US006225451B1

(12) United States Patent
Ballinger et al.

(10) Patent No.: US 6,225,451 B1
(45) Date of Patent: May 1, 2001

(54) CHROMOSOME 11-LINKED CORONARY HEART DISEASE SUSCEPTIBILITY GENE CHD1

(75) Inventors: Dennis G. Ballinger, Menlo Park, CA (US); Wei Ding, Salt Lake City, UT (US); Susanne Wagner, Murray, UT (US); Mark A. Hess, Salt Lake City, UT (US)

(73) Assignee: Myriad Genetics, Inc., Salk Lake City, UT (US)

( * ) Notice: Subject to any disclaimer, the term of this patent is extended or adjusted under 35 U.S.C. 154(b) by 0 days.

(21) Appl. No.: 09/262,773

(22) Filed: Mar. 4, 1999

Related U.S. Application Data

(60) Provisional application No. 60/080,934, filed on Apr. 6, 1998.

(51) Int. Cl.[7] .............................. C07H 21/04; C12Q 1/68
(52) U.S. Cl. ................................ 536/22.1; 435/6
(58) Field of Search ................. 435/6; 536/22.1

(56) References Cited

PUBLICATIONS

Hillier et al., "The WashU–Merck EST Project," EMBL Sequence Database, Jun. 7, 1996.*
Hillier et al., "WashU–merck EST Project 1997," EMBL Sequence Database, Apr. 25, 1997.*
Lee et al., "Zinc finger protein," EMBL Sequence Database, Nov. 1, 1996.*
Stokes et al., "DNA binding and chromatin localization properties of CHD1," Molecular and Cellular Biology, vol. 15, No. 5, May 1995, pp. 2745–2753.*
Woodage et al., "Characterization of the CHD family of proteins," Proc. Natl. Acad. Sci. USA, vol. 94, Oct. 1997, pp. 11472–11477.*
Monaco et al., "Homo sapiens ZNF202 beta (ZNF202) mRNA, complete cds," EMBL Sequence Database, Nov. 16, 1998.*
Monaco et al., "Molecular Cloning and Characterization of ZN202: a New Gene at 11g23.3. Encoding Testis–specific Zinc Finger Proteins," Geonomics 52, No. 3, Sep. 15, 1997, 358–362.*
Myriad Genetics, Inc., Mar. 10, 1998 Press Release "Myriad and Novartis Discover Important Cardiovascular Disease Gene."*
Kardassis et al. 1996, Hypertension 27: 980–1008.*
Ktistaki et al. 1994, Nucleic Acids Research 22 (22): 4689–4696.*

* cited by examiner

Primary Examiner—Jeffrey Fredman
Assistant Examiner—Arun Chakrabarti
(74) Attorney, Agent, or Firm—Fish & Neave; James F. Haley, Jr., Esq.; Stanley D. Liang

(57) ABSTRACT

Human coronary heart disease susceptibility gene (CHD1), some alleles of which are related to susceptibility to coronary heart disease. Germline mutations in the CHD1 gene and their use in the diagnosis of predisposition to coronary heart disease and to metabolic disorders, including hypoalphalipoproteinemia, familial combined hyperlipidemia, insulin resistant syndrome X or multiple metabolic disorder, obesity, diabetes and dyslipidemic hypertension. Presymptomatic therapy of individuals who carry deleterious alleles of the CHD1 gene (including gene therapy, protein replacement therapy, and administration of protein mimetics and inhibitors). The screening of drugs for dyslipidemic therapy.

21 Claims, 12 Drawing Sheets

```
KRAB consensus          esVtFkDVavdFseEEWqilLdPaQrkLYrdVMLENFrnlvsl
in some KRAB domains       gl                  qd           kd       ey
CHD zincfinger          GLVTFKDVAVcFSQDqWsdLDPtQKefYgEYvLEedcgiVvs
                                                            ↓
                                              diabetes sample 35  E
```

FIG.4

Figure 6B:
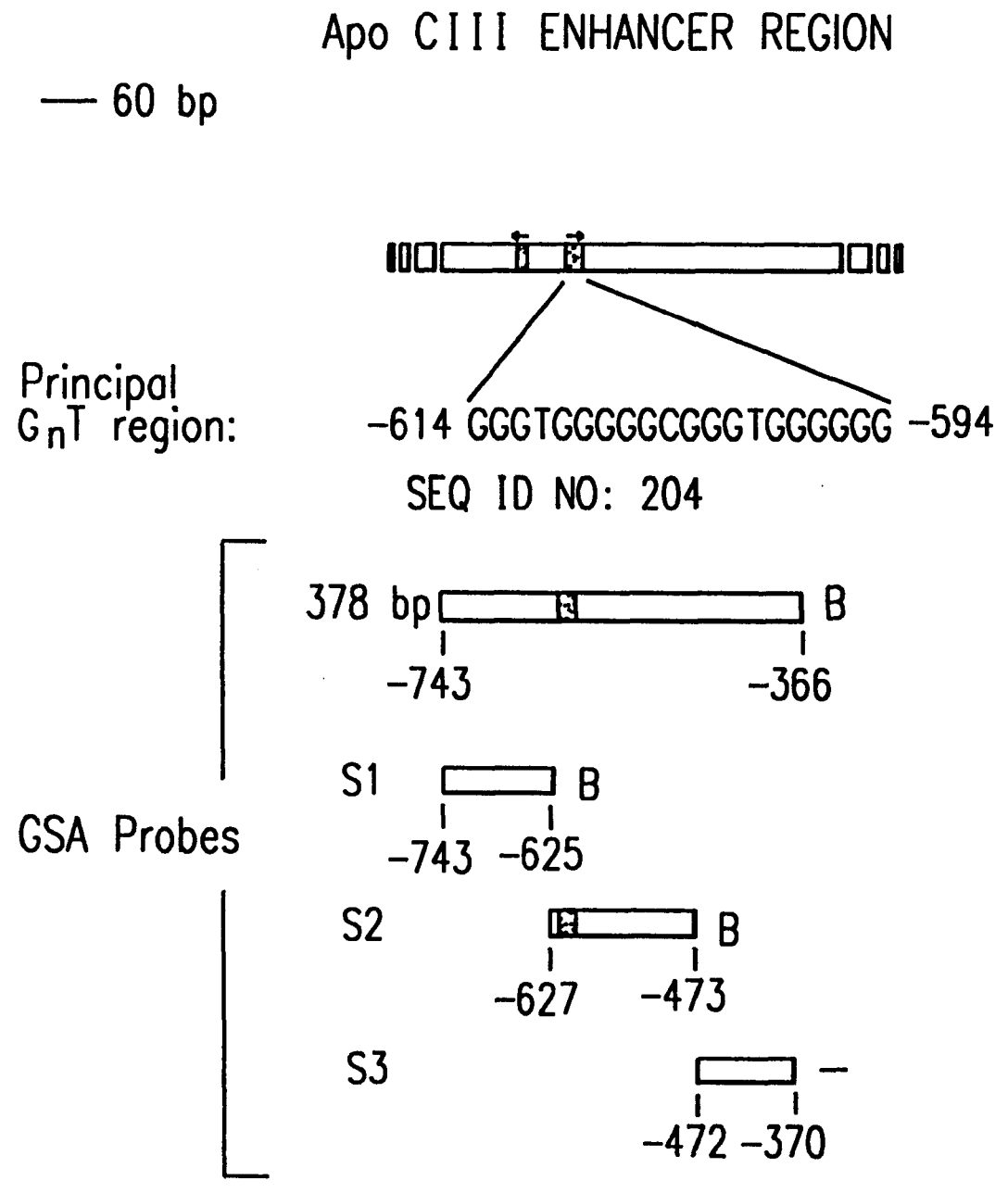

Apo CIII ENHANCER REGION

— 60 bp

Principal $G_nT$ region: −614 GGGTGGGGGCGGGTGGGGGG −594
SEQ ID NO: 204

GSA Probes:

CHD1-SCAN DOMAIN  FRRFRYQEAASPREALIRLRELCHQWLRPERRTKEQILELLVEQFLTVLPGELQSWVRGQRPESGEEAVTLVEGLQ
SCAN CONSENSUS    FRQICYQEtsGPREALSRLRELCRqWLRPEIHTKEQILELLVLEQFLtILPgELIawVrehhPESGEEaVtIvEDLq

FIG.8

CHROMOSOME 11-LINKED CORONARY HEART DISEASE SUSCEPTIBILITY GENE CHD1

This utility application claims benefit under 35 U.S.C. §119(e) of U.S. Provisional Application (formerly U.S. application Ser. No. 09/034,941, converted to a provisional application on Mar. 3, 1999) filed Mar. 4, 1998, and also claims benefit under 35 U.S.C. §119(e) of U.S. Provisional Application Ser. No. 60/080,934, filed Apr. 6, 1998.

TECHNICAL FIELD OF THE INVENTION

The present invention relates generally to the field of human genetics. The present invention specifically relates to a human coronary heart disease susceptibility gene (CHD1), some alleles of which are related to susceptibility to coronary heart disease. More specifically, the present invention relates to germline mutations in the CHD1 gene and their use in the diagnosis of predisposition to coronary heart disease and to metabolic disorders, including hypoalphalipoproteinemia, familial combined hyperlipidemia, insulin resistant syndrome X or multiple metabolic disorder, obesity, diabetes and dyslipidemic hypertension.

The invention also relates to presymptomatic therapy of individuals who carry deleterious alleles of the CHD1 gene (including gene therapy, protein replacement therapy, and administration of protein mimetics and inhibitors).

Also within the scope of this invention is the screening of drugs for coronary heart disease or metabolic disorder therapy.

The invention further relates to the screening in patients of the CHD1 gene for mutations, such screening is useful for diagnosing the predisposition to coronary heart disease and to metabolic disorders, including hypoalphalipoproteinemia, familial combined hyperlipidemia, insulin resistant syndrome X or multiple metabolic disorder, obesity, diabetes and dyslipidemic hypertension.

Also within the scope of this invention are binding assays utilizing the proteins of the invention.

Also within the scope of this invention are antibodies directed against protein products encoded by the CHD1 gene, hybridomas secreting the antibodies, and diagnostic kits comprising those antibodies.

Methods for using the CHD1 polypeptides, CHD1 DNA sequences, polynucleotide primers, and antisense sequences directed at the CHD1 locus and the aforementioned antibodies are also within the scope of this invention.

BACKGROUND OF THE INVENTION

Coronary heart disease (CHD) or coronary artery disease (CAD) is one of the major causes of death in the United States, accounting for about a third of all mortality. Studies of early CHD sib pairs have identified several risk factors that contribute to CHD (Goldstein, et al., 1973; Hazzard, et al., 1973; and Williams, et al., 1990)*. These dyslipidemic phenotypes and their frequency in cases of early familial coronary disease include: familial hypercholesterolemia (high LDL cholesterol), 3–4%; Type III hyperlipidemia (Apo E2/E2 genotype), 0.5 to 3%; low HDL-cholesterol (HDL-C, also called hypobetalipoproteinemia), 20 to 30%; familial combined hyperlipidemia (FCH—high LDL-cholesterol and/or high triglycerides and/or high VLDL-cholesterol), 20–36%; familial hypertriglyceridemia, about 20%; high Lp(a), 16 to 19%; high homocysteine, 15 to 30%; or no known concordant risk factors 10 to 20% (Williams, et al., 1990). Thus, a familial history of CHD is a risk factor independent of known physiological abnormalities (Hopkins, et al., 1988, Jorde, et al., 1990).

\* A list of References is appended herein, providing full citations of the references.

Several metabolic disorders are associated with increased risk of CHD. These include familial dyslipidemic hypertension (Williams, et al., 1990; Williams, et al., 1993), insulin-dependent diabetes mellitus (IDDM), non-insulin-dependent diabetes mellitus (NIDDM), maturity onset diabetes of the young (MODY), insulin resistant syndrome X (Castro-Cabezas, et al., 1993; Kawamoto, et al., 1996; Landsberg, 1996; Hjermann, 1992; Vague and Raccah, 1992), hyperthyroidism and hypothyroidism (de Bruin, et al., 1993; Blangero, et al., 1996) and obesity (Iverius, et al., 1985). Recent analyses indicate the possibility that a single defect, perhaps the amount of visceral body fat, may underlie many of these syndromes (Hopkins, et al., 1996).

The underlying genetic causes of the majority of CHD deaths are not known. In addition, the genetics of many of the underlying metabolic disorders are not completely understood. These metabolic disorders are generally described as "genetically complex". In addition, the disorders themselves are fairly common in the population, so one possibility is that common alleles at some loci predispose to the disorders, making these alleles difficult to distinguish from common (non-causal) polymorphisms. In addition, the disease causing alleles may have low penetrance. The diseases also develop over a large number of years, thus creating the situation that a relatively minor alteration in the function of the predisposing gene(s) can, over a lifetime, have severe metabolic and phenotypic consequences. Thus, the disease-causing alleles may not be obviously deleterious to gene function. Finally, many metabolic diseases show significant co-morbidity, raising the possibility that multiple phenotypes might be associated with a single gene. The penetrances of the individual disorders may be influenced by different alleles of the gene or by environmental or genetic background effects, and may differ between or within families segregating mutations in the predisposing gene(s).

Some risk factors appear relatively simple genetically. For instance, lipoprotein (a) (Lp(a)) levels are strongly correlated with CHD. Greater than 95% of the variation in Lp(a) protein levels is associated with the gene itself, and is mostly related to the number of Kringle repeats in the gene (DeMeester, et al., 1995). The role of the LDL receptor in lipid metabolism and CHD is another example. The familial hypercholesterolemia (FH) syndrome is a rare syndrome (affecting about 1 in 500 individuals) characterized by very high low-density lipoprotein (LDL)-cholesterol, and very early CHD, usually manifest in the 20s or 30s. Early family studies identified and clinically defined obligate FH heterozygotes, and allowed for the positional cloning of the gene responsible for FH, the LDL receptor. About half of FH index cases can be found to carry mutations in the LDL receptor gene, and at least 373 distinct mutations have been identified in the LDL receptor to date (a database of identified mutations can be found at www.ucl.ac.uk/fh/). These mutations cover the full extent of possible deleterious mutations. Included are point mutations that alter the function of the receptor or the expression of the gene, small insertions and deletions causing frameshifts in the coding region and large genomic rearrangements that cause substantial alterations in the gene's structure, resulting in altered gene expression.

On the other hand, some dyslipidemias appear to be genetically quite complex. For instance, about half of the variation in high-density lipoprotein-C (HDL-C) levels appear to be genetically determined (Friedlander, et al., 1986a; Friedlander, et al., 1986b; Moll, et al., 1989; Perusse, et al., 1989; Prenger, et al., 1992; Cohen, et al., 1994). Defects in several genes are known to cause low HDL-C including apolipoprotein AI (ApoAI) deficiency, apolipoprotein B (ApoB) polymorphisms (Peacock et al., 1992), lipoprotein lipase (LPL) deficiency and lecithin:cholesterol acetyltransferase (LCAT) deficiency (recently reviewed in Funke, 1997). However, in aggregate these known genetic defects account for only a very small proportion of individuals with low HDL. Some studies have shown association of HDL-C levels with the hepatic triglyceride lipase and ApoAI, CIII AIV loci (e.g. Cohen, et al., 1994), indicating that a significant portion of the genetic effects may come from these loci, though other studies have failed to find such an association (Bu, et al., 1994; Maheny, et al., 1995; Marcil, et al., 1996). Additionally, the ApoAI, CIII and AIV loci have been associated with familial combined hyperlipidimia (FCH) in some studies (Wojciechowski, et al., 1991; Tybjaerg-Hansen, et al., 1993, Dallinga-Thie, et al., 1997), but not others (Xu, et al., 1994).

Another complexity of the dyslipidemias is illustrated by the LPL gene. Heterozygotes for some LPL mutations show higher triglycerides and lower HDL-C, and no elevation in LDL-C, and high systolic blood pressure when compared with control individuals (Sprecher, et al., 1996; Deeb, et al., 1996). However there is a significant variation in the extent of these abnormalities when different mutations are compared (Sprecher, et al., 1996). In addition, some LPL mutations are found in individuals with a more classic familial combined hyperlipidemia (FCH), having high LDL-C as well as high TG and low HDL-C (Yang, et al., 1996), and some with insulin-resistant syndrome X (Tenkanen, et al., 1994). Other reports fail to find linkage of FCH with LPL, even in families segregating known LPL mutations (e.g. de Bruin, et al., 1996).

Another illustrative set of examples are the MODY genes (Maturity Onset Diabetes of the Young). In combination, the MODY genes account for about 130 of every 10,000 diabetics. Positional cloning and candidate gene mutation screening have identified causal mutations in four transcription factors regulating pancreatic gene expression (HNF-1α, Yamagata, et al., 1996; HNF-4α, Yamagata, et al., 1996b, HNF 1β, Horikawa et al., 1997; and IPF1 Stoffers, et al., 1997) and in glucokinase, a pancreatic beta-cell molecule involved in the sensing of glucose levels. Interestingly, some of the transcription factor mutations are frameshifts, implying a total loss of functional protein from the altered allele. These results indicate that half-normal levels of these transcription factors can have a very specific physiological effect, and disease phenotype, in spite of their synthesis in a large variety of tissues.

SUMMARY OF THE INVENTION

The present invention solves the problems referred to above by providing means to diagnose, prevent and treat coronary heart disease and metabolic disorders, including hypoalphalipoproteinemia, familial combined hyperlipidemia, insulin resistant syndrome X or multiple metabolic disorder, obesity, diabetes and dyslipidemic hypertension.

More specifically, this invention provides human coronary heart disease susceptibility gene (CHD1), some alleles of which are related to susceptibility to coronary heart disease and to metabolic disorders related to lipid metabolism. This invention also relates to germline mutations in the CHD1 gene, and methods and systems for using the germline mutations of the CHD1 gene in the diagnosis of predisposition to metabolic disorders.

The present invention also provides the means necessary for production of gene-based therapies directed at coronary heart disease or metabolic disorders. These therapeutic agents may take the form of polynucleotides comprising all or a portion of the CHD1 locus placed in appropriate vectors or delivered to target cells in direct ways such that the function of the CHD1 protein is interfered with or reconstituted.

The invention further comprises the use of polypeptides of the invention for the treatment or prevention of CHD. Therapeutic agents may also take the form of polypeptides based on either a portion of or the entire protein sequence of CHD1; such isolated polypeptides as well as pharmaceutical compositions comprising them are also provided by this invention. These may functionally replace the activity of CHD1 in vivo, or interfere with normal CHD1 function.

Also within the scope of this invention are methods and systems for presymptomatic therapy of individuals who carry deleterious alleles of the CHD1 gene.

The present invention also provides isolated antibodies (e.g. monoclonal antibodies), that specifically bind to epitopes of an isolated polypeptide encoded by the CHD1 locus.

Also provided by this invention are methods and systems for the screening in patients of the CHD1 gene for mutations, such screening is useful for diagnosing the predisposition to coronary heart disease and to metabolic disorders. Such methods may further comprise the step of amplifying a portion of the CHD1 locus, and may further include a step of providing a set of polynucleotides that are primers for amplification of said portion of the CHD1 locus. Such methods may also include a step of providing the complete set of short polynucleotides defined by the sequence of CHD1 or discrete subsets of that sequence, all single-base substitutions of that sequence or discrete subsets of that sequence, all 1-, 2-, 3-, or 4-base deletions of that sequence or discrete subsets of that sequence, and all 1-, 2-, 3-, or 4-base insertions in that sequence or discrete subsets of that sequence. This invention also provides methods for using and kits comprising the above-mentioned antibodies to identify mutant forms of CHD1 polypeptides or to detect aberrant levels of expression of CHD1 polypeptides in biological samples. Such methods are useful for identifying mutations for use in either diagnosis of the predisposition to coronary heart disease or the diagnosis or prognosis of metabolic disorders.

This invention further provides isolated polynucleotides comprising all or a portion of the CHD1 locus or comprising a mutated CHD1 locus, preferably at least eight bases and not more than about 300 kilobases (kb) in length. Such polynucleotides may also be antisense polynucleotides. The present invention also provides a recombinant construct comprising such an isolated polynucleotide, for example, a recombinant construct suitable for expression of a polypeptide comprising a CHD1 wild-type or mutant polypeptide, or a portion of either, in a transformed host cell.

Also within the scope of this invention are methods of detecting a polynucleotide comprising a portion of the CHD1 locus or its expression product in an analyte. Such methods may further comprise the step of amplifying the portion of the CHD1 locus, and may further include a step of providing a set of polynucleotides that are primers for amplification of said portion of the CHD1 locus. The method is useful for either diagnosis of the predisposition to coronary heart disease or the diagnosis or prognosis of metabolic disorders.

Also provided by the present invention are kits for detecting in an analyte a polynucleotide comprising a portion of the CHD1 locus, kits comprising a polynucleotide complementary to the portion of the CHD1 locus packaged in a suitable container, and instructions for their use.

Also within the scope of this invention are methods of preparing a polynucleotide comprising polymerizing nucleotides to yield a sequence comprised of at least eight consecutive nucleotides of the CHD1 locus; and methods of preparing a polypeptide comprising polymerizing amino acids to yield a sequence comprising at least five amino acids encoded within the CHD1 locus.

Also within the scope of this invention are methods to screen drugs (e.g. binding assays) for inhibition or restoration of CHD1 gene product function as a therapy for coronary heart disease or metabolic disorders.

It is a discovery of the present invention that the CHD1 locus, certain alleles of which predispose individuals to coronary heart disease or to metabolic disorders related to lipid metabolism, is a gene encoding multiple CHD1 proteins, some of which have been found to have sequence motifs characteristic of the zinc finger category of transcription factors, and the KRAB motif, implicated in protein-protein interactions. This gene is termed CHD1 herein. It is a discovery of the present invention that mutations in the CHD1 locus in the germline are indicative of a predisposition to coronary heart disease or to metabolic disorders related to lipid metabolism. The mutational events of the CHD1 locus can involve deletions, insertions and point mutations within the coding sequence and the non-coding sequence, as well as within the regulatory sequence.

It is also a discovery of the present invention that the CHD1 protein is a sequence specific DNA binding protein that binds and may regulate the expression of genes involved in lipid metabolism or implicated in CHD and metabolic disorders.

This diagram shows genomic DNA and the order of markers (coded as in Table 3) in the CHD1 region. It also shows a set of BACs and PACs (e.g. B91=BAC 91; P254= PAC 254), and the recombinants found in families linked to chromosome 11q23. The recombinants are shown with solid lines representing the region shared with the haplotype segregating with disease in the family, the arrowhead at the recombinant marker, and the region between the last recombinant marker and the first non-recombinant marker is stippled. The width of the lines represent the relative confidence of linkage in the family in which the recombinant is found, with the thicker lines representing more likely linkage to 11q23. The kindred and individual carrying the recombinant chromosome are listed to the right of each line.

Figure 2:
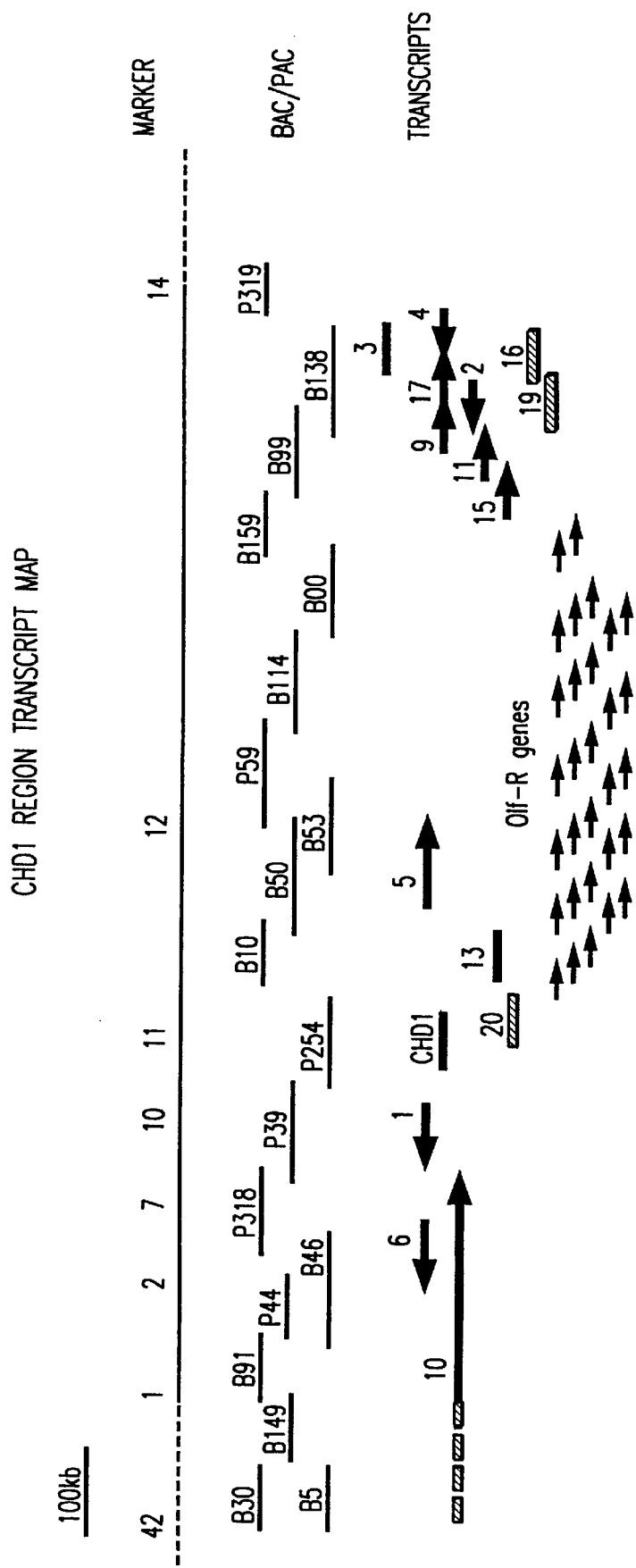

FIG. 2. CHD1 region transcript map. A diagram of the CHD1 region, showing the location of BACs and PACs, identified transcripts and the location of CHD1. Genomic DNA is represented by the top line, with the positions of some genetic markers (coded as in Table 3). The BACs and PACs (e.g., B91=BAC 91; P254=PAC 254) that form a genomic contig across the region spanning markers 1 to 14 are shown below the genomic DNA. Below these, the candidate genes that were screened for mutations in CHD families are shown in their approximate locations. A set of almost 40 olfactory receptor (Olf-R) genes in the middle of the CHD1 region are also shown. CHD1 is located on PAC 254.

Figure 3:
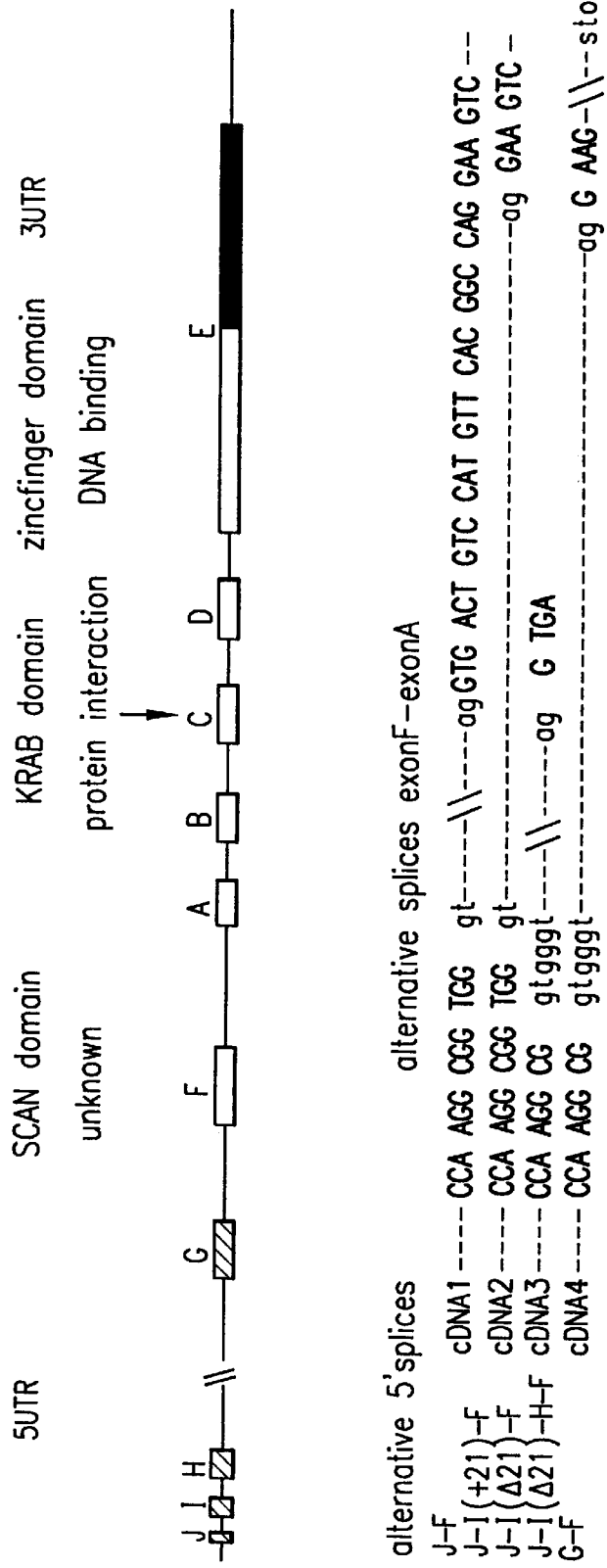

FIG. 3. CHD1 alternative transcripts. A diagram of the CHD1 transcription unit showing the exons of CHD1 and alternative transcripts of CHD1. Diagram of the alternatively spliced products of the CHD1 locus. Ten exons of the CHD1 gene are diagramed as boxes, filled boxes are 5' and 3' untranslated regions (UTR) of the transcripts. cDNA1 to cDNA4 indicate four alternative splices between exons A and F that affect the protein coding capacity of CHD1. The five observed 5' alternative splices are also shown; these may occur in any combinations with cDNAs 1 to 4. The approximate locations and functions of conserved sequence motifs of CHD1 proteins are also shown.

FIG. 4. CHD1 KRAB domain mutation in a diabetic proband. A human KRAB domain consensus sequence (SEQ ID NO: 199) is listed on the top line, with the most highly conserved amino acids in upper case. The middle line (SEQ ID NO: 200) shows particular amino acids contained in at least 15% of human KRAB domains. The bottom line (SEQ ID NO: 201) gives the sequences of the CHD1 KRAB domain; amino acids conserved with the consensus are in upper case. The arrow indicates the position of a mutation (K872E) found in a DNA sample from an obese diabetic who has low HDL (SEQ ID NO: 202) (see text).

Figure 5A:
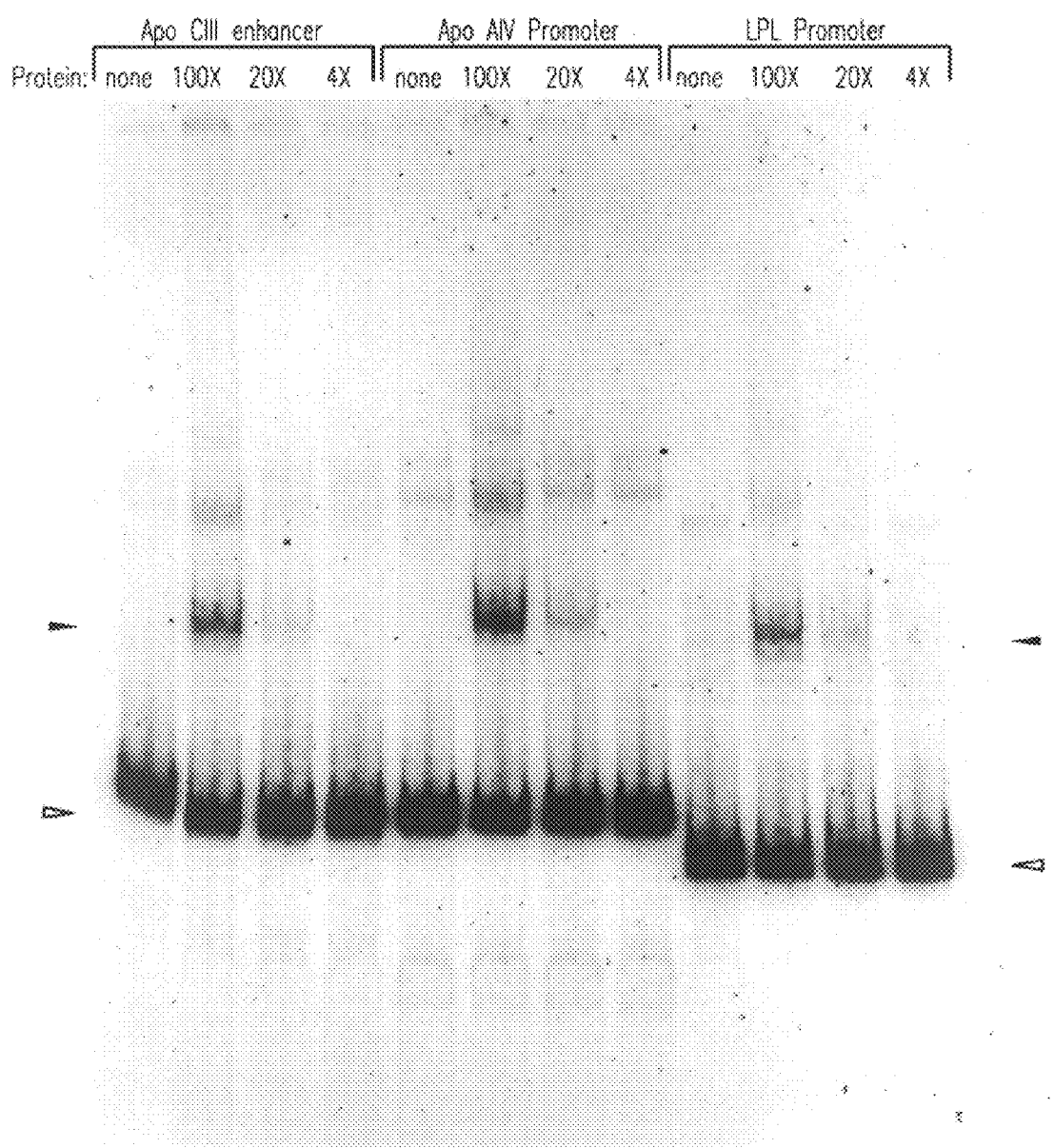

FIG. 5A. Mobility shift of gene promoter fragments by CHD1.ZnF3-8 protein. Promoter regions amplified by PCR were end labeled with $^{32}P$ and incubated with purified CG7 GST-fusion protein (zinc fingers 3 through 8). No d(I:C) competitor was used. Relative to the start of transcription, the probes spanned: −573 to −165 (apolipoprotein AIV), −743 to −366 (apolipoprotein CIII, Kardassis, et al, 1996), −532 to −187 (Lipoprotein Lipase). The molar protein:probe ratio is indicated above each lane. 100× protein corresponds to approximately 140 nM in the binding reaction. Open arrowheads indicate free probe. Filled arrowheads indicate the principal shifted species.

Figure 5B:
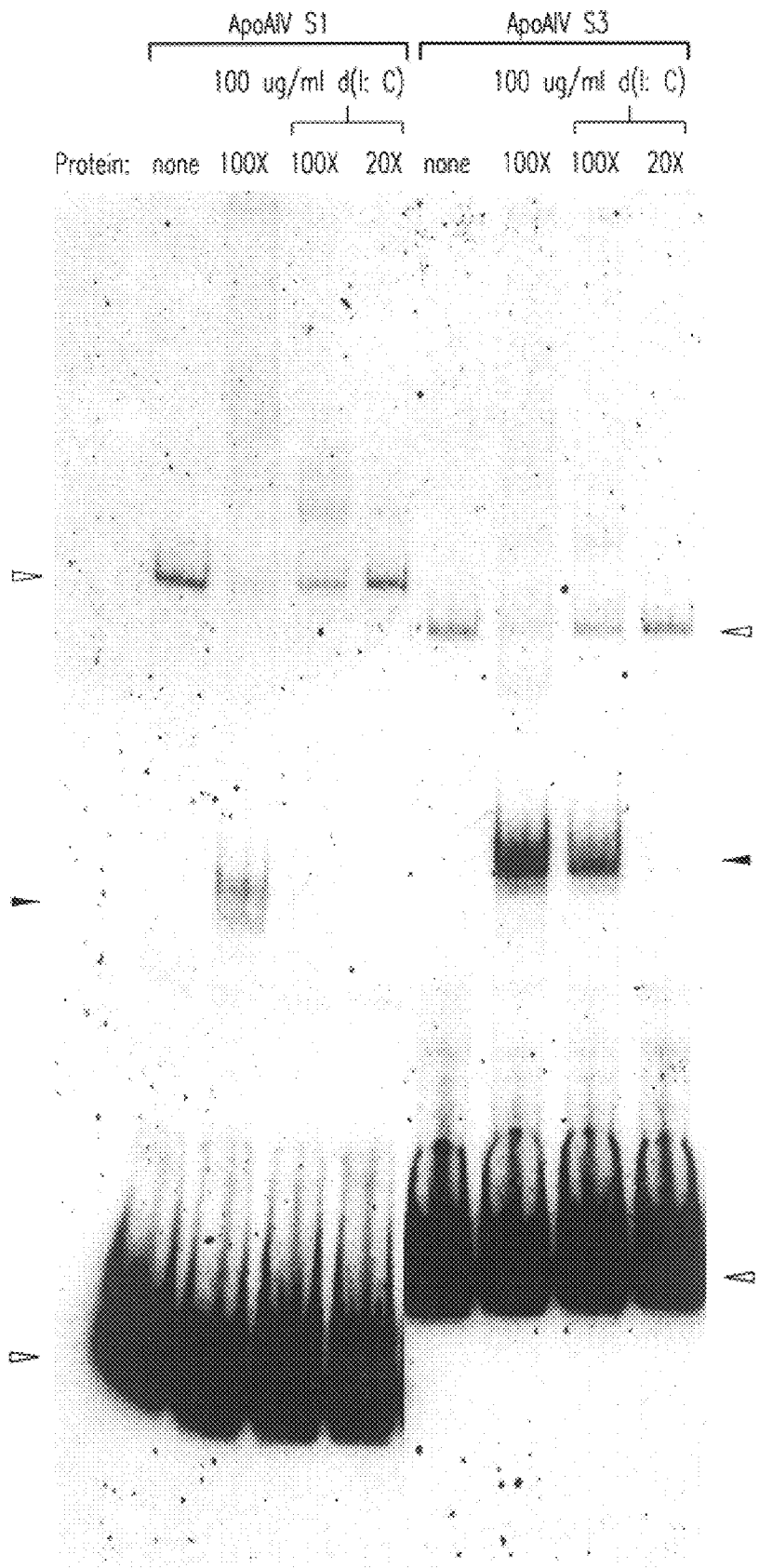

FIG. 5B. Mobility shift of Apolipoprotein AIV gene promoter subfragments by CHD1.ZnF3-8 Protein. The promoter fragment (−573 to −165) shifted by CHD1 GST fusion protein was trisected by PCR amplification to 3 adjacent, non-overlapping regions (2 are shown: S1, −573 to −447 and S3, −328 to −165). $^{32}P$ end-labeled products were incubated with purified CHD1 GST-fusion protein (zinc fingers 3 through 8). The molar protein:probe ratio and addition of non-specific competitor are indicated above each lane. 100× protein corresponds to approximately 140 nM in the binding reaction. Open arrowheads indicate free probe. Filled arrowheads indicate the principal shifted species. Note that the weak shift of fragment S1 is fully competed by d(I:C), indicating that it is due to non-specific binding.

Figure 5C:
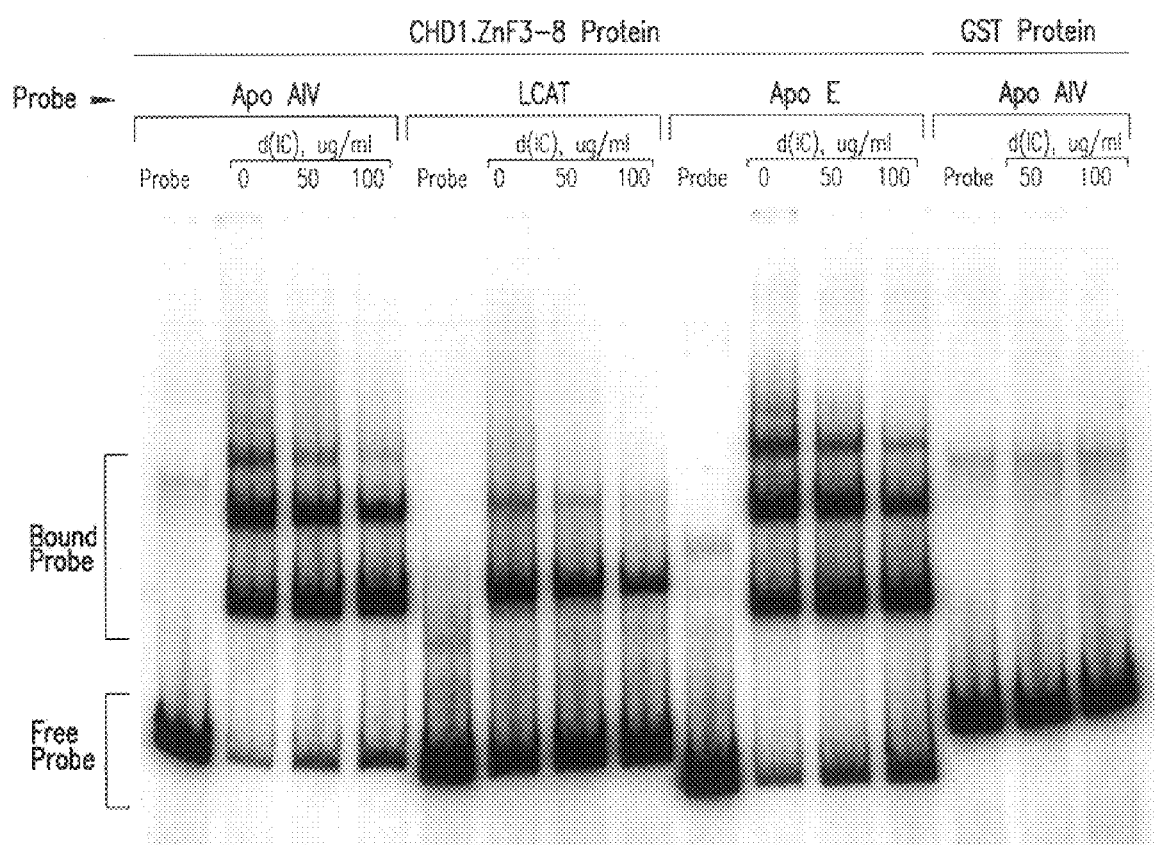

FIG. 5C. Mobility shift of gene promoter fragments by CHD1.ZnF3-8 protein. PCR amplified promoter regions were end labeled with $^{32}P$ and incubated with purified CHD1 GST-fusion protein (zinc fingers 3 through 8). Poly d(I:C) competitor was used as indicated. Relative to the start of transcription, the probes spanned: −573 to −165 (Apolipoprotein AIV, Apo AIV), −1304 to −968 (Lecithin:cholesterol acetyltransferase, LCAT), −324 to +16 (Apolipoprotein E, Apo E). The molar protein:probe ratio in the binding reaction was 100× (GST, 250×); protein concentration was approximately 140 nmolar (GST, 340 nmolar).

Figure 6A:
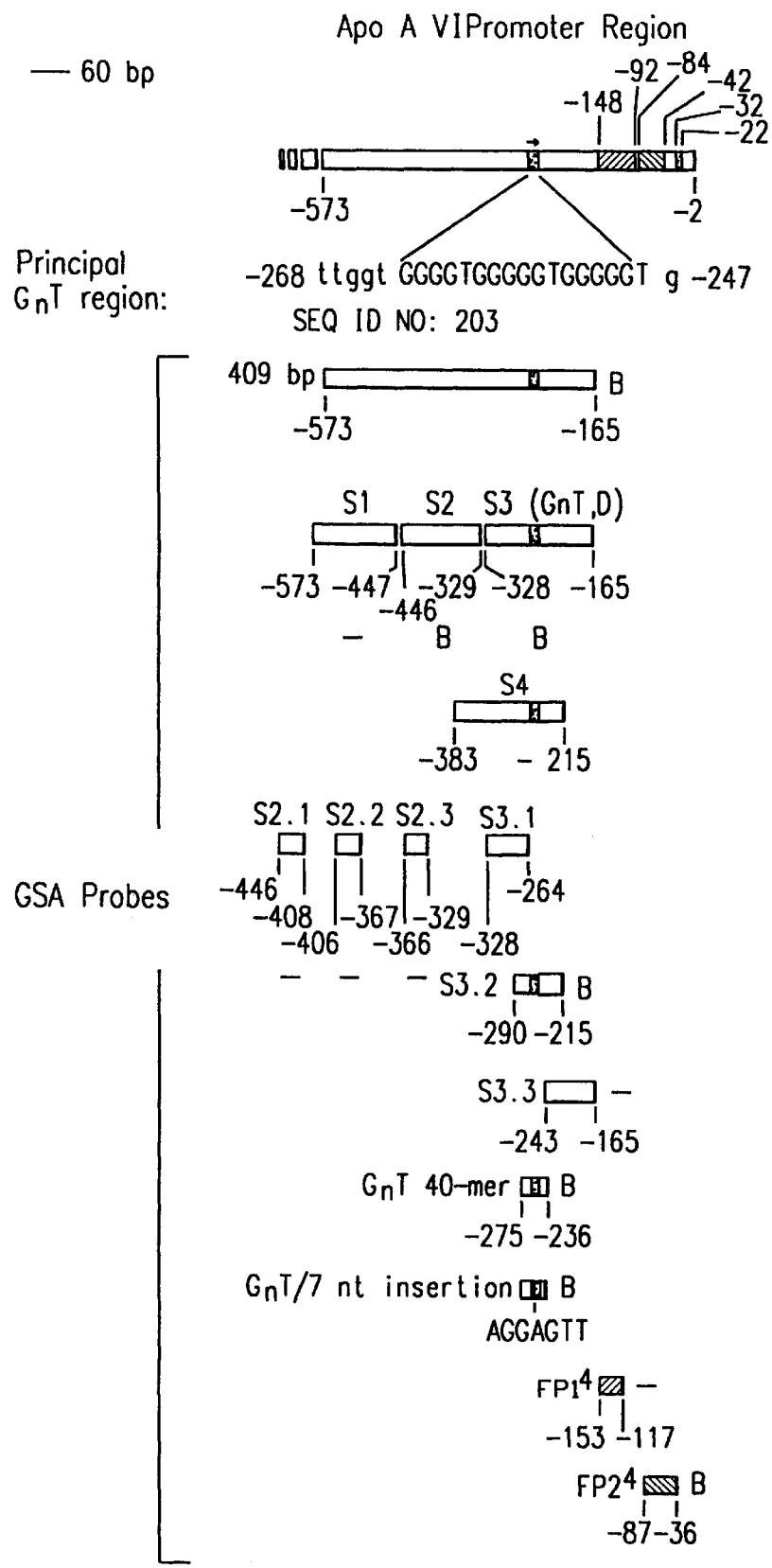
Figure 6C:
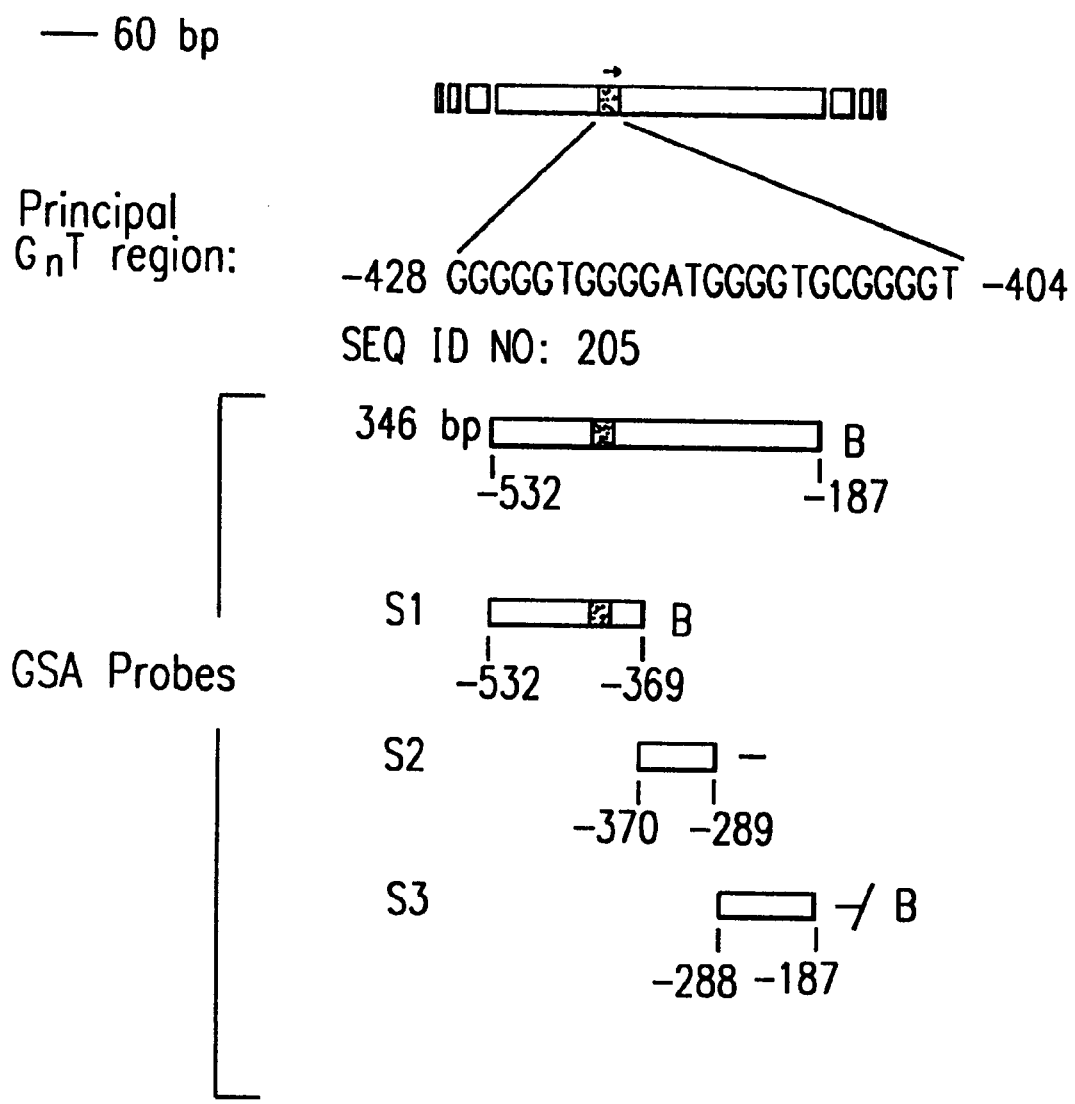

FIG. 6. Diagrammatic summary of gel shift assay results for fragments of the Apolipoprotein AIV promoter (FIG. 6A), the Apolipoprotein CIII enhancer (FIG. 6B) and the lipoprotein lipase (LPL) promoter (FIG. 6C). Fragments marked with "B" bind to CHD1.ZnF3-8 as detected by a probe mobility shift on polyacrylamide gels; those marked "−" were not detectably shifted under the same conditions; and those marked "−/B" bound very weakly. GSA probes indicate promoter fragments tested. Principal GnT region gives the sequence of each fragment with the highest degree of conservation with the GGGGT consensus (see text). The stippled boxes indicate these consensus sequences, and some of the defined protein binding sites in Apo AIV promoter (Kardassis, et al., 1996). The sequence ttg-gtGGGGTGGGGGTGGGGGTg in FIG. 6A is SEQ ID NO: 203. The sequence GGGTGGGGGCGGGTGGGGGG in FIG. 6B is SEQ ID NO: 204. The sequence GGGGGTGGG-GATGGGGTGCGGGGT in FIG. 6C is SEQ ID NO: 205.

Figure 7:
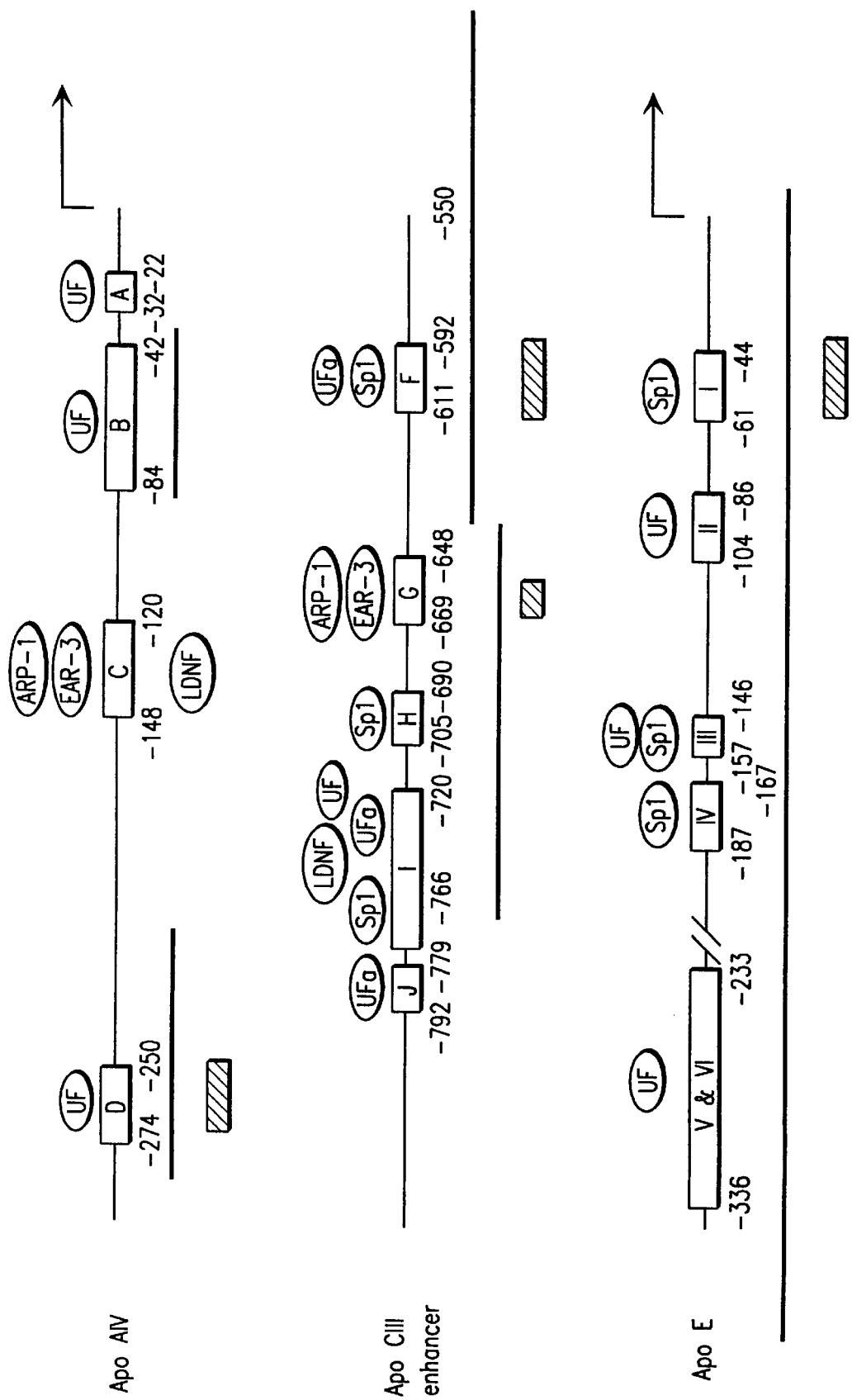

FIG. 7. The regulatory regions of the ApoAIV gene, the ApoCIII enhancer, and the ApoE gene, and fragments that bind CHD1.ZnF.3-8. Diagrams of promoter fragments from these genes, adapted from Kardassis, et al., 1996, showing regions that bind proteins from nuclear extracts, and which are important for regulation of the respective genes. The ovals indicate transcription factors that bind to particular motifs; UF, unknown factor; LDNF, ligand-dependent nuclear factor (e.g., HNF-4). Below each promoter diagram are shown the following: Promoter fragment that binds CHD1.Znf3.8 (solid line); CHD1 consensus binding sequence block (stippled boxes).

FIG. 8. The amino acid sequence of the CHD1 SCAN domain (SEQ ID NO: 207) is aligned to a consensus sequence (SEQ ID NO: 208) derived from homology analysis of SCAN domain containing zinc-finger proteins in the Genbank database.

DETAILED DESCRIPTION OF THE INVENTION

This invention relates to wild-type and mutant CHD1 polypeptides and DNA sequences encoding them, antibodies directed against those polypeptides, compositions comprising the polypeptides, DNA sequences or antibodies, and methods for identifying additional CHD1 mutant polypeptides and antibodies and methods for the detection, treatment and prevention of human coronary heart disease and related metabolic disorders related to lipid metabolism, including hypoalphalipoproteinemia, familial combined hyperlipidemia, insulin resistant syndrome X or multiple metabolic disorder, obesity, diabetes and dyslipidemic hypertension.

In order that the invention herein described may be fully understood, the following detailed description is set forth.

The term "metabolic disorders" refers to one or more conditions afflicting a human patient, either present individually or in combination, associated with a susceptibility to CHD. In particular, the term includes any dyslipidemia wherein the serum level of lipid is in the bottom 10% or top 90% of the population, based on age and sex corrected population values reported by the LRC. An individual can be classified as dyslipidemic if any of the following values fall within the above defined ranges: total serum cholesterol, LDL-cholesterol, VLDL-cholesterol, HDL-cholesterol or triglycerides. Used herein, "metabolic disorders" also includes other syndromes that can accompany alterations in serum lipid levels. These syndromes include: insulin-dependent diabetes mellitus (IDDM), non-insulin-dependent diabetes mellitus (NIDDM), hyperthyroidism, hypothyroidism, dyslipidemic hypertension, obesity, insulin resistance or multiple metabolic syndrome (or insulin resistant syndrome X). These conditions may be present in a particular individual or family independently or in any combination.

The term "amplification of polynucleotides" refers to methods such as the polymerase chain reaction (PCR), ligation amplification (or ligase chain reaction, LCR) and amplification methods based on the use of Q-beta replicase for the purpose of amplifying polynucleotides. Also useful for this purpose are, without limitation, strand displacement amplification (SDA) and nucleic acid sequence based amplification (NASBA). These methods are well known and widely practiced in the art. See, e.g., U.S. Pat. Nos. 4,683,195 and 4,683,202 and Innis et al., 1990 (for PCR); and Wu et al., 1989a (for LCR); U.S. Pat. Nos. 5,270,184 and 5,455,166 (for SDA); and U.S. Pat. No. 5,409,818, Kievits et al., 1991 and Compton, 1991 for NASBA. Reagents and hardware for conducting PCR are commercially available. Primers useful for amplifying sequences from the CHD1 region are preferably complementary to, and hybridize specifically to, sequences in the CHD1 region or in regions that flank a target region therein. CHD1 sequences generated by amplification may be sequenced directly. Alternatively, but less desirably, the amplified sequence(s) may be cloned prior to sequence analysis. One method for the direct cloning and sequence analysis of enzymatically amplified genomic segments has been described by Scharf, 1986.

The term "to encode" refers to the following: a polynucleotide is said to "encode" a polypeptide if, in its native state or when manipulated by methods well known to those skilled in the art, it can be transcribed and/or translated to produce the mRNA for and/or the polypeptide or a fragment thereof. The anti-sense strand is the complement of such a nucleic acid, and the encoding sequence can be deduced therefrom.

The terms "isolated" or "substantially pure" nucleic acid or polynucleotide (e.g., an RNA, DNA or a mixed polymer) is one that is substantially separated from other cellular components that naturally accompany a native human sequence or protein, e.g., ribosomes, polymerases, many other human genome sequences and proteins. The term embraces a nucleic acid sequence that has been removed from its naturally occurring environment, and includes recombinant or cloned DNA isolates and chemically synthesized analogs or analogs that are biologically synthesized by heterologous systems.

The term "CHD1 alleles" refers to normal alleles (also referred to as wild-type alleles) of the CHD1 locus as well as alleles carrying variations that predispose individuals to develop coronary heart disease or metabolic disorders. Such predisposing alleles are also called "CHD1 susceptibility alleles" or "CHD1 mutant alleles".

The terms "CHD1 Locus", "CHD1 gene", "CHD1 nucleic acids" or "CHD1 polynucleotide" each refer to polynucleotides, which are in the CHD1 region. Some of these DNAs are likely to direct the expression, in normal or abnormal tissues, of CHD1 wild-type and mutant alleles, said mutant alleles predispose an individual to develop coronary heart disease or metabolic disorders. The locus is indicated in part by mutations that predispose individuals to develop coronary heart disease or metabolic disorders. These mutations fall within the CHD1 region described infra.

The CHD1 locus is intended to include CHD1 coding sequences, intervening sequences and regulatory elements controlling transcription and/or translation. The CHD1 locus is intended to include all allelic variations of the DNA sequence.

The term "CHD1 nucleic acids" or "CHD1 polynucleotides" is also extended to refer to nucleic acids that encode a CHD1 polypeptide, CHD1 polypeptide fragment, homologs and variants of CHD1, protein fusions and deletions of any of the above. These nucleic acids comprise a sequence which is either derived from, or substantially similar to a natural CHD1-encoding gene or one having substantial homology with a natural CHD1-encoding gene or a portion thereof.

The polynucleotide compositions of this invention include RNA, cDNA, genomic DNA, synthetic forms, and mixed polymers, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.) Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

The term "CHD1 region" refers to a portion of human chromosome 11 bounded by the markers D11S924 to D11S912. This region contains the CHD1 locus, including the CHD1 gene.

The terms "CHD1 locus", "CHD1 allele" and "CHD1 region" all refer to the double-stranded DNA comprising the locus, allele, or region, as well as either of the single-stranded DNAs comprising the locus, allele or region.

The term a "portion" of the CHD1 locus or region or allele is defined as having a minimal size of at least about eight nucleotides, or preferably about 15 nucleotides, or more preferably at least about 25 nucleotides, and may have a minimal size of at least about 40 nucleotides. This definition includes all sizes in the range of 8–40 nucleotides as well as greater than 40 nucleotides.

The term "regulatory sequences" refers to those sequences normally within 100 kilobases (kb) of the coding region of a locus, but they may also be more distant from the coding region, which affect the expression of the gene. Such regulation of expression comprises transcription of the gene, and translation, splicing, and stability of the messenger RNA.

The term "operably linked" refers to a juxtaposition wherein the components so described are in a relationship permitting them to function in their intended manner. For instance, a promoter is operably linked to a coding sequence if the promoter affects its transcription or expression. The term "operably linked" may refer to functional linkage between a nucleic acid expression control sequence (e.g., a promoter, enhancer, or array of transcription factor binding sites) and a second nucleic acid sequence, wherein the expression control sequence directs transcription of the nucleic acid corresponding to the second sequence.

The term "vector" or "recombinant DNA cloning vehicle" refers to a specifically designed nucleic acid, polynucleotide or DNA molecule capable of autonomous existence and replication in an appropriate host cell. The vector comprises a member selected from the group comprising plasmid, bacteriophage, and artificial chromosome construct. This vehicle or vector may "carry" inserted DNA, said inserted DNA may comprise CHD1 polynucleotide or nucleic acid. The vector may allow expression of one or more genes carried on the inserted DNA in an appropriate host cell. The expressed gene product may be a polypeptide or RNA. The vector may allow expression of the antisense RNA of a gene. The vector may allow for production of antisense RNA or DNA of the inserted gene or genes in a cell-free system by methods well known in the art (Maniatis et al., 1982; Sambrook et al., 1989; Ausubel et al., 1992). The vector may exist in a host cell or in substantially pure form. The vector may exist in a host cell as an autonomous replicating unit or an autonomous unit, or alternatively it may integrate into the genome of the host cell.

The "vector" may be a recombinant DNA or polynucleotide molecule comprising all or part of the CHD1 region. The recombinant construct may be capable of replicating autonomously in a host cell. Alternatively, the recombinant construct may become integrated into the chromosomal DNA of the host cell. Such a recombinant polynucleotide comprises a polynucleotide of genomic DNA, cDNA, semi-synthetic, or synthetic origin which, by virtue of its origin or manipulation, 1) is not associated with all or a portion of a polynucleotide with which it is associated in nature; 2) is linked to a polynucleotide other than that to which it is linked in nature; or 3) does not occur in nature.

Therefore, recombinant polynucleotides comprising sequences otherwise not naturally occurring are provided by this invention. Although the wild-type sequence may be employed, it will often be altered, e.g., by deletion, substitution or insertion.

Genomic DNA or cDNA libraries of various types may be screened as natural sources of the nucleic acids of the present invention, or such nucleic acids may be provided by amplification of sequences resident in genomic DNA or other natural sources, e.g., by PCR. The choice of cDNA libraries normally corresponds to a tissue source which is abundant in mRNA for the desired proteins. Phage libraries are normally preferred, but other types of libraries may be used. Clones of a library are spread onto plates, transferred to a substrate for screening, denatured and probed for the presence of desired sequences.

The DNA sequences used in this invention will usually comprise at least about five codons (15 nucleotides), more usually at least about 7–15 codons, and most preferably, at least about 35 codons. One or more introns may also be present. This number of nucleotides is usually about the minimal length required for a successful probe that would hybridize specifically with an CHD1-encoding sequence.

Techniques for nucleic acid manipulation are described generally, for example, in Sambrook et al., 1989 or Ausubel et al., 1992. Reagents useful in applying such techniques, such as restriction enzymes and the like, are widely known in the art and commercially available from such vendors as New England BioLabs, Boehringer Mannheim, Amersham, Promega Biotech, U.S. Biochemicals, New England Nuclear, and a number of other sources. The recombinant nucleic acid sequences used to produce fusion proteins of the present invention may be derived from natural or synthetic sequences. Many natural gene sequences are obtainable from various cDNA or from genomic DNA libraries using appropriate probes. See, GenBank, National Institutes of Health.

The term "recombinant nucleic acid, polynucleotide or DNA" refers to a nucleic acid molecule which is not naturally occurring, or which is made by the artificial combination of two otherwise separated segments of sequence. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site, for example, for a restriction endonuclease. Alternatively, it is performed to join together nucleic acid segments of desired functions to generate a desired combination of functions.

The term "probes" refer to polynucleotide probes for the purpose of detecting polynucleotide polymorphisms associated with CHD1 alleles which predispose to coronary heart disease or metabolic disorders, or are associated with coronary heart disease or metabolic disorders by hybridization. Each probe is designed to form a stable hybrid with that of the target sequence, under highly stringent to moderately stringent hybridization and wash conditions. If it is expected that a probe will be perfectly complementary to the target sequence, high stringency conditions will be used. Hybridization stringency may be lessened if some mismatching is expected, for example, if variants are expected with the result that the probe will not be completely complementary. Conditions are chosen which rule out nonspecific/adventitious bindings, that is, which minimize noise. (It should be noted that throughout this disclosure, if it is simply stated that "stringent" conditions are used that is meant to be read as "high stringency" conditions are used.) Since such indications identify neutral DNA polymorphisms as well as mutations, these indications need further analysis to demonstrate detection of an CHD1 susceptibility allele.

Probes for CHD1 alleles may be derived from the sequences of the CHD1 region or its cDNAs. The probes may be of any suitable length, which span all or a portion of the CHD1 region, and which allow specific hybridization to the CHD1 region. If the target sequence contains a sequence identical to that of the probe, the probes may be short, e.g., in the range of about 8–30 base pairs, since the hybrid will be relatively stable under even highly stringent conditions. If some degree of mismatch is expected with the probe, i.e., if it is suspected that the probe will hybridize to a variant region, a longer probe may be employed which hybridizes to the target sequence with the requisite specificity.

The probes will include an isolated polynucleotide attached to a label or reporter molecule and may be used to isolate other polynucleotide sequences, having sequence similarity by standard methods. For techniques for preparing and labeling probes see, e.g., Sambrook et al., 1989 or Ausubel et al., 1992. Other similar polynucleotides may be selected by using homologous polynucleotides. Alternatively, polynucleotides encoding these or similar polypeptides may be synthesized or selected by use of the redundancy in the genetic code. Various codon substitutions may be introduced, e.g., by silent changes (thereby producing various restriction enzyme recognition sites) or to optimize expression for a particular system. Mutations may be introduced to modify the properties of the polypeptide, perhaps to change ligand-binding affinities, interchain or intermolecular affinities, or the polypeptide degradation or turnover rate.

Probes comprising synthetic oligonucleotides or other polynucleotides of the present invention may be derived from naturally occurring or recombinant single- or double-stranded polynucleotides, or be chemically synthesized. Probes may also be labeled by nick translation, Klenow fill-in reaction, or other methods known in the art.

Portions of the polynucleotide sequence having at least about eight nucleotides, usually at least about 15 nucleotides, and fewer than about 6 kilobases (kb), usually fewer than about 1.0 kb, from a polynucleotide sequence encoding CHD1 are preferred as probes. This definition therefore includes probes of sizes 8 nucleotides through 6000 nucleotides. The probes may also be used to determine whether mRNA encoding CHD1 is present in a cell or tissue.

The term "substantial homology or similarity" when referring to a nucleic acid or fragment thereof indicates that when optimally aligned (with appropriate nucleotide insertions or deletions) with the other nucleic acid (or its complementary strand), there is nucleotide sequence identity in at least about 60% of the nucleotide bases, usually at least about 70%, more usually at least about 80%, preferably at least about 90%, and more preferably at least about 95–98% of the nucleotide bases.

Alternatively, substantial homology or similarity exists when a nucleic acid or fragment thereof hybridizes to another nucleic acid (or a complementary strand thereof) under selective hybridization conditions, to a strand, or to its complement. Selectivity of hybridization exists when hybridization which is substantially more selective than total lack of specificity occurs. Typically, selective hybridization will occur when there is at least about 55% homology over a stretch of at least about 14 nucleotides, preferably at least about 65%, more preferably at least about 75%, and most preferably at least about 90%. See, Kanehisa, 1984. The length of homology comparison, as described, may be over longer stretches, and in certain embodiments will often be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides.

Nucleic acid hybridization will be affected by such conditions as salt concentration, temperature, or organic solvents, in addition to the base composition, length of the complementary strands, and the number of nucleotide base mismatches between the hybridizing nucleic acids, as will be readily appreciated by those skilled in the art. Stringent temperature conditions will generally include temperatures in excess of 30° C., typically in excess of 37° C., and preferably in excess of 45° C. Stringent salt conditions will ordinarily be less than 1000 mM, typically less than 500 mM, and preferably less than 200 mM. However, the combination of parameters is much more important than the measure of any single parameter. See, e.g., Wetmur and Davidson, 1968. Probe sequences may also hybridize specifically to duplex DNA under certain conditions to form triplex or other higher order DNA complexes. The preparation of such probes and suitable hybridization conditions are well known in the art.

The term "target region" refers to a region of the nucleic acid which is amplified and/or detected. The term "target sequence" refers to a sequence with which a probe or primer will form a stable hybrid under desired conditions.

The terms "analyte polynucleotide", "polynucleotide in analyte", and "analyte strand" refer to a single- or double-stranded polynucleotide which is suspected of containing a target sequence, and which may be present in a variety of types of samples, including biological samples.

The terms "CHD1 protein" or "CHD1 polypeptide" refers to a protein or polypeptide encoded by the CHD1 locus, variants or fragments thereof. The term "polypeptide" refers to a polymer of amino acids and its equivalent and does not refer to a specific length of the product; thus, peptides, oligopeptides and proteins are included within the definition of a polypeptide. This term also does not refer to, or exclude modifications of the polypeptide, for example, glycosylations, acetylations, phosphorylations, and the like. Included within the definition are, for example, polypeptides containing one or more analogs of an amino acid (including, for example, unnatural amino acids, etc.), polypeptides with substituted linkages as well as other modifications known in the art, both naturally and non-naturally occurring. Ordinarily, such polypeptides will be at least about 50% homologous to the native CHD1 sequence, preferably in excess of about 90%, and more preferably at least about 95% homologous. Also included are proteins encoded by DNA which hybridize under high or low stringency conditions, to CHD1-encoding nucleic acids and closely related polypeptides or proteins retrieved by antisera to the CHD1 protein(s).

The length of polypeptide sequences compared for homology will generally be at least about 16 amino acids, usually at least about 20 residues, more usually at least about 24 residues, typically at least about 28 residues, and preferably more than about 35 residues.

The term "protein modifications or fragments" refers to CHD1 polypeptides or fragments thereof that are substantially homologous to primary structural sequence but which include, e.g., in vivo or in vitro chemical and biochemical modifications or which incorporate unusual amino acids. Such modifications include, for example, acetylation, carboxylation, phosphorylation, glycosylation, ubiquitination, labeling, e.g., with radionuclides, and various enzymatic modifications, as will be readily appreciated by those well skilled in the art. A variety of methods for labeling polypeptides and of substituents or labels useful for such purposes are well known in the art, and include radioactive isotopes such as $^{32}$P, ligands which bind to labeled antiligands (e.g., antibodies), fluorophores, chemiluminescent agents, enzymes, and antiligands which can serve as specific binding pair members for a labeled ligand. The choice of label depends on the sensitivity required, ease of conjugation with the primer, stability requirements, and available instrumentation. Methods of labeling polypeptides are well known in the art. See Sambrook et al., 1989 or Ausubel et al., 1992.

Besides substantially full-length polypeptides, the present invention provides for biologically active fragments of the polypeptides. Significant biological activities include ligand-binding, immunological activity and other biological activities characteristic of CHD1 polypeptides. Immunological activities include both immunogenic function in a target immune system, as well as sharing of immunological epitopes for binding, serving as either a competitor or substitute antigen for an epitope of the CHD1 protein. As used herein, "epitope" refers to an antigenic determinant of a polypeptide. An epitope could comprise three amino acids in a spatial conformation which is unique to the epitope. Generally, an epitope consists of at least five such amino acids, and more usually consists of at least 8–10 such amino acids. Methods of determining the spatial conformation of such amino acids are known in the art.

For immunological purposes, tandem-repeat polypeptide segments may be used as immunogens, thereby producing highly antigenic proteins. Alternatively, such polypeptides will serve as highly efficient competitors for specific binding. Production of antibodies specific for CHD1 polypeptides or fragments thereof is described below.

The term "fusion protein" refers to fusion polypeptides comprising CHD1 polypeptides and fragments. Homologous polypeptide fusions may be between two or more CHD1 polypeptide sequences or between the sequences of CHD1 and a related protein. Heterologous fusions may be constructed which would exhibit a combination of properties or activities of the derivative polypeptides. For example, ligand-binding or other domains may be "swapped" between CHD1 and other polypeptides or polypeptide fragments. A fusion protein may have the DNA binding domain of CHD1 and the transcription activation domain of another protein (for example, the transcriptional activation domain of the yeast GAL4 protein (Ma and Ptashne, 1987)). Such homologous or heterologous fusion polypeptides may display altered strength or specificity of binding. A heterologous polypeptide or polypeptide fragment may confer a new activity on CHD1. For example, a fusion between CHD1 or a portion of CHD1 to the Schistosoma japonicum glutathione-S-transferase (GST) may be made. This fusion protein can bind to glutathione sepharose or agarose beads, whereas CHD1 cannot. Fusion partners include, inter alia, GST, immunoglobulins, bacterial beta-galactosidase, trpE, protein A, β-lactamase, α amylase, maltose binding protein, alcohol dehydrogenase, polyhistidine (for example, six histidine at the amino and/or carboxyl terminus of the polypeptide), green fluorescent protein, yeast α mating factor, GAL4 transcription activation or DNA binding domain, and luciferase. See Godowski et al., 1988.

Fusion proteins will typically be made by either recombinant nucleic acid methods, as described above, or may be chemically synthesized. Techniques for the synthesis of polypeptides are described, for example, in Merrifield, 1963.

The term "protein purification" refers to various methods for the isolation of the CHD1 polypeptides or fusion polypeptides comprising CHD1 polypeptides from other biological material, such as from cells transformed with recombinant nucleic acids encoding CHD1, and are well known in the art. For example, such polypeptides may be purified by immunoaffinity chromatography employing, for instance, the antibodies provided by the present invention. Various methods of protein purification are well known in the art, and include those described in Deutscher, 1990 and Scopes, 1982.

The terms "isolated", "substantially pure", "purified", "purified and isolated" and "substantially homogeneous" are used interchangeably to describe a protein or polypeptide that has been separated from components that accompany it in its natural state. A monomeric protein is substantially pure when at least about 60 to 75% of a sample exhibits a single polypeptide sequence. A substantially pure protein will typically comprise about 60 to 90% W/W of a protein sample, more usually about 95%, and preferably will be over 99% pure. Protein purity or homogeneity may be indicated by a number of means well known in the art, such as polyacrylamide gel electrophoresis of a protein sample, followed by visualizing a single polypeptide band upon staining the gel with a stain well known in the art. For certain purposes, higher resolution may be provided by using HPLC or other means well known in the art for purification.

A CHD1 protein is substantially free of naturally associated components when it is separated from the native contaminants that accompany it in its natural state. Thus, a polypeptide that is chemically synthesized or synthesized in a cellular system different from the cell from which it naturally originates will be substantially free from its naturally associated components. A protein may also be rendered substantially free of naturally associated components by isolation, using protein purification techniques well known in the art.

A polypeptide produced as an expression product of an isolated and manipulated genetic sequence is an "isolated polypeptide," as used herein, even if expressed in a homologous cell type. Synthetically made forms or molecules expressed by heterologous cells are inherently isolated molecules.

The terms "substantial homology" or "substantial identity", when referring to polypeptides, indicate that the polypeptide or protein in question exhibits at least about 30% identity with an entire naturally-occurring protein or a portion thereof, usually at least about 70% identity, and preferably at least about 95% identity.

The term "substantially similar function" refers to the function of a modified nucleic acid or a modified polypeptide (or protein) with reference to the wild-type CHD1 nucleic acid or wild-type CHD1 polypeptide. The modified polypeptide will be substantially homologous to the wild-type CHD1 polypeptide and will have substantially the same function. The modified polypeptide may have an altered amino acid sequence and/or may contain modified amino acids. In addition to the similarity of function, the modified polypeptide may have other useful properties, such as a longer half-life. The similarity of function (activity) of the modified polypeptide may be substantially the same as the activity of the wild-type CHD1 polypeptide. Alternatively, the similarity of function (activity) of the modified polypeptide may be higher than the activity of the wild-type CHD1 polypeptide. The modified polypeptide is synthesized using conventional techniques, or is encoded by a modified nucleic acid and produced using conventional techniques. The modified nucleic acid is prepared by conventional techniques. A nucleic acid with a function substantially similar to the wild-type CHD1 gene function produces the modified protein described above.

Homology, for polypeptides, is typically measured using sequence analysis software. See, e.g., the Sequence Analysis Software Package of the Genetics Computer Group, University of Wisconsin Biotechnology Center, 910 University Avenue, Madison, Wis. 53705. Protein analysis software matches similar sequences using measure of homology assigned to various substitutions, deletions and other modifications. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine.

The term a polypeptide "fragment", "portion" or "segment" refers to a stretch of amino acid residues of at least about five to seven contiguous amino acids, often at least about seven to nine contiguous amino acids, typically at least about nine to 13 contiguous amino acids and, most preferably, at least about 20 to 30 or more contiguous amino acids.

The polypeptides of the present invention, if soluble, may be coupled to a solid-phase support, e.g., nitrocellulose, nylon, column packing materials (e.g., Sepharose beads), magnetic beads, glass wool, plastic, metal, polymer gels, cells, or other substrates. Such supports may take the form, for example, of beads, wells, dipsticks, or membranes.

The term "antibodies" refers to polyclonal and/or monoclonal antibodies and fragments thereof, and immunologic binding equivalents thereof, which are capable of specifically binding to the CHD1 polypeptides and fragments thereof or to polynucleotide sequences from the CHD1 region, particularly from the CHD1 locus or a portion thereof. The term "antibodies" is used both to refer to a homogeneous molecular entity, or a mixture such as a serum product made up of a plurality of different molecular entities. Polypeptides may be prepared synthetically in a peptide synthesizer or as fusion proteins as described above and coupled to a carrier molecule (e.g., keyhole limpet hemocyanin) and injected over several months into rabbits, mice, goats, etc. Sera is tested for immunoreactivity to the CHD1 polypeptide or fragment. Monoclonal antibodies may be made by injecting mice with the protein polypeptides, fusion proteins or fragments thereof. Monoclonal antibodies are screened by ELISA and tested for specific immunoreactivity with CHD1 polypeptide or fragments thereof. See, Harlow and Lane, 1988. These antibodies will be useful in assays and as pharmaceuticals.

Once a sufficient quantity of desired polypeptide has been obtained, it may be used for various purposes. A typical use is the production of antibodies specific for binding. These antibodies may be either polyclonal or monoclonal, and may be produced by in vitro or in vivo techniques well known in the art. For production of polyclonal antibodies, an appropriate target immune system, typically mouse or rabbit, is selected. Substantially purified antigen is presented to the immune system in a fashion determined by methods appropriate for the animal and by other parameters well known to immunologists. Typically the injections are performed in footpads, intramuscularly, intraperitoneally, or intradermally. Of course, other species may be substituted for mouse or rabbit. Polyclonal antibodies are then purified using techniques known in the art, adjusted for the desired specificity.

An immunological response is usually assayed with an immunoassay. Normally, such immunoassays involve some purification of a source of antigen, for example, that produced by the same cells and in the same fashion as the antigen. A variety of immunoassay methods are well known in the art. See, e.g., Harlow and Lane, 1988, or Goding, 1986.

Monoclonal antibodies with affinities of $10^{-8}$ $M^{-1}$ or preferably $10^{-9}$ to $10^{-10}$ $M^{-1}$ or stronger are typically made by standard procedures as described, e.g., in Harlow and Lane, 1988 or Goding, 1986. Briefly, appropriate animals are selected and the desired immunization protocol followed. After the appropriate period of time, the spleens of such animals are excised and individual spleen cells fused, typically, to immortalized myeloma cells under appropriate selection conditions. Thereafter, the cells are clonally separated and the supernatants of each clone tested for their production of an appropriate antibody specific for the desired region of the antigen.

Other suitable techniques involve in vitro exposure of lymphocytes to the antigenic polypeptides, or alternatively, to selection of libraries of antibodies in phage or similar vectors. See Huse et al., 1989. The polypeptides and antibodies of the present invention may be used with or without modification. Frequently, polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent agents, chemiluminescent agents, magnetic particles and the like. Patents teaching the use of such labels include U.S. Pat. Nos. 3,817,837; 3,850,752; 3,939,350; 3,996,345; 4,277,437; 4,275,149 and 4,366,241. Also, recombinant immunoglobulins may be produced (see U.S. Pat. No. 4,816,567).

The term "epitope" refers to a region of a polypeptide that provokes a response by an antibody. This region needs not comprise consecutive amino acids. The term epitope is also known in the art as "antigenic determinant".

The term a "biological sample" refers to a sample of tissue or fluid suspected of containing an analyte polynucleotide or polypeptide from an individual including, but not limited to, e.g., plasma, serum, spinal fluid, lymph fluid, the external sections of the skin, respiratory, intestinal, and genitourinary tracts, tears, saliva, blood cells, tumors, organs, tissue and samples of in vitro cell culture constituents.

The terms "diagnosing" and "prognosing," as used in the context of coronary heart disease or metabolic disorders, are used to indicate 1) the classification of disease states as coronary heart disease or metabolic disorders;

2) the determination of the severity of the coronary heart disease or metabolic disorders;

3) the monitoring of the disease progression, prior to, during and after treatment.

The practice of the present invention employs, unless otherwise indicated, conventional techniques of chemistry, molecular biology, microbiology, recombinant DNA, genetics, and immunology. See, e.g., Maniatis et al., 1982; Sambrook et al., 1989; Ausubel et al., 1992; Glover, 1985; Anand, 1992; Guthrie and Fink, 1991. A general discussion of techniques and materials for human gene mapping, including mapping of human chromosome 11, is provided, e.g., in White and Lalouel, 1988.

Strategy for the Molecular Cloning of CHD1

Starting from a region on chromosome 11 of the human genome, a region which contains a genetic locus, CHD1, which causes susceptibility to coronary heart disease and metabolic disorders, has been identified.

Figure 1:
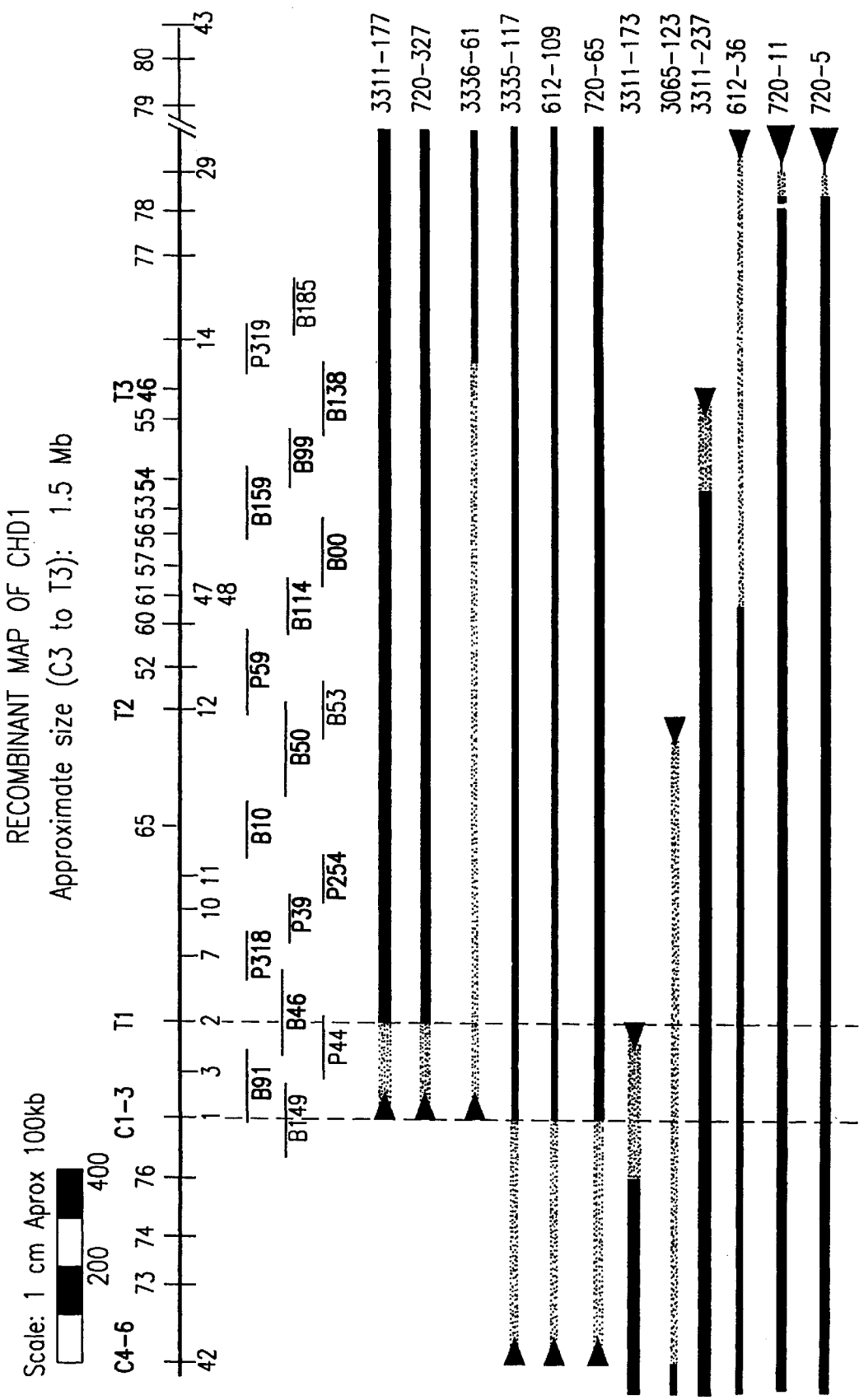
FIG. 1. Recombinant map of CHD1. A diagram showing the order of genetic markers neighboring CHD1, a schematic map of BACs and PACs spanning the CHD1 region and recombinants in several potentially linked families.

The region containing the CHD1 locus was identified using a variety of genetic techniques. Genetic mapping techniques initially defined the CHD1 region in terms of recombination with genetic markers. Based upon studies of large extended families ("kindreds") with multiple cases of coronary heart disease and metabolic disorders, a chromosomal region has been pinpointed that contains the CHD1 gene as well as putative susceptibility alleles in the CHD1 locus. Two meiotic breakpoints have been discovered on the distal side of the CHD1 locus which are expressed as recombinants between genetic markers and the disease locus, and two recombinants on the proximal side of the CHD1 locus. Thus, a region which contains the CHD1 locus is physically bounded by these markers. FIG. 1 shows the order of these markers.

Population Resources

Large, well-documented Utah kindreds are especially important in providing good resources for human genetic studies. Each large kindred independently gives evidence whether or not an CHD1 susceptibility allele is segregating in that family. Recombinants informative for localization and isolation of the CHD1 locus could be obtained only from kindreds large enough to confirm the presence of a susceptibility allele. Large sibships are especially important for studying coronary heart disease, since penetrance of CHD1 susceptibility alleles may be reduced both by age and sex, making informative sibships difficult to find. Furthermore, large sibships are essential for constructing haplotypes of deceased individuals by inference from the haplotypes of their close relatives. Example 1 shows how kindreds were selected.

Genetic Mapping

Given a set of informative families, genetic markers are essential for linking a disease to a region of a chromosome. Such markers include restriction fragment length polymorphisms (RFLPs) (Botstein et al., 1980), markers with a variable number of tandem repeats (VNTRs) (Jeffreys et al., 1985; Nakamura et al., 1987), and an abundant class of DNA polymorphisms based on short tandem repeats (STRs), especially repeats of CpA (Weber and May, 1989; Litt et al., 1989). To generate a genetic map, one selects potential genetic markers and tests them using DNA extracted from members of the kindreds being studied.

Genetic markers useful in searching for a genetic locus associated with a disease can be selected on an ad hoc basis, by densely covering a specific chromosome, or by detailed analysis of a specific region of a chromosome. A preferred method for selecting genetic markers linked with a disease involves evaluating the degree of informativeness of kindreds to determine the ideal distance between genetic markers of a given degree of polymorphism, then selecting markers from known genetic maps, which are ideally spaced for maximal efficiency. Informativeness of kindreds is measured by the probability that the markers will be heterozygous in unrelated individuals. It is also most efficient to use STR markers, which are detected by amplification of the target nucleic acid sequence using PCR; such markers are highly informative, easy to assay (Weber and May, 1989), and can be assayed simultaneously using multiplexing strategies (Skolnick and Wallace, 1988), greatly reducing the number of experiments required. This linkage analysis is described in Example 2.

Once linkage has been established, one needs to find markers that flank the disease locus, i.e., one or more markers proximal to the disease locus, and one or more markers distal to the disease locus. Where possible, candidate markers can be selected from a known genetic map. Where none is known, new markers can be identified by the STR technique, as shown in Example 2.

Genetic mapping is usually an iterative process. In the present invention, it began by defining flanking genetic markers around the CHD1 locus, then replacing these flanking markers with other markers that were successively closer to the CHD1 locus. As an initial step, recombination events, defined by large extended kindreds, helped specifically to localize the CHD1 locus as either distal or proximal to regionally localized specific genetic markers.

Contig Assembly

Given a genetically defined interval flanked by meiotic recombinants, one needs to generate a contig of genomic clones that spans that interval. Publicly available resources, such as the Whitehead integrated maps of the human genome provide aligned chromosome maps of genetic markers, other sequence tagged sites (STSs), radiation hybrid map data, and CEPH yeast artificial chromosome (YAC) clones. From the map data, one can often identify a set of yeast artificial chromosomes (YACs) that span the genetically defined interval. Oligonucleotide primer pairs for markers located in the interval can be synthesized and used to screen libraries of bacterial artificial chromosomes (BACs) and P1 artificial chromosomes (PACs). Successive rounds of BAC/PAC library screening with BAC or PAC end markers enables the completion of a BAC/PAC clone contig that spans the genetically defined interval. A set of overlapping but non-redundant BAC and PAC clones that span this interval (FIGS. 1 and 2) (the minimum tiling path) can then be selected for use in subsequent molecular cloning protocols. Contig assembly is described in Example 3.

Genomic Sequencing

Given a minimum tiling path of BAC and PAC clones across a defined interval, one useful gene finding strategy is to generate an almost complete genomic sequence of that interval. Random genomic clone sublibraries can be prepared from each BAC or PAC clone in the minimum tiling path. Individual sublibrary clones sufficient in number to generate an, on average, 6x redundant sequence of each BAC or PAC can then be end-sequenced with vector primers. These sequences can be assembled into sequence contigs, and these contigs placed in a local genomic sequence database. One can search the genomic sequence contigs for sequence similarity with known genes and expressed sequence tags (ESTs), examine them for the presence of long open translational reading frames, and characterize them for CpG dinucleotide frequency. Genomic sequencing is described in Example 4.

Hybrid Selection

Given a minimum tiling path of BAC and PAC clones across a defined interval, another useful gene finding strategy is to obtain cDNA clones cognate to the minimum tiling path BACs and PACs. One preferred cDNA cloning strategy is hybrid selection. cDNA can be prepared from a number of human tissues and human cell lines in such a manner that the cDNA molecules have PCR primer binding sites (anchors) at each end. This cDNA can be affinity captured with the minimum tiling path BACs and PACs. Captured cDNA can then be amplified by PCR using the anchor primers and then cloned. Individual clones can then be end-sequenced with vector primers. The sequences of these cDNA clones can be analyzed for similarity to genomic sequence contigs generated from BACs and PACs on the minimum tiling path. One can then identify individual exons of genes in the genetically defined interval by parsing the sequences of true-positive hybrid selected clones across these genomic sequence contigs. Hybrid selection is described in Example 5.

RACE and Inter-exon PCR

While hybrid selection is an efficient approach to the initial identification of novel genes located within a defined interval of the genome, the approach is not often the most efficient way to complete the cloning of those genes. Rapid amplification of cDNA ends (RACE) provides a PCR based method to identify new 5' and 3' cDNA sequences. cDNA can be prepared from a number of human tissues in a manner such that the cDNA molecules have PCR primer binding sites (anchors) at their 5' ends, 3' ends, or both. PCR amplification from this cDNA with 5' end anchor primers and gene specific reverse primers can generate 5' RACE products. Similarly, PCR amplification with 3' end anchor primers and gene specific forward primers can generate 3' RACE products. cDNA cloning techniques can also miss exons that lie between already known exons of a gene; for instance, this can easily occur if a particular exon is only included in a relatively rare splice variant of a transcript. Combinatorial inter-exon PCR is an effective strategy for detecting these exons. One can design a forward primer based on sequences from the first known exon of the gene and a set of reverse primers, one based on the sequence of each of the downstream exons (or any subset thereof) of the gene. Then one can amplify by PCR from cDNA of tissues and cell lines thought to express the gene, using all the combinations of the forward primer with each reverse primer. Combinations as complex as a forward primer from each exon paired with a reverse primer from each exon, subject only to the limitation that the forward primer should be from an exon upstream of the exon from which the reverse primer was designed, can be tried. PCR products that differ in length from the expected product can be purified. In either RACE or combinatorial inter-exon PCRs, the PCR products can either be purified and then sequenced directly or first cloned and then sequenced. RACE and inter-exon PCR are described in Example 5.

cDNA Library Screening

Another useful strategy for finding new 5', 3', or internal sequences is cDNA library screening. One can make or purchase bacteriophage lambda cDNA libraries prepared from RNA from tissues or cell lines thought to express the gene. One then screens plaque lifts from those libraries with labeled nucleic acid probes based on the currently known sequences of the gene of interest. Individual positive clones are purified, and then the clone inserts can be sequenced.

Mutation Screening

Proof that any particular gene located within the genetically defined interval is CHD1 is obtained by finding sequences in DNA or RNA extracted from affected kindred members that create abnormal CHD1 gene products or abnormal levels of CHD1 gene product. Such CHD1 susceptibility alleles will co-segregate with the disease in large kindreds. They will also be present at a much higher frequency in non-kindred individuals with coronary heart disease or metabolic disorders than in individuals in the general population. Whether one is comparing CHD1 sequences from coronary heart disease or dyslipidemic cases to those from unaffected individuals, the key is to find mutations that are serious enough to cause obvious disruption to the normal function of the gene product. These mutations can take a number of forms. The most severe forms are frame shift mutations or large deletions causing the gene to encode an abnormal protein or one causing significantly altered protein expression. Less severe disruptive mutations would include small in-frame deletions and nonconservative base pair substitutions. Each of these mutations would have a significant effect on the protein produced, such as changes to or from a cysteine residue, from a basic to an acidic amino acid or vice versa, from a hydrophobic to hydrophilic amino acid or vice versa, or would affect secondary, tertiary or quaternary protein structure. Small deletions or base pair substitutions could also significantly alter protein expression by changing the level of transcription, splice pattern, mRNA stability, or translation efficiency of the CHD1 transcript. Silent mutations or those resulting in conservative amino acid substitutions would not generally be expected to disrupt protein function. Mutation screening is described in Example 6.

Useful Diagnostic Techniques

According to the diagnostic and prognostic method of the present invention, alteration of the wild-type CHD1 locus is detected. In addition, the method can be performed by detecting the wild-type CHD1 locus and confirming the lack of a predisposition to metabolic disorders at the CHD1 locus. "Alteration of a wild-type gene" encompasses all forms of mutations including deletions, insertions and point mutations in the coding and noncoding regions. Deletions may be of the entire gene or of only a portion of the gene. Point mutations may result in stop codons, frameshift mutations or amino acid substitutions. Such mutations may be present in individuals either with or without symptoms of coronary heart disease or metabolic disorders. In addition, there may be differences in the drug response or prognosis of symptomatic individuals that carry mutations in CHD1 compared to those that do not. The finding of CHD1 mutations thus provides both diagnostic and prognostic information. Point mutations or deletions may alter the protein produced by CHD1, impairing its function. Point mutations or deletions may occur in regulatory regions, such as in the promoter of the gene, leading to loss or diminution of expression of the mRNA. Point mutations or deletions may also abolish proper RNA processing, leading to reduction or loss of expression of the CHD1 gene product, expression of an altered CHD1 gene product, or to a decrease in mRNA stability or translation efficiency.

Useful diagnostic techniques include, but are not limited to, fluorescent in situ hybridization (FISH), direct DNA sequencing, PFGE analysis, Southern blot analysis, single stranded conformation analysis (SSCA), RNase protection assay, allele-specific oligonucleotide (ASO) analysis, dot blot analysis and PCR-SSCP, as discussed in detail further below. Also useful is the recently developed technique of DNA microchip technology.

Predisposition to coronary heart disease or metabolic disorders can be ascertained by testing any tissue of a human for mutations of the CHD1 gene. For example, a person who has inherited a germline CHD1 mutation would be prone to develop coronary heart disease or metabolic disorders. This can be determined by testing DNA from any tissue of the person's body. Most simply, blood can be drawn and DNA extracted from the cells of the blood. In addition, prenatal diagnosis can be accomplished by testing fetal cells, placental cells or amniotic cells for mutations of the CHD1 gene. Alteration of a wild-type CHD1 allele, whether, for example, by point mutation or deletion, can be detected by any of the means discussed herein.

There are several methods that can be used to detect DNA sequence variation. Direct DNA sequencing, either manual sequencing or automated fluorescent sequencing can detect sequence variation. For a gene such as CHD1, manual sequencing is very labor-intensive, but under optimal conditions, mutations in the coding sequence of a gene are rarely missed. Another approach is the single-stranded conformation polymorphism assay (SSCA) (Orita et al., 1989). This method does not detect all sequence changes, especially if the DNA fragment size is greater than 200 bp, but can be optimized to detect most DNA sequence variation. The reduced detection sensitivity is a disadvantage, but the increased throughput possible with SSCA makes it an attractive, viable alternative to direct sequencing for mutation detection on a research basis. The fragments with shifted mobility on SSCA gels are then sequenced to determine the exact nature of the DNA sequence variation. Other approaches based on the detection of mismatches between the two complementary DNA strands include clamped denaturing gel electrophoresis (CDGE) (Sheffield et al., 1991), heteroduplex analysis (HA) (White et al., 1992) and chemical mismatch cleavage (CMC) (Grompe et al., 1989). None of the methods described above will detect large deletions, duplications or insertions, nor will they detect a regulatory mutation that affects transcription or translation of the protein. Other methods that might detect these classes of mutations such as a protein truncation assay or the asymmetric assay, detect only specific types of mutations and would not detect missense mutations. A review of currently available methods of detecting DNA sequence variation can be found in a recent review by Grompe (1993). Once a mutation is known, an allele specific detection approach such as allele specific oligonucleotide (ASO) hybridization can be utilized to rapidly screen large numbers of other samples for that same mutation.

Detection of point mutations may be accomplished by molecular cloning of the CHD1 allele(s) and sequencing the allele(s) using techniques well known in the art. Alternatively, the gene sequences can be amplified directly from a genomic DNA preparation from the tissue, using known techniques, as exemplified in Example 6. The DNA sequence of the amplified sequences can then be determined.

There are seven well known methods for a more complete, yet still indirect, test for confirming the presence of a susceptibility allele:

1) single-stranded conformation analysis (SSCA) (Orita et al., 1989);
2) denaturing gradient gel electrophoresis (DGGE or CDGE) (Wartell et al., 1990; Sheffield et al., 1989 and 1991);
3) RNase protection assays (Finkelstein et al., 1990; Kinszler et al., 1991);
4) allele-specific oligonucleotides (ASOs) (Conner et al., 1983);
5) the use of proteins that recognize nucleotide mismatches, such as the E. coli mutS protein (Modrich, 1991);
6) allele-specific PCR (Rano and Kidd, 1989); and
7) single nucleotide extension assays.

For allele-specific PCR, primers are used that hybridize at their 3' ends to a particular CHD1 mutation. If the particular CHD1 mutation is not present, an amplification product is not observed. Amplification Refractory Mutation System (ARMS) can also be used, as disclosed in European Patent Application Publication No. 0332435 and in Newton et al., 1989. For single nucleotide extension assays, primers are used with their 3' ends at the nucleotide prior to a particular CHD1 mutation. The primers are then extended separately with each of the four dideoxynucleotides. Only those nucleotides complementary to the allele(s) present in an individual will be added to the oligonucleotide. The genotype of the individual can be inferred from the pattern of nucleotides added in the extension assay. Insertions and deletions of genes can also be detected by cloning, sequencing and amplification. In addition, restriction fragment length polymorphism (RFLP) probes for the gene or surrounding marker genes can be used to score alteration of an allele or an insertion in a polymorphic fragment. Such a method is particularly useful for screening relatives of an affected individual for the presence of the CHD1 mutation found in that individual. Other techniques for detecting insertions and deletions as known in the art can be used.

In the first three methods (SSCA, DGGE or CDGE and RNase protection assay), a new electrophoretic band appears. SSCA detects a band that migrates differentially because the sequence change causes a difference in single-strand, intramolecular base pairing. RNase protection involves cleavage of the mutant polynucleotide into two or more smaller fragments. DGGE detects differences in migration rates of mutant sequences compared to wild-type sequences, using a denaturing gradient gel. In an allele-specific oligonucleotide assay, an oligonucleotide is designed that detects a specific sequence, and the assay is performed by detecting the presence or absence of a hybridization signal. In the mutS assay, the protein binds only to sequences that contain a nucleotide mismatch in a heteroduplex between mutant and wild-type sequences.

Mismatches, according to the present invention, are hybridized nucleic acid duplexes in which the two strands are not 100% complementary. Lack of total homology may be due to deletions, insertions, inversions or substitutions.

Mismatch detection can be used to detect point mutations in the gene or in its mRNA product. While these techniques are less sensitive than sequencing, they are simpler to perform on a large number of samples. An example of a mismatch cleavage technique is the RNase protection method. In the practice of the present invention, the method involves the use of a labeled riboprobe that is complementary to the human wild-type CHD1 gene coding sequence. The riboprobe and either mRNA or DNA isolated from the tumor tissue are annealed (hybridized) together and subsequently digested with the enzyme RNase A which is able to detect some mismatches in a duplex RNA structure. If a mismatch is detected by RNase A, it cleaves at the site of the mismatch. Thus, when the annealed RNA preparation is separated on an electrophoretic gel matrix, if a mismatch has been detected and cleaved by RNase A, an RNA product will be detected that is smaller than the full length duplex RNA for the riboprobe and the mRNA or DNA. The riboprobe does not need to be the full length of the CHD1 mRNA or gene but can be a segment of either. If the riboprobe comprises only a segment of the CHD1 mRNA or gene, it will be desirable to use a number of these probes to screen the whole mRNA sequence for mismatches.

In similar fashion, DNA probes can be used to detect mismatches, through enzymatic or chemical cleavage. See, e.g., Cotton et al., 1988; Shenk et al., 1975; Novack et al., 1986. Alternatively, mismatches can be detected by shifts in the electrophoretic mobility of mismatched duplexes relative to matched duplexes. See, e.g., Cariello, 1988. With either riboprobes or DNA probes, the cellular mRNA or DNA, that might contain a mutation, can be amplified using PCR (see below) before hybridization. Changes in DNA of the CHD1 gene can also be detected using Southern hybridization, especially if the changes are gross rearrangements, such as large deletions and insertions.

DNA sequences of the CHD1 gene that have been amplified by the polymerase chain reaction may also be screened using allele-specific probes. These probes are nucleic acid oligomers, each of which contains a region of the CHD1 gene sequence harboring a known mutation. For example, one oligomer may be about 30 nucleotides in length (although shorter and longer oligomers are also usable as well recognized by those of skill in the art), corresponding to a portion of the CHD1 gene sequence. By use of a battery of such allele-specific probes, PCR amplification products can be screened to identify the presence of a previously identified mutation in the CHD1 gene. Hybridization of allele-specific probes with amplified CHD1 sequences can be performed, for example, on a nylon filter. Hybridization to a particular probe under high stringency hybridization conditions indicates the presence of the same mutation in the tumor tissue as in the allele-specific probe.

The newly developed technique of nucleic acid analysis via microchip technology is also applicable to the present invention. In this technique, thousands of distinct oligonucleotide probes are embedded in an array on a silicon or glass chip. Nucleic acid to be analyzed is fluorescently labeled and hybridized to the probes on the chip. It is also possible to study nucleic acid-protein interactions using these nucleic acid microchips. Using this technique one can determine the presence of mutations or even sequence the nucleic acid being analyzed, or one can measure expression levels of a gene of interest. A major advantage of this method is that parallel processing of many, even thousands, of probes at once can be accomplished and thereby increase the rate of analysis tremendously. Several papers that use this technique have been published (Hacia et al., 1996; Ramsay, 1998, and Schena et al., 1996).

The most definitive test for mutations in a candidate locus is to directly compare genomic CHD1 sequences from coronary heart disease or metabolic disorders patients with those from a control population. Alternatively, one could sequence messenger RNA after amplification, e.g., by PCR, thereby eliminating the necessity of determining the exon structure of the candidate gene.

Mutations from coronary heart disease or metabolic disorder patients falling outside the coding region of CHD1 can be detected by examining the non-coding regions, such as introns and regulatory sequences near or within the CHD1 gene. An early indication that mutations in noncoding regions are important may come from Northern blot experiments that reveal messenger RNA molecules of abnormal size or abundance in coronary heart disease or metabolic disorder patients as compared to control individuals.

Alteration of CHD1 mRNA expression can be detected by any techniques known in the art. These include Northern blot analysis, PCR amplification and RNase protection. Diminished mRNA expression indicates an alteration of the wild-type CHD1 gene. Alteration of wild-type CHD1 genes can also be detected by screening for alteration of wild-type CHD1 protein. For example, monoclonal antibodies immunoreactive with CHD1 can be used to screen a tissue. Lack of cognate antigen would indicate a CHD1 mutation. Antibodies specific for products of mutant alleles could also be used to detect mutant CHD1 gene product. Such immunological assays can be done in any convenient formats known in the art. These include Western blots, immunohistochemical assays and ELISA assays. Any means for detecting an altered CHD1 protein can be used to detect alteration of wild-type CHD1 genes. Functional assays, such as protein binding determinations, can be used. In addition, assays can be used that detect CHD1 biochemical function, for instance, DNA binding. Finding a mutant CHD1 gene product indicates presence of a mutant CHD1 allele.

Mutant CHD1 genes or gene products can also be detected in other human body samples, such as serum, stool, urine, sputum and buccal swabs. The same techniques discussed above for detection of mutant CHD1 genes or gene products in tissues can be applied to other body samples. Cells are sloughed off from tissues and appear in such body samples. In addition, the CHD1 gene product itself may be secreted into the extracellular space and found in these body samples even in the absence of cells. By screening such body samples, a simple diagnosis can be achieved.

The primer pairs of the present invention are useful for determination of the nucleotide sequence of a particular CHD1 allele using PCR. The pairs of single-stranded DNA primers can be annealed to sequences within or surrounding the CHD1 gene on chromosome 11 in order to amplify the DNA comprising the CHD1 gene itself. A complete set of these primers allows synthesis of all of the nucleotides of the CHD1 gene coding sequences, i.e., the exons. The set of primers preferably allows synthesis of both intron and exon sequences. Allele-specific primers can also be used. Such primers anneal only to particular CHD1 mutant alleles, and thus will only amplify a product in the presence of the mutant allele as a template.

In order to facilitate subsequent cloning of amplified sequences, primers may have restriction enzyme recognition sequences appended to their 5' ends. Thus, all nucleotides of the primers are derived from CHD1 sequences or sequences adjacent to CHD1, except for the few nucleotides necessary to form a restriction enzyme recognition site. Such enzymes and recognition sites are well known in the art. The primers themselves can be synthesized using techniques well known in the art. Generally, the primers can be made using commercially-available oligonucleotide synthesizing machines. Given the sequence of the CHD1 gene shown in SEQ ID NOs: 1, 3, 5, and 7, design of particular primers is well within the skill of the art.

The nucleic acid probes provided by the present invention are useful for a number of purposes. They can be used in Southern hybridization to genomic DNA and in the RNase protection method for detecting point mutations already discussed above. The probes can be used to detect PCR amplification products. They may also be used to detect mismatches with the CHD1 gene or mRNA using other techniques.

The presence of an altered (or a mutant) CHD1 gene that produces a protein having a loss of function, or altered function, may correlate to an increased risk of coronary heart disease or metabolic disorders. In order to detect a CHD1 gene mutation, a biological sample is prepared and analyzed for a difference between the sequence of the CHD1 allele being analyzed and the sequence of the wild-type CHD1 allele. Mutant CHD1 alleles can be initially identified by any of the techniques described above. The mutant alleles are then sequenced to identify the specific mutation of the particular mutant allele. Alternatively, mutant CHD1 alleles can be initially identified by identifying mutant (altered) CHD1 proteins, using conventional techniques. The mutant alleles are then sequenced to identify the specific mutation for each allele. The mutations, especially those which lead to an altered function of the CHD1 protein, are then used for the diagnostic and prognostic methods of the present invention.

CHD1 Gene Structure

As detailed in Example 7, The CHD1 gene sequence has been determined. Ten exons and about 20 kb of contiguous flanking genomic DNA have been sequenced. Four polypeptides, due to alternative splicing, are predicted to be encoded by this locus based on the sequence data. Transcripts encoding all four proteins have been observed in cDNAs from various sources.

More than four alternatively spliced transcripts are predicted and observed to encode these four CHD1 proteins. Four cDNAs, cDNA 1–4, begin in exon F. These cDNAs encode the four alternative proteins, starting at the AUG in exon F and their 5' untranslated regions are described below. The presence of five exons upstream of exon F, exons G, H, I (+21), I (−21) and J allows for additional 5' untranslated regions to be added on to any of cDNAs 1–4. Several combinations have been observed: J-F-rest of any one of cDNA 1–4, J-I(+21)-F-rest of any one of cDNA 1–4, J-I(−21)-F-rest of any one of cDNA 1–4, J-I(−21)-H-F-rest of any one of cDNA 1–4 and G-F-rest of any one of cDNA 1–4. Other combinations are also predicted.

These alternative 5' exons that encode 5' untranslated regions may give rise to an additional level of regulation of gene expression. For example, the presence of a particular 5' untranslated region in a transcript may give rise to mRNA transcript with greater half life in a cell than the presence of one of the other 5' untranslated regions. Another example of such is that the 5' untranslated regions may regulate the relative abundances of cDNAs 1–4 through regulation of alternative splicing.

The CHD1 protein has domains with significant sequence homology to protein domains in the database (FIG. 3). One such domain is a set of eight C2H2 zinc-finger motifs. Zinc-finger motifs often serve as nucleic acid binding motifs, and can also serve as protein interaction motifs. A leucine-rich SCAN domain is found near the N-terminus of all of the alternative proteins (amino acids 49–125). This domain is found in at least 10 other putative transcription factors, but its function is currently unknown (Williams et al. 1995, Lee et al., 1997). FIG. 8 displays a comparison between the CHD1 SCAN domain and a consensus SCAN domain sequence derived from homology analysis of SCAN domain containing zinc-finger proteins in the GenBank database. Yeast-two-hybrid experiments as well as in vitro interaction studies indicate that the SCAN domain acts as a protein-protein interaction surface leading to homo- and/or heterodimerization of two SCAN containing peptides, polypeptides or proteins. The functional form of CHD1 may therefore include a homo- and/or heterodimer of different CHD1 isoforms or CHD1 and other SCAN domain containing zinc-finger proteins. Precedents for transcription factors acting as dimers include members of the bZIP family, bHLH proteins and nuclear receptors (Kouzarides and Ziff, 1988, Fairman et al. 1993, Fawell et al., 1990). A third domain, the KRAB domain (amino acids 235–276 in the protein encoded by cDNA1), is found in many zinc-finger containing transcription factors. It is often a site for protein-protein interaction, and it has been observed as a transcriptional repression domain (Kim et al., 1996, Moosmann et al., 1996). These motifs together suggest that CHD1 serves as a sequence-specific DNA-binding transcription factor. The presence of a KRAB domain raises the possibility that at least one function of CHD1 is that of a repressor: it binds to its cognate binding sites on CHD1 target genes and turns these genes off or reduces the level of transcription of these genes.

Two of the alternative cDNAs (−3 and −4) encode small proteins largely identical to the N-terminus of the longer protein products (−1 and −2, respectively). Tagged fusion proteins have identified the subcellular localization of some of these proteins. The protein encoded by cDNA1 is largely localized to the nucleus, whereas the protein encoded by cDNA3 is found to be diffuse throughout the cell. These localizations were monitored by fusing the relevant CHD1 open reading frame to green fluorescent protein under the control of the cytomegalovirus promoter, transfecting these constructs into 293 cells and monitoring expression microscopically.

The presence of multiple protein products raises the possibility that their relative proportion may influence function. For example, the N-terminus may interact with another protein, call it "protein X", and target protein X to the transcriptional control region of relevant genes. The presence of a fragment of the CHD1 protein that also binds protein X but lacks a DNA binding motif could regulate the effective concentration of protein X, and the function of the protein complex bound to the regulatory region. Such alternative transcripts retaining only partial function have been described for transcription factors and found to serve as competitive regulators (Chen et al., 1994, Arshura et al., 1995, and Walker et al., 1996).

Preparation of Recombinant or Chemically Synthesized Nucleic Acids; Vectors, Transformation, Host Cells Large amounts of the polynucleotides of the present invention may be produced by replication in a suitable host cell. Natural or synthetic polynucleotide fragments coding for a desired fragment will be incorporated into recombinant polynucleotide constructs, usually DNA constructs, capable of introduction into and replication in a prokaryotic or eukaryotic cell. Usually the polynucleotide constructs will be suitable for replication in a unicellular host, such as yeast or bacteria, but may also be intended for introduction to (with and without integration into the genome) cultured mammalian or plant or other eukaryotic cell lines. The purification of nucleic acids produced by the methods of the present invention is described, e.g., in Sambrook et al., 1989 or Ausubel et al., 1992.

The polynucleotides of the present invention may also be produced by chemical synthesis, e.g., by the phosphoramidite method described by Beaucage and Caruthers, 1981 or the triester method according to Matteucci and Caruthers, 1981, and may be performed on commercial, automated oligonucleotide synthesizers. A double-stranded fragment may be obtained from the single-stranded product of chemical synthesis either by synthesizing the complementary strand and annealing the strands together under appropriate conditions or by adding the complementary strand using DNA polymerase with an appropriate primer sequence.

Polynucleotide constructs prepared for introduction into a prokaryotic or eukaryotic host may comprise a replication system recognized by the host, and comprises the intended polynucleotide fragment encoding the desired polypeptide, preferably with transcription and translational initiation regulatory sequences operably linked to the polypeptide-encoding polynucleotide segment. Expression vectors may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional termination sequences, and mRNA stabilizing sequences. Secretion signals may also be included where appropriate, whether from a native CHD1 protein or from other receptors or from secreted polypeptides of the same or related species. These secretion signals thereby allow the protein to cross and/or lodge in cell membranes, and thus attain its functional topology, or be secreted from the cell. Such vectors may be prepared by means of standard recombinant techniques well known in the art and discussed, for example, in Sambrook et al., 1989 or Ausubel et al. 1992.

An appropriate promoter and other necessary vector sequences will be selected so as to be functional in the host, and may include, when appropriate, those naturally associated with CHD1 genes. Examples of workable combinations of cell lines and expression vectors are described in Sambrook et al., 1989, or Ausubel et al., 1992; see also, e.g., Metzger et al., 1988. Many useful vectors are known in the art and may be obtained from such vendors as Stratagene, New England Biolabs, Promega Biotech, and others. Promoters such as the trp, lac and phage promoters, tRNA promoters and glycolytic enzyme promoters may be used in prokaryotic hosts. Useful yeast promoters include promoter regions for metallothionein, 3-phosphoglycerate kinase or other glycolytic enzymes such as enolase or glyceraldehyde-3-phosphate dehydrogenase, enzymes responsible for maltose and galactose utilization, and others. Vectors and promoters suitable for use in yeast expression are further described in Hitzeman et al., EP 73,675A. Appropriate non-native mammalian promoters might include the early and late promoters from SV40 (Fiers et al., 1978) or promoters derived from murine Moloney leukemia virus, mouse tumor virus, cytomegalovirus, avian sarcoma viruses, adenovirus II, bovine papilloma virus or polyoma. In addition, the construct may be joined to an amplifiable gene (e.g., DHFR) so that multiple copies of the gene may be made. For appropriate enhancer and other expression control sequences, see also Enhancers and Eukaryotic Gene Expression, Cold Spring Harbor Press, Cold Spring Harbor, N.Y. (1983).

While such expression vectors may replicate autonomously, they may also replicate by being inserted into the genome of the host cell, by methods well known in the art.

Expression and cloning vectors will likely contain a selectable marker, a gene encoding a protein necessary for survival or growth of a host cell transformed with the vector. The presence of this gene ensures growth of only those host cells bearing the cloning vehicle. Typical selection genes encode proteins that a) confer resistance to antibiotics or other toxic substances, e.g. ampicillin, neomycin, methotrexate, etc.;

b) complement auxotrophic deficiencies; or c) supply critical nutrients not available from complex media, e.g., the gene encoding D-alanine racemase for Bacilli.

The choice of the proper selectable marker will depend on the host cell, and appropriate markers for different hosts are well known in the art.

The vectors containing the nucleic acids of interest can be transcribed in vitro, and the resulting RNA introduced into the host cell by well-known methods, e.g., by injection (see, Kubo et al., 1988), or the vectors can be introduced directly into host cells by methods well known in the art, which vary depending on the type of cellular host, including electroporation; transfection employing calcium chloride, rubidium chloride, calcium phosphate, DEAE-dextran, or other substances; microprojectile bombardment; lipofection; infection (where the vector is an infectious agent, such as a retroviral genome); and other methods. See generally, Sambrook et al., 1989 and Ausubel et al., 1992. The introduction of the polynucleotides into the host cell by any method known in the art, including, inter alia, those described above, will be referred to herein as "transformation." The cells into which nucleic acids described above have been introduced are meant to also include the progeny of such cells.

Large quantities of the nucleic acids and polypeptides of the present invention may be prepared by expressing the CHD1 nucleic acids or portions thereof in vectors or other expression vehicles in compatible prokaryotic or eukaryotic host cells. The most commonly used prokaryotic hosts are strains of *Escherichia coli,* although other prokaryotes, such as *Bacillus subtilis* or Pseudomonas may also be used.

Mammalian or other eukaryotic host cells, such as those of yeast, filamentous fungi, plant, insect, amphibian or avian species, may also be useful for production of the proteins of the present invention. Propagation of mammalian cells in culture is per se well known. See, Jakoby and Pastan, 1979. Examples of commonly used mammalian host cell lines are VERO and HeLa cells, Chinese hamster ovary (CHO) cells, and WI38, BHK, and COS cell lines. An example of a commonly used insect cell line is SF9. However, it will be appreciated by the skilled practitioner that other cell lines may be appropriate, e.g., to provide higher expression, desirable glycosylation patterns, or other features.

Clones are selected by using markers, the choice of which depends on the mode of the vector construction. The marker may be on the same or a different DNA molecule, preferably the same DNA molecule. In prokaryotic hosts, the transformant may be selected, e.g., by resistance to ampicillin, tetracycline or other antibiotics. Production of a particular product based on temperature sensitivity may also serve as an appropriate marker.

Prokaryotic or eukaryotic cells transformed with the polynucleotides of the present invention will be useful not only for the production of the nucleic acids and polypeptides of the present invention, but also, for example, in studying the characteristics of CHD1 polypeptides.

Antisense polynucleotide sequences are useful in preventing or diminishing the expression of the CHD1 locus, as will be appreciated by those skilled in the art. For example, polynucleotide vectors containing all or a portion of the CHD1 locus or other sequences from the CHD1 region (particularly those flanking the CHD1 locus) may be placed under the control of a promoter in an antisense orientation and introduced into a cell. Expression of such an antisense construct within a cell will interfere with CHD1 transcription and/or translation and/or replication.

The probes and primers based on the CHD1 gene sequences disclosed herein are used to identify homologous CHD1 gene sequences and proteins in other species. These CHD1 gene sequences and proteins are used in the diagnostic/prognostic, therapeutic and drug screening methods described herein for the species from which they have been isolated.

Biochemical Characterization of the CHD1 Gene

CHD1 protein consisting of the last six zinc fingers has been purified as a GST-fusion protein. A consensus DNA site (GGGGT) for this protein was selected by in vitro DNA binding studies by a method as described in Morris et al., 1994. This consensus DNA site is found to exist in multiple copies in the regulatory regions upstream of several genes involved in lipid metabolism.

GST-CHD1 fusion protein binds specifically to promoter fragments of, inter alia, the ApoIV, ApoCIII, ApoE, LCAT, and LPL genes in in vitro DNA binding studies (FIGS. 5 and 6). A full summary of the promoters shown to bind to CHD1 is provided in Table 12.

The genes to whose promoters CHD1 binds can be grouped according to function. The first class is a set of apolipoprotein genes that encode structural components of circulating lipoproteins. The second class is a set of genes encoding enzymes known to influence lipoprotein composition. The third class is a set of genes implicated directly in the etiology of atherosclerosis, angiogenesis, diabetes, obesity and metabolic syndrome X. Six genes whose promoter fragments are bound by CHD1 encode proteins with no known involvement in CHD or metabolic disorders related to liplid metabolism. Example 8 provides a detailed analysis of these three classes of genes.

In addition to these genes, CHD1 has been found to bind to a promoter fragment of the HNF4 gene (hepatic nuclear factor 4). Transfection assays indicate that CHD1 represses transcription from this promoter suggesting that CHD1 may regulate HNF4 expression in vivo. Pathological consequences of CHD1 dysfunction are likely include deregulation of HNF4 expression that may be counteracted by agonists/antagonists of HNF4.

HNF4 is a member of the nuclear receptor superfamily, a class of ligand-activated transcription factors. HNF4 functions as a major regulator of liver-specific gene expression, and is involved in the expression of apolipoproteins AI, AII, AIV B and CIII (Kardassis et al., 1996). Mutations in HNF4 have been identified in MODY1 (maturity-onset diabetes of the young) cases (Yamagata et al., 1996, Furuta et al., 1997) linking HNF4 to diabetes. As a ligand-activated nuclear receptor HNF4 presents an excellent target for drug development.

The above experiments that establish CHD1 as a sequence-specific DNA binding protein are described in detail in Example 8.

Analysis of the CHD1 Gene

Further structure and function studies are determined according to methods detailed in Example 10. These studies are intended to establish the role of CHD1 in transcription regulation of its target genes, and the biological significance of this role. Furthermore, these studies are intended to discover functional partners of CHD1, and to establish structure and function of the protein.

CHD1 of a Diabetic Patient Has a Mutation in KRAB Domain and Polymorphisms in CHD1 Promoter Sequence Example 9 describes polymorphisms in CHD1 in CHD1 and CEPH control cases.

Particularly notable is a mutation of CHD1 in a diabetic patient. This mutation changes a Lysine to Glutamic Acid within the KRAB domain. A change in charge in a putative protein-protein interaction domain is highly significant. This mutant protein may be unable to interact with a target protein. The lack of such interaction may have significant consequence to the expression of CHD1 target genes and thus to lipid metabolism.

Additionally, genomic sequences including exonJ and promoter elements for CHD1 have been identified (Example 7). Five polymorphisms and one insertion were found in CHD and CEPH samples. Their position and frequencies are listed in Table 17.

Methods of Use: Nucleic Acid Diagnosis and Diagnostic Kits

To detect the presence of a CHD1 allele predisposing an individual to coronary heart disease or metabolic disorders, a biological sample such as blood is prepared and analyzed for the presence or absence of susceptibility alleles of CHD1. Results of these tests and interpretive information are returned to the health care provider for communication to the tested individual. Such diagnoses may be performed by diagnostic laboratories, or, alternatively, diagnostic kits are manufactured and sold to health care providers or to private individuals for self-diagnosis.

Initially, the screening method involves amplification of the relevant CHD1 sequences. In a preferred embodiment of the invention, the screening method involves a non-PCR based strategy. Such screening methods include two-step label amplification methodologies that are well known in the art. Both PCR and non-PCR based screening strategies can detect target sequences with a high level of sensitivity.

The most popular method used today is target amplification. Here, the target nucleic acid sequence is amplified with polymerases. One particularly preferred method using polymerase-driven amplification is the polymerase chain reaction (PCR). This preferred method is exemplified in Example 6. The polymerase chain reaction and other polymerase-driven amplification assays can achieve over a million-fold increase in copy number through the use of polymerase-driven amplification cycles. Once amplified, the resulting nucleic acid can be sequenced or used as a substrate for DNA probes, or for incorporation into cloning vectors.

When the probes are used to detect the presence of the target sequences (for example, in screening for susceptibility to coronary heart disease or metabolic disorders), the biological sample to be analyzed, such as blood or serum, may be treated, if desired, to extract the nucleic acids. The sample nucleic acid may be prepared in various ways to facilitate detection of the target sequence; e.g. denaturation, restriction digestion, electrophoresis or dot blotting. The targeted region of the analyte nucleic acid usually must be at least partially single-stranded to form hybrids with the targeting sequence of the probe. If the sequence is naturally single-stranded, denaturation will not be required. However, if the sequence is double-stranded, the sequence will probably need to be denatured. Denaturation can be carried out by various techniques known in the art.

Analyte nucleic acid and probe are incubated under conditions that promote stable hybrid formation of the target sequence in the probe with the putative targeted sequence in the analyte. The region of the probes used to bind to the analyte can be made completely complementary to the targeted region of human chromosome 11. Therefore, high stringency conditions are desirable in order to prevent false positives. Conditions of high stringency, however, are used only if the probes are complementary to regions of the chromosome that are unique in the genome. The stringency of hybridization is determined by a number of factors during hybridization and during the washing procedure, including temperature, ionic strength, base composition, probe length, and concentration of formamide. These factors are outlined in, for example, Maniatis et al., 1982 and Sambrook et al., 1989. Under certain circumstances, the formation of higher order hybrids, such as triplexes, quadraplexes, etc., may be desired to provide the means of detecting target sequences.

Detection, if any, of the resulting hybrid is usually accomplished by the use of labeled probes. Alternatively, the probe may be unlabeled, but may be detectable by specific binding with a ligand that is labeled, either directly or indirectly. Suitable labels and methods for labeling probes and ligands are known in the art. These labels and methods comprise radioactive labels that may be incorporated by known methods (e.g., nick translation, random priming or end-labeling by T4 polynucleotide kinase), biotin, fluorescent groups, chemiluminescent groups (e.g., dioxetanes, particularly triggered dioxetanes), enzymes, antibodies and etc. Variations of this basic scheme are known in the art, and include those variations that facilitate separation of the hybrids to be detected from extraneous materials and/or that amplify the signal from the labeled moiety. A number of these variations are reviewed in Matthews and Kricka, 1988; Landegren et al., 1988; Mittlin, 1989; U.S. Pat. No. 4,868,105, and in EPO Publication No. 225,807.

As noted above, non-PCR based screening assays are also contemplated in this invention. This procedure hybridizes a nucleic acid probe (or an analog such as a methyl phosphonate backbone replacing the normal phosphodiester), to the low level DNA target. This probe may have an enzyme covalently linked to the probe, such that the covalent linkage does not interfere with the specificity of the hybridization. This complex consisting of enzyme, probe, conjugate and target nucleic acid can then be isolated away from the free probe enzyme conjugate. A substrate is then added for enzyme detection. Enzymatic activity is observed as a change in color development or luminescent output resulting in a $10^3$–$10^6$ increase in sensitivity. For an example relating to the preparation of oligodeoxynucleotide-alkaline phosphatase conjugates and their use as hybridization probes see Jablonski et al., 1986.

Two-step label amplification methodologies are known in the art. These assays work on the principle that a small ligand (such as digoxigenin, biotin, or the like) is attached to a nucleic acid probe capable of specifically binding CHD1. Exemplary probes are those described in Tables 7 and 8 of this patent application. Allele-specific probes are also contemplated within the scope of this example and exemplary allele-specific probes include probes encompassing the predisposing or potentially predisposing mutations.

In one example, the small ligand attached to the nucleic acid probe is specifically recognized by an antibody-enzyme conjugate. In one embodiment of this example, digoxigenin is attached to the nucleic acid probe. Hybridization is detected by an antibody-alkaline phosphatase conjugate that acts on a chemiluminescent substrate. For methods for labeling nucleic acid probes according to this embodiment see Martin et al., 1990. In a second example, the small ligand is recognized by a second ligand-enzyme conjugate that is capable of specifically complexing to the first ligand. A well known embodiment of this example is the biotin-avidin type of interactions. For methods for labeling nucleic acid probes and their use in biotin-avidin based assays see Rigby et al., 1977 and Nguyen et al., 1992.

Also within the scope of this invention are the nucleic acid probe assays employing a cocktail of nucleic acid probes capable of detecting CHD1. Thus, in one example to detect the presence of CHD1 in a cell sample, more than one probe complementary to CHD1 is employed and in particular the number of different probes is alternatively 2, 3, or 5 different nucleic acid probe sequences. In another example, to detect the presence of mutations in the CHD1 gene sequence in a patient, more than one probe complementary to CHD1 is employed where the cocktail includes probes capable of binding to the allele-specific mutations identified in populations of patients with alterations in CHD1. In this embodiment, any number of probes can be used, and will preferably include probes corresponding to the major gene mutations identified as predisposing an individual to coronary heart disease or metabolic disorders. Some candidate probes contemplated include probes comprising the allele-specific mutations identified in Tables 7 and 8 and those comprising the CHD1 regions corresponding to SEQ ID Nos: 1, 3, 5, 7, 9 and 206, both 5' and 3' to the mutation site.

Methods of Use: Peptide Diagnosis and Diagnostic Kits

The genetic defect underlying CHD or metabolic disease can also be detected on the basis of the alteration of wild-type CDH1 polypeptide. Such alterations can be determined by sequence analysis in accordance with conventional techniques. More preferably, antibodies (polyclonal or monoclonal) are used to detect differences in, or the absence of, CDH1 peptides. The antibodies may be prepared as defined under "antibodies" (further shown in Examples 11 and 12). Other techniques for raising and purifying antibodies are well known in the art and any such techniques may be chosen to achieve the preparations claimed in this invention. In a preferred embodiment of the invention, antibodies will immunoprecipitate CDH1 proteins from solution as well as react with CDH1 protein on Western or immunoblots of polyacrylamide gels. In another preferred embodiment, antibodies will detect CDH1 proteins in paraffin or frozen tissue sections, using immunocytochemical techniques.

Preferred embodiments relating to methods for detecting CHD1 or its mutations include enzyme-linked immunosorbent assays (ELISA), radioimmunoassays (RIA), immunoradiometric assays (IRMA) and immunoenzymatic assays (IEMA), including sandwich assays using monoclonal and/or polyclonal antibodies. Exemplary sandwich assays are described by David et al. in U.S. Pat. Nos. 4,376,110 and 4,486,530, hereby incorporated by reference, and exemplified in Example 14.

Methods of Use: Drug Screening

This invention is particularly useful for screening compounds by using the CHD1 polypeptide or binding fragment thereof in any of a variety of drug screening techniques.

The CHD1 polypeptide or fragment employed in such a test may either be free in solution, affixed to a solid support (as shown in Example 13), or borne on a cell surface. One method of drug screening utilizes eukaryotic or prokaryotic host cells stably transformed with recombinant polynucleotides expressing the CDH1 polypeptide or fragment. Such cells, either in viable or fixed form, can be used for standard binding assays, preferably in competitive binding assays.

One may measure, for example, (a) the formation of complexes formed between a CDH1 polypeptide or fragment and the drug candidate being tested; or (b) the degree to which the formation of a complex between a CDH1 polypeptide or fragment and a known ligand such as a specific polypeptide or DNA sequence is interfered with by the drug candidate being tested. An example of method (a) is provided in Example 13, wherein the drug candidates are peptides.

Thus, the present invention provides methods of screening for drugs comprising interaction between a drug candidate with a CHD1 polypeptide or fragment thereof and assaying (I) for the presence of a complex between the drug candidate and the CHD1 polypeptide or fragment, or (ii) for the presence of a complex between the CDH1 polypeptide or fragment and a ligand such as a polypeptide or DNA sequence, by methods well known in the art. In such competitive binding assays the CHD1 polypeptide or fragment is typically labeled. Free CHD1 polypeptide or fragment is separated from that present in a protein:protein or protein:DNA complex, and the amount of free (i.e., uncomplexed) label is a measure of the binding of the drug candidate to CHD1 or its interference with CDH1:ligand binding, respectively.

Another technique for drug screening provides high throughput screening for compounds having suitable binding affinity to the CHD1 polypeptides and is described in detail in Geysen, PCT application WHO 84/03564, published on Sep. 13, 1984. Briefly, large numbers of different small peptide test compounds are synthesized on a solid substrate, such as plastic pins or some other surface. The peptide test compounds are reacted with CHD1 polypeptide and washed. Bound CHD1 polypeptide is then detected by methods well known in the art.

Purified CHD1 can be coated directly onto plates for use in the aforementioned drug screening techniques. Non-neutralizing antibodies to the polypeptide can be used to capture antibodies to immobilize the CHD1 polypeptide on the solid phase.

This invention also contemplates the use of competitive drug screening assays in which neutralizing antibodies capable of specifically binding to the CDH1 polypeptide compete with a test compound for binding to the CDH1 polypeptide or fragments thereof. In this manner, the antibodies can be used to detect the presence of any test compound sharing one or more antigenic determinants of the CDH1 polypeptide.

A further technique for drug screening involves the use of host eukaryotic cell lines or cells (such as described above) that have a nonfunctional CHD1 gene. These host cell lines or cells are defective at the CHD1 polypeptide level. The host cell lines or cells are grown in the presence of the candidate drug compound. The rate of growth of the host cells is measured to determine if the compound is capable of regulating the growth of CHD1 defective cells.

A further technique for drug screening involves the use of host prokaryotic or eukaryotic cell lines or cells (such as described above) that have a reporter gene construct under the transcriptional regulation of the CHD1 high-affinity DNA recognition sequences (see Example 8), and that express either endogenous or exogenous CHD1 polypeptide or fragment. The host cell lines or cells are then exposed to a drug compound. The rate of transcription of the reporter gene is then monitored to determine if the compound is capable of altering its expression.

As described in Example 8, CDH1 is a sequence-specific DNA binding protein. It may be possible to use oligonucleotides comprising the CDH1 DNA recognition sequence as an inhibitor.

Methods of Use: Rational Drug Design

The goal of rational drug design is to produce structural analogs of biologically active polypeptides of interest or of small molecules with which they interact (e.g., agonists, antagonists, inhibitors) in order to fashion drugs which are, for example, more active or stable forms of the polypeptide, or which, e.g., enhance or interfere with the function of a polypeptide in vivo. See, e.g., Hodgson, 1991. In one approach, one first determines the three-dimensional structure of a protein of interest (e.g., CHD1 polypeptide) or, for example, of the CHD1-receptor or ligand complex or, for example, of the CHD1-nucleic acid complex, by x-ray crystallography or nuclear magnetic resonance (NMR) in solution, by computer modeling—most typically, by a combination of approaches. Less often, useful information regarding the structure of a polypeptide may be gained by modeling based on the structure of homologous proteins. An example of rational drug design is the development of HIV protease inhibitors (Erickson et al., 1990). In addition, peptides (e.g., CHD1 polypeptide) are analyzed by the "alanine scan" approach (Wells, 1991). In this technique, a particular amino acid residue is replaced by Ala, and its effect on the peptide's activity is determined. Each of the amino acid residues of the peptide is analyzed in this manner to determine the functionally important regions of the peptide (i.e. the peptide is alanine "scanned").

It is also possible to isolate a target-specific antibody, selected by a functional assay, and then to solve its crystal structure. In principle, this approach yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original protein. The anti-ids could then be used to identify and isolate peptides from banks of chemically or biologically produced banks of peptides. Selected peptides would then act as the pharmacore.

Thus, one may design drugs that have, for example, improved CHD1 polypeptide activity or stability or that act as inhibitors, agonists, antagonists, etc. of CDH1 polypeptide activity. By virtue of the availability of cloned CHD1 sequences, sufficient amounts of the CHD1 polypeptide may be made available to perform such analytical studies as x-ray crystallography. In addition, the knowledge of the CDH1 protein sequence provided herein will guide those employing computer modeling techniques in place of, or in addition to, x-ray crystallography.

Methods of Use: Gene Therapy

According to the present invention, a method is also provided that supply wild-type CHD1 function to a cell carrying mutant CHD1 alleles. Supplying such a function should suppress phenotypic expression of coronary heart disease or metabolic disorders in the recipient cell or in an organism bearing such cell. The wild-type CDH1 gene or a part of the gene may be introduced into the cell in a vector such that the gene remains extrachromosomal, or integrates at a random location into the cellular DNA. In such situations, the gene will be expressed by the cell from the extrachromosomal or chromosomal location, respectively. If a gene fragment is introduced and expressed in a cell carrying a mutant CDH1 allele, the gene fragment should encode a part of the CDH1 protein that is required for suppression of the coronary heart disease or metabolic disorders phenotype. More preferred is the situation where the wild-type CHD1 gene or a part thereof is introduced into the mutant cell in such a way that it recombines with the endogenous mutant CHD1 gene present in the cell, especially if the mutant allele is a dominant allele (a cell bearing a dominant CDH1 mutant allele is phenotypically mutant even in the presence of a wild-type allele). Such recombination requires a double recombination event that results in the correction of the CDH1 gene mutation. Vectors for introduction of genes both for recombination and for extrachromosomal maintenance are known in the art, and any suitable vector may be used. Methods for introducing DNA into cells such as electroporation, calcium phosphate coprecipitation and viral transduction are known in the art, and the choice of method is within the competence of the person of ordinary skill in the art. Cells transformed with the wild-type CDH1 gene can be used as model systems to study metabolic disorders and drug treatments that alter cellular metabolism.

As generally discussed above, the CDH1 gene or fragment, where applicable, may be employed in gene therapy methods in order to increase the amount of the expression products of such genes. Such gene therapy is particularly appropriate for use in cells in which the level of CDH1 polypeptide is absent or diminished compared to normal cells. It may also be useful to increase the level of expression of a given CHD1 gene even in those cells in which the mutant gene is expressed at a "normal" level, but the gene product is not fully functional. It may also be useful to increase the levels of CDH1 in normal cells, providing the cell or host with a more atheroprotective phenotype.

Gene therapy would be carried out according to generally accepted methods, for example, as described by Friedman, 1991. Cells from a patient's tissue of interest (i.e. bone marrow or liver) would be first analyzed by the diagnostic methods described above, to ascertain the production of CHD1 polypeptide in the cells. A virus or plasmid vector (see further details below), containing a copy of the CHD1 gene linked to expression control elements and possibly capable of replicating inside the cells, is prepared. Suitable vectors are known, such as disclosed in U.S. Pat. No. 5,252,479 and PCT published application WHO 93/07282. The vector is then injected into the patient into the appropriate target tissue or systemically, or used to infect cells in vitro, and the cells then used to repopulate or supplement the patient's tissues. If the transfected gene is not permanently incorporated into the genome of each of the targeted cells, the treatment may have to be repeated periodically.

Gene transfer systems known in the art may be useful in the practice of the gene therapy methods of the present invention. These include viral and nonviral transfer methods. A number of viruses have been used as gene transfer vectors, including papovaviruses, e.g., SV40 (Madzak et al., 1992), adenovirus (Berkner, 1992; Berkner et al., 1988; Gorziglia and Kapikian, 1992; Quantin et al., 1992; Rosenfeld et al., 1992; Wilkinson et al., 1992; Stratford-Perricaudet et al., 1990), vaccinia virus (Moss, 1992), adeno-associated virus (Muzyczka, 1992; Ohi et al., 1990), herpes viruses including HSV and EBV (Margolskee, 1992; Johnson et al., 1992; Fink et al., 1992; Breakfield and Geller, 1987; Freese et al., 1990), and retroviruses of avian (Brandyopadhyay and Temin, 1984; Petropoulos et al., 1992), murine (Miller, 1992; Miller et al., 1985; Sorge et al., 1984; Mann and Baltimore, 1985; Miller et al., 1988), and human origin (Shimada et al., 1991; Helseth et al., 1990; Page et al., 1990; Buchschacher and Panganiban, 1992). Most human gene therapy protocols have been based on disabled murine retroviruses.

Nonviral gene transfer methods known in the art include chemical techniques such as calcium phosphate coprecipitation (Graham and van der Eb, 1973; Pellicer et al., 1980); mechanical techniques, for example microinjection (Anderson et al., 1980; Gordon et al., 1980; Brinster et al., 1981; Constantini and Lacy, 1981); membrane fusion-mediated transfer via liposomes (Felgner et al., 1987; Wang and Huang, 1989; Kaneda et al, 1989; Stewart et al., 1992; Nabel et al., 1990; Lim et al., 1992); and direct DNA uptake and receptor-mediated DNA transfer (Wolff et al., 1990; Wu et al., 1991; Zenke et al., 1990; Wu et al., 1989b; Wolff et al., 1991; Wagner et al., 1990; Wagner et al., 1991; Cotten et al., 1990; Curiel et al., 1991a; Curiel et al., 1991b). Viral-mediated gene transfer can be combined with direct in vivo gene transfer using liposome delivery, allowing one to direct the viral vectors to the tumor cells and not into the surrounding nondividing cells. Alternatively, the retroviral vector producer cell line can be injected into tissues (Culver et al., 1992). These producer cells would then provide a continuous source of vector particles. This technique has been approved for use in humans with inoperable brain tumors.

In an approach that combines biological and physical gene transfer methods, plasmid DNA of any size is combined with a polylysine-conjugated antibody specific to the adenovirus hexon protein, and the resulting complex is bound to an adenovirus vector. The trimolecular complex is then used to infect cells. The adenovirus vector permits efficient binding, internalization, and degradation of the endosome before the coupled DNA is damaged.

Liposome/DNA complexes have been shown to be capable of mediating direct in vivo gene transfer. While in standard liposome preparations the gene transfer process is nonspecific, localized in vivo uptake and expression have been reported in tumor deposits, for example, following direct in situ administration (Nabel, 1992), and may apply to particular tissues.

Gene transfer techniques that target DNA directly to liver or other target tissues, are preferred. Receptor—mediated gene transfer, for example, is accomplished by the conjugation of DNA (usually in the form of covalently closed supercoiled plasmid) to a protein ligand via polylysine. Ligands are chosen on the basis of the presence of the corresponding ligand receptors on the cell surface of the target cell/tissue type. These ligand-DNA conjugates can be injected directly into the blood if desired and are directed to the target tissue where receptor binding and internalization of the DNA-protein complex occurs. To overcome the problem of intracellular destruction of DNA, coinfection with adenovirus can be included to disrupt endosome function.

Methods of Use: Peptide Therapy

Peptides that have CHD1 activity can be supplied to cells with mutant or missing CDH1 alleles. Protein can be produced by expression of the cDNA sequence in bacteria, for example, using known expression vectors. Alternatively, CHD1 polypeptide can be extracted from CHD1-producing mammalian cells. In addition, the techniques of synthetic chemistry can be employed to synthesize CDH1 protein. Any of such techniques can provide the composition of the present invention comprising the CDH1 protein. The composition is substantially free of other human proteins. This is most readily accomplished by synthesis in a microorganism or in vitro.

Active CDH1 molecules can be introduced into cells by microinjection or by use of liposomes, for example. Alternatively, some molecules may be taken up by cells, actively or by diffusion. Extracellular application of the CDH1 gene product may be sufficient to affect phenotype.

Supply of molecules with CDH1 activity should lead to partial reversal of the altered metabolic state. Other molecules with CDH1 activity (for example, peptides, drugs or organic compounds) may also be used to effect such a reversal. Modified polypeptides having substantially similar function are also used for peptide therapy.

Methods of Use: Transformed Hosts

Similarly, cells and animals that carry a mutant CDH1 allele can be used as model systems to study and test for substances with potential as therapeutic agents. The cells are typically cultured epithelial cells. These may be isolated from individuals with CDH1 mutations. Alternatively, the cell line can be engineered to carry the mutation in the CHD1 allele, as described above. After a test substance is applied to the cells, the phenotype of the cell is determined. Any metabolic trait of mutant cell lines, such as lipid metabolism or glucose metabolism can be assayed. Assays for each of these traits are known in the art.

Animals for testing therapeutic agents can be selected after mutagenesis of whole animals or after treatment of germline cells or zygotes. The latter approach includes insertion of mutant CHD1 alleles, usually from a second animal species, as well as insertion of disrupted homologous genes. Alternatively, the endogenous CHD1 gene(s) of the animals may be disrupted by insertion or deletion mutation or other genetic alterations using conventional techniques (Capecchi, 1989; Valancius and Smithies, 1991; Hasty et al., 1991; Shinkai et al., 1992; Mombaerts et al., 1992; Philpott et al., 1992; Snouwaert et al., 1992; Donehower et al., 1992). After test substances have been administered to the animals, appropriate metabolic profiles must be assessed. If the test alters cellular or organismal metabolism in an appropriate way, then the test substance is a candidate therapeutic agent for the treatment of the metabolic disorders identified herein. These animal models provide an extremely important testing vehicle for potential therapeutic products.

The following are examples that illustrate the methods of this invention. the examples are included for the purposes of illustration only and the present invention is limited only by the claims. Standard techniques well known in the art or the techniques specifically described below were utilized.

EXAMPLE 1

Ascertain and Study Kindreds Likely to Have a Chromosome 11-Linked Coronary Heart Disease Susceptibility Locus Extensive coronary heart disease prone kindreds were ascertained from index cases with early coronary heart disease (before the age of 50 for men or 55 for women). These probands were contacted, and those with familial history of coronary heart disease were recruited for lipid profiling. Large kindreds were expanded from those with extensive clustering of coronary heart disease or dyslipidemia. The large number of meioses present in these large kindreds provided the power to detect whether the CHD1 locus was segregating, and increased the opportunity for informative recombinants to occur within the small region being investigated. This vastly improved the chances of establishing linkage to the CHD1 region, and greatly facilitated the reduction of the CHD1 region to a manageable size, which permits identification of the CHD1 locus itself.

Each kindred was extended through all available connecting relatives and to all informative first degree relatives of each proband or affected relative. Medical records or death certificates were obtained for confirmation of coronary heart disease. Each key connecting individual and all informative individuals were invited to participate by providing a blood sample from which DNA was extracted, and for extensive lipid profiling, and medical histories were gathered. We also sampled spouses, siblings, and offspring of deceased cases so that the genotype of the deceased cases could be inferred from the genotypes of their relatives.

The criteria for selection of kindreds to analyze for CHD1 linkage were: 1) genotypes available, or inferable, for 6 or more coronary heart disease or dyslipidemic cases, and 2) at least genotyped cases within a second degree of relationship to another genotyped case.

The families were analyzed for the presence of a number of different dyslipidemic phenotypes. All of the data presented are for a low HDL cholesterol phenotype, with three liability classes. The liability classes were: Class 1, strongly, affected, HDL-C less than 10% of population (corrected for age and sex); Class 2, weakly affected, HDL-C greater than 10% but less than 25%; Class 3, HDL-C greater than 25%. Each individual was scrutinized for the presence of factors that might confound HDL-C levels, and the phenotype corrected accordingly. Confounding factors included body mass index, alcohol consumption and prescription drug use.

EXAMPLE 2

Selection of Kindreds that are Linked to Chromosome 11 and Localization of CHD1 to a Small Interval Nuclear pellets were extracted from 16 ml of ACD blood, and DNA extracted with phenol and chloroform, precipitated with ethanol, and resuspended in Tris-EDTA. The markers used for genotyping were short tandem repeat (STR) loci at 11q23 which flanked the most likely CHD1 location as indicated from preliminary genomic search data. The region showing preliminary linkage was from D11S924 to D11S912, an interval of about 20 cM (centiMorgans).

Two-point linkage analysis was performed with the package LINKAGE (Lathrop et al., 1984; 1985) using the FASTLINK implementation (Cottingham et al., 1993; Schaffer et al., 1994). The statistical analysis for the inheritance of susceptibility to coronary heart disease used the model described in Table 1.

This model assumed a rare autosomal dominant susceptibility locus (gene frequency of 0.01) and allowed for a sporadic rate of coronary heart disease. Marker allele frequencies were estimated from unrelated individuals present in the kindreds. A total of 42 kindreds were analyzed with at least nine markers from the region (see Table 3 for a list of markers). Most of these were haplotyped by hand, and segregating haplotypes were assigned as rare alleles at a single locus. The genotypes and haplotypes were analyzed for linkage using a number of different dyslipidemic phenotypes.

TABLE 1

Model Used in the Analysis of CHD1-linked Kindreds

| Phenotype | Liability | penetrance (AA) | penetrance (Aa) | penetrance (aa) |
| --- | --- | --- | --- | --- |
| 2 (affected) | 1 | 0.025 | 0.5 | 0.5 |
| 2 (affected) | 2 | 0.15 | 0.35 | 0.35 |
| 1 (unaffected) | 3 | 0.6 | 0.8 | 0.8 |

Linkage in the presence of heterogeneity was assessed by the admixture test (A-test) of Ott (1986). HOMOG, which postulates two family types, linked and unlinked, was used. Multipoint linkage analysis was performed using VITESSE (O'Connell et al., 1995). The size of the pedigrees made more-than-five-point analyses impossible. The multipoint results in FIG. 2 represent a walking three-point analysis, with the disease phenotype placed between each pair of adjacent markers in all intervals but the exterior ones, in which the two closest markers were used.

Two point linkage analysis of the haplotype (or 2-point linkage to marker D11S1353, if a haplotype was not generated), yielded strongly suggestive linkage. Six kindreds showed individual evidence for linkage (LOD>0.2). The heterogeneity LOD score was 3.64, with an alpha (proportion of linked families) of 0.25. The posterior probability of linkage was 0.98, with a likelihood ratio of 4359. Individual LOD scores for the families are shown in Table 2.

TABLE 2

Haplotype Heterogeneity LOD Scores
for High-risk Coronary Heart
Disease Kindreds

| Pedigree | LOD (theta = 0) | Max LOD (theta) |
|---|---|---|
| 3311 | 3.449 | 3.449 (0.00) |
| 68801 | 1.454 | 1.454 (0.00) |
| 72001 | 1.327 | 1.327 (0.00) |
| 3077 | 0.567 | 0.567 (0.00) |
| 3065 | 0.395 | 0.402 (0.01) |
| 652* | 0.401 | 0.401 (0.00) |
| 604* | 0.002 | 0.337 (0.10) |
| 604** | 0.311 | 1.119 (0.05) |

*based on 2-point LOD scores (pedigrees were not haplotyped)
**based on 5-point LOD score

EXAMPLE 3

Contig Assembly

Genomic clone contig assembly in the CHD1 region started from the 1993–94 Genethon human genetic linkage map (Gyapay, et al., 1994). YACs located in the interval between D11S1353 and D11S933 were ordered from Genome Systems. Primer pairs for markers located in the interval between D11S1353 and D11S933 were synthesized and used to screen a BAC library at Myriad. Markers that were negative on that BAC library were used to screen the BAC and PAC libraries at Genome Systems. To generate additional starting points for physical mapping, several inter-alu PCR fragments from the YACs were sent to Genome Systems to use as probes of their BAC libraries. DNA preparations were prepared from the BACs and PACs from these screens. End sequences were obtained by dye terminator sequencing with vector primers on ABI 377 sequencers, and by radioactive cycle sequencing. Primer pairs defining BAC or PAC end markers were designed from these sequences. These new markers were checked against the YACs and a human chromosome 11-containing rodent cell line to ensure that they mapped to the correct chromosome and within the correct interval. These new markers were checked against the already identified BACs/PACs to determine the positions of these clones relative to each other. The outside markers from each clone contig were used to screen the Myriad BAC library; those that were negative on that BAC library were used to screen the BAC and PAC libraries at Genome Systems. Repeated cycles of library screening and marker development allowed for the construction of a BAC/PAC contig that spanned the minimal recombinant interval (FIG. 2).

As shown in the physical map of the CHD1 region (FIG. 2), a 15 clone BAC/PAC contig spans the interval between D11S1353 and D1S933 (markers 1 and 14, see Table 3). Based on the genetic data described in detail above, the CHD1 locus must lie in the interval between the markers 1 and 54 (FIG. 1 and Table 3). This interval is spanned by a 15 clone BAC/PAC contig. Based on the sizes and map positions of the YACs in the region, the sizes of these BACs and PACs in the contig and extensive sequencing of those BACs and PACs, we estimate the size of the minimal genetically defined interval containing CHD1 to be about 1 megabase.

TABLE 3

Markers in the CHD1 Region

| MARKER | CODE | SOURCE |
|---|---|---|
| D11S1353 | 1 | CEPH |
| D11S488 | 2 | CEPH |
| D11S936 | 3 | CEPH |
| D11S1316 | 7 | CEPH |
| D11S964 | 10 | HUGO/UT |
| D11S836 | 11 | HUGO |
| D11S1328 | 12 | CEPH |
| D11S933 | 14 | CEPH |
| D11S934 | 29 | CEPH |
| D11S924 | 42 | CEPH |
| D11S912 | 43 | HUGO |
| B138-1 | 46 | Myriad |
| B114-4 | 47 | Myriad |
| B114-2 | 48 | Myriad |
| P59-a | 52 | Myriad |
| B159-a | 53 | Myriad |
| B159-b | 54 | Myriad |
| B138-a | 55 | Myriad |
| B159-c | 56 | Myriad |
| B00-1 | 57 | Myriad |
| B114-7 | 60 | Myriad |
| B114-8 | 61 | Myriad |
| B10-a | 65 | Myriad |
| D11S925 | 73 | CEPH |
| D11S4089 | 74 | CEPH |
| D11S4167 | 76 | CEPH |
| D11S4158 | 77 | CEPH |
| D11S1896 | 78 | CEPH |
| D11S4151 | 79 | CEPH |
| D11S4110 | 80 | CEPH |

EXAMPLE 4

Genomic Sequencing

BAC or PAC DNA was sheared by sonication. To generate blunt-ended fragments, the sonicated DNA was incubated with mung-bean nuclease (Pharmacia Biotech) followed by treatment with a Pfu polishing kit (Stratagene). The DNA fragments were fractionated by size on a 0.8% TAE agarose gel, and fragments in the size range of 1.0–1.6 kb were excised under longwave (365 nm) ultraviolet light. The excised gel slice was rotated 180 degrees relative to the original direction of electrophoresis and then placed into a new gel tray containing 1.0% GTG-Seaplaque low melting temperature agarose (FMC corporation) before the gel solidified. Electrophoresis was repeated for the same time and voltage as the first run, resulting in a concentration of the DNA fragments in a small volume of agarose, and the gel slice containing the DNA fragments was once again excised from the gel. The DNA fragments were purified from the agarose by incubating the gel slice with beta-agarase (New England Biolabs), followed by removal of the agarose monomers using disposable microconcentrators (Amicon) that employ a 50,000 Daltons molecular weight cutoff filter. DNA fragments were ligated into the Hinc II site of the plasmid pMYG2, a pBluescript (Stratagene) derivative where the polylinker has been replaced by the pMYG2 polylinker (Table 4). The vector was prepared by digestion with Hinc II followed by dephosphorylation with calf alkaline phosphatase (Boehringer Mannheim).

TABLE 4

Cloning Sites in pMYG1 and pMYG2

| Name | Sequence | |
|---|---|---|
| pMYG2 polylinker | ATGACCATAGTCGACCTGGCCGTCGTT | (SEQ ID NO: 15) |
| pMYG1 polylinker | ATGACCATAGTCGACGGATCCGTCGACCTGGCCGTCGTT | (SEQ ID NO: 16) |

Ligated products were transformed into DH5-α *E. coli* competent cells (Life Technologies, Inc.) and plated on LB plates containing ampicillin, IPTG, and Bluo-gal (Sigma; Life Technologies, Inc.). White colonies were used to inoculate individual wells of 1 ml 96-well microtiter plates (Beckman) containing 200 microliters of LB media supplemented with ampicillin at 50 micrograms per milliliter. The plates were incubated for 16–20 hours in a shaking incubator at 37° Celsius. After incubation, 20 microliters of dimethyl sulfoxide were added to each well and the plates were stored frozen. The inserts of random-sheared clones were amplified from *E. coli* cultures by PCR with vector primers, and the PCR products were sequenced with M13 forward or reverse fluorescent energy transfer (FET) dye-labeled primers on ABI 377 sequencers.

DNA sequencing gel files were examined for lane tracking accuracy and adjusted where necessary before data extraction. ABI sample files resulting from gel files were converted to the Standard Chromatogram Format (SCF) and trimmed of sequencing vector (pMYG1 or pMYG2). Trimmed sequences were assembled using Acem.bly (Thierry-Mieg et al., 1995; Durbin and Thierry-Mieg, 1991). Contiguous sequence resulting from automatic assembly was screened for residual vector sequence (both sequencing vector and cloning vector) as well as for bacterial contamination using BLAST (Altschul et al., 1990).

Remaining sequences were arranged according to sequence similarity to overlapping genomic clones. Repetitive sequence was masked from the sequence contigs using xblast (Claverie and States, 1993). These masked sequences were placed in a Genetic Data Environment (GDE) (Smith et al., 1994) local database for subsequent similarity searches. Similarities among genomic DNA sequences and hybrid-selected cDNA clones as well as GenBank entries—both DNA and protein—were identified using BLAST. The DNA sequences were also characterized with respect to short period repeats, CpG content, and long open reading frames.

EXAMPLE 5

Gene Identification cDNA Preparation. First-strand cDNA molecules were synthesized from Poly(A) enriched RNA from different human tissues (listed in Table 5) using the tailed random primer FSnnN10 (all primers are listed in Table 6) or the tailed oligo-deoxythymidine primer FSnnT12 and Superscript II reverse transcriptase (Gibco BRL) in reverse transcription reactions. In all oligonucleotides 'nn' refers to a dinucleotide specific for the tissue source (Table 5), and 'N' refers to any of the four nucleotides. Long first strand cDNA molecules were purified by NaOH treatment and separated on Sepharose CL-4B columns. Degenerate overhang ligation was used to "anchor" the 5' end of the cDNA. A double stranded oligonucleotide (UCA.B annealed to UCA.T7) was ligated onto the 5' ends (5' relative to mRNA) of the cDNA using T4 DNA ligase. Anchored double-stranded cDNA molecules were then repurified on Sepharose CL-4B columns. For hybrid selection, island hopping and RACE, cDNA from a mixture of tissues were first expanded by amplification using UCP.A AND FS, and long products were purified by fractionation on Sepharose CL-4B.

Hybrid selection was performed by a modified procedure of Lovett et al. (1991). Selection probes were prepared from purified BACs or PACs by digestion with Hinf I and Exonuclease III. The single-stranded probe was photolabelled with photobiotin (Gibco BRL) according to the manufacturer's recommendations. Probe, cDNA and Cot-1 DNA and poly A RNA were hybridized overnight at 40° C. in 2.4M TEA-Cl, 10 mM NaPO$_4$, 1 mM EDTA. Hybridized cDNAs were captured on streptavidin-paramagnetic particles (Dynal), eluted, re-amplified with UCP.A AND FS, and large cDNA molecules (>400 bp) were fractionated by gel electrophoresis and purified from the gel. The selected, amplified cDNA molecules were hybridized with an additional aliquot of probe and Cot-1 DNA. Captured and eluted products were amplified again with UCP.A AND FS, size-selected by gel electrophoresis, and cloned into dephosphorylated pUC18 digested with Hinc II. Ligation products were transformed into XL2-Blue ultra-competent cells (Stratagene).

Insert-containing clones were identified by blue/white selection on Xgal or Bluo-gal plates. Inserts were amplified by colony PCR with vector primers. The colony PCR products were arrayed on a dot-blot apparatus, and filters hybridized separately with Cot-1 DNA or probe DNA prepared by the "nick translation" method. Probe positive, Cot-1 negative clones were then sequenced on ABI 377 sequencers. Alignment of these cDNA sequences to corresponding genomic sequences, and parsing of the cDNA sequences across those genomic sequences revealed exons, allowing for the initial characterization of genes located within the region.

Inter-exon (island hopping) PCR: Following sequence analysis of the first hybrid selected clones that originated from CHD1, several primers were designed to try to amplify CHD1 products from various tissue cDNAs. Internal exons and the 3' terminal exons (identified as sequences in the dbEST database that were homologous to genomic sequences adjacent to known exons of CHD1) were identified and confirmed by amplification using the primer pairs described in Table 6 (i.e. IH.F1 and IH.R1 formed one such a primer pair). Amplified products were fractionated by gel electrophoresis and purified and either directly sequenced using dye terminator chemistry or cloned and sequenced as described above for hybrid selection.

5' RACE: The 5' end exon of CHD1 was identified by a modified RACE protocol. Amplified cDNA molecules from liver and brain were further amplified through two rounds of nested PCR, using the primer pairs GS1 or NR1 and UCP.A followed by GS2 or any of NR2–NR6 and UCP.B (Table 6). In the first round of PCR, the gene-specific primer was at about 5-fold excess over the anchor primer (UCP.A) to increase the proportion of specifically primed products. Amplified products were subjected tp gel electrophoresis, purified, cloned and sequenced as described above for hybrid selection. The primers NR3 through NR6 allow for 5' RACE specific to each of cDNAs 1–4.

TABLE 5

Tissue Sources for cDNA

| Tissue | Two-base code |
|---|---|
| Human Liver or Hepatocyte | AC |
| Human Small Intestine | CT |
| Human Kidney | AG |
| Human Placenta | CA |
| Human Lymphocyte | CG |
| Human Cheek epithelium | CC |
| Human Fetal Liver | AA |
| Human Fetal Brain | AT |
| Human Testes | GG |
| Human Thymus | GA |
| Mouse Liver | TA |
| Patient Blood Draw | AT |

TABLE 6

Oligonucleotides Used for cDNA synthesis, Hybrid Selection and Island Hopping (respectively (SEQ ID NOS: 17–37))

| Name | Sequence |
|---|---|
| FsnnN10 | GTCAGATCTACTACGTACAGnnNNNNNNNNNN |
| FsnnT12 | GTCAGATCTACTACGTACAGnnTTTTTTTTTTTT |
| UCA.B | (PO$_4$)GTGACTAATCGATACGCGTGTGAAGGTGC |
| UCA.T7 | CCTTCACACGCGTATCGATTAGTCACNNNNNNNN(NH$_2$) |
| FS OR Fsr | GTCAGATCTACTACGTACAG |
| UCP.A | CACCTTCACACGCGTATCG |
| UCP.B | CCTTCACACGCGTATCGATTAG |
| GS1 | ACATGGACAGTCACCGCCT |
| GS2 | ACAGTCACCGCCTTGGTCT |
| IH.F1 | GCTGGTGGAGGGTTTGCAGA |
| IH.R1 | CTGTGTATATCCTCCAAACT |
| IH.F2 | GGAATGTGGAAAAAGTTACACAC |
| IH.R2 | CTCTTCCTCACCTCCCTTAG |

TABLE 6-continued

Oligonucleotides Used for cDNA synthesis, Hybrid Selection and Island Hopping (respectively (SEQ ID NOS: 17–37))

| Name | Sequence |
|---|---|
| IH.F3 | GTGAGGAGATCTGCTTTCAG |
| IH.R3 | CAGGTTCAACACTTTCCGTG |
| NR1 | CTCATTAGGTGACTCAGGCTC |
| NR2 | GACTCAGGCTCCGCTCCTA |
| NR3 | AACATGGACAGTCACCCAC |
| NR4 | CTCTGACAGGACTTCCCAC |
| NR5 | TGAACATGGACAGTCACCGC |
| NR6 | CCTCTGACAGGACTTCCGC |

EXAMPLE 6

Mutation Screening

Both genomic DNA and cDNA were used as templates for mutation screening.

Genomic DNA: Using genomic DNAs from CHD kindred members, population control individuals and diabetes affecteds, nested PCR amplifications were performed to generate PCR products of the candidate genes that were screened for CHD1 mutations. The primers listed in Table 7 were used to produce amplicons of the CHD1 gene. Using the outer primer pair for each exon (a and p), 1–10 ng of genomic DNA were subjected to a 23–26 cycle primary amplification by PCR, after which the PCR products were diluted 60-fold and re-amplified using nested M13-tailed primers (b and q or c and r, etc.) for another 20–25 cycles; either TaqPlus (Stratagene) or AmpliTaq Gold (Perkin Elmer) was used in the PCRs. In general, the PCR conditions used were an initial denaturation step at 95° C. for 1 minute (TaqPlus) or 10 minutes (AmpliTaq Gold), followed by cycles of denaturation at 96° C. (12 seconds), annealing at 55° C. (15 seconds) and extension at 72° C. (45–60 seconds). PCR products were sequenced with M13 forward or reverse fluorescent energy transfer (FET) dye-labeled primers on ABI 377 sequencers. Chromatograms were analyzed for the presence of polymorphisms or sequence aberrations in either the Macintosh program Sequencher (Gene Codes) or the Java program Mutscreen (Myriad, proprietary).

TABLE 7

Oligonucleotides for Mutation Screening from Genomic DNA (respectively (SEQ ID NOS: 38–175))

| name | alias | sequence | genomic positions |
|---|---|---|---|
| primary amplicon for exons A and B | | | |
| MS7A1F1 | ms7.1a1 | CCG TGA CAA CCA AGA ACT TCC | 11260 |
| MS7A1R1 | ms7.1p1 | GTT TAG TAT GGC TTA TGC CCA GTG | 12079 |
| MS7A1F2 | ms7.1a2 | CTC CCG TGA CAA CCA AGA AC | 11257 |
| MS7A1R2 | ms7.1p2 | GTG AGC TTA AAA CTG GCA AGA GTG | 12126 |

TABLE 7-continued

Oligonucleotides for Mutation Screening from
Genomic DNA (respectively (SEQ ID NOS: 38-175))

| name | alias | sequence | genomic positions |
|---|---|---|---|
| secondary amplicon for exon A | | | |
| MS7.1F1 | ms7.1b1 | GTT TTC CCA GTC ACG ACG CCA AGA ACT TCC TCC TGA CTC | 11269 |
| MS7.1R1 | ms7.1q1 | AGG AAA CAG CTA TGA CCA TCT T GGT ATA GGA GAA ATG TCC C | 11605 |
| MS7.1F2 | ms7.1b2 | GTT TTC CCA GTC ACG ACG CTT CCT CCT GAC TCC ATG GTG AC | 11276 |
| MS7.1R2 | ms7.1q2 | AGG AAA CAG CTA TGA CCA TCT CCT TGC CTG CCT TCT GC | 11582 |
| secondary amplicon for exon B | | | |
| MS7.2F1 | ms7.1c1 | GTT TTC CCA GTC ACG ACG GGG GCA TGC TGC ATA TTA CTG | 11876 |
| MS7.2R1 | ms7.1r1 | AGG AAA CAG CTA TGA CCA TGT GAG CTT AAA ACT GGC AAG AGT G | 12126 |
| MS7.2F2 | ms7.1c2 | GTT TTC CCA GTC ACG ACG GCC CAG ATT TTT GCC CAT TAT TG | 11854 |
| MS7.2R2 | ms7.1r2 | AGG AAA CAG CTA TGA CCA TGT GCA TCC TGC TTC ACC TGT TTA G | 12097 |
| primary amplicon for exons C and D | | | |
| MS7A2F1 | ms7.2a1 | CGT TAA AGT GTC AAG TAG GGA G | 12577 |
| MS7A2R1 | ms7.2p1 | CCG AAG TTC ACA AAA CTA TTC | 14343 |
| MS7A2F2 | ms7.2a2 | GTT AAA GTG TCA AGT AGG GAG C | 12578 |
| MS7A2R2 | ms7.2p2 | GAC TAA ATG GAA TGC CTG TC | 14047 |
| secondary amplicon for exon C | | | |
| MS7.3F1 | ms7.2b1 | GTT TTC CCA GTC ACG ACG CCG TAG CAT CAC GTT TTG | 12832 |
| MS7.3R1 | ms7.2q1 | AGG AAA CAG CTA TGA CCA TGA TCT CTG GGC TTA GAA CAC TC | 13046 |
| MS7.3F2 | ms7.2b2 | GTT TTC CCA GTC ACG ACG CTT CAA CAG GGA CAA AAT ACG | 12804 |
| MS7.3R2 | ms7.2q2 | AGG AAA CAG CTA TGA CCA TGG AAA AAG ATC TCT GGG CTT AG | 13053 |
| secondary amplicon for exon D | | | |
| MS7.4F1 | ms7.2c1 | GTT TTC CCA GTC ACG ACG GAA TTG TTG AGC CAA TCG TG | 13493 |
| MS7.4R1 | ms7.2r1 | AGG AAA CAG CTA TGA CCA TGA AGC ACT GCC TAG AGG AAC TG | 13721 |
| MS7.4F2 | ms7.2c2 | GTT TTC CCA GTC ACG ACG GGG AAT TGT TGA GCC AAT CGT G | 13491 |
| MS7.4R2 | ms7.2r2 | AGG AAA CAG CTA TGA CCA TGA GAG CGG GGC CCT ACA GAG | 13746 |
| primary amplicon for exon E | | | |
| MS7.5F1 | ms7.3a1 | GCA TTC CAT TTA GTC TTG CCA TC | 14033 |
| MS7.5R1 | ms7.3p1 | GCT GAC AAG AGG GCT TTT CC | 15216 |
| MS7.5R2 | ms7.3p2 | GTT GCA GGA AGA GGT AAT GTC AG | 15282 |
| MS7.5R3 | ms7.3p3 | CAT CCC CTC AAG GCG TAG AG | 15336 |
| secondary amplicons for exon E | | | |
| MS7.5AF1 | ms7.3b1 | GTT TTC CCA GTC ACG ACG GCT ACA | |

TABLE 7-continued

Oligonucleotides for Mutation Screening from
Genomic DNA (respectively (SEQ ID NOS: 38–175))

| name | alias | sequence | genomic positions |
|---|---|---|---|
| | | GTG ACC CCC TTT TTC | 14105 |
| MS7.5AR1 | ms7.3q1 | AGG AAA CAG CTA TGA CCA TGT CTA ACA AGG TGG GAG TTA CAA G | 14434 |
| MS7.5AF2 | ms7.3b2 | GTT TTC CCA GTC ACG ACG CAG TGA CCC CCT TTT TCC TC | 14109 |
| MS7.5AR2 | ms7.3q2 | AGG AAA CAG CTA TGA CCA TGG GAG TTA CAA GTG AAG CTC TTT C | 14422 |
| MS7.5BF1 | ms7.3c1 | GTT TTC CCA GTC ACG ACG GGC ATC ATG ACT GTT CTG TG | 14375 |
| MS7.5BR1 | ms7.3r1 | AGG AAA CAG CTA TGA CCA TGG GTT TTT CTC CAG TAT GTG TC | 14715 |
| MS7.5BF2 | ms7.3c2 | GTT TTC CCA GTC ACG ACG GAG GCA TCA TGA CTG TTC TG | 14373 |
| MS7.5CF1 | ms7.3d1 | GTT TTC CCA GTC ACG ACG ACA CAG GCT GAG AGA ACT CCA TC | 14596 |
| MS7.5CR1 | ms7.3s1 | AGG AAA CAG CTA TGA CCA TGC TCT TCC CAC ATT CGT TGC | 14994 |
| MS7.5CR2 | ms7.3s2 | AGG AAA CAG CTA TGA CCA TAC TGC GCT GTG GGT GAA G | 14927 |
| MS7.5DF1 | ms7.3e1 | GTT TTC CCA GTC ACG ACG CTC TAC CTC TGC AGC GAG TG | 14881 |
| MS7.5DR1 | ms7.3t1 | AGG AAA CAG CTA TGA CCA TCC TTA GGT GAG GGC TGA AAG | 15183 |
| MS7.5DR2 | ms7.3t2 | AGG AAA CAG CTA TGA CCA TCT CTT CCT CAC CTC CCT TAG | 15197 |
| MS7.5DF2 | ms7.3e2 | GTT TTC CCA GTC ACG ACG GCT GCT GAG GAA CTC TAC C | 14869 |
| primary amplicon for intron GF | | | |
| MS7.6A1 | ms7.6a1 | CTC CGT CAT GGT TGG TGT TTC | 9606 |
| MS7.6P1 | ms7.6p1 | CTC CTT TGT CCG CCT CTC TG | 10506 |
| MS7.6A2 | ms7.6a2 | CAC ATC TCC GTC ATG GTT GGT G | 9601 |
| MS7.6P2 | ms7.6p2 | GCT CCT TTG TCC GCC TCT CTG | 10507 |
| secondary amplicon for intron GF | | | |
| MS7.6B1 | ms7.6c1 | GTT TTC CCA GTC ACG ACG GGT GGT TGG GGA AAA GAG GA | 10032 |
| MS7.6Q1 | ms7.6r1 | AGG AAA CAG CTA TGA CCA TCG GAA GCG TCG GAA GTT CTG | 10415 |
| MS7.6B2 | ms7.6c2 | GTT TTC CCA GTC ACG ACG GGC TAT GGT GGT TGG GGA AAA G | 10026 |
| MS7.6Q2 | ms7.6r2 | AGG AAA CAG CTA TGA CCA TGA AGC GTC GGA AGT TCT GGT G | 10413 |
| MS7.6C1 | ms7.6b1 | GTT TTC CCA GTC ACG ACG GTA CTG CAG GGA TCT TAG GAA | 9778 |
| MS7.6R1 | ms7.6q1 | AGG AAA CAG CTA TGA CCA TCA GCC TGA GTT CAA TCA TAA TC | 10102 |
| MS7.6C2 | ms7.6b2 | GTT TTC CCA GTC ACG ACG GAG TAC TGC AGG GAT CTT AGG A | 9776 |

TABLE 7-continued

Oligonucleotides for Mutation Screening from
Genomic DNA (respectively (SEQ ID NOS: 38-175))

| name | alias | sequence | genomic positions |
|---|---|---|---|
| MS7.6R2 | ms7.6q2 | AGG AAA CAG CTA TGA CCA TGA CAA CAG CCT GAG TTC AAT C | 10107 |
| primary amplicon for exon F | | | |
| MS7.15F1 | ms7.5a1 | CAG GGC CCT TGG AAG AAA ATC | 10158 |
| MS7.15R1 | ms7.5p1 | GAA CCC ACG GCT CAA CAT TC | 10936 |
| MS7.15F2 | ms7.5a2 | CTA TGG TGG TTG GGG AAA AGA | 10028 |
| MS7.15R2 | ms7.5p2 | CGG CTC AAC ATT CAA AGA AGG | 10929 |
| secondary amplicon for exon F | | | |
| MS7.16F1 | ms7.5b1 | GTT TTC CCA GTC ACG ACG GGG GCT AAT GAC AGT GTG AG | 10203 |
| MS7.16R1 | ms7.5q1 | AGG AAA CAG CTA TGA CCA T GAC GGT AAG AAA TTG TTC CAG | 10548 |
| MS7.16F2 | ms7.5b2 | GTT TTC CCA GTC ACG ACG GGA AGA AAA TCC TCG CTG TG | 10168 |
| MS7.16R2 | ms7.5q2 | AGG AAA CAG CTA TGA CCA T CTC CAG GTA GGA CGG TAA GAA | 10558 |
| MS7.17F1 | ms7.5c1 | GTT TTC CCA GTC ACG ACG CTA GAG CTG CTT GTG CTG G | 10513 |
| MS7.17R1 | ms7.5r1 | AGG AAA CAG CTA TGA CCA T CAT GGG GCT CAT GGT ATA TG | 10800 |
| MS7.17F2 | ms7.5c2 | GTT TTC CCA GTC ACG ACG GTG CTG GAA CAA TTT CTT AC | 10525 |
| MS7.17R2 | ms7.5r2 | AGG AAA CAG CTA TGA CCA T CAT GGT ATA TGA GCA ACC C | 10791 |
| primary amplicon for exon G | | | |
| MS7.7A1 | ms7.7a1 | GGT GCC ATC ACT CTT CTA AGC | 9355 |
| MS7.7P1 | ms7.7p1 | CAT CTC CTG CCT GGA CTA CTG | 9826 |
| MS7.7A2 | ms7.7a2 | GAT AAT AGC TGG TGC CAT CAC | 9345 |
| MS7.7P2 | ms7.7p2 | CCC TTC TCT TCC TTC CTA CAG | 9870 |
| secondary amplicon for exon G | | | |
| MS7.7B1 | ms7.7b1 | GTT TTC CCA GTC ACG ACG ATA CAT TTA ATG CTC ATA GGC | 9385 |
| MS7.7Q1 | ms7.7q1 | AGG AAA CAG CTA TGA CCA TGCA AAG TAC AAC AGA ATT ACC | 9767 |
| MS7.7B2 | ms7.7b2 | GTT TTC CCA GTC ACG ACG GCC ATC ACT CTT CTA AGC AA | 9358 |
| MS7.7Q2 | ms7.7q2 | AGG AAA CAG CTA TGA CCA TGCT CTA ACT TCC TAA GAT CCC | 9806 |
| primary amplicon for 3' UTR | | | |
| MS7.9F1 | ms7.4a1 | GTG GGA AGA GCT TCA GTC GC | 14984 |
| MS7.9R1 | ms7.4p1 | CTT GCC ACT CCC ACA ATC AGA | 16512 |
| MS7.9F2 | ms7.4a2 | CGT CAG GCA TCA GAG AAC AC | 15015 |
| MS7.9R2 | ms7.4p2 | CCA CTC CCA CAA TCA GAG AAG | 16508 |
| secondary amplicons for 3' UTR | | | |
| MS7.10F1 | ms7.4b1 | GTT TTC CCA GTC ACG ACG CAC TTA ATT AGG CAT CAG AGG | 15094 |

TABLE 7-continued

Oligonucleotides for Mutation Screening from Genomic DNA (respectively (SEQ ID NOS: 38-175))

| name | alias | sequence | genomic positions |
|---|---|---|---|
| MS7.10R1 | ms7.4q1 | AGG AAA CAG CTA TGA CCA TGA CGA TAT AGG AAC CAC GAC | 15456 |
| MS7.10F2 | ms7.4b2 | GTT TTC CCA GTC ACG ACG GCA TCA GAG GAC CCA CTC AG | 15105 |
| MS7.10R2 | ms7.4q2 | AGG AAA CAG CTA TGA CCA TGT AGA GGC AGG TGC ACT CCA G | 15393 |
| MS7.11F1 | ms7.4c1 | GTT TTC CCA GTC ACG ACG CAA CCT GAA TTG AGG CTT CTC | 15351 |
| MS7.11R1 | ms7.4r1 | AGG AAA CAG CTA TGA CCA TGAC AGC GAG GGA TCT ATG C | 15675 |
| MS7.11F2 | ms7.4c2 | GTT TTC CCA GTC ACG ACG GAA TTG AGG CTT CTC CTT CAC | 15357 |
| MS7.12F1 | ms7.4d1 | GTT TTC CCA GTC ACG ACG GCT TTG CAC ACA TTC ACA | 15631 |
| MS7.12R1 | ms7.4s1 | AGG AAA CAG CTA TGA CCA TCA AAC ACT ACC ATC TCA CTT G | 16979 |
| MS7.12F2 | ms7.4d2 | GTT TTC CCA GTC ACG ACG GTT TGC GTC CTG ATG GCT TTG | 15616 |
| MS7.12R2 | ms7.4s2 | AGG AAA CAG CTA TGA CCA TGG TGT GAA GGG GTT GGT GG | 16065 |
| MS7.13F1 | ms7.4e1 | GTT TTC CCA GTC ACG ACG GAA GCC TCT TTC CAT ACG AG | 15835 |
| MS7.13R1 | ms7.4t1 | AGG AAA CAG CTA TGA CCA TAG TTT CCA AAT CCC CTT ACT C | 16106 |
| MS7.13F2 | ms7.4e2 | GTT TTC CCA GTC ACG ACG CAG AAG CCT CTT TCC ATA CG | 15835 |
| MS7.13R2 | ms7.4t2 | AGG AAA CAG CTA TGA CCA TGT TTC CAA ATC CCC TTA CTC A | 16105 |
| MS7.14F1 | ms7.4f1 | GTT TTC CCA GTC ACG ACG CAT TCC CTC ATA TGC ACA AG | 16026 |
| MS7.14R1 | ms7.4u1 | AGG AAA CAG CTA TGA CCA TGA ACC TTT AAC TGG CAA CAG A | 16453 |
| MS7.14F2 | ms7.4f2 | GTT TTC CCA GTC ACG ACG CAC AGG GGT CGT ATG AGT AAG | 16072 |
| MS7.14R2 | ms7.4u2 | AGG AAA CAG CTA TGA CCA TGG CCA TCA TGA GAT GCT AC | 16424 |
| primary amplicon for intron FA | | | |
| MS7.8A1 | | CCG TCC TAC CTG GAG AAC TAC | 10544 |
| MS7.8P1 | | CCT GGT GTG GAC GCT GCT CTG | 11501 |
| MS7.8P2 | | CCG CTC TCC TGC AGG GTC TGG | 11532 |
| secondary amplicons for intron FA | | | |
| MS7.8B1 | | GTT TTC CCA GTC ACG ACG CGA GGA GGC AGT GAC GCT GGT G | 10599 |
| MS7.8Q1 | | AGG AAA CAG CTA TGA CCA TCC CAC GGC TCA ACA TTC AAA GA | 10933 |
| MS7.8Q2 | | AGG AAA CAG CTA TGA CCA TCA CGG CTC AAC ATT CAA AGA AG | 10931 |
| MS7.8C1 | | GTT TTC CCA GTC ACG ACG AGG GGG | |

TABLE 7-continued

Oligonucleotides for Mutation Screening from
Genomic DNA (respectively (SEQ ID NOS: 38—175))

| name | alias | sequence | genomic positions |
|---|---|---|---|
| | | TCT CAG CCA CCA AAG | 10869 |
| MS7.8R1 | | AGG AAA CAG CTA TGA CCA TAA GGA GGA GCT GAA GGT TAT C | 11170 |
| MS7.8C2 | | GTT TTC CCA GTC ACG ACG AAG GGT CAT GGC TTT GGT TTT | 10887 |
| MS7.8R2 | | AGG AAA CAG CTA TGA CCA TGG GAT GCG CAG GCC TGC ACT G | 11132 |
| MS7.8D1 | | GTT TTC CCA GTC ACG ACG CAG GCT GGG GGT GGT GAG AGA | 11090 |
| MS7.8S1 | | AGG AAA CAG CTA TGA CCA TCC GCT CCT AAA TGC ACC GTC T | 11382 |
| MS7.8D2 | | GTT TTC CCA GTC ACG ACG GGG AAG GAA CCT TGG GTG ACA | 11063 |
| MS7.8S2 | | AGG AAA CAG CTA TGA CCA TGC AGC TCA TTA GGT GAC TCA G | 11406 |
| primary amplicon for promoter 1 | | | |
| MS7.9A1 | | CTA TGA ATA CCT TCT AGT GGG | 8183 |
| MS7.9F1 | | CAA AAT CCT GGG AAT GAC ACG | 9269 |
| MS7.9A2 | | GTG CCT GTT ACG TGC CAG TGC | 8122 |
| MS7.9P2 | | CAC CAG CTA TTA TCT TTC TAA | 9358 |
| secondary amplicon for promoter 1 | | | |
| MS7.9B1 | | GTT TTC CCA GTC ACG ACG GAT AGT AAA AGC ATA ATG GAG | 8309 |
| MS7.9Q1 | | AGG AAA CAG CTA TGA CCA TAG CTT CAT GTC TTC TGA GAT G | 8613 |
| MS7.9B2 | | GTT TTC CCA GTC ACG ACG GAT ATG GTG AAT AAT CAA GAG | 8288 |
| MS7.9Q2 | | AGG AAA CAG CTA TGA CCA TCT CAA GCT TCA TGT CTT CTG A | 8617 |
| MS7.9C1 | | GTT TTC CCA GTC ACG ACG GAA ATG GGA TCA AAG AAA ACA | 8573 |
| MS7.9R1 | | AGG AAA CAG CTA TGA CCA TCT TGG CAA ACG TGC TCA TGT C | 8896 |
| MS7.9C2 | | GTT TTC CCA GTC ACG ACG GTA GGG GAA ATG GGA TCA AAG | 8568 |
| MS7.9R2 | | AGG AAA CAG CTA TGA CCA TCG AGC TCT CTT GGC AAA CGT G | 8903 |
| MS7.9D1 | | GTT TTC CCA GTC ACG ACG GTG ATG GAA GGA TCT TAG ATA | 8847 |
| MS7.9S1 | | AGG AAA CAG CTA TGA CCA TCT TTA CAA TCA GCC CCC AAT C | 9244 |
| MS7.9D2 | | GTT TTC CCA GTC ACG ACG GAT GGA AGG ATC TTA GAT AGG | 8849 |
| MS7.9S2 | | AGG AAA CAG CTA TGA CCA TGC CCC CAA TCT ATT TTT CAA G | 9232 |
| primary amplicon for exons H and I | | | |
| MS7.10.A1 | | CTG CCT TGG AAT CTG TAC TGA C | 451 |

TABLE 7-continued

Oligonucleotides for Mutation Screening from
Genomic DNA (respectively (SEQ ID NOS: 38-175))

| name | alias | sequence | genomic positions |
|---|---|---|---|
| MS7.10P1 | | AGC CCC AGC ACA GAC CTA TTA C | 1288 |
| MS7.10A2 | | GCG CTT TGA TAA CCC TGT CTG C | 433 |
| MS7.10P2 | | CAG GTG CTT ATA GTA AGT TTG A | 1218 |
| secondary amplicons for exons H and I | | | |
| MS7.10B1 | | GTT TTC CCA GTC ACG ACG GCA GCG CTA GAT CCC AGG CTC T | 530 |
| MS7.10Q1 | | AGG AAA CAG CTA TGA CCA TCC CAC CCT CTT ATG CTA GAT AG | 825 |
| MS7.10B2 | | GTT TTC CCA GTC ACG ACG GCG CTA GAT CCC AGG CTC TCA C | 533 |
| MS7.10Q2 | | AGG AAA CAG CTA TGA CCA TAA CCC TGC CCA CCC TCT TAT GC | 833 |
| MS7.10C1 | | GTT TTC CCA GTC ACG ACG AAA CGC CTG GGA TTC ATA ATC T | 868 |
| MS7.10R1 | | AGG AAA CAG CTA TGA CCA TAA GGG GTC TAG AAC TGT TTC AC | 1100 |
| MS7.10C2 | | GTT TTC CCA GTC ACG ACG CCT GGG ATT CAT AAT CTT TCA C | 872 | cDNA: Total RNAs prepared from CHD kindred lymphocytes were treated with DNase I (Boehringer Mannheim) to remove contaminating genomic DNA, and then converted to heteroduplex cDNA with a mix of N10 random primers and a tailed oligo dT primer, and Superscript II reverse transcriptase (Life Technologies) in a reverse transcription reaction. These cDNA molecules were used as the template for nested PCR amplifications to generate the cDNA PCR products of the candidate genes that were screened for CHD1 mutations. Using the outer primer pair (Table 8) for each amplicon, 10 ngs of cDNA were subjected to a 20 cycle primary amplification, after which the PCR products were diluted 100-fold and reamplified using nested M13-tailed primers for another 25–30 cycles. The cDNAs were amplified by PCR using TaqPlus DNA polymerase (Stratagene) using the "hot-start" technique. Conditions used were an initial denaturation step at 95° C. for 30 seconds followed by a pause at 80° C. while the polymerase/nucleotide mixture was added to the template/primer mixtures. The "hot-start" was followed by cycles of denaturation at 96° C. (4 seconds), annealing at 55° C. (10 seconds) and extension at 72° C. (60 seconds). PCR products were fractionated by gel electrophoresis and purified and then sequenced with M13 forward or reverse fluorescent energy transfer (FET) dye-labeled primers on ABI 377 sequencers. The sequences of these products were analyzed in GDE to determine their exon structure. Chromatograms were analyzed for the presence of polymorphisms or sequence aberrations in either the Macintosh program Sequencher (Gene Codes) or the Java program Mutscreen (Myriad, proprietary).

EXAMPLE 7

CHD1 Gene Structure

The CHD1 gene sequence has been determined. Ten exons and about 20 kb of contiguous flanking genomic DNA has been sequenced. SEQ ID NO: 9 is the sequence for CHD1 including exons and flanking genomic sequence. The DNA sequence of SEQ ID NO: 206 differs from SEQ ID NO: 9 by a single G/C base-pair deletion at position 533 of SEQ ID NO: 9. The DNA sequence of SEQ ID NO: 206 may be produced by deleting one G/C base-pair at position 533 by in vitro mutagenesis procedures or recombinant DNA protocols well known in the art (see, e.g., Ausulbel et al, 1992) from the DNA sequence produced by the methods described above.

SEQ ID NO: 209 is the genomic sequence of ExonJ and the promoter region of CHD1. The last nucleotide of SEQ ID NO: 209 is one nucleotide before the first nucleotide of SEQ ID NO: 9 or SEQ ID NO: 206. SEQ ID NO: 210 is the genomic sequence of CHD1 comprising SEQ ID NO: 209 and SEQ ID NO: 9. Position 1 to position 2,933 of SEQ ID NO: 210 is SEQ ID NO: 209 and position 2,934 to 23,071 is SEQ ID NO: 9.

SEQ ID NO: 1 is the sequence of an alternative CHD1 transcript (cDNA1). SEQ ID NO: 3 is the sequence of an alternative CHD1 transcript (cDNA2).

TABLE 8

Oligonucleotides for Mutation Screening from cDNA (respectively (SEQ ID NOS: 176-189)

| names | sequence | genomic position | CDNA position |
|---|---|---|---|
| primary amplicon for exonA | | | |
| MC7.1A1 | GTG CTG GAA CAA TTT CTT ACC G | 10525 | 365 |
| MC7.1P1 | CCC AAG GCT CTT CCT CTC TAA C | 13596 | 986 |
| MC7.1A1 | CAG ATC CTA GAG CTG CTT GTG C | 10507 | 347 |
| MC7.1P2 | GGC TCT TGA GTC TCC TGA GGC | 13633 | 1023 |
| secondary amplicon for exonA | | | |
| MC7.1B1 | GTT TTC CCA GTC ACG ACG CCA TGT TCA CGG CCA GGA AGT C | 11329 | 508 |
| MC7.1Q1 | AGG AAA CAG CTA TGA CCA T GGC CAT CCT GGT GTG GAC GCT GCT CTC | 11500 | 681 |
| MC7.1Q2 | AGG AAA CAG CTA TGA CCA T GGC CAT CTC GCT CTC CTG CAG GGT CTC | 11921 | 712 |
| MC7.1C1 | GTT TTC CCA GTC ACG ACG GTT GCT CTT CTT ACT GCT CTG | 11983 | 773 |
| MC7.1R1 | AGG AAA CAG CTA TGA CCA TGG CCA TCTT CTT CCA AGA CAT ATT CTC | 12977 | 906 |
| MC7.1C2 | GTT TTC CCA GTC ACG ACG CTC AGA GAT GGT TGC TCT TC | 11973 | 763 |
| primary amplicon for 3UTR | | | |
| MC7.4A1 | GAA ACC ATT CAC GTG CCC TAC C | 15045 | 1951 |
| MC7.4P1 | GAC AGT TTC CAA ATC CCC TTA C | 16109 | 3015 |
| MC7.4A2 | CTC GTC AGG CAT CAG AGA ACA C | 15013 | 1919 |
| MC7.4P2 | GTG CAT ATG AGG GAA TGT GAA C | 16042 | 2948 |

SEQ ID NO: 5 is the sequence of an alternative CHD1 transcript (cDNA3). SEQ ID NO: 7 is the sequence of an alternative CHD1 transcript (cDNA4). SEQ ID No: 10 is the sequence of alternative 5' exon J. SEQ ID No: 11 is the sequence of alternative 5' exon I(−21). SEQ ID No: 12 is the sequence of alternative 5' exon I(+21). SEQ ID No: 13 is the sequence of alternative 5' exon H. SEQ ID No: 14 is the sequence of alternative 5' exon G. The alternative transcripts represent alternative splice donors and acceptors at the ends of intronFA (FIG. 3). Sequence ID NO.: 2 is the protein encoded by cDNA1; sequence ID NO.: 4 by cDNA2; sequence ID NO.: 6 by cDNA3; and sequence ID NO.: 8 by cDNA4. These sequences are shown in Table 9. The genomic nucleotide positions of the alternative splices are described in Table 10. Alternative transcripts encoding all four alternative proteins have been detected in cDNAs from various sources. Different tissues contain the alternative transcripts at different relative abundances.

In addition, many forms of alternative 5' exons exist. The combination that have been observed are: J-F, J-I(+21)-F, J-I(−21)-F, J-I(−21)-H-F, G-F (see FIG. 3). These alternatives change the 5' untranslated region of the messages, and can be found in any combination with cDNAs 1–4, which all start at exon F.

TABLE 9

CHD1 DNA and Protein Sequences

CHD1 cDNA1    SEQ ID NO:1
GGCCCTTGGAAGAAAATCCTCGCTGTGTCCAGGCTGAGGCGGGGGGCTAATGACA

GTGTGAGCTCTAGATGGTGTGAGACCACCCCAAAGCCAAGAAATGGCTACAGCCG

TGGAACCAGAGGACCAGGATCTTTGGGAAGAAGAGGGAATTCTGATGGTGAAACT

GGAAGATGATTTCACCTGTCGGCCAGAGTCTGTCTTACAGAGGGATGACCCGGTG

CTGGAAACCTCCCACCAGAACTTCCGACGCTTCCGCTACCAGGAGGCAGCAAGCC

CTAGAGAAGCTCTCATCAGACTCCGAGAACTTTGTCACCAGTGGCTGAGACCAGA

GAGGCGGACAAAGGAGCAGATCCTAGAGCTGCTTGTGCTGGAACAATTTCTTACC

TABLE 9-continued

CHD1 DNA and Protein Sequences

```
GTCCTACCTGGAGAACTACAGAGCTGGGTGCGGGCCAACGGCCAGAAAGTGGCG
AGGAGGCAGTGACGCTGGTGGAGGGTTTGCAGAAACAACCCAGGAGACCAAGGCG
GTGGGTGACTGTCCATGTTCACGGCCAGGAAGTCCTGTCAGAGGAGACGGTGCAT
TTAGGAGCGGAGCCTGAGTCACCTAATGAGCTGCAGGATCCTGTGCAAAGCTCGA
CCCCCGAGCAGTCTCCTGAGGAAACCACACAGAGCCCAGATCTGGGGGCACCGGC
AGAGCAGCGTCCACACCAGGAAGAGGAGCTCCAGACCCTGCAGGAGAGCGAGGTC
CCAGTGCCCGAGGACCCAGACCTTCCTGCAGAGAGGAGCTCTGGAGACTCAGAGA
TGGTTGCTCTTCTTACTGCTCTGTCACAGGGACTGGTAACGTTCAAGGATGTGGC
CGTATGQTTTTCCCAGGACCAGTGGAGTGATCTGGACCCAACACAGAAAGAGTTC
TATGGAGAATATGTCTTGGAAGAAGACTGTGGAATTGTTGTCTCTCTGTCATTTC
CAATCCCCAGACCTGATGAGATCTCCCAGGTTAGAGAGGAAGAGCCTTGGGTCCC
AGATATCCAAGAGCCTCAGGAGACTCAAGAGCCAGAAATCCTGAGTTTTACCTAC
ACAGGAGATAGGAGTAAAGATGAGGAAGAGTGTCTGGAGCAGGAAGATCTGAGTT
TGGAGGATATACACAGGCCTGTTTTGGGAGAACCAGAAATTCACCAGACTCCAGA
TTGGGAAATAGTCTTTGAGGACAATCCAGGTAGACTTAATGAAAGAAGATTTGGT
ACTAATATTTCTCAAGTGAATAGTTTTGTGAACCTTCGGGAAACTACACCCGTCC
ACCCCTGTTAGGGAGGCATCATGACTGTTCTGTGTGTGGAAAGAGCTTCACTTG
TAACTCCCACCTTGTTAGACACCTGAGGACTCACACAGGAGAGAAACCCTATAAA
TGTATGGAATGTGGAAAAAGTTACACACGAAGCTCACATCTTGCCAGGCACCAAA
AGGTTCACAAGATGAACGCGCCTTACAAATATCCCCTAAACCGGAAGAATTTGGA
AGAGACCTCCCCTGTGACACAGGCTGAGAGAACTCCATCAGTGGAGAAACCCTAT
AGATGTGATGATTGCGGAAAGCACTTCCGCTGGACTTCAGACCTTGTCAGACATC
AGAGGACACATACTGGAGAAAAACCCTTCTTTTGTACTATTTGTGGCAAAAGCTT
CAGCCAGAAATCTGTGTTAACAACACACCAAAGAATCCACCTGGGAGGCAAACCC
TACTTGTGTGGAGAGTGTGGTGAGGACTTCAGTGAACACAGGCGGTACCTGGCGC
ACCGGAAGACGCACGCTGCTGAGGAACTCTACCTCTGCAGCGAGTGCGGGCGCTG
CTTCACCCACAGCGCAGCGTTCGCCAAGCACTTGAGAGGACACGCCTCAGTGAGG
CCCTGCCGATGCAACGAATGTGGGAAGAGCTTCAGTCGCAGGGACCACCTCGTCA
GGCATCAGAGAACACACACTGGGGAGAAACCATTCACGTGCCCTACCTGTGGAAA
AAGCTTCAGCAGAGGATATCACTTAATTAGGCATCAGAGGACCCACTCAGAAAAG
ACCTCCTAGCTAGGTCCCCATGTGAGGAGATCTGCTTTCAGCCCTCACCTAAGGG
AGGTGAGGAAGAGGAAAAGCCCTCTTGTCAGCCTGGGAAGACCTTTTCGAGGGAG
TCTCCCTGACCTGCTCAGATCTGACATTACCTCTTCCTGCAACTAAACACGAGCC
TGGGCAGAACCTCTCAGCCTTCCTCTACGCCTTGAGGGGATGTTTCATCCAAAGT
ACAACCTGAATTGAGGCTTCTCCTTCACTGGAGTGCACCTGCCTCTACCTCATGG
GTATAAAGTAGGAGAACTAAGAGACTTAAGAGGTCGTGGTTCCTATATCGTCCAA
AAAATAGGCTGTTACATATCCTAAAGACTGCTCAACAGCTTCAAGTTGAAAGTGG
CCAAGGACAGCCCCTTAGGTTTGGGAAGGGACGAGCCTGAAGGATTCTGTCTTTA
```

TABLE 9-continued

CHD1 DNA and Protein Sequences

CTGGGGTCAAATCTTAAAGCACACAGCTCTGGACTCAAGACAGGAGGTTTGCGTC

CTGATGGCTTTGCACACATTCACAGGATAACTGCATAGATCCCTCGCTGTCTGAT

TCACTTCTTACCATGCACTTTCCTTTGATGCTGAGGAGAAATGGAAGTGGGCGAA

AAATCTCAAGGCTGCTTCATGTGGACCTTGTCAAGCTGCTCCCTCCCCCAGCGTC

AAATTGTTATCAGGTGCCAAACACTGCTAGAAAGGAGGGCCTAGTCAGAAGCCTC

TTTCCATACGAGTTTTGGTTTTGTTTTTAATATTTTTTTCTATTAAAATACTCAT

GCATTTAACCTTCCCGTTATTCAACCAGTCTCTTGGTTGCATCCCTAGCACTTCT

ACTACAAGTGAGATGGTAGTGTTTGAGTGCTTATTGAGTAAAGCATAATTCGGTC

ATAATGAAATCGTTCACATTCCCTCATATGCACAAGCCACCAACCCCTTCACAC

CCCCCTTCACAGGGGTCGTATGAGTAAGGGGATTTGGAAACTGTCAACTTACAAA

GGCACTATAACAATTACAGAATCATGATTGCCATGGGCCACTTTATTTACATGAA

GACAACTGGAGAACGACTAAGACCAAATTATGGAAAATAAGAAAAAGCTGTTGCT

GGCAAGACCATCAAGACTGTTCTGACACCCTGTCCCCATCATCCCTGACTGAGTA

CTCTGACATCACGGAAAGTGTTGAACCTGGGACCCTGAGGAATTCACCAGGAGTA

AATGGCTTTCATGTAAAAAAAAA

CHD1 CDNA2     SEQ ID NO: 3
GGCCCTTGGAAGAAAATCCTCGCTGTGTCCAGGCTGAGGCGGGGGGCTAATGACA

GTGTGAGCTCTAGATGGTGTGAGACCACCCCAAAGCCAAGAAATGGCTACAGCCG

TGGAACCAGAGGACCAGGATCTTTGGGAAGAAGAGGGAATTCTGATGGTGAAACT

GGAAGATGATTTCACCTGTCGGCCAGAGTCTGTCTTACAGAGGGATGACCCGGTG

CTGGAAACCTCCCACCAGAACTTCCGACGCTTCCGCTACCAGGAGGCAGCAAGCC

CTAGAGAAGCTCTCATCAGACTCCGAGAACTTTGTCACCAGTGGCTGAGACCAGA

GAGGCGGACAAAGGAGCAGATCCTAGAGCTGCTTGTGCTGGAACAATTTCTTACC

GTCCTACCTGGAGAACTACAGAGCTGGGTGCGGGCCAACGGCCAGAAAGTGGCG

AGGAGGCAGTGACGCTGGTGGAGGGTTTGCAGAAACAACCCAGGAGACCAAGGCG

GTGGGAAGTCCTGTCAGAGGAGACGGTGCATTTAGGAGCGGAGCCTGAGTCACCT

AATGAGCTGCAGGATCCTGTGCAAAGCTCGACCCCCGAGCAGTCTCCTGAGGAAA

CCACACAGAGCCCAGATCTGGGGGCACCGGCAGAGCAGCGTCCACACCAGGAAGA

GGAGCTCCAGACCCTGCAGGAGAGCGAGGTCCCAGTGCCCGAGGACCCAGACCTT

CCTGCAGAGAGGAGCTCTGGAGACTCAGAGATGGTTGCTCTTCTTACTGCTCTGT

CACAGGGACTGGTAACGTTCAAGGATGTGGCCGTATGCTTTTCCCAGGACCAGTG

GAGTGATCTGGACCCAACACAGAAAGAGTTCTATGGAGAATATGTCTTGGAAGAA

GACTGTGGAATTGTTGTCTCTCTGTCATTTCCAATCCCCAGACCTGATGAGATCT

CCCAGGTTAGAGAGGAAGAGCCTTGGGTCCCAGATATCCAAGAGCCTCAGGAGAC

TCAAGAGCCAGAAATCCTGAGTTTTACCTACACAGGAGATAGGAGTAAAGATGAG

GAAGAGTGTCTGGAGCAGGAAGATCTGAGTTTGGAGGATATACACAGGCCTGTTT

TGGGAGAACCAGAAATTCACCAGACTCCAGATTGGGAAATAGTCTTTGAGGACAA

TCCAGGTAGACTTAATGAAAGAAGATTTGGTACTAATATTTCTCAAGTGAATAGT

TTTGTGAACCTTCGGGAAACTACACCCGTCCACCCCCTGTTAGGGAGGCATCATG

TABLE 9-continued

CHD1 DNA and Protein Sequences

ACTGTTCTGTGTGTGGAAAGAGCTTCACTTGTAACTCCCACCTTGTTAGACACCT

GAGGACTCACACAGGAGAGAAACCCTATAAATGTATGGAATGTGGAAAAAGTTAC

ACACGAAGCTCACATCTTGCCAGGCACCAAAAGGTTCACAAGATGAACGCGCCTT

ACAAATATCCCCTAAACCGGAAGAATTTGGAAGAGACCTCCCCTGTGACACAGGC

TGAGAGAACTCCATCAGTGGAGAAACCCTATAGATGTGATGATTGCGGAAAGCAC

TTCCGCTGGACTTCAGACCTTGTCAGACATCAGAGGACACATACTGGAGAAAAAC

CCTTCTTTTGTACTATTTGTGGCAAAAGCTTCAGCCAGAAATCTGTGTTAACAAC

ACACCAAAGAATCCACCTGGGAGGCAAACCCTACTTGTGTGGAGAGTGTGGTGAG

GACTTCAGTGAACACAGGCGGTACCTGGCGCACCGGAAGACGCACGCTGCTGAGG

AACTCTACCTCTGCAGCGAGTGCGGGCGCTGCTTCACCCACAGCGCAGCGTTCGC

CAAGCACTTGAGAGGACACGCCTCAGTGAGGCCCTGCCGATGCAACGAATGTGGG

AAGAGCTTCAGTCGCAGGGACCACCTCGTCAGGCATCAGAGAACACACACTGGGG

AGAAACCATTCACGTGCCCTACCTGTGGAAAAAGCTTCAGCAGAGGATATCACTT

AATTAGGCATCAGAGGACCCACTCAGAAAAGACCTCCTAGCTAGGTCCCCATGTG

AGGAGATCTGCTTTCAGCCCTCACCTAAGGGAGGTGAGGAAGAGGAAAAGCCCTC

TTGTCAGCCTGGGAAGACCTTTTCGAGGGAGTCTCCCTGACCTGCTCAGATCTGA

CATTACCTCTTCCTGCAACTAAACACGAGCCTGGGCAGAACCTCTCAGCCTTCCT

CTACGCCTTGAGGGGATGTTTCATCCAAAGTACAACCTGAATTGAGGCTTCTCCT

TCACTGGAGTGCACCTGCCTCTACCTCATGGGTATAAAGTAGGAGAACTAAGAGA

CTTAAGAGGTCGTGGTTCCTATATCGTCCAAAAAATAGGCTGTTACATATCCTAA

AGACTGCTCAACAGCTTCAAGTTGAAAGTGGCCAAGGACAGCCCCTTAGGTTTGG

GAAGGGACGAGCCTGAAGGATTCTGTCTTTACTGGGGTCAAATCTTAAAGCACAC

AGCTCTGGACTCAAGACAGGAGGTTTGCGTCCTGATGGCTTTGCA

CACATTCACAGGATAACTGCATAGATCCCTCGCTGTCTGATTCACTTCTTACCAT

GCACTTTCCTTTGATGCTGAGGAGAAATGGAAGTGGGCGAAAAATCTCAAGGCTG

CTTCATGTGGACCTTGTCAAGCTGCTCCCTCCCCCAGCGTCAAATTGTTATCAGG

TGCCAAACACTGCTAGAAAGGAGGGCCTAGTCAGAAGCCTCTTTCCATACGAGTT

TTGGTTTTGTTTTTAATATTTTTTTCTATTAAAATACTCATGCATTTAACCTTCC

CGTTATTCAACCAGTCTCTTGGTTGCATCCCTAGCACTTCTACTACAAGTGAGAT

GGTAGTGTTTGAGTGCTTATTGAGTAAAGCATAATTCGGTCATAATGAAATCGTT

CACATTCCCTCATATGCACAAGCCCACCAACCCCTTCACACCCCCCTTCACAGGG

GTCGTATGAGTAAGGGGATTTGGAAACTGTCAACTTACAAAGGCACTATAACAAT

TACAGAATCATGATTGCCATGGGCCACTTTATTTACATGAAGACAACTGGAGAAC

GACTAAGACCAAATTATGGAAAATAAGAAAAAGCTGTTGCTGGCAAGACCATCAA

GACTGTTCTGACACCCTGTCCCCATCATCCCTGACTGAGTACTCTGACATCACGG

AAAGTGTTGAACCTGGGACCCTGAGGAATTCACCAGGAGTAAATGGCTTTCATGT

AAAAAAAAA

CHD1 CDNA3   SEQ ID NO: 5
GGCCCTTGGAAGAAAATCCTCGCTGTGTCCAGGCTGAGGCGGGGGGCTAATGACA

TABLE 9-continued

CHD1 DNA and Protein Sequences

GTGTGAGCTCTAGATGGTGTGAGACCACCCCAAAGCCAAGAAATGGCTACAGCCG

TGGAACCAGAGGACCAGGATCTTTGGGAAGAAGAGGGAATTCTGATGGTGAAACT

GGAAGATGATTTCACCTGTCGGCCAGAGTCTGTCTTACAGAGGGATGACCCGGTG

CTGGAAACCTCCCACCAGAACTTCCGACGCTTCCGCTACCAGGAGGCAGCAAGCC

CTAGAGAAGCTCTCATCAGACTCCGAGAACTTTGTCACCAGTGGCTGAGACCAGA

GAGGCGGACAAAGGAGCAGATCCTAGAGCTGCTTGTGCTGGAACAATTTCTTACC

GTCCTACCTGGAGAACTACAGAGCTGGGTGCGGGCCAACGGCCAGAAAGTGGCG

AGGAGGCAGTGACGCTGGTGGAGGGTTTGCAGAAACAACCCAGGAGACCAAGGCG

GTGACTGTCCATGTTCACGGCCAGGAAGTCCTGTCAGAGGAGACGGTGCATTTAG

GAGCGGAGCCTGAGTCACCTAATGAGCTGCAGGATCCTGTGCAAAGCTCGACCCC

CGAGCAGTCTCCTGAGGAAACCACACAGAGCCCAGATCTGGGGGCACCGGCAGAG

CAGCGTCCACACCAGGAAGAGGAGCTCCAGACCCTGCAGGAGAGCGAGGTCCCAG

TGCCCGAGGACCCAGACCTTCCTGCAGAGAGGAGCTCTGGAGACTCAGAGATGGT

TGCTCTTCTTACTGCTCTGTCACAGGGACTGGTAACGTTCAAGGATGTGGCCGTA

TGCTTTTCCCAGGACCAGTGGAGTGATCTGGACCCAACACAGAAAGAGTTCTATG

GAGAATATGTCTTGGAAGAAGACTGTGGAATTGTTGTCTCTCTGTCATTTCCAAT

CCCCAGACCTGATGAGATCTCCCAGGTTAGAGAGGAAGAGCCTTGGGTCCCAGAT

ATCCAAGAGCCTCAGGAGACTCAAGAGCCAGAAATCCTGAGTTTTACCTACACAG

GAGATAGGAGTAAAGATGAGGAAGAGTGTCTGGAGCAGGAAGATCTGAGTTTGGA

GGATATACACAGGCCTGTTTTGGGAGAACCAGAAATTCACCAGACTCCAGATTGG

GAAATAGTCTTTGAGGACAATCCAGGTAGACTTAATGAAAGAAGATTTGGTACTA

ATATTTCTCAAGTGAATAGTTTTGTGAACCTTCGGGAAACTACACCCGTCCACCC

CCTGTTAGGGAGGCATCATGACTGTTCTGTGTGTGGAAAGAGCTTCACTTGTAAC

TCCCACCTTGTTAGACACCTGAGGACTCACACAGGAGAGAAACCCTATAAATGTA

TGGAATGTGGAAAAAGTTACACACGAAGCTCACATCTTGCCAGGCACCAAAAGGT

TCACAAGATGAACGCGCCTTACAAATATCCCCTAAACCGGAAGAATTTGGAAGAG

ACCTCCCCTGTGACACAGGCTGAGAGAACTCCATCAGTGGAGAAACCCTATAGAT

GTGATGATTGCGGAAAGCACTTCCGCTGGACTTCAGACCTTGTCAGACATCAGAG

GACACATACTGGAGAAAAACCCTTCTTTTGTACTATTTGTGGCAAAAGCTTCAGC

CAGAAATCTGTGTTAACAACACACCAAAGAATCCACCTGGGAGGCAAACCCTACT

TGTGTGGAGAGTGTGGTGAGGACTTCAGTGAACACAGGCGGTACCTGGCGCACCG

GAAGACGCACGCTGCTGAGGAACTCTACCTCTGCAGCGAGTGCGGGCGCTGCTTC

ACCCACAGCGCAGCGTTCGCCAAGCACTTGAGAGGACACGCCTCAGTGAGGCCCT

GCCGATGCAACGAATGTGGGAAGAGCTTCAGTCGCAGGGACCACCTCGTCAGGCA

TCAGAGAACACACACTGGGAGAAACCATTCACGTGCCCTACCTGTGGAAAAAGC

TTCAGCAGAGGATATCACTTAATTAGGCATCAGAGGACCCACTCAGIAAAGACCT

CCTAGCTAGGTCCCCATGTGAGGAGATCTGCTTTCAGCCCTCACCTAAGGGAGGT

GAGGAAGAGGAAAAGCCCTCTTGTCAGCCTGGGAAGACCTTTTCGAGGGAGTCTC

CCTGACCTGCTCAGATCTGACATTACCTCTTCCTGCAACTAAACACGAGCCTGGG

TABLE 9-continued

CHD1 DNA and Protein Sequences

CAGAACCTCTCAGCCTTCCTCTACGCCTTGAGGGGATGTTTCATCCAAAGTACAA
CCTGAATTGAGGCTTCTCCTTCACTGGAGTGCACCTGCCTCTACCTCATGGGTAT
AAAGTAGGAGAACTAAGAGACTTAAGAGGTCGTGGTTCCTATATCGTCCAAAAAA
TAGGCTGTTACATATCCTAAAGACTGCTCAACAGCTTCAAGTTGAAAGTGGCCAA
GGACAGCCCCTTAGGTTTGGGAAGGGACGAGCCTGAAGGATTCTGTCTTTACTGG
GGTCAAATCTTAAAGCACACAGCTCTGGACTCAAGACAGGAGGTTTGCGTCCTGA
TGGCTTTGCACACATTCACAGGATAACTGCATAGATCCCTCGCTGTCTGATTCAC
TTCTTACCATGCACTTTCCTTTGATGCTGAGGAGAAATGGAAGTGGGCGAAAAAT
CTCAAGGCTGCTTCATGTGGACCTTGTCAAGCTGCTCCCTCCCCCAGCGTCAAAT
TGTTATCAGGTGCCAAACACTGCTAGAAAGGAGGGCCTAGTCAGAAGCCTCTTTC
CATACGAGTTTTGGTTTTGTTTTAATATTTTTTTCTATTAAAATACTCATGCAT
TTAACCTTCCCGTTATTCAACCAGTCTCTTGGTTGCATCCCTAGCACTTCTACTA
CAAGTGAGATGGTAGTGTTTGAGTGCTTATTGAGTAAAGCATAATTCGGTCATAA
TGAAATCGTTCACATTCCCTCATATGCACAAGCCCACCAACCCCTTCACACCCCC
CTTCACAGGGGTCGTATGAGTAAGGGGATTTGGAAACTGTCAACTTACAAAGGCA
CTATAACAATTACAGAATCATGATTGCCATGGGCCACTTTATTTACATGAAGACA
ACTGGAGAACGACTAAGACCAAATTATGGAAAATAAGAAAAAGCTGTTGCTGGCA
AGACCATCAAGACTGTTCTGACACCCTGTCCCATCATCCCTGACTGAGTACTCT
GACATCACGGAAAGTGTTGAACCTGGGACCCTGAGGAATTCACCAGGAGTAAATG
GCTTTCATGTAAAAAAAAA

CHD1 cDNA4  SEQ ID NO: 7

GGCCCTTGGAAGAAAATCCTCGCTGTGTCCAGGCTGAGGCGGGGGGCTAATGACA
GTGTGAGCTCTAGATGGTGTGAGACCACCCCAAAGCCAAGAAATGGCTACAGCCG
TGGAACCAGAGGACCAGGATCTTTGGGAAGAAGAGGGAATTCTGATGGTGAAACT
GGAAGATGATTTCACCTGTCGGCCAGAGTCTGTCTTACAGAGGGATGACCCGGTG
CTGGAAACCTCCCACCAGAACTTCCGACGCTTCCGCTACCAGGAGGCAGCAAGCC
CTAGAGAAGCTCTCATCAGACTCCGAGAACTTTGTCACCAGTGGCTGAGACCAGA
GAGGCGGACAAAGGAGCAGATCCTAGAGCTGCTTGTGCTGGAACAATTTCTTACC
GTCCTACCTGGAGAACTACAGAGCTGGGTGCGGGGCCAACGGCCAGAAAGTGGCG
AGGAGGCAGTGACGCTGGTGGAGGGTTTGCAGAAACAACCCAGGAGACCAAGGCG
GAAGTCCTGTCAGAGGAGACGGTGCATTTAGGAGCGGAGCCTGAGTCACCTAATG
AGCTGCAGGATCCTGTGCAAAGCTCGACCCCCGAGCAGTCTCCTGAGGAAACCAC
ACAGAGCCCAGATCTGGGGGCACCGGCAGAGCAGCGTCCACACCAGGAAGAGGAG
CTCCAGACCCTGCAGGAGAGCGAGGTCCCAGTGCCCGAGGACCCAGACCTTCCTG
CAGAGAGGAGCTCTGGAGACTCAGAGATGGTTGCTCTTCTTACTGCTCTGTCACA
GGGACTGGTAACGTTCAAGGATGTGGCCGTATGCTTTTCCCAGGACCAGTGGAGT
GATCTGGACCCAACACAGAAAGAGTTCTATGGAGAATATGTCTTGGAAGAAGACT
GTGGAATTGTTGTCTCTCTGTCATTTCCAATCCCCAGACCTGATGAGATCTCCCA
GGTTAGAGAGGAAGAGCCTTGGGTCCCAGATATCCAAGAGCCTCAGGAGACTCAA

TABLE 9-continued

CHD1 DNA and Protein Sequences

GAGCCAGAAATCCTGAGTTTTACCTACACAGGAGATAGGAGTAAAGATGAGGAAG
AGTGTCTGGAGCAGGAAGATCTGAGTTTGGAGGATATACACAGGCCTGTTTTGGG
AGAACCAGAAATTCACCAGACTCCAGATTGGGAAATAGTCTTTGAGGACAATCCA
GGTAGACTTAATGAAAGAAGATTTGGTACTAATATTTCTCAAGTGAATAGTTTTG
TGAACCTTCGGGAAACTACACCCGTCCACCCCCTGTTAGGGAGGCATCATGACTG
TTCTGTGTGTGGAAAGAGCTTCACTTGTAACTCCCACCTTGTTAGACACCTGAGG
ACTCACACAGGAGAGAAACCCTATAAATGTATGGAATGTGGAAAAAGTTACACAC
GAAGCTCACATCTTGCCAGGCACCAAAAGGTTCACAAGATGAACGCGCCTTACAA
ATATCCCCTAAACCGGAAGAATTTGGAAGAGACCTCCCCTGTGACACAGGCTGAG
AGAACTCCATCAGTGGAGAAACCCTATAGATGTGATGATTGCGGAAAGCACTTCC
GCTGGACTTCAGACCTTGTCAGACATCAGAGGACACATACTGGAGAAAAACCCTT
CTTTTGTACTATTTGTGGCAAAAGCTTCAGCCAGAAATCTGTGTTAACAACACAC
CAAAGAATCCACCTGGGAGGCAAACCCTACTTGTGTGGAGAGTGTGGTGAGGACT
TCAGTGAACACAGGCGGTACCTGGCGCACCGGAAGACGCACGCTGCTGAGGAACT
CTACCTCTGCAGCGAGTGCGGGCGCTGCTTCACCCACAGCGCAGCGTTCGCCAAG
CACTTGAGAGGACACGCCTCAGTGAGGCCCTGCCGATGCAACGAATGTGGGAAGA
GCTTCAGTCGCAGGGACCACCTCGTCAGGCATCAGAGAACACACACTGGGGAGAA
ACCATTCACGTGCCCTACCTGTGGAAAAAGCTTCAGCAGAGGATATCACTTAATT
AGGCATCAGAGGACCCACTCAGAAAAGACCTCCTAGCTAGGTCCCCATGTGAGGA
GATCTGCTTTCAGCCCTCACCTAAGGGAGGTGAGGAAGAGGAAAAGCCCTCTTGT
CAGCCTGGGAAGACCTTTTCGAGGGAGTCTCCCTGACCTGCTCAGATCTGACATT
ACCTCTTCCTGCAACTAAACACGAGCCTGGGCAGAACCTCTCAGCCTTCCTCTAC
GCCTTGAGGGGATGTTTCATCCAAAGTACAACCTGAATTGAGGCTTCTCCTTCAC
TGGAGTGCACCTGCCTCTACCTCATGGGTATAAAGTAGGAGAACTAAGAGACTTA
AGAGGTCGTGGTTCCTATATCGTCCAAAAAATAGGCTGTTACATATCCTAAAGAC
TGCTCAACAGCTTCAAGTTGAAAGTGGCCAAGGACAGCCCCTTAGGTTTGGGAAG
GGACGAGCCTGAAGGATTCTGTCTTTACTGGGGTCAAATCTTAAAGCACACAGCT
CTGGACTCAAGACAGGAGGTTTGCGTCCTGATGGCTTTGCACACATTCACAGGAT
AACTGCATAGATCCCTCGCTGTCTGATTCACTTCTTACCATGCACTTTCCTTTGA
TGCTGAGGAGAAATGGAAGTGGGCGAAAAATCTCAAGGCTGCTTCATGTGGACCT
TGTCAAGCTGCTCCCTCCCCCAGCGTCAAATTGTTATCAGGTGCCAAACACTGCT
AGAAAGGAGGGCCTAGTCAGAAGCCTCTTTCCATACGAGTTTTGGTTTTGTTTTT
AATATTTTTTCTATTAAAATACTCATGCATTTAACCTTCCCGTTATTCAACCAG
TCTCTTGGTTGCATCCCTAGCACTTCTACTACAAGTGAGATGGTAGTGTTTGAGT
GCTTATTGAGTAAAGCATAATTCGGTCATAATGAAATCGTTCACATTCCCTCATA
TGCACAAGCCCACCAACCCCTTCACACCCCCCTTCACAGGGGTCGTATGAGTAAG
GGGATTTGGAAACTGTCAACTTACAAAGGCACTATAACAATTACAGAATCATGAT
TGCCATGGGCCACTTTATTTACATGAAGACAACTGGAGAACGACTAAGACCAAAT

TABLE 9-continued

CHD1 DNA and Protein Sequences

TATGGAAAATAAGAAAAAGCTGTTGCTGGCAAGACCATCAAGACTGTTCTGACAC

CCTGTCCCCATCATCCCTGACTGACTACTCTGACATCACGGAAAGTGTTGAACCT

GGGACCCTGAGGAATTCACCAGGAGTAAATGGCTTTCATGTAAAAAAAAA

CHD1 Genomic DNA    SEQ ID NO: 206
CCTCCTCTCAGATTGCTTAAGATCATCTCCGGGGGCTCCTTGCCCCGGCTAGCCC

CATCTCCTTACACCACCAAGCCCCCCTCACCCCAGCACACACCCAGATACACTCA

CCCGTGATCTTGTCACCTGTGATGATAGTATGTCCTTGGCGTCCATTTGGCCAGA

GCTTTTCAGCTGTCACTGTGACAGACCCTGAGGTTCCCCTCAAGCCAGTAGCTGC

TGTCTCCACTTGCAACTTTCCTCTCCTCCCACTCCTAACAGCCAGTTTTGGCACC

TCTTCTCAGCACCTGCGTTACTTTTAGCAGGAGTATACCTACTTCTTGAGTGTCT

TGATTAAAAATTTGTTTTTGTGCCATGGATAGGCTGTGTTCCTTCAGAAAGGTGT

CAGTCTAATTTTTGTTTTTCTGAACAATGAATGTTCTCATCTTCTAGGCGCTTTG

ATAACCCTGTCTGCCTTGGAATCTGTACTGACCTCCCCAGAGGGAGACTCTTAGA

CCCAGCCTTTCTTGAACAACCTTGGTCCTGGGGAGCACGCTAGATCCCAGGCTCT

CACTTAGAGGCTGGGCTTAGAACTGTTGCTTTTTCTCTATCCACGCTCTGCAGGT

GACACCCAGGGCAGCTACACTCAGAAGCCACAAGGAATGCTAGTGGAGCCCCTCA

TCCCTCCCAGCTTCTCTTCCAAGCTGCCCCGTGGGGCTTGATCCAGGAAGCTACT

TCAGAAAGGTTGTGGGATAGCCTTGGGAGGAGGTTTGTTGGTGGGAAGCGTGTGA

ACCGGAACAGTCTTGGATAACTTTCTGCTGTTACTATCTAGCATAAGAGGGTGGG

CAGGGTTGGAGAGAGGACAGGAATTTTTCCTCCTAGGACCAAACGCCTGGGATTC

ATAATCTTTCACCCTTTCTCCTCCAGCTATACCCTTTTTGTACTCTGTGTATATA

CTATATTGCAGTAGACAATCATTCCAAGGGTACAACAAGGTTTACCACAATGTGA

GGGACTCAGCCATTGCAAATTGTACAGATGAGGTAAGTTACAGGTTTACATTTTT

TTTTCCCAGTAAATTTGGCACAGATTTAAAATGTGAAACAGTTCTAGACCCCTTG

TTTTTGCTGTTCTCTCACCAGCAAACCCTTTAGTTTGGCCAGCAATGGCTTTCTG

CATGAACTTCAGATTTACTTCATTTGCTAGGTGGTGGTTCTCAAACTTACTATAA

GCACCTGAAGGGCTAGTTAAACGCATATTGCTGGGGCCCACCCCTAGAGTTTCTG

GTAATAGGTCTGTGCTGGGGCTTGAGAATTTATGCTTCTAACAAGGCTCAGGTAC

TGATGCTGCAGATCTGGGTTCTTCACTTTGAGAACAACTACCTTTTGGCCAAATG

TGATATACGTATTGCAGTAGGTTGAGGTTCAGAATACCTTTGTTTGAGTACTTCT

GTGTTGGAAACTAGTAATCTGATCTTTTATAGATAATCACTTAGGTCTGAATATT

CTGTTCGCAAAATTAAGAAAGCGTACTTAAAACAACTGAATGCTATATGCCAAAT

TTGAGGTGAAATATTGATGAGTTCTTCCCCTTGATTTTCTTAATTCTCTTGATAG

GGGCTTCACGTTTTGATCAAAAATATTACACCTGTATTCTGGGCTTTTGCTGTGA

ATTCCTAGTATTGCTAAAATTCTGCAATTTCTTAACTACCTGTTAAGTTCCTCAA

GGTCAGAGCTTCTGCTTTTTTTATCTTTCTTTGCCCAGCACCTTGAATAGTGTGG

GACACGTAATTGACGCTCAGTAGATATTTGTGTATTGAACTCCATCCCTTGTCCT

CCTCCCCTCTTGATGTTTTTCTCTACTGGCCTTATGCTACACAGTAAAGCAGGGC

ATGATTATGCCACTTGATTACCCCCAAGAGATTGGAATAAATGCTAATGCCAAAT

TABLE 9-continued

CHD1 DNA and Protein Sequences

TCCTACAGCTATCCCTGTGAATGGTTTATTACCCAGGAGCCCTGACACTGGCTGA

TTTCTGAATTTTCAGTGCTTCTGTAATATATACTAGTTGGGGGAGGAGAAATAGA

AAGCTTAAACTCAATGTGCGTTTATTGAATACCTTTTCTACTAAGGGCTTGACAA

AGTGGTAGGCACTGGAATATAAAAATGAATAAGGAGACCCTTGCTCTCGAGGCA

GGGCCCACAGTGGGAGACAGACGTTAAGCCATGCCCACGACAAGAATGACTTCT

GAGATTCCTTCTTTGGATCATGATTTAGTCTTCAGTGGAAACCTGGTACTCCTCA

GATTCCTCTGGTTCAACAGGCGGGATCCCATCCCTTATCATCTCCTCAAATGCT

AAAGGACCCTTGAGCAAAGCCAGGAGGAAGTCATCTAGACGTGAAACAGGGAGTA

TCCACACAGGCTGTGTTAATGACAAAGCTAAAAACATAGTAAATGACTTTTGAAT

TTACTGCTGTTATGAATTATCTATAGCAACACCTCAGGTCAGCTCTGTTATATAT

GTTATTGTGTTATTTCCCATTAAATGATGGTTCCTCTGACTATCTGATTGGCATT

GACTATGTTTGTTGTAGGGATTGCATACATCTAGTTTAACTCTGGCTGTCAAATG

AGAGAGCAGTTACTCTTATCAGGATGGGTGTCAGGTTTGATGTCCCCTCCTTTTC

CTGCTTCAGGTTAATTTGTCATGTTCTGTTTTAAACTGAGGCATATAGCTTGACC

TCCTTTATTTAGGCCATTAACTGCTCTGGGGTAGTTTTCCTGAAGGTTAAAAAGC

CTAGCTTCATGATGGAGGTTAATCAACATGACCATGATGGCCAGGTGTATAAATC

TGGCCTCTTAAAAATCTGTATTTGAGGCTGGGTGCAGTGGCTCACACCTGTAATC

CTAACACTTTGGGAGGCCAAAGCTGGCAGATCACTTGAGCCCAGGTATTTGAGAC

CAGCCTGGGCAACATGGCAAGACCCCTTCTCTATwAAAAATTTAAACATTAGCTG

GGCATGGTGGCATGTGCTGTAGTCCCAGATACTTAGGAGGCTGGGGTGGGAGGAT

GGCCTGAACCTGGGAGGCAGAGATTGCAGTGAGTTGTGATCTTGCCACTGCACTC

CAGTCTTAGCAACAGAGTAAACCCTATCTCAAAACTTAAAAATCTGTGTTTGGCC

CCTAGCCGTCCTCAGCTCTTGAGTAAATCTCAGCATCCTAGGCTGTTACATTATG

GCCCAAATATTCAATAGAGATGCTGTATATCCTTGTTCCTCTCAAAACCCCTCCT

CATCACCATCAAAAAGCTGGTTTAGTTCTCTACCTTTAGATAAAGAATCATCCCA

AGACTCAACATGAGCTGCCGTGACTTGTCCAAGATGACACCTCTTTACAATGTAG

AGCAGTGGACAGAACACAGGTCACCCTCCGCCGAAAGCAACTATCTACTGTCTAA

CATTGCCTCCTAGGCCTGCCATATATAACCATCAAAAACATTTTAGTTTAGAATA

AAGTGAATTGTTACAATTTTTATTTTTCATTTTTGTGTTTACATTTACTCTCAAT

GACATGTTTATTCCCACCTAATATCTTGAGGCTAACCACAAAATCTGCAGCATTT

CCAGGCAGAAGATACTTGTGACTTCCCTGTACTATCCACTACATACTTGACCTCT

TTCTCTTTCTTCCTGTCTTCCCTTTCTCTATACCTTATTATCTTTCTTTGGAACC

TCTTGTAACAAATTTTGAGCCATTTCTCCCCTCACTACTCAAATATCACTTTTAT

GAAGGGGCGGGGGGAAACTTAGGTGGCAAAAATATTTTACAGAAACAGTTTTAA

ACATGTTTTGAAGCATACTGGTCACGTGTTAGAAGGCCAAAAGCCAGGGAATTCA

TTCCCTTTCATTCATTGTGCTGTCTAGGTTAAGTTTTCACAGGACTTCTTGGTAC

ACTGAGTTTGCCTCAGATTGTCTCCTGCCAGTTACAGGGAGTGGAGAGGACTTTG

ATATATTGGTAATTAGAAGCATTSCYGATATGGTCTTCGGTGGGAGAACCTGTGT

CTAAGGTTCCTTCTCATCTGTATTCCAACACTTTCATTTAATCCTACTTCATAAG

TABLE 9-continued
CHD1 DNA and Protein Sequences

```
TGCCTCCAAAGCAAGGATTTTTTTTTGGTTTAGCATGGTTTCTTTGATATAACA
ATAGACCGACCAAGATTTTCCTTATGCCATCTGTTTTTTGTAATTATGATGCAA
TAGAGAACTGTTTGCTTGTTTATCATTTAAATCTTGCCTTCTTCCCAAAACGATT
TCAAATAGCTTGAAGGAAAATGAATAAAATATATTGAGCACCTACCCTATGCCAG
ACTCTATACTGAAGGGTTTCTATAGGTTATTTCATTTACTCCTTAAAACAACCAC
ATGAGATAAGTAGTATTAGCCACATTTTTGAGGATAAGACTGAGGCTTAGGGAAA
TTGTGTTACAAGGCTAATAAGCGAGGTCAGGGATTCGAGGTCAGGGATTCAAACC
CAGCGTGCCAAGGCCACTAACCATTATGTGGAAAGCTTAGGTAAGCGCTTGTATA
TAGGACAATCAAGAATAAAAGAATATGTCCATTAGAAGGATTGTACTGGGCTAAT
CTTTCGTTTTAAAGAACAGCAGCAGCATTGGAAAAGAGCGGTTAACAGTTTTTAT
TAGCCAATTTCTATTCTAGAACACTGAGAGGAGCTGTTGACAGGCCCTGGTTAGC
CCCAGCAAGTAGTTGTATTAAAATTACCAAACTATAGGCCTGCATTAAGGTATAA
AATAAGAATGGGGACTGGAAGGGATATAAATATCTGCTAAATATAATAATTTCAG
TTCTAATCACTATTTTCTTCTGAAGATTATTTGCCAGTACATAGGCAGATCACTG
TCTCTCCTTTAGGTTGATGGTATATGACTACAGACTTTGTCATTTAGGGTCCAGA
AAGATCACCCTAGCTAGTAGCGTTTTAAGGTAGAGAACTAGATATTGTTTCATTG
CCTGTGGTTTTCTGTTCTTGTAAGAGAATTGAGCTTGGGTCTTCACTGCCACGTG
ACACCTTCAGATAAGGGGCAGAGACAGCTGGCCTGAGGATTGTACAGAGGTCTTA
CCTTGATAGCTCCTCTCCAATCCTATGCATCCTAGGAACACTCAAGACACTAGGT
TGTATCTTTGCAGATACTGTTTTAGTGTCTTCTGGAACCAAGTCTCTTACTTAAT
CCTGGCCTGGTTTCATATTCTCTCTATTGTATTCTCTCTATAGTTTTTGTCTTAC
TCTGGAACTCTTCCAAGGACAGACATTGAAGAAAGGTATTAGAATAGCAAAGGCA
ACAAATTGCAAGGTATACTTATGGCATAGCACATCCCATTAATTATAGAATAAAA
ACACAACATCTGTTTTCTGCCTCTAATATTAAATCTTGACATTTGCACAACACAT
TTTAGTTCATAAAGCTCTCATATCTCAGATAATCACTGAGTTAGGAGACTGGTTA
TCTGCAGAGGGCTTTATCCTTTACAAGGGCTCTTGGGTACGTTACTTCACGAAAC
CCTCAGGGAAGCTCCAGTTTCTTGGGGATCTGGGGCCGGGGCATATGTCTTTGGA
TACCCAGTTTGGTGCTGTGCACAGCACTGCTGTACCTCCTATTCATTTCCCATCT
CTTACCCCACAAAGACTCCTTCCTTCATTCCTTCTATTGCTGATCTGTTTTCCTT
CATCTTCCTAGGCTGCCAAAGTAAATGCAAAACAAGCACCAGAAATCTCAGCTTG
TGATTTCTGAAGGGCATTTTTAAATGGCAAGTTTGGTGTGGCACTGTTACATGTT
CTTTTTTCTTTGGAGAGCAAAGCCCTTTGAGAGAGCAGGAACTCTTCTGTCAATG
CATACGTTGTAGGATCCATACTGTGGAATCTCTTGTACCTAGTGCTGCGTGAAAA
CAATGAGGATTCCAAGTCTACTTCACTGGACATCGGTTCTCAAACTTTTAAGATA
CTAGAAGTCCTTTTATTAAGCCAAAAGACCCTATGTATTAATTCTGTCTTCCAGG
GGTAGGAGTTGGGGTGGGGTTTGGAAAGCTTTGTCTGGATAAATAATTAGTATTG
TAGTTCCATTTATTTGATGTCTGATTTTGCGCTTATTAAAATTGATTTAAATCCT
CAATGGAAAATGATTTTTTTTTTTCAAATGCCAAGTGTTGTGTGACTTGCATTTG
```

TABLE 9-continued

CHD1 DNA and Protein Sequences

GATTATTCCCGGTGCAACCTGAAGATTCCTTGTGATGAGTTGTGGTTCCATCATC

TTGGGAACCACTAAGAGAATTCTGTTTTACTCACAATCCAAACAATAAATGTTTT

TTTCCCTATGTATGCCTTTATCCAGCACACAGTTTGCTAGACTTATGGATGAATA

TGGGTTAATATAACATGGTATCTATCCTTCTGGAAACAGACTTTTAAAACCTTAC

TAAGCATTCTCTGCATTCATCAAATGTGAAGTGAGTGCCTGGTGTGTGCCAGGCA

TCGAGCTGGGCACAGCATATCCCTGCCCTCAGAGCTTTACAGTCCAGTGAGTTCA

ACAGAAGATGAACAGTTTTGATGACACAAAAAATAGACACATGTGCATGCTGTGA

TAGGGGGAGATACAAgTTCCTGTGGAAGCATCATCTGGGAGGACCAGGGAAGGCA

TCTTGGAAAAACTGAGCTCTGAAAGATGGATAGAGTTAACCACATGAAGAGTGGA

GAAGGGTACTTCAGACAAGGTGAACAGCATCAGGAAAGCCCAGGGAGGGTATAGA

AAAGAAAGAACAGTAATTCTTGCAGTGGCTTTCAATGGGAGTGGCAGTCATGGAA

GGAAGGAGAGGTAGCAGGGACCAGCTTTTGAAGGGCTTTGTGTATCACATTTTAA

GAAGTTTAAATTTTAACCTAAGGTCACTGGGAAGCCATTGGCAGATTTTGTATGT

TAGGAAGTTCACCACTCACCTACTTGGAGTATTGCAGGTGGAGCTAATGTGGATG

GGCCTCCTGCCCATTATTAAATCCTGTTCCTGTCAGGAACAGGACAGCCCATGCT

GTCTCTCCCTGTGTGTCTGTCTCTCCCTGTGTGTCTGTCTCTCTCTCTCTCTCTG

TCTCTCTCTCAAAAGCTAAAGGAAAGCGCATAGGTTCCAGAAGGAAAAAGAAA

TAACCACTAGAAAAATAAGTATAAGCTGACTTTACCATGGCGCAGTGAGATTCCA

AACCAAAATAAGGTTTCTAGGGATTGAGCTTTTAATACTGGTACTCCAACAGGGA

GATAGGACTTGGGAAACTGACGCTGTGTGAAAGTTACAGAATTAAGCAGCCTGCA

AACCTGGACCTTTGAAAATCGTCCTACTGACCCAGGAAAAGTGCAAGGAAGTGGG

TTCTCCAGAACCTTGGGTAGGCCAAACATTACTTGAAGGCATCGATCTAAATAAT

ACACAAAAGCATTATTCAGGAACACCCTGAGAAATTAACATAAAAACTGATTTGG

CCAGGCATGGTGGCTCAGCCTCTGGTAACAGTGCTTTGGGAGGCCAAGGTTGGAA

AATCACTTGAGGCCAGGAGATCCAGGCTGTAGTGAGCTATGATTGTACTACTGCA

CTCCAGCCTGGGCAACAGAGGGAGAGTCTTAAAAAAGCAAACTGTCCAAGATCAT

TGAAACCATTAGCACTTAGGAAGAAACAAATGAAATTACATTCAAGGGGGTCACA

TTTAAATCCAGGGCTCTCAGGACTCCCAAAGTAAAAGATGGACATAAAATAAAA

AAATTACAAGCCACTTGAGAAAAAAATAAATCACCATGAGGTAGAGATAGCAGAG

GAAAAATTACACATGAAGATCTAGGAATTAGGGAGCTATCCAAGATAGACTGTGA

AAGTATGTTGCAAGTGACTGAGGGTAATGAAAAAAATGTCATAAGAGCATGAATT

AGAAGCGTTTTGAGAAAGAATGAAGATAATGTGGTCATTGACTGTAAACTCATTT

GATGGGCAACGATAGATGAGACACAGCTATTAAGAGTGGATCGATAACCTTGAAT

GTGGATGTGAGGCAACTGTAGTATAGCACAAAAAGGTTGAGAAATGATGGAGCCC

TTAAGCTGCTTGTGGACACTGGTCTGGAGGGGACAGGACCAAGAAAACCAGTCA

TGGAGGTTGAACTAAGTCATCTCTCCAATGTATCCGTGCCTGTTACGTGCCAGTG

CCGTTTAGGAGCAGAGGATATTGTAATTTTTTTTAAAGTTCCTATGAATACCTTC

TAGTGGGTCATAATGGCTCAACCGGGAAATGGCAGTAGAGATGAAGAGATGGATG

GATTCGAAAGACATTTTTTGGAAGTTGGAATTAACAGGATATGGTGAATAATCAA

TABLE 9-continued

CHD1 DNA and Protein Sequences

GAGATAGTAAAAGCATAATGGAGGAAACAATGGTTCTTCCTGTTACCATAGGAAG

AAGCTTTGGAGTAGAGTTTTATTCATTTTAAATGCATTTATTGTGCACTTTATTA

TAGGTATTGGAGATTGATGGAAAATAGTCTCTGACCTCAAAGAGTTTCACAGGAA

AGATGAGCGATGGCTATGTAATATGACCAATACTGGGATAGAGAGGTGCCCAGGT

CACTACGGGAGGACTTAGGTGATTTCTAACTATGTCTGAGAGTAGGGGAAATGGG

ATCAAAGAAAACATCTCAGAAGACATGAAGCTTGAGCTTATGTCTTGAAAAATTT

AAAGTTTAACCTAACCAAGGATAAAGAATCAGAAGAAACAGCATATTCAAAAGCT

AAAGAACACGGGACTCTTGTGTGCTTTGCATGTACACACGTGTGTGCGTGTGTGT

CTGAAAGGATTGGAGAGGAGGGCGAAGAGAATAACAAGATGAACGTCAACCTAAT

GTAGAATGTTTGAAGTTTGTATTTCACTTAACAAGACAGCGGGGAGTGATGGAAG

GATCTTAGATAGGAAAGGGACATGAGCACGTTTGCCAAGAGAGCTCGTTCTGGTC

ATAGTGGGTACGTGAAGGTGACAAATCTGGAGGCAGATAGCTCACATTTGGAGGC

AGCTQCAGTCATCCAGATGAGAAGTGAGAGGGACCTAAGCTGTAAATTGTGGGAA

TAAAGACAAGACCCGTTAAAAAGAAAGAGAACACACCATGTAGCGTGGAAAGGAG

AAGGGTGGAGAGTAGCCTGTGCAGAAGGAACAACCTTCAAAAAGACATGGAAGAC

TGAAAAGACACCCTGTTGTAGGGAGATCAGCAATGCATTTTTTATAACCAGGTGA

TACAGGGAAAGGGTAGGATCTGAAGCTTGAAAAATAGATTGGGGGCTGATTGTAA

AGAGCTTCGTGTCATTCCCAGGATTTTGGAACTGATTTTACTAACATGAAAAAGG

TTTTGTTTTAAAATACTGAGTAATATAGTTGGAACTATAATTTAGAAAGATAATA

GCTGGTGCCATCACTCTTCTAAGCAAAGATAGTAATACATTTAATGCTCATAGGC

TTTAGTAATACATTTAATCCTTACAGTAAGCCTATTAGATAAAAACCATTATTAT

CTCCCTTCTATAGACAGAGAAACTGGCATTAGGAGAATGAGAACTTGCCTATGGT

CCCACTCTGGAAATACCTAGTAAGCGACAGAGCCAGGATTCAAACCCAGGCAGCT

TGACTCCAGAACTTTCGCTCATAACCTTACACATCTCCGTCATGGTTGGTGTTTC

TCAACCATGGATACACATTCGAACTGCATGTAGCATCTCTAAACATACAGTTACC

TGAATTGACTGAATCAGAGTGTCTGAAAAATGATGTGTGATACTATGTTTTGCAA

AATCTCCACAGGTAATTCTGTTGTACTTTGCTTATAGTTGAGTACTGCAGGGATC

TTAGGAAGTTAGAGCAGTAGTCCAGGCAGGAGATGATGAAGGCTCAGACTAAAGC

AGTCTGTAGGAAGGAAGAGAAGGGAACCGGTTTGGAGACTTAAGCGGGGGAATTG

GCAGTATTTGTGAAGTGGAAATGCAGTATTTTCTTGTAGAGTATGAACCTTGCCT

AGGAAAGGGAGTAGAGGACCATACCTTTAGTTGTAAATTATCCTCTCCCAACTGG

ATCTGTTGATTTATGGCTATGGTGGTTGGGAAAAGAGGATTTAACCATTTGAAG

AAGTTTGTGTAGAGGATTATGATTGAACTCAGGCTGTTGTCCTTGTGTATAGTTT

CATGCTTATACTCTTGTTTGTCTTTACTTCTCTATCCAGGGCCCTTGGAAGAAAA

TCCTCGCTGTGTCCAGGCTGAGGCGGGGGCTAATGACAGTGTGAGCTCTAGATG

GTGTGAGACCACCCCAAAGCCAAGAAATGGCTACAGCCGTGGAACCAGAGGACCA

GGATCTTTGGGAAGAAGAGGGAATTCTGATGGTGAAACTGGAAGATGATTTCACC

TGTCGGCCAGAGTCTGTCTTACAGAGGGATGACCCGGTGCTGGAAACCTCCCACC

TABLE 9-continued

CHD1 DNA and Protein Sequences

AGAACTTCCGACGCTTCCGCTACCAGGAGGCAGCAAGCCCTAGAGAAGCTCTCAT

CAGACTCCGAGAACTTTGTCACCAGTGGCTGAGACCAGAGAGGCGGACAAAGGAG

CAGATCCTAGAGCTGCTTGTGCTGGAACAATTTCTTACCGTCCTACCTGGAGAAC

TACAGAGCTGGGTGCGGGGCCAACGGCCAGAAAGTGGCGAGGAGGCAGTGACGCT

GGTGGAGGGTTTGCAGAAACAACCCAGGAGACCAAGGCGGTGGGTGAGGAGGGGG

AGTCCtGATCTGTGTGATGTGGAGGGGACTATTTGCTGGAAGGCTGGATTTGCG

GGGAGAGCTTGCAGGATCCCCATAAATTATTAGTGGCTCTGCCCTTGGGTTGCTC

ATATACCATGAGCCCCATGGATTAGGGGATGTGTGTATGAATGTGACTTTCT

GGATATTGGAACACCTGTATAGGGACCATCTGAGGGGgTCTCAGCCACCAAAGGG

TCATGGCTTTGGTTTTCCCTTCTTTGAATGTTGAGCCGTGGGTTCCTGGAGAGGA

GAATTTTGTGACTTCCTCGAAGGTTCTCATAGATCCCCAGTCACAGATCCCCCTT

CCTGGCTGGTCAGCTAGGGAAGCAGGCAGCAAGGAGAGCTGCAGGTGGGACAGGT

GGAGATGGGAAGGAACCTTGGGTGACAGGGGCCCAGGCTGGGGGTGGTGAGAGAG

CAGTGCAGGCCTGCGCATCCCCTGCCTTGTCCTGGGGAGGATAACCTTCAGCTCC

TCCTTGCCTGCTCCATTGAAACTGGAGTTTCCCCTCCTTGTCTGGGTCCCTCTGG

GAGTGTTTTCTCTAGGCATCTTCTCCTAAAATAAGCTCCCGTGACAACCAAGAAC

TTCCTCCTGACTCCATGGTGACTGGAAGTTGGAATTATTCCCAGGTGACTGTCCA

TGTTCACGGCCAGGAAGTCCTGTCAGAGGAGACGGTGCATTTAGGAGCGGAGCCT

GAGTCACCTAATGAGCTGCAGGATCCTGTGCAAAGCTCGACCCCCGAGCAGTCTC

CTGAGGAAACCACACAGAGCCCAGATCTGGGGGCACCGGCAGAGCAGCGTCCACA

CCAGGAAGAGGAGCTCCAGACCCTGCAGGAGAGCGGTGGGAAGCATCAGCAGAAA

GGGGGGATTGTGGCAGAAGGCAGGCAAGGAGGGGGACATTTCTCCTATACCAAGG

AAGCTGGGTAGATAGACTGTATGGAAAGACATCACAGAATCCAGGATGTCAAGAG

GAGACAGTACCGCCAGCTAGAGTCCCCCATAAACAGGGCCAAGCTTAGACAGCAG

ATTGTTGCTTGTTCTCTTGGCATTCTGATAGTCTCATAGGTGATGGGATTGGGAT

ATGGGAGCTACCCTTAGGCCAGTTTCTTGGTTCCCATAATAGAAAGGATAGGGCC

ACCTTCCTACCAAAGATGGTGGGGATGCCCAGATTTTTGCCCATTATTGGGCA

TGCTGCATATTACTGATCTTTGCCTTCTTTTCTTCATAGAGGTCCCAGTGCCCGA

GGACCCAGACCTTCCTGCAGAGAGGAGCTCTGGAGACTCAGAGATGGTTGCTCTT

CTTACTGCTCTGTCACAGGTGTGCCCTAGTTACCTCTGTACCACAGAGAATTTGT

TTGAAGAACCACTGGGCATAAGCCATACTAAACAGGTGAAGCAGGATGCACATTT

ACACTCTTGCCAGTTTTAAGCTCACAGTTCTGCAGGTACCTGGAAGGGGAGGAGA

TAATGAGATAAATTATCATACCTTATATTGGATCCACAGGCACCAACACCAGTTT

ATTTGCCATTGACTAGAAGAACTAACAAAATGGGATTATTTTGTAACACTCCAGT

ACAACTGCGAAGTTGTCAAATGAGGGTTTTTAGTTTTTTTTTTTTAAAGGAA

TAAATTTGATAGTCATTTGTAAGTATGACAGACTGTACTGCTGAGACATTTAGGA

AGTATTCACCATGATCAAAGCTCTGAAACTAAGCCATGTGGCTGGAGAAAAAGAA

ATAGAATTCATGTATGGTTTTAGATTGTAATCTAACTGAGGAAAAAAGTCTTGTT

TTGGCTATAGAGTATAGAAAACTATTGAAAGTGATTAGAGTCTTTAGGGAAAGTGT

TABLE 9-continued

CHD1 DNA and Protein Sequences

ACTAGAAAAGATGAATTTTGCAGAAATGTATATAGCGTTAAAGTGTCAAGTAGGG
AGCTGAATGATGATTTTTAAGACCTTTCCTAAATTTTAAACAATACCTTAAAGAA
GAAGAACATAAGCTGGTCCTCAGGAAAAGTGGTGGAGTTGGAGGGGGCAGGGCCA
GTGCCACAGGGGACACATGGCTCCCCCGAGAATGAGTTTAAGCAGCCCGCCACTC
AAGCTCCTTTCATCTCCTAGAGGAGTCCACCTATTGTGTGACCTTCAACAGGGAC
AAAATACGAGGCTACCCGTAGCATCACGTTTTGATGAAATCCTTATGTGGTTTCA
GGGACTGGTAACGTTCAAGGATGTGGCCGTATGCTTTTCCCAGGACCAGTGGAGT
GATCTGGACCCAACACAGAAAGAGTTCTATGGAGAATATGTCTTGGAAGAAGACT
GTGGAATTGTTGTCTCTCTGTGTAAGGAATTTCAAGTATTCTAGAGTGTTCTAAG
CCCAGAGATCTTTTTCCTGCTGGAAATTTTGGGGGATCTTAGACCTTAGATTGTA
TGCAGTGAACTTCTCTTATGCCTTCCCCACCAATAAAATTGAGGGATTAGGTGAA
AAATACGGTGTCCTTTCAAGTAAAAGATAAATGGATGGAAATGGAAACCTCTAAT
AGGAAAACAAACTTGTAATATTACAGCTTTAGTGCAGAAATATTTGAAGTAAGCA
CATGAGTTTTAAAACAGTAAGAGTTGGAGATAATCTTTCTTGAATATGGGAAAAG
AGGATAAGGTGTACAATGGTATAATTATTAAGTTGCAGGTGAAAACCACAAGAAA
GGCAAGAGATACGCAGTCCTTGGTTAAAAGTACACAAACTAAAGAGATGAAAGAT
TTCATCACCTGAGCTAGCTATGTATTTGCCCCACAACCTACCAAATAGAAAAGGA
CCGCTCTTAACACAGGGAATTGTTGAGCCAATCGTGATATCCTATTTTCCCTCTC
TTGAGCAGCATTTCCAATCCCCAGACCTGATGAGATCTCCCAGGTTAGAGAGGAA
GAGCCTTGGGTCCCAGATATCCAAGAGCCTCAGGAGACTCAAGAGCCAGAAATCC
TGAGTTTTACCTACACAGGTGAGGAATGACAAAAACGGTGTTACCCACCCTGAGC
CAGCAGTTCCTCTAGGCAGTGCTTCTCTCTCTGTAGGGCCCCGCTCTCATCAG
TTCTTCTAACATGTCAGCCAGTACTGCTTTCTCCCTCTGACAGCCATTTCTTCTG
TCATTGCCCTCCTCTTTTCTCCTCCCATCATTTGTCTGATAGCAATGTAATACAA
AAGGGTGAAAGAAAAATGTTAACTTTTGGAATTGCAGCTATACCATTTACTGTAC
AATTCCCTTAAACCCTCGATTCTCAATCTCTGCATTTGTAAAATGAAGATTATAT
TTGTGCATACCAAGGTTTGTTGATAGCATAAAAATATGAGAAAGTGCTTGGCACA
GGACAGGCATTCCATTTAGTCTTGCCATCTCAAAACCCTTTGTAAAAATCTCCCC
ATTGTGTAGAAGGCATTGTTGCCGCTACAGTGACCCCCTTTTTCCTCTCACCCTT
TCTACAGGAGATAGGAGTAAAGATGAGGAAGAGTGTCTGGAGCAGGAAGATCTGA
GTTTGGAGGATATACACAGGCCTGTTTTGGGAGAACCAGAAATTCACCAGACTCC
AGATTGGGAAATAGTCTTTGAGGACAATCCAGGTAGACTTAATGAAAGAAGATTT
GGTACTAATATTTCTCAAGTGAATAGTTTTGTGAACCTTCGGGAAACTACACCCG
TCCACCCCCTGTTAGGGAGGCATCATGACTGTTCTGTGTGTGGAAAGAGCTTCAC
TTGTAACTCCCACCTTGTTAGACACCTGAGGACTCACACAGGAGAGAAACCCTAT
AAATGTATGGAATGTGGAAAAAGTTACACACGAAGCTCACATCTTGCCAGGCACC
AAAAGGTTCACAAGATGAACGCGCCTTACAAATATCCCCTAAACCGGAAGAATTT
GGAAGAGACCTCCCCTGTGACACAGGCTGAGAGAACTCCATCAGTGGAGAAACCC

TABLE 9-continued

CHD1 DNA and Protein Sequences

TATAGATGTGATGATTGCGGAAAGCACTTCCGCTGGACTTCAGACCTTGTCAGAC

ATCAGAGGACACATACTGGAGAAAAACCCTTCTTTTGTACTATTTGTGGCAAAAG

CTTCAGCCAGAAATCTGTGTTAACAACACACCAAAGAATCCACCTGGGAGGCAAA

CCCTACTTGTGTGGAGAGTGTGGTGAGGACTTCAGTGAACACAGGCGGTACCTGG

CGCACCGGAAGACGCACGCTGCTGAGGAACTCTACCTCTGCAGCGAGTGCGGGCG

CTGCTTCACCCACAGCGCAGCGTTCGCCAAGCACTTGAGAGGACACGCCTCAGTG

AGGCCCTGCCGATGCAACGAATGTGGGAAGAGCTTCAGTCGCAGGGACCACCTCG

TCAGGCATCAGAGAACACACACTGGGGAGAAACCATTCACGTGCCCTACCTGTGG

AAAAAGCTTCAGCAGAGGATATCACTTAATTAGGCATCAGAGGACCCACTCAGAA

AAGACCTCCTAGCTAGGTCCCCATGTGAGGAGATCTGCTTTCAGCCCTCACCTAA

GGGAGGTGAGGAAGAGGAAAAGCCCTCTTGTCAGCCTGGGAAGACCTTTTCGAGG

GAGTCTCCCTGACCTGCTCAGATCTGACATTACCTCTTCCTGCAACTAAACACGA

GCCTGGGCAGAACCTCTCAGCCTTCCTCTACGCCTTGAGGGGATGTTTCATCCAA

AGTACAACCTGAATTGAGGCTTCTCCTTCACTGGAGTGCACCTGCCTCTACCTCA

TGGGTATAAAGTAGGAGAACTAAGAGACTTAAGAGGTCGTGGTTCCTATATCGTC

CAAAAAATAGGCTGTTACATATCCTAAAGACTGCTCAACAGCTTCAAGTTGAAAG

TGGCCAAGGACAGCCCCTTAGGTTTGGGAAGGGACGAGCCTGAAGGATTCTGTCT

TTACTGGGGTCAAATCTTAAAGCACACAGCTCTGGACTCAAGACAGGAGGTTTGC

GTCCTGATGGCTTTGCACACATTCACAGGATAACTGCATAGATCCCTCGCTGTCT

GATTCACTTCTTACCATGCACTTTCCTTTGATGCTGAGGAGAAATGGAAGTGGGC

GAAAAATCTCAAGGCTGCTTCATGTGGACCTTGTCAAGCTGCTCCCTCCCCCAGC

GTCAAATTGTTATCAGGTGCCAaaCACTGCTAGAAAGGAGGGCCTAGTCAGAAGC

CTCTTTCCATACGAGTTTTGGTTTTGTTTTTAATATTTTTTTCTATTAAAATACT

CATGCATTTAACCTTCCCGTTATTCAACCAGTCTCTTGGTTGCATCCCTAGCACT

TCTACTACAAGTGAGATGGTAGTGTTTGAGTGCTTATTGAGTAAAGCATAATTCG

GTCATAATGAAATCGTTCACATTCCCTCATATGCACAAGCCCACCAACCCCTTCA

CACCCCCCTTCACAGGGGTCGTATGAGTAAGGGGATTTGGAAACTGTCAACTTAC

AAAGGCACTATAACAATTACAGAATCATGATTGCCATGGGCCACTTTATTTACAT

GAAGACAACTGGAGAACGACTAAGACCAAATTATGGAAAATAAGAAAAAGCTGTT

GCTGGCAAGACCATCAAGACTGTTCTGACACCCTGTCCCATCATCCCTGACTGA

GTACTCTGACATCACGGAAAGTGTTGAACCTGGGACCCTGAGGAATTCACCAGGA

GTAAATGGCTTTCATGTATTTGTGTTGTTTGCTTTTTCTTACGTGATTTTATGTT

CATAGAGCTAGAAAGTAGCATCTCATGATGGCCCAACAATCTCTGTTGCCAGTTA

AAGGTTCCTTGGAGATGAGGCTGAATAATTATGAACCTCACCTTCTCTGATTGTG

GGAGTGGCAAGAACTGGGGAGACGTCCTCCATAAGTGGAGCACAGGGTATGGGGT

TAAAGCATGACAGGGAGAGTCTTCTGTGCCTGGTTTCTTCTCCTCTATCTCATAA

TGCATTATGGGCCCGAGGAATAGGGGAGGGTTAATAAGACTCCAACCCTAATGGC

CCAACAGGGAAATTCTCATTTTGGTCGATGATATTCTGATGGACTGGTTTGGTCT

TAATACCAGTCAACCGTTGTCCTTCTGGAAATATACATATATGAAATAAATAAAG

TABLE 9-continued

CHD1 DNA and Protein Sequences

```
GTAACACTTGCAGCCAAGTTCCCTGGTTTCTGGGACTTCCCATCTTACCCATTCC
TTTTCCAGGGCTTCAGTGTCCTGATACTTCTGAGGGTGGTTCATACTCAAATAGA
TCTGGGAGTACAGAGTATTTTTCCTTGAGGAAAGGAAGGGTTGGGATGATTAGCA
GAGTCCGGTGAAACATATGCACTCTGAGATAAGATCCAAGCCTGGAGTTTGCAGA
AGATACTGTCCTAATAAGCAGGCATTTCTAAACCAAGTATCTAAGCCTAAGCACA
GCTTGTCCTGGGTGAAATGTCTGCCACAAAAGATAGTTTCTCCTAGCTCAGACTT
AACCATTTATAAAGGTTGGTAAAATACTGGCAGTGACAACAAATTGACTTTTTAA
TTTTCTTATTTGCATTATTCCAATAAATGAAAATCTGTCAGAGTTCTACATGAGG
GAAAGCTTGTGAGGCTGGGCCGGTTTGTTGGAACATCAAATAGTCCTTAATTACT
GATCTCCCTGCAGAGTTTCATATGCTGACACTAAATCTCTGGTCCCTTTTGTAAA
TTACTGAATTTTCTGAGGTTCTGGGAGGGACATGTTGTCTCCCAAATCTGAACAA
ACACAACCACAGTGTGCAGCGGCAGGAAAGAAGTAGTGCAGCTGAGCGTGAGCAG
GGAGGTTGGAGCACAGGGTGTGTATTCGGAGGGGTCCCCTCTAGTATCTTGTGAG
CAGTAGAATTCTAGCATCCTTGAATACCATACTAAGTTTCTGAGGGAGAAAACGG
TGGGATTTTAAAGATATTATTTGGAGGAAGTTAATACGCTACTTAATTAACAGAA
TTGGCAGGTGGTTGGAAATGTGCTAAAGAGGTATGACACATTAAAAATGATAATA
TAAGGATGTTTGACCAGATAATTTAGGAATAACCAAGGAATATTTAACCTCTTCA
CCACAAAGTCCGAGGAGAAATAAATGCCCAAGAGATCAAGCCAAAATACATTTTT
ATTATCTGGGACTTAGGCCTCATATTCCGGAGCAGAATCCGGTAAACTCAGATGA
ACTCCATGGAGAATTTCATAAATCAGATTAACATCAAGGTACTAAAATCAAAACC
CACTAAGAAACCTGTTGCCCCCTTCAAAGCACAACTGAAGTAATGGATCTAATAG
AAGATACATTGTTTGCACTGAGCAGTAGAGTAGTAGAGGAGAAAAGCCCAGAGAT
GGCACAGACAAGTTGTTCCAGTCCCCTTCAGTCAAGGCCTCTGGACCACCACCCT
GCCACAGGCGAAAAATGGGATATTTAATAaATAaAAAATTTTGATTCACCAGACT
GGCTGAAAGGACAGTAaTCCAaATGAGAGTTAACGGCTCCATAGTAGTTTTCTAG
AATGAAAGCTGAACTGAGAAATAGTAACTGATGACATGTTGAGCAGGTTAATAAT
TTGGTACCCTTCCACACCAGTATTTGTTTGTTTGTTTTGAGATGGAGTCTC
GCTCTGTCGCCCAGGCTGGAGTGCAGTGGCGTGATCTCGGCTCACTGCAAGCTCC
GCCTCCCGGGTTCACGCCATTCTCCTGCCTCAGCCTCCCAGGAAGCTGGGACTA
CAGGCACCCACCACCACGCCCGGCTGATTTTCTGTAATTTTGGTAGAGACGGGGT
TTCACCATGTTAGCCAGGATGGTCTCGATCTCCTGACCTTGTGATCCGCCTGCCT
TGGCCTCCCAAAGTGCTGGGATTGCAAGCGTGAGCCACCGCACCTGGCCCCACAC
CAGTATTTTAAAAATAGTTTGTTTTACCTCTAGCGTCTTCCCTCAGCTGACCTA
AATAGTCCAGCCACAATAGCTGAGAGAAGTATACCTACAATTATTTCCATCTCCT
TATATTTCTAGTGATGTTGGCTGACTAACCCACTAATCTAGTTTATGGGAGAGGG
AAAGACTGAAAGAGCCACAAAGTGGATGGCCAACCCACGTGATTACTAACCTTTA
TTGTGGCAAAGTAACTGATACAATGTTTCAAATGTAAGCACATCTCCTTGGAATA
AGTGGAATAACTTAATTCATCCTTGCGGAAGTCCTGAGGATCAAGCAAGGAGGAG
```

TABLE 9-continued

CHD1 DNA and Protein Sequences

CCCAGCTTTCTTTAGACACCACCTTTTTTATCTTTAATAACAAAAAGGAACAAAG

TGATTGTCAGACCAGCACAAAGATACCTCTTAATGTGCAATTTCTATTCTCTTTA

GTGTGTGTGAGTGCACGCATGCACGTGTGTACACCGAGGTTTCAGGTAGAAGGAG

GAATGCAATTCAAATTCTAAAAAAGGAATCAGTCAGCACAAACTAGTTTATTTGG

CAATTCATAAAGATAGGGACTCTTCAGAGGAGGTTGAGAGCATTGTAGGGTTATG

TAAAGACTTCCAGAAGCTGTAAAGACTTCCAGAAGCAAGAAGATTCAACCATCTA

AAACGCCATGCAGGAAAATAGCCAAACCTTCTCCATTTAAGTAGAGAATAAATCT

TAGTAGCGTTCTCTGCAGAATATAACAACGCTGCAAAAAGGCCATTTCACAGGAA

TATAATCAAAACTGCAGATTCTCAGGGTTTCCCGTAAGACGACTTCTCTGCTCTT

CTGTTTGTGGTTTCTTTTTTAGTTGTACATCTCTCCTAGACAAGTCCAAGGAACT

ACTAACGAGAAGATTTCAGGAAGAGGCCTACAGCAATTGCTTGGTGCTTGGGTTC

ATTTGCGGAATCTTGGCAACAGGTCTACAGAGAAGCAGTTCCACGGCAAAAGAGC

TGTGGGGCAGTTGAATAATCCATCCAAACAATGAGGAGTAAACCCTGAGTCAAGA

AACCAGCAAAAAGCAGAAGACTGGGTCAGCAAATAAAGGGAGAAGATCCTTGCCT

CCTTCAGTGCCCCTAGCATGATATTCTGAAAGGCCCTCCACTAAAATACAACTAC

AGTTTTAATAAATTACTAAAATAGAGAATAGAAGTAGTATGTAAGTTGGGATAGG

GTGATCTGAATTAAGTGTTTTAACATTCATGAACTGTTCAGGACAAAAGCTGTAA

GATATTGGTTAACCTCAACATTGTTAAATTAAGTGTGCACTGTAGTATCAAAGAT

ACTCATAAGAATGGAGAGAGTAATTTTCTAAATAGTGGAGGGAAAATAGGAATTA

ATTTTTTTCAAAAGTGGGACTTAGGTTGTCTAAAGAAAGGCCAAAAAAAGCATAA

AAAGATGAAAAAATAGAACTACGAAGAACACAGCCCAAATATATGAATAAAATAG

GTAAATTATAACAAAGTATATACAACAGATATACAAAAATAGTGATTTTTTTTT

TTTTTTT

CHD1 exonJ    SEQ ID NO: 10
GGTGTTCCGACCCGCTAGGCCCCGCGCGGCTCGGATCCGGCGGCGCTGTTTCGGT

CGGGAGTGGGTGGGAGAGAAGCCGGGGCAGGGGAGGAGCCGCCGGAGCTGTCGGA

GCCG

CHD exonI(-21)    SEQ ID NO: 11
TGACACCCAGGGCAGCTACACTCAGAAGCCACAAGGAATGCTAGTGGAGCCCCTC

ATCCCTCCCAGCTTCTCTTCCAAGCTGCCCCGTGGGGCTTGATCCAGGAAGCTAC

TTCAGAAAG

CHD1 exonI(+21)    SEQ ID NO:12
TGACACCCAGGGCAGCTACACTCAGAAGCCACAAGGAATGCTAGTGGAGCCCCTC

ATCCCTCCCAGCTTCTCTTCCAAGCTGCCCCGTGGGGCTTGATCCAGGAAGCTAC

TTCAGAAAGGTTGTGGGATAGCCTTGGGAG

CHD1 exonH    SEQ ID NO:13
CTATACCCTTTTTGTACTCTGTGTATATACTATATTGCAGTAGACAATCATTCCA

AGGGTACAACAAGGTTTACCACAATGTGAGGGACTCAGCCATTGCAAATTGTACA

GATGAG

CHD1 exonG    SEQ ID NO: 14
ATAACCTTACACATCTCCGTCATGGTTGGTGTTTCTCAACCATGGATACACATTC TABLE 9-continued CHD1 DNA and Protein Sequences

GAACTGCATGTAGCATCTCTAAACATACAGTTACCTGAATTGACTGAATCAGAGT

GTCTGAAAAATGATGTGTGATACTATGTTTTGCAAAATCTCCACAG

CHD1 protein encoded by cDNA1      SEQ ID NO:2

MATAVEPEDQDLWEEEGILMVKLEDDFTCRPESVLQRDDPVLETSHQNFRRFRYQ

EAASPREALIRLRELCHQWLRPERRTKEQILELLVLEQFLTVLPGELQSWVRGQR

PESGEEAVTLVEGLQKQPRRPRRWVTVHVHGQEVLSEETVHLGAEPESPNELQDP

VQSSTPEQSPEETTQSPDLGAPAEQRPHQEEELQTLQESEVPVPEDPDLPAERSS

GDSEMVALLTALSQGLVTFKDVAVCFSQDQWSDLDPTQKEFYGEYVLEEDCGIVV

SLSFPIPRPDEISQVREEEPWVPDIQEPQETQEPEILSFTYTGDRSKDEEECLEQ

EDLSLEDIHRPVLGEPEIHQTPDWEIVFEDNPGRLNERRFGTNISQVNSFVNLRE

TTPVHPLLGRHHDCSVCGKSFTCNSHLVRHLRTHTGEKPYKCMECGKSYTRSSHL

ARHQKVHKMNAPYKYPLNRKNLEETSPVTQAERTPSVEKPYRCDDCGKHFRWTSD

LVRHQRTHTGEKPFFCTICGKSFSQKSVLTTHQRIHLGGKPYLCGECGEDFSEHR

RYLAHRKTHAAEELYLCSECGRCFTHSAAFAKHLRGHASVRPCRCNECGKSFSRR

DHLVRHQRTHTGEKPFTCPTCGKSFSRGYHLIRHQRTHSEKTS

CHD1 protein encoded by cDNA2      SEQ ID NO: 4
MATAVEPEDQDLWEEEGILMVKLEDDFTCRPESVLQRDDPVLETSHQNFRRFRYQ

EAASPREALIRLRELCHQWLRPERRTKEQILELLVLEQFLTVLPGELQSWVRGQR

PESGEEAVTLVEGLQKQPRRPRRWEVLSEETVHLGAEPESPNELQDPVQSSTPEQ

SPEETTQSPDLGAPAEQRPHQEEELQTLQESEVPVPEDPDLPAERSSGDSEMVAL

LTALSQGLVTFKDVAVCFSQDQWSDLDPTQKEFYGEYVLEEDCGIVVSLSFPIPR

PDEISQVREEEPWVPDJQEPQETQEPEILSFTYTGDRSKDEEECLEQEDLSLEDI

HRPVLGEPEIHQTPDWEIVFEDNPGRLNERRFGTNISQVNSFVNLRETTPVHPLL

GRHHDCSVCGKSFTCNSHLVRHLRTHTGEKPYKCMECGKSYTRSSHLARHQKVHK

MNAPYKYPLNRKNLEETSPVTQAERTPSVEKPYRCDDCGKHFRWTSDLVRHQRTH

TGEKPFFCTICGKSFSQKSVLTTHQRIHLGGKPYLCGECGEDFSEHRRYLAHRKT

HAAEELYLCSECGRCFTHSAAFAKHLRGHASVRPCRCNECGKSFSRRDHLVRHQR

THTGEKPFTCPTCGKSFSRGYHLIRHQRTHSEKTS

CHD1 protein encoded by cDNA3      SEQ ID NO: 6
MATAVEPEDQDLWEEEGILMVKLEDDFTCRPESVLQRDDPVLETSHQNFRRFRYQ

EAASPREALIRLRELCHQWLRPERRTKEQILELLVLEQFLTVLPGELQSWVRGQR

PESGEEAVTLVEGLQKQPRRPRR

CHD1 protein encoded by cDNA4      SEQ ID NO: 8
MATAVEPEDQDLWEEEGILMVKLEDDFTCRPESVLQRDDPVLETSHQNFRRFRYQ

EAASPREALIRLRELCHQWLRPERRTKEQILELLVLEQFLTVLPGELQSWVRGQR

PESGEEAVTLVEGLQKQPRRPRRKSCQRRRCI

CHD1 Genomic DNA-A      SEQ ID NO: 9
CCTCCTCTCAGATTGCTTAAGATCATCTCCGCGGGCTCCTTGCCCCGGCTAGCCC

CATCTCCTTACACCACCAAGCCCCCCTCACCCCAGCACACACCCAGATACACTCA

CCCGTGATCTTGTCACCTGTGATGATAGTATGTCCTTGGCGTCCATTTGGCCAGA

GCTTTTCAGCTGTCACTGTGACAGACCCTGAGGTTCCCCTCAAGCCAGTAGCTGC

TABLE 9-continued

CHD1 DNA and Protein Sequences

TGTCTCCACTTGCAACTTTCCTCTCCTCCCACTCCTAACAGCCAGTTTTGGCACC

TCTTCTCAGCACCTGCGTTACTTTTAGCAGGAGTATACCTACTTCTTGAGTGTCT

TGATTAAAAATTTGTTTTTGTGCCATGGATAGGCTGTGTTCCTTCAGAAAGGTGT

CAGTCTAATTTTTGTTTTTCTGAACAATGAATGTTCTCATCTTCTAGGCGCTTTG

ATAACCCTGTCTGCCTTGGAATCTGTACTGACCTCCCCAGAGGGAGACTCTTAGA

CCCAGCCTTTCTTGAACAACCTTGGTCCTGGGGAGCAGCGCTAGATCCCAGGCTC

TCACTTAGAGGCTGGGCTTAGAACTGTTGCTTTTTCTCTATCCACGCTCTGCAGG

TGACACCCAGGGCAGCTACACTCAGAAGCCACAAGGAATGCTAGTGGAGCCCCTC

ATCCCTCCCAGCTTCTCTTCCAAGCTGCCCCGTGGGCTTGATCCAGGAAGCTAC

TTCAGAAAGGTTGTGGGATAGCCTTGGGAGGAGGTTTGTTGGTGGGAAGCGTGTG

AACCGGAACAGTCTTGGATAACTTTCTGCTGTTACTATCTAGCATAAGAGGGTGG

GCAGGGTTGGAGAGAGGACAGGAATTTTTCCTCCTAGGACCAAACGCCTGGGATT

CATAATCTTTCACCCTTTCTCCTCCAGCTATACCCTTTTTGTACTCTGTGTATAT

ACTATATTGCAGTAGACAATCATTCCAAGGGTACAACAAGGTTTACCACAATGTG

AGGGACTCAGCCATTGCAAATTGTACAGATGAGGTAAGTTACAGGTTTACATTTT

TTTTTCCCAGTAAATTTGGCACAGATTTAAAATGTGAAACAGTTCTAGACCCCTT

GTTTTTGCTGTTCTCTCACCAGCAAACCCTTTAGTTTGGCCAGCAATGGCTTTCT

GCATGAACTTCAGATTTACTTCATTTGCTAGGTGGTGGTTCTCAAACTTACTATA

AGCACCTGAAGGGCTAGTTAAACGCATATTGCTGGGGCCCACCCCTAGAGTTTCT

GGTAATAGGTCTGTGCTGGGGCTTGAGAATTTATGCTTCTAACAAGGCTCAGGTA

CTGATGCTGCAGATCTGGGTTCTTCACTTTGAGAACAACTACCTTTTGGCCAAAT

GTGATATACGTATTGCAGTAGGTTGAGGTTCAGAATACCTTTGTTTGAGTACTTC

TGTGTTGGAAACTAGTAATCTGATCTTTTATAGATAATCACTTAGGTCTGAATAT

TCTGTTCGCAAAATTAAGAAAGCGTACTTAAAACAACTGAATGCTATATGCCAAA

TTTGAGGTGAAATATTGATGAGTTCTTCCCCTTGATTTTCTTAATTCTCTTGATA

GGGGCTTCACGTTTTGATCAAAAATATTACACCTGTATTCTGGGCTTTTGCTGTG

AATTCCTAGTATTGCTAAAATTCTGCAATTTCTTAACTACCTGTTAAGTTCCTCA

AGGTCAGAGCTTCTGCTTTTTTATCTTTCTTTGCCCAGCACCTTGAATAGTGTG

GGACACGTAATTGACGCTCAGTAGATATTTGTGTATTGAACTCCATCCCTTGTCC

TCCTCCCCTCTTGATGTTTTTCTCTACTGGCCTTATGCTACACAGTAAAGCAGGG

CATGATTATGCCAQTTGATTACCCCCAAGAGATTGGAATAAATGCTAATGCCAAA

TTCCTACAGCTATCCCTGTGAATGGTTTATTACCCAGGAGCCCTGACACTGGCTG

ATTTCTGAATTTTCAGTGCTTCTGTAATATATACTAGTTGGGGGAGGAGAAATAG

AAAGCTTAAACTCAATGTGCGTTTATTGAATACCTTTTCTACTAAGGGCTTGACA

AAGTGGTAGGCACTGGAATATAAAAATGAATAAGGAGACCCTTGCTCTCGAGGC

AGGGCCCACAGTGGGGAGACAGACGTTAAGCCATGCCCACGACAAGAATGACTTC

TGAGATTCCTTCTTTGGATCATGATTTAGTCTTCAGTGGAAACCTGGTACTCCTC

AGATTCCTCTGGTTCAACAGGCGGGATCCCATCCCTTATCATCTCCTCAAATGC

TABLE 9-continued

CHD1 DNA and Protein Sequences

TAAAGGACCCTTGAGCAAAGCCAGGAGGAAGTCATCTAGACGTGAAACAGGGAGT

ATCCACACAGGCTGTGTTAATGACAAAGCTAAAAACATAGTAAATGACTTTTGAA

TTTACTGCTGTTATGAATTATCTATAGCAACACCTCAGGTCAGCTCTGTTATATA

TGTTATTGTGTTATTTCCCATTAAATGATGGTTCCTCTGACTATCTGATTGGCAT

TGACTATGTTTGTTGTAGGGATTGCATACATCTAGTTTAACTCTGGCTGTCAAAT

GAGAGAGCAGTTACTCTTATCAGGATGGGTGTCAGGTTTGATGTCCCCTCCTTTT

CCTGCTTCAGGTTAATTTGTCATGTTCTGTTTTAAACTGAGGCATATAGCTTGAC

CTCCTTTATTTAGGCCATTAACTGCTCTGGGGTAGTTTTCCTGAAGGTTAAAAAG

CCTAGCTTCATGATGGAGGTTAATCAACATGACCATGATGGCCAGGTGTATAAAT

CTGGCCTCTTAAAAATCTGTATTTGAGGCTGGGTGCAGTGGCTCACACCTGTAAT

CCTAACACTTTGGGAGGCCAAAGCTGGCAGATCACTTGAGCCCAGGTATTTGAGA

CCAGCCTGGGCAACATGGCAAGACCCCTTCTCTATWAAAAATTTAAACATTAGCT

GGGCATGGTGGCATGTGCTGTAGTCCCAGATACTTAGGAGGCTGGGGTGGGAGGA

TGGCCTGAACCTGGGAGGCAGAGATTGCAGTGAGTTGTGATCTTGCCACTGCACT

CCAGTCTTAGCAACAGAGTAAACCCTATCTCAAAACTTAAAAATCTGTGTTTGGC

CCCTAGCCGTCCTCAGCTCTTGAGTAAATCTCAGCATCCTAGGCTGTTACATTAT

GGCCCAAATATTCAATAGAGATGCTGTATATCCTTGTTCCTCTCAAAACCCCTCC

TCATCACCATCAAAAAGCTGGTTTAGTTCTCTACCTTTAGATAAAGAATCATCCC

AAGACTCAACATGAGCTGCCGTGACTTGTCCAAGATGACACCTCTTTACAATGTA

GAGCAGTGGACAGAACACAGGTCACCCTCCGCCGAAAGCAACTATCTACTGTCTA

ACATTGCCTCCTAGGCCTGCCATATATAACCATCAAAAACATTTTAGTTTAGAAT

AAAGTGAATTGTTACAATTTTTATTTTTCATTTTTGTGTTTACATTTACTCTCAA

TGACATGTTTATTCCCACCTAATATCTTGAGGCTAACCACAAAATCTGCAGCATT

TCCAGGCAGAAGATACTTGTGACTTCCCTGTACTATCCACTACATACTTGACCTC

TTTCTCTTTCTTCCTGTCTTCCCTTTCTCTATACCTTATTATCTTTCTTTGGAAC

CTCTTGTAACAAATTTTGAGCCATTTCTCCCCTCACTACTCAzATATCACTTTTA

TGAAGGGGCGGGGGGGAAACTTAGGTGGCAAAAATATTTTACAGAAACAGTTTTA

AACATGTTTTGAAGCATACTGGTCACGTGTTAGAAGGCCAAAAGCCAGGGAATTC

ATTCCCTTTCATTCATTGTGCTGTCTAGGTTAAGTTTTCACAGGACTTCTTGGTA

CACTGAGTTTGCCTCAGATTGTCTCCTGCCAGTTACAGGGAGTGGAGAGGACTTT

GATATATTGGTAATTAGAAGCATTsCyGATATGGTCTTCGGTGGGAGAACCTGTG

TCTAAGGTTCCTTCTCATCTGTATTCCAACACTTTCATTTAATCCTACTTCATAA

GTGCCTCCAAAGCAAGGATTTTTTTTTGGTTTAGCATGGTTTCTTTGATATAAC

AATAGACCGACCAAGATTTTCCTtATGCCATCTGTTTTTTTGTAATTATGATGCA

ATAGAGAACTGTTTGCTTGTTTATCATTTAAATCTTGCCTTCTTCCCAAAACGAT

TTCAAATAGCTTGAAGGAAAATGAATAAAATATATTGAGCACCTACCCTATGCCA

GACTCTATACTGAAGGGTTTCTATAGGTTATTTCATTTACTCCTTAAAACAACCA

CATGAGATAAGTAGTATTAGCCACATTTTTGAGGATAAGACTGAGGCTTAGGGAA

ATTGTGTTACAAGGCTAATAAGCGAGGTCAGGGATTCGAGGTCAGGGATTCAAAC

TABLE 9-continued

CHD1 DNA and Protein Sequences

CCAGCGTGCCAAGGCCACTAACCATTATGTGGAAAGCTTAGGTAAGCGCTTGTAT
ATAGGACAATCAAGAATAAAAGAATATGTCCATTAGAAGGATTGTACTGGGCTAA
TCTTTCGTTTTAAAGAACAGCAGCAGCATTGGAAAAGAGCGGTTAACAGTTTTTA
TTAGCCAATTTCTATTCTAGAACACTGAGAGGAGCTGTTGACAGGCCCTGGTTAG
CCCCAGCAAGTAGTTGTATTAAAATTACCAAACTATAGGCCTGCATTAAGGTATA
AAATAAGAATGGGGACTGGAAGGGATATAAATATCTGCTAAATATAATAATTTCA
GTTCTAATCACTATTTTCTTCTGAAGATTATTTGCCAGTACATAGGCAGATCACT
GTCTCTCCTTTAGGTTGATGGTATATGACTACAGACTTTGTCATTTAGGGTCCAG
AAAGATCACCCTAGCTAGTAGCGTTTTAAGGTAGAGAACTAGATATTGTTTCATT
GCCTGTGGTTTTCTGTTCTTGTAAGAGAATTGAGCTTGGGTCTTCACTGCCACGT
GACACCTTCAGATAAGGGGCAGAGACAGCTGGCCTGAGGATTGTACAGAGGTCTT
ACCTTGATAGCTCCTCTCCAATCCTATGCATCCTAGGAACACTCAAGACACTAGG
TTGTATCTTTGCAGATACTGTTTTAGTGTCTTCTGGAACCAAGTCTCTTACTTAA
TCCTGGCCTGGTTTCATATTCTCTCTATTGTATTCTCTCTATAGTTTTTGTCTTA
CTCTGGAACTCTTCCAAGGACAGACATTGAAGAAAGGTATTAGAATAGCAAAGGC
AACAAATTGCAAGGTATACTTATGGCATAGCACATCCCATTAATTATAGAATAAA
AACACAACATCTGTTTTCTGCCTCTAATATTAAATCTTGACATTTGCACAACACA
TTTTAGTTCATAAAGCTCTCATATCTCAGATAATCACTGAGTTAGGAGACTGGTT
ATCTGCAGAGGGCTTTATCCTTTACAAGGGCTCTTGGGTACGTTACTTCACGAAA
CCCTCAGGGAAGCTCCAGTTTCTTGGGGATCTGGGGCCGGGGCATATGTCTTTGG
ATACCCAGTTTGGTGCTGTGCACAGCACTGCTGTACCTCCTATTCATTTCCCATC
TCTTACCCCACAAAGACTCCTTCCTTCATTCCTTCTATTGCTGATCTGTTTTCCT
TCATCTTCCTAGGCTGCCAAAGTAAATGCAAAACAAGCACCAGAAATCTCAGCTT
GTGATTTCTGAAGGGCATTTTTAAATGGCAAGTTTGGTGTGGCACTGTTACATGT
TCTTTTTTCTTTGGAGAGCAAAGCCCTTTGAGAGAGCAGGAACTCTTCTGTCAAT
GCATACGTTGTAGGATCCATACTGTGGAATCTCTTGTACCTAGTGCTGCGTGAAA
ACAATGAGGATTCCAAGTCTACTTCACTGGACATCGGTTCTCAAACTTTTAAGAT
ACTAGAAGTCCTTTTATTAAGCCAAAAGACCCTATGTATTAATTCTGTCTTCCAG
GGGTAGGAGTTGGGGTGGGGTTTGGAAAGCTTTGTCTGGATAAATAATTAGTATT
GTAGTTCCATTTATTTGATGTCTGATTTTGCGCTTATTAAAATTGATTTAAATCC
TCAATGGAAAATGATTTTTITTTTTCAAATGCCAAGTGTTGTGTGACTTGCATTT
GGATTATTCCCGGTGCAACCTGAAGATTCCTTGTGATGAGTTGTGGTTCCATCAT
CTTGGGAACCACTAAGAGAATTCTGTTTTACTCACAATCCAAACAATAAATGTTT
TTTTCCCTATGTATGCCTTTATCCAGCACACAGTTTGCTAGACTTATGGATGAAT
ATGGGTTAATATAACATGGTATCTATCCTTCTGGAAACAGACTTTTAAAACCTTA
CTAAGCATTCTCTGCATTCATCAAATGTGAAGTGAGTGCCTGGTGTGTGCCAGGC
ATCGAGCTGGGCACAGCATATCCCTGCCCTCAGAGCTTTACAGTCCAGTGAGTTC
AACAGAAGATGAACAGTTTTGATGACACAAAAAATAGACACATGTGCATGCTGTG

TABLE 9-continued

CHD1 DNA and Protein Sequences

```
ATAGGGGGAGATACAAgTTCCTGTGGAAGCATCATCTGGGAGGACCAGGGAAGGC
ATCTTGGAAAAACTGAGCTCTGAAAGATGGATAGAGTTAACCACATGAAGAGTGG
AGAAGGGTACTTCAGACAAGGTGAACAGCATCAGGAAAGCCCAGGGAGGGTATAG
AAAAGAAAGAACAGTAATTCTTGCAGTGGCTTTCAATGGGAGTGGCAGTCATGGA
AGGAAGGAGAGGTAGCAGGGACCAGCTTTTGAAGGGCTTTGTGTATCACATTTTA
AGAAGTTTAAATTTTAACCTAAGGTCACTGGGAAGCCATTGGCAGATTTTGTATG
TTAGGAAGTTCACCACTCACCTACTTGGAGTATTGCAGGTGGAGCTAATGTGGAT
GGGCCTCCTGCCCATTATTAAATCCTGTTCCTGTCAGGAACAGGACAGCCCATGC
TGTCTCTCCCTGTGTGTCTGTCTCTCCCTGTGTGTCTGTCTCTCTCTCTCTCT
GTCTCTCTCTCAAAAGCTAAAGGAAAGCGCATAGGTTCCAGAAGGAAAAAGAA
ATAACCACTAGAAAAATAAGTATAAGCTGACTTTACCATGGCGCAGTGAGATTCC
AAACCAAAATAAGGTTTCTAGGGATTGAGCTTtTAATACTGGTACTCCAACAGGG
AGATAGGACTTGGGAAACTGACGCTGTGTGAAAGTTACAGAATTAAGCAGCCTGC
AAACCTGGACCTTTGAAAATCGTCCTACTGACCCAGGAAAAGTGCAAGGAAGTGG
GTTCTCCAGAACCTTGGGTAGGCCAAACATTACTTGAAGGCATCGATCTAAATAA
TACACAAAAGCATTATTCAGGAACACCCTGAGAAATTAACATAAAAACTGATTTG
GCCAGGCATGGTGGCTCAGCCTCTGGTAACAGTGCTTTGGGAGGCCAAGGTTGGA
AAATCACTTGAGGCCAGGAGATCCAGGCTGTAGTGAGCTATGATTGTACTACTGC
ACTCCAGCCTGGGCAACAGAGGGAGAGTCTTAAAAAAGCAAACTGTCCAAGATCA
TTGAAACCATTAGCACTTAGGAAGAAACAAATGAAATTACATTCAAGGGGGTCAC
ATTTAAATCCAGGGCTCTCAGGACTCCCAAAGTAAAAAGATGGACATAAAATAAA
AAAATTACAAGCCACTTGAGAAAAAAATAAATCACCATGAGGTAGAGATAGCAGA
GGAAAAATTACACATGAAGATCTAGGAATTAGGGAGCTATCCAAGATAGACTGTG
AAAGTATGTTGCAAGTGACTGAGGGTAATGAAAAAAATGTCATAAGAGCATGAAT
TAGAAGCGTTTTGAGAAAGAATGAAGATAATGTGGTCATTGACTGTAAACTCATT
TGATGGGCAACGATAGATGAGACACAGCTATTAAGAGTGGATCGATAACCTTGAA
TGTGGATGTGAGGCAACTGTAGTATAGCACAAAAAGGTTGAGAAATGATGGAGCC
CTTAAGCTGCTTGTGGACACTGGTCTGGAGGGGACAGGACCAAGAAAACCAGTC
ATGGAGGTTGAACTAAGTCATCTCTCCAATGTATCCGTGCCTGTTACGTGCCAGT
GCCGTTTAGGAGCAGAGGATATTGTAATTTTTTTAAAGTTCCTATGAATACCTT
CTAGTGGGTCATAATGGCTCAACCGGGAAATGGCAGTAGAGATGAAGAGATGGAT
GGATTCGAAAGACATTTTTTGGAAGTTGGAATTAACAGGATATGGTGAATAATCA
AGAGATAGTAAAAGCATAATGGAGGAAACAATGGTTCTTCCTGTTACCATAGGAA
GAAGCTTTGGAGTAGAGTTTTATTCATTTTAAATGCATTTATTGTGCACTTTATT
ATAGGTATTGGAGATTGATGGAAAATAGTCTCTGACCTCAAAGAGTTTCACAGGA
AAGATGAGCGATGGCTATGTAATATGACCAATACTGGGATAGAGAGGTGCCCAGG
TCACTACGGGAGGACTTAGGTGATTTCTAACTATGTCTGAGAGTAGGGGAAATGG
GATCAAAGAAAACATCTCAGAAGACATGAAGCTTGAGCTTATGTCTTGAAAAATT
TAAAGTTTAACCTAACCAAGGATAAAGAATCAGAAGAAACAGCATATTCAAAAGC
```

TABLE 9-continued

CHD1 DNA and Protein Sequences

TAAAGAACACGGGACTCTTGTGTGCTTTGCATGTACACACGTGTGTGCGTGTGTG

TCTGAAAGGATTGGAGAGGAGGGCGAAGAGAATAACAAGATGAACGTCAACCTAA

TGTAGAATGTTTGAAGTTTGTATTTCACTTAACAAGACAGCGGGGAGTGATGGAA

GGATCTTAGATAGGAAAGGGACATGAGCACGTTTGCCAAGAGAGCTCGTTCTGGT

CATAGTGGGTACGTGAAGGTGACAAATCTGGAGGCAGATAGCTCACATTTGGAGG

CAGCTGCAGTCATCCAGATGAGAAGTGAGAGGGACCTAAGCTGTAAATTGTGGGA

ATAAAGACAAGACCCGTTAAAAAGAAAGAGAACACACCATGTAGCGTGGAAAGGA

GAAGGGTGGAGAGTAGCCTGTGCAGAAGGAACAACCTTCAAAAAGACATGGAAGA

CTGAAAAGACACCCTGTTGTAGGGAGATCAGCAATGCATTTTTTATAACCAGGTG

ATACAGGGAAAGGGTAGGATCTGAAGCTTGAAAAATAGATTGGGGCTGATTGTA

AAGAGCTTCGTGTCATTCCCAGGATTTTGGAACTGATTTTACTAACATGAAAAG

GTTTTGTTTTAAAATACTGAGTAATATAGTTGGAACTATAATTTAGAAAGATAAT

AGCTGGTGCCATCACTCTTCTAAGCAAAGATAGTAATACATTTAATGCTCATAGG

CTTTAGTAATACATTTAATCCTTACAGTAAGCCTATTAGATAAAAACCATTATTA

TCTCCCTTCTATAGACAGAGAAACTGGCATTAGGAGAATGAGAACTTGCCTATGG

TCCCACTCTGGAAATACCTAGTAAGCGACAGAGCCAGGATTCAAACCCAGGCAGC

TTGACTCCAGAACTTTCGCTCATAACCTTACACATCTCCGTCATGGTTGGTGTTT

CTCAACCATGGATACACATTCGAACTGCATGTAGCATCTCTAAACATACAGTTAC

CTGAATTGACTGAATCAGAGTGTCTGAAAAATGATGTGTGATACTATGTTTTGCA

AAATCTCCACAGGTAATTCTGTTGTACTTTGCTTATAGTTGAGTACTGCAGGGAT

CTTAGGAAGTTAGAGCAGTAGTCCAGGCAGGAGATGATGAAGGCTCAGACTAAAG

CAGTCTGTAGGAAGGAAGAGAAGGGAACCGGTTTGGAGACTTAAGCGGGGAATT

GGCAGTATTTGTGAAGTGGAAATGCAGTATTTTCTTGTAGAGTATGAACCTTGCC

TAGGAAAGGGAGTAGAGGACCATACCTTTAGTTGTAAATTATCCTCTCCCAACTG

GATCTGTTGATTTATGGCTATGGTGGTTGGGGAAAAGAGGATTTAACCATTTGAA

GAAGTTTGTGTAGAGGATTATGATTGAACTCAGGCTGTTGTCCTTGTGTATAGTT

TCATGCTTATACTCTTGTTTGTCTTTACTTCTCTATCCAGGGCCCTTGGAAGAAA

ATCCTCGCTGTGTCCAGGCTGAGGCGGGGGGCTAATGACAGTGTGAGCTCTAGAT

GGTGTGAGACCACCCCAAAGCCAAGAAATGGCTACAGCCGTGGAACCAGAGGACC

AGGATCTTTGGGAAGAAGAGGGAATTCTGATGGTGAAACTGGAAGATGATTTCAC

CTGTCGGCCAGAGTCTGTCTTACAGAGGGATGACCCGGTGCTGGAAACCTCCCAC

CAGAACTTCCGACGCTTCCGCTACCAGGAGGCAGCAAGCCCTAGAGAAGCTCTCA

TCAGACTCCGAGAACTTTGTCACCAGTGGCTGAGACCAGAGAGGCGGACAAAGGA

GCAGATCCTAGAGCTGCTTGTGCTGGAACAATTTCTTACCGTCCTACCTGGAGAA

CTACAGAGCTGGGTGCGGGCCAACGGCCAGAAAGTGGCGAGGAGGCAGTGACGC

TGGTGGAGGGTTTGCAGAAACAACCCAGGAGACCAAGGCGGTGGGTGAGGAGGGG

GAGTCCTGATCTGTGTGATGTGGAGGGGGACTATTTGCTGGAAGGCTGGATTTGC

GGGGAGAGCTTGCAGGATCCCCATAAATTATTAGTGGCTCTGCCCTTGGGTTGCT

TABLE 9-continued

CHD1 DNA and Protein Sequences

CATATACCATGAGCCCCATGGATTAGGGGATGTGTGTATGAATGTGACTTTC

TGGATATTGGAACACCTGTATAGGGACCATCTGAGGGGgTCTCAGCCACCAAAGG

GTCATGGCTTTGGTTTTCCCTTCTTTGAATGTTGAGCCGTGGGTTCCTGGAGAGG

AGAATTTTGTGACTTCCTCGAAGGTTCTCATAGATCCCCAGTCACAGATCCCCCT

TCCTGGCTGGTCAGCTAGGGAAGCAGGCAGCAAGGAGAGCTGCAGGTGGGACAGG

TGGAGATGGGAAGGAACCTTGGGTGACAGGGGCCCAGGCTGGGGGTGGTGAGAGA

GCAGTGCAGGCCTGCGCATCCCCTGCCTTGTCCTGGGGAGGATAACCTTCAGCTC

CTCCTTGCCTGCTCCATTGAAACTGGAGTTTCCCCTCCTTGTCTGGGTCCCTCTG

GGAGTGTTTTCTCTAGGCATCTTCTCCTAAAATAAGCTCCCGTGACAACCAAGAA

CTTCCTCCTGACTCCATGGTGACTGGAAGTTGGAATTATTCCCAGGTGACTGTCC

ATGTTCACGGCCAGGAAGTCCTGTCAGAGGAGACGGTGCATTTAGGAGCGGAGCC

TGAGTCACCTAATGAGCTGCAGGATCCTGTGCAAAGCTCGACCCCCGAGCAGTCT

CCTGAGGAAACCACACAGAGCCCAGATCTGGGGGCACCGGCAGAGCAGCGTCCAC

ACCAGGAAGAGGAGCTCCAGACCCTGCAGGAGAGCGGTGGGAAGCATCAGCAGAA

AGGGGGGATTGTGGCAGAAGGCAGGCAAGGAGGGGGACATTTCTCCTATACCAAG

GAAGCTGGGTAGATAGACTGTATGGAAAGACATCACAGAATCCAGGATGTCAAGA

GGAGACAGTACCGCCAGCTAGAGTCCCCCATAAACAGGGCCAAGCTTAGACAGCA

GATTGTTGCTTGTTCTCTTGGCATTCTGATAGTCTCATAGGTGATGGGATTGGGA

TATGGGAGCTACCCTTAGGCCAGTTTCTTGGTTCCCATAATAGAAAGGATAGGGC

CACCTTCCTACCAAAGATGGTGGGGATGCCCAGATTTTTGCCCATTATTGGGGC

ATGCTGCATATTACTGATCTTTGCCTTCTTTTCTTCATAGAGGTCCCAGTGCCCG

AGGACCCAGACCTTCCTGCAGAGAGGAGCTCTGGAGACTCAGAGATGGTTGCTCT

TCTTACTGCTCTGTCACAGGTGTGCCCTAGTTACCTCTGTACCACAGAGAATTTG

TTTGAAGAACCACTGGGCATAAGCCATACTAAACAGGTGAAGCAGGATGCACATT

TACACTCTTGCCAGTTTTAAGCTCACAGTTCTGCAGGTACCTGGAAGGGGAGGAG

ATAATGAGATAAATTATCATACCTTATATTGGATCCACAGGCACCAACACCAGTT

TATTTGCCATTGACTAGAAGAACTAACAAAATGGATTATTTTGTAACACTCCAG

TACAACTGCGAAGTTGTCAAATGAGGGTTTTTTAGTTTTTTTTTTTTTAAAGGA

ATAAATTTGATAGTCATTTGTAAGTATGACAGACTGTACTGCTGAGACATTTAGG

AAGTATTCACCATGATCAAAGCTCTGAAACTAAGCCATGTGGCTGGAGAAAAAGA

AATAGAATTCATGTATGGTTTTAGATTGTAATCTAACTGAGGAAAAAAGTCTTGT

TTTGGCTATAGAGTATAGAAACTATTGAAAGTGATTAGAGTCTTTAGGGAAAGTG

TACTAGAAAAGATGAATTTTGCAGAAATGTATATAGCGTTAAAGTGTCAAGTAGG

GAGCTGAATGATGATTTTTAAGACCTTTCCTAAATTTTAAACAATACCTTAAAGA

AGAAGAACATAAGCTGGTCCTCAGGAAAAGTGGTGGAGTTGGAGGGGCAGGGCC

AGTGCCACAGGGGACACATGGCTCCCCCGAGAATGAGTTTAAGCAGCCCGCCACT

CAAGCTCCTTTCATCTCCTAGAGGAGTCCACCTATTGTGTGACCTTCAACAGGGA

CAAAATACGAGGCTACCCGTAGCATCACGTTTTGATGAAATCCTTATGTGGTTTC

AGGGACTGGTAACGTTCAAGGATGTGGCCGTATGCTTTTCCCAGGACCAGTGGAG

TABLE 9-continued

CHD1 DNA and Protein Sequences

TGATCTGGACCCAACACAGAAAGAGTTCTATGGAGAATATGTCTTGGAAGAAGAC

TGTGGAATTGTTGTCTCTCTGTGTAAGGAATTTCAAGTATTCTAGAGTGTTCTAA

GCCCAGAGATCTTTTTCCTGCTGGAAATTTTGGGGGATCTTAGACCTTAGATTGT

ATGCAGTGAACTTCTCTTATGCCTT(CCCACCAATAAAATTGAGGGATTAGGTGA

AAAATACGGTGTCCTTTCAAGTAAAAGATAAATGGATGGAAATGGAAACCTCTAA

TAGGAAAACAAACTTGTAATATTACAGCTTTAGTGCAGAAATATTTGAAGTAAGC

ACATGAGTTTTAAAACAGTAAGAGTTGGAGATAATCTTTCTTGAATATGGGAAAA

GAGGATAAGGTGTACAATGGTATAATTATTAAGTTGCAGGTGAAAACCACAAGAA

AGGCAAGAGATACGCAGTCCTTGGTTAAAAGTACACAAACTAAAGAGATGAAAGA

TTTCATCACCTGAGCTAGCTATGTATTTGCCCCACAACCTACCAAATAGAAAAGG

ACCGCTCTTAACACAGGGAATTGTTGAGCCAATCGTGATATCCTATTTTCCCTCT

CTTGAGCAGCATTTCCAATCCCCAGACCTGATGAGATCTCCCAGGTTAGAGAGGA

AGAGCCTTGGGTCCCAGATATCCAAGAGCCTCAGGAGACTCAAGAGCCAGAAATC

CTGAGTTTTACCTACACAGGTGAGGAATGACAAAAACGGTGTTACCCACCCTGAG

CCAGCAGTTCCTCTAGGCAGTGCTTCTCTCTCTGTAGGGCCCCGCTCTCATCA

GTTCTTCTAACATGTCAGCCAGTACTGCTTTCTCCCTCTGACAGCCATTTCTTCT

GTCATTGCCCTCCTCTTTTCTCCTCCCATCATTTGTCTGATAGCAATGTAATACA

AAAGGGTGAAAGAAAAATGTTAACTTTTGGAATTGCAGCTATACCATTTACTGTA

CAATTCCCTTAAACCCTCGATTCTCAATCTCTGCATTTGTAAAATGAAGATTATA

TTTGTGCATACCAAGGTTTGTTGATAGCATAACAATATGAGAAAGTGCTTGGCAC

AGGACAGGCATTCCATTTAGTCTTGCCATCTCAAAACCCTTTGTAAAAATCTCCC

CATTGTGTAGAAGGCATTGTTGCCGCTACAGTGACCCCCTTTTTCCTCTCACCCT

TTCTACAGGAGATAGGAGTAAAGATGAGGAAGAGTGTCTGGAGCAGGAAGATCTG

AGTTTGGAGGATATACACAGGCCTGTTTTGGGAGAACCAGAAATTCACCAGACTC

CAGATTGGGAAATAGTCTTTGAGGACAATCCAGGTAGACTTAATGAAAGAAGATT

TGGTACTAATATTTCTCAAGTGAATAGTTTTGTGAACCTTCGGGAAACTACACCC

GTCCACCCCCTGTTAGGGAGGCATCATGACTGTTCTGTGTGTGGAAAGAGCTTCA

CTTGTAACTCCCACCTTGTTAGACACCTGAGGACTCACACAGGAGAGAAACCCTA

TAAATGTATGGAATGTGGAAAAAGTTACACACGAAGCTCACATCTTGCCAGGCAC

CAAAAGGTTCACAAGATGAACGCGCCTTACAAATATCCCCTAAACCGGAAGAATT

TGGAAGAGACCTCCCCTGTGACACAGGCTGAGAGAACTCCATCAGTGGAGAAACC

CTATAGATGTGATGATTGCGGAAAGCACTTCCGCTGGACTTCAGACCTTGTCAGA

CATCAGAGGACACATACTGGAGAAAAACCCTTCTTTTGTACTATTTGTGGCAAAA

GCTTCAGCCAGAAATCTGTGTTAACAACACACCAAAGAATCCACCTGGGAGGCAA

ACCCTACTTGTGTGGAGAGTGTGGTGAGGACTTCAGTGAACACAGGCGGTACCTG

GCGCACCGGAAGACGCACGCTGCTGAGGAACTCTACCTCTGCAGCGAGTGCGGGC

GCTGCTTCACCCACAGCGCAGCGTTCGCCAAGCACTTGAGAGGACACGCCTCAGT

GAGGCCCTGCCGATGCAACGAATGTGGGAAGAGCTTCAGTCGCAGGGACCACCTC

TABLE 9-continued

CHD1 DNA and Protein Sequences

GTCAGGCATCAGAGAACACACACTGGGGAGAAACCATTCACGTGCCCTACCTGTG

GAAAAAGCTTCAGCAGAGGATATCACTTAATTAGGCATCAGAGGACCCACTCAGA

AAAGACCTCCTAGCTAGGTCCCCATGTGAGGAGATCTGCTTTCAGCCCTCACCTA

AGGGAGGTGAGGAAGAGGAAAAGCCCTCTTGTCAGCCTGGGAAGACCTTTTCGAG

GGAGTCTCCCTGACCTGCTCAGATCTGACATTACCTCTTCCTGCAACTAAACACG

AGCCTGGGCAGAACCTCTCAGCCTTCCTCTACGCCTTGAGGGGATGTTTCATCCA

AAGTACAACCTGAATTGAGGCTTCTCCTTCACTGGAGTGCACCTGCCTCTACCTC

ATGGGTATAAAGTAGGAGAACTAAGAGACTTAAGAGGTCGTGGTTCCTATATCGT

CCAAAAAATAGGCTGTTACATATCCTAAAGACTGCTCAACAGCTTCAAGTTGAAA

GTGGCCAAGGACAGCCCCTTAGGTTTGGGAAGGGACGAGCCTGAAGGATTCTGTC

TTTACTGGGGTCAAATCTTAAAGCACACAGCTCTGGACTCAAGACAGGAGGTTTG

CGTCCTGATGGCTTTGCACACATTCACAGGATAACTGCATAGATCCCTCGCTGTC

TGATTCACTTCTTACCATGCACTTTCCTTTGATGCTGAGGAGAAATGGAAGTGGG

CGAAAAATCTCAAGGCTGCTTCATGTGGACCTTGTCAAGCTGCTCCCTCCCCCAG

CGTCAAATTGTTATCAGGTGCCAaaCACTGCTAGAAAGGAGGGCCTAGTCAGAAG

CCTCTTTCCATACGAGTTTTGGTTTTGTTTTAATATTTTTTCTATTAAAATAC

TCATGCATTTAACCTTCCCGTTATTCAACCAGTCTCTTGGTTGCATCCCTAGCAC

TTCTACTACAAGTGAGATGGTAGTGTTTGAGTGCTTACCGAGTAAAGCATAATTC

GGTCATAATGAAATCGTTCACATTCCCTCATATGCACAAGCCCACCAACCCCTTC

ACACCCCCTTCACAGGGGTCGTATGAGTAAGGGGATTTGGAAACTGTCAACTTA

CAAAGGCACTATAACAATTACAGAATCATGATTGCCATGGGCCACTTTATTTACA

TGAAGACAACTGGAGAACGACTAAGACCAAATTATGGAAAATAAGAAAAAGCTGT

TGCTGGCAAGACCATCAAGACTGTTCTGACACCCTGTCCCCATCATCCCTGACTG

AGTACTCTGACATCACGGAAAGTGTTGAACCTGGGACCCTGAGGAATTCACCAGG

AGTAAATGGCTTTCATGTATTTGTGTTGTTTGCTTTTTCTTACGTGATTTTATGT

TCATAGAGCTAGAAAGTAGCATCTCATGATGGCCCAACAATCTCTGTTGCCAGTT

AAAGGTTCCTTGGAGATGAGGCTGAATAATTATGAACCTCACCTTCTCTGATTGT

GGGAGTGGCAAGAACTGGGGAGACGTCCTCCATAAGTGGAGCACAGGGTATGGGG

TTAAAGCATGACAGGGAGAGTCTTCTGTGCCTGGTTTCTTCTCCTCTATCTCATA

ATGCATTATGGGCCCGAGGAATAGGGGAGGGTTAATAAGACTCCAACCCTAATGG

CCCAACAGGGAAATTCTCATTTTGGTCGATCATATTCTGATGGACTGGTTTGGTC

TTAATACCAGTCAACCGTTGTCCTTCTGGAAATATACATATATGAAATAAATAAA

GGTAACACTTGCAGCCAAGTTCCCTGGTTTCTGGGACTTCCCATCTTACCCATTC

CTTTTCCAGGGCTTCAGTGTCCTGATACTTCTGAGGGTGGTTCATACTCAAATAG

ATCTGGGAGTACAGAGTATTTTTCCTTGAGGAAAGGAAGGGTTGGGATGATTAGC

AGAGTCCGTGAAACATATGCACTCTGAGATAAGATCCAAGCCTGGAGTTTGCAG

AAGATACTGTCCTAATAAGCAGGCATTTCTAAACCAAGTATCTAAGCCTAAGCAC

AGCTTGTCCTGGGTGAAATGTCTGCCACAAAAGATAGTTTCTCCTAGCTCAGACT

TAACCATTTATAAAGGTTGGTAAAATACTGGCAGTGACAACAAATTGACTTTTTA

TABLE 9-continued

CHD1 DNA and Protein Sequences

ATTTTCTTATTTGCATTATTCCAATAAATGAAAATCTGTCAGAGTTCTACATGAG
GGAAAGCTTGTGAGGCTGGGCCGGTTTGTTGGAACATCAAATAGTCCTTAATTAC
TGATCTCCCTGCAGAGTTTCATATGCTGACACTAAATCTCTGGTCCCTTTTGTAA
ATTACTGAATTTTCTGAGGTTCTGGGAGGGACATGTTGTCTCCCAAATCTGAACA
AACACAACCACAGTGTGCAGCGGCAGGAAAGAAGTAGTGCAGCTGAGCGTGAGCA
GGGAGGTTGGAGCACAGGGTGTGTATTCGGAGGGGTCCCCTCTAGTATCTTGTGA
GCAGTAGAATTCTAGCATCCTTGAATACCATACTAAGTTTCTGAGGGAGAAAACG
GTGGGATTTTAAAGATATTATTTGGAGGAAGTTAATACGCTACTTAATTAACAGA
ATTGGCAGGTGGTTGGAAATGTGCTAAAGAGGTATGACACATTAAAAATGATAAT
ATAAGGATGTTTGACCAGATAATTTAGGAATAACCAAGGAATATTTAACCTCTTC
ACCACAAAGTCCGAGGACAAATAAATGCCCAAGAGATCAAGCCAAAATACATTTT
TATTATCTGGGACTTAGGCCTCATATTCCGGAGCAGAATCCGGTAAACTCAGATG
AACTCCATGGAGAATTTCATAAATCAGATTAACATCAAGGTACTAAAATCAAAAC
CCACTAAGAAACCTGTTGCCCCCTTCAAAGCACAACTGAAGTAATGGATCTAATA
GAAGATACATTGTTTGCACTGAGCAGTAGAGTAGTAGAGGAGAAAAGCCCAGAGA
TGGCACAGACAAGTTGTTCCAGTCCCCTTCAGTCAAGGCCTCTGGACCACCACCC
TGCCACAGGCGAAAAATGGGATATTTAATAaATAaAAaATTTTGATTCACCAGAC
TGGCTGAAAGGACAGTAaTCCAaATGAGAGTTAACGGCTCCATAGTAGTTTTCTA
GAATGAAAGCTGAACTGAGAAATAGTAACTGATGACATGTTGAGCAGGTTAATAA
TTTGGTACCCTTCCACACCAGTATTTGTTTGTTTGTTTGTTTTGAGATGGAGTCT
CGCTCTGTCGCCCAGGCTGGAGTGCAGTGGCGTGATCTCGGCTCACTGCAAGCTC
CGCCTCCCGGGTTCACGCCATTCTCCTGCCTCAGCCTCCCCAGGAAGCTGGGACT
ACAGGCACCCACCACCACGCCCGGCTGATTTTCTGTAATTTTGGTAGAGACGGGG
TTTCACCATGTTAGCCAGGATGGTCTCGATCTCCTGACCTTCTCATCCGCCTGCC
TTGGCCTCCCAAAGTGCTGGGATTGCAAGCGTGAGCCACCGCACCTGGCCCCACA
CCAGTATTTTTAAAAATAGTTTGTTTTACCTCTAGCGTCTTCCCTCAGCTGACCT
AAATAGTCCAGCCACAATAGCTGAGAGAAGTATACCTACAATTATTTCCATCTCC
TTATATTTCTAGTGATGTTGGCTGACTAACCCACTAATCTAGTTTATGGGAGAGG
GAAAGACTGAAAGAGCCACAAAGTGGATGGCCAACCCACGTGATTACTAACCTTT
ATTGTGGCAAAGTAACTGATACAATGTTTCAAATGTAAGCACATCTCCTTGGAAT
AAGTGGAATAACTTAATTCATCCTTGCGGAAGTCCTGAGGATCAAGCAAGGAGGA
GCCCAGCTTTCTTTAGACACCACCTTTTTTATCTTTAATAACAAAAAGGAACAAA
GTGATTGTCAGACCAGCACAAAGATACCTCTTAATGTGCAATTTCTATTCTCTTT
AGTGTGTGTGAGTGCACGCATGCACGTGTGTACACCGAGGTTTCAGGTAGAAGGA
GGAATGCAATTCAAATTCTAAAAAAGGAATCAGTCAGCACAAACTAGTTTATTTG
GCAATTCATAAAGATAGGGACTCTTCAGAGGAGGTTGAGAGCATTGTAGGGTTAT
GTAAAGACTTCCAGAAGCTGTAAAGACTTCCAGAAGCAAGAAGATTCAACCATCT
AAAACGCCATGCAGGAAAATAGCCAAACCTTCTCCATTTAAGTAGAGAATAAATC

TABLE 9-continued

CHD1 DNA and Protein Sequences

TTAGTAGCGTTCTCTGCAGAATATAACAACGCTGCAAAAAGGCCATTTCACAGGA
ATATAATCAAAACTGCACATTCTCAGGGTTTCCCGTAAGACGACTTCTCTGCTCT
TCTGTTTGTGGTTTCTTTTTTAGTTGTACATCTCTCCTAGACAAGTCCAAGGAAC
TACTAACGAGAAGATTTCAGGAAGAGGCCTACAGCAATTGCTTGGTGCTTGGGTT
CATTTGCGGAATCTTGGCAACAGGTCTACAGAGAAGCAGTTCCACGGCAAAAGAG
CTGTGGGCAGTTGAATAATCCATCCAAACAATGAGGAGTAAACCCTGAGTCAAG
AAACCAGCAAAAAGCAGAAGACTGGGTCAGCAAATAAAGGGAGAAGATCCTTGCC
TCCTTCAGTGCCCCTAGCATGATATTCTGAAAGGCCCTCCACTAAAATACAACTA
CAGTTTTAATAAATTACTAAAATAGAGAATAGAAGTAGTATGTAAGTTGGGATAG
GGTGATCTGAATTAAGTGTTTTAACATTCATGAACTGTTCAGGACAAAAGCTGTA
AGATATTGGTTAACCTCAACATTGTTAAATTAAGTGTGCACTGTAGTATCAAAGA
TACTCATAAGAATGGAGAGAGTAATTTTCTAAATAGTGGAGGGAAAATAGGAATT
AATTTTTTTCAAAAGTGGGACTTAGGTTGTCTAAAGAAAGGCCAAAAAAAGCATA
AAAAGATGAAAAAATAGAACTACGAAGAACACAGCCCAAATATATGAATAAAATA
GAATAAATAGTAACTACCATTTAAGATAGAGATTGTCAGAATGGGTAAAAAAAA
AGTAAATTATAACAAAGTATATACAACAGATATACAAAAATAGTGATTTTTTTTT
TTTTTTTT

CHD1 ExonJ and Promoter Sequence    SEQ ID NO: 209
GTCATTAGCTTTATCCATTGACAAAATCTCTTTTCTTCGCCAAACTTGTCAGGCT
TCTGAAACTTCTCCTAGGGCTATCGGCGTACTTCCTTGTAAAATCTACTGTTAGC
AAAGAACTCTAAGTCCTTTGGCAGGAACACCCCCATCCTTGATATCTGACCATCC
TTAATACCTGGTCAGTGTCCTCATCCTCCATCATGCCCCAGGTGATGTCTGATCA
ACCTGGCCTGTCTTCAGCAAGAATCCTATTAGGTTGACTTAGCCAGAATCCGCCT
TAAGCCTGATGTTTCCCCTTAGTAATTTTCAATCCATCGACGTCCCAAACTCCAA
AAAAAGTTCCTTGACTATAAATTCCCACTTGCCCATTCTGTATTCAGAGTTCAGC
CCAATCTCTCATCCCTACAGCAAGACTTCATTGCAGTGGTTTCTTTACCTTTCCT
GGTCCTGAATAAGGTCTCCCTTACCATGCTCTAACAAGTATCACTGAATAATTTT
TCCTTTAACACTGTAATGCATTAAATGTTTAGAAGAAGATGTTTATGTATTATTT
ATGCACTTAATACCAATATTTTAAAATATTCAATGAGATTTACAGAGAAAAATAT
TTGGTACACAGTAGGCTTTCATGAAATGTATATTTCTCTTTGTATTGGGTAATTT
TATGTGTCAACTTGACTAGCTAAGGGATGCCCAGACAACAGAAAACATTATTAGT
CGGTGTGTCTGTGAGGGTCTTTCTGGCCAATATGGTGAAACCCCCTCTCTACTAA
AAATACACACACACAAAAAAAaaatagctgggcatggtggcacatgcctgtaatc
ccagctattcgggaggctgaggcaggagaattgcttgaacccaggaggcagacat
tgcagtaagccgagatcgctgggcgacagagcaagactctgtccaaaaaaaaaaa
aaaaaaaaaaaagagAgAgAGAGATTAGCATTTCAATCAGTaGACTGAGTAAaG
AAAATCACTCTCACCACTATGCGTAGGCACCATCCAATCCATTGAGGGCCCAAAT
AGTATAAAAAGGCAGGGAAAAGTAAATTCACCTCTCTCTTCTTGAGCTGGGACAT
CATCTCCTCCTGCTCTCTGGCCTTCAGACACCAGCACCTCAATCCCTTTCCAGTT TABLE 9-continued CHD1 DNA and Protein Sequences

CTCAGGCCTTCAGCTTTAGACTGAATTATACCACCAACCTCCTTATTTCTCCAGC

CTTATAATAAATCTCCTTTTATATGTTTATACATACCCCGTGTGAAAGGAAAGTG

ATTTGGGGCCCCCAAAATCACTAAAGGGAAAATTCATGCTGGGAACTGCTTAGGG

CAAACCTGCCTCCCCTTCTATTCAAAGTCACCTCTCTGCTCACTGAGATAAATGC

ATATCTGATTGCCTCCTTCCGGAGAGGCTAATCAGCAACTCAATGCAACCATTTG

TGTCTTATCTACCTATGACCTGGAAGCCCCCTCCCCGCTTTGAGTTGTCCTGCCT

TCTGGGTTCACACCTATTAGTTCTGTTTCGCTAATACACTGCCGCTCCACCAAAA

GTAACTAATCCTTTGGTTCAAACCCAGTAAACAGATCCCAGCAATGTGTCCCATG

AAAAGGAAGTGGCACATGGCACGTGGAGAGTGGTGACTTACAGGGTAAAAGGGAC

AGAGAGCAAAGGAAAATGTCAGGTATGGGCAGAAAGGTCACCGAACAGACAAAAA

TGAACAAATGAGATCAGGGAAGACAGCCTGAAAGTAAAGAAATACGAAGCAACAC

TCAAAGGAAAAGAAAGAACAGTGATaCCATAACTATTTTCTTTCTGAGCTTCTGA

TGTTCCATTCAGTTCATGTGCAATGTATCATTTAGTCCTCAGAGTAACGGTATTA

TTATGCCCGTTTTATATGATGCaCAATAGGGTTCAAAGATGGAGAGATTCGGCCG

AGGCCCTGCTGCTGATGGTGACTGCAAGAGCCAGTATTCAAACCTAACGCTGCCC

TTTTCTACCATGTTGCAGCGGACAATGCAAAGAAAAAAAAAATCAAGAAAAACACG

TAGAGGTATCCAAATGAAAACAAACACACAAAAGATCAAAAACAGAAAAGAAAAA

AGAAAAGAAAAAGAAAACCCTTGCAGAAGGTATGCCTGTAAATGAAAGGCCCAAG

ATGTTAATTTATTCGCTGCAGAGTGGAGTTAGGGGTCGCGGACGGCAGCTGTGGG

GTCCGAGGCTTCTTCGCACTGGGTCCTTGGGGAGCACTGAGCCGCAACCCGCGGA

GGGCGCATAGAGAGGATCAAACCTCCCACAGCCTAGAAAGGCTCCTACTCGGCGA

GAAGGCGGGCGAGCGATCGCTTCCGGTTCCGGGCGCAAAGGCCCCACGTGTTCC

GACCCGCTAGGCCCCGCGCGGCTCGGATCCGGCGGCGCTGTTTCGGTCGGGAGTG

GGTGGGAGAGAAGCCGGGGCAGGGGAGGAGCCGCCGGAGCTGTCGGAGCCGTGAG

TCCTGAGTGGGCTGGGCTGGGCCGGGCCGGGCTGGACCGGGCCGGACCAGATCGG

GCAGAGCCGGGCAGGGCGGnGAGGAGGGGGAGGGACCGGGAGACCCCGGCCCCCC

AGAGTCTGGGGAAATCGCCGTGTCCTGGGGAAGGGGTGCCGCCGGTGTACTGAGG

GTGCCGAGACGTTGTGGTCTCTGTGTTTCCTGGTGGCCGGAGCCAGTATCTCCGG

GGACACGGATGGCGCTCCCGGCTTCCTTTCCTTTCCAGCCACCGCCCTCCGCCCC

CTCCTGGGGCCTGCAGAAATGTAGTTAGTCCGTACCTCGTACCTCCTAACGCTTC

CGCGCCAACTGTCCCCCGGAACCGAGGGAGGAGTGGTCTAGGCCCCTTTATTTT

CCGCAGCTTTTTCTTACC

CHD1 Genomic DNA Comprising CHD1 ExonJ and Promoter
Sequence    SEQ ID NO: 210
GTCATTAGCTTTATCCATTGACAAAATCTCTTTTCTTCGCCAAACTTGTCAGGCT

TCTGAAACTTCTCCTAGGGCTATCGGCGTACTTCCTTGTAAAATCTACTGTTAGC

AAAGAACTCTAAGTCCTTTGGCAGGAACACCCCCATCCTTGATATCTGACCATCC

TTAATACCTGGTCAGTGTCCTCATCCTCCATCATGCCCCAGGTGATGTCTGATCA

ACCTGGCCTGTCTTCAGCAAGAATCCTATTAGGTTGACTTACGGAGAATCCGCCT

TAAGCCTGATGTTTCCCCTTAGTAATTTTCAATCCATCGACGTCCCAAACTCCAA

TABLE 9-continued

CHD1 DNA and Protein Sequences

```
AAAAAGTTCCTTGACTATAAATTCCCACTTGCCCATTCTGTATTCAGAGTTCAGC

CCAATCTCTCATCCCTACAGCAAGACTTCATTGCAGTGGTTTCTTTACCTTTCCT

GGTCCTGAATAAGGTCTCCCTTACCATGCTCTAACAAGTATCACTGAATAATTTT

TCCTTTAACACTGTAATGCATTAAATGTTTAGAAGAAGATGTTTATGTATTATTT

ATGCACTTAATACCAATATTTTAAAATATTCAATGAGATTTACAGAGAAAAATAT

TTGGTACACAGTAGGCTTTCATGAAATGTATATTTCTCTTTGTATTGGGTAATTT

TATGTGTCAACTTGACTAGCTAAGGGATGCCCAGACAACAGAAAACATTATTAGT

CGGTGTGTCTGTCAGGGTCTTTCTGGCCAATATGGTGAAACCCCCTCTCTACTAA

AAATACACACACAAAAAAAaaatagctgggcatggtggcacatgcctgtaatc ccagctattcgggaggctgaggcaggagaattgcttgaacccaggaggcagacat tgcagtaagccgagatcgctgggcgacagagcaagactctgtccaaaaaaaaaa aaaaaaaaaaaagagAgAgAGAGATTAGCATTTGAATCAGTaGACTGAGTAAaG

AAAATCACTCTCACCACTATGCGTAGGCACCATCCAATCCATTGAGGGCCCAAAT

AGTATAAAAAGGCAGGGAAAAGTAAATTCACCTCTCTCTTCTTGAGCTGGGACAT

CATCTCCTCCTGCTCTCTGGCCTTCAGACACCAGCACCTCAATCCCTTTCCAGTT

CTCAGGCCTTCAGCTTTAGACTGAATTATACCACCAACCTCCTTATTTCTCCAGC

TTGCAGTAAGCAGATCCTCCCACTTCTCAACGTCCATAATTATGTAAGCCAACTC

CTTATAATAAATCTCCTTTTATATGTTTATACATACCCCGTGTGAAAGGAAAGTG

ATTTGGGGCCCCAAAATCACTAAAGGGAAAATTCATGCTGGGAACTGCTTAGGG

CAAACCTGCCTCCCCTTCTATTCAAAGTCACCTCTCTGCTCACTGAGATAAATGC

ATATCTGATTGCCTCCTTCCGGAGAGGCTAATCAGCAACTCAATGCAACCATTTG

TGTCTTATCTACCTATGACCTGGAAGCCCCCTCCCCGCTTTGAGTTGTCCTGCCT

TCTGGGTTCACACCTATTAGTTCTGTTTCGCTAATACACTGCCGCTCCACCAAA

GTAACTAATCCTTTGGTTCAAACCCAGTAAACAGATCCCAGCAATGTGTCCCATG

AAAAGGAAGTGGCACATGGCACGTGGAGAGTGGTGACTTACAGGGTAAAAGGGAC

AGAGAGCAAAGGAAAATGTCAGGTATGGGCAGAAAGGTCACCGAACAGACAAAAA

TGAACAAATGAGATCAGGGAAGACAGCCTGAAAGTAAAGAAATACGAAGCAACAC

TCAAAGGAAAAGAAAGAACAGTGATaCCATAACTATTTTCTTTCTGAGCTTCTGA

TGTTCCATTCAGTTCATGTGCAATGTATCATTTAGTCCTCAGAGTAACGGTATTA

TTATGCCCGTTTTATATGATGCaCAATAGGGTTCAAAGATGGAGAGATTCGGCCG

AGGCCCTGCTGCTGATGGTGACTGCAAGAGCCAGTATTCAAACCTAACGCTGCCC

TTTTCTACCATGTTGCAGCGGACAATGCAAAGAAAAAAAAATCAAGAAAAACACG

TAGAGGTATCCAAATGAAAACAAACACACAAAAGATCAAAAACAGAAAAGAAAAA

AGAAAAGAAAAAGAAAACCCTTGCAGAAGGTATGCCTGTAAATGAAAGGCCCAAG

ATGTTAATTTATTCGCTGCAGAGTGGAGTTAGGGGTCGCGGACGGCAGCTGTGGG

GTCCGAGGCTTCTTCGCACTGGGTCCTTGGGGAGCACTGAGCCGCAACCCGCGGA

GGGCGCATAGAGAGGATCAAACCTCCCACAGCCTAGAAAGGCTCCTACTCGGCGA

GAAGGCGGGCGAGCGATCGCTTCCGGTTCCGGGCGCAAAGGCCCCACGTGTTCC
```

TABLE 9-continued

CHD1 DNA and Protein Sequences

GACCCGCTAGGCCCCGCGCGGCTCGGATCCGGCGGCGCTGTTTCGGTCGGGAGTG

GGTGGGAGAGAAGCCGGGGCAGGGGAGGAGCCGCCGGAGCTGTCGGAGCCGTGAG

TCCTGAGTGGGCTGGGCTGGGCCGGGCCGGGCTGGACCGGGCCGGACCAGATCGG

GCAGAGCCGGGCAGGGCGGnGAGGAGGGGGAGGGACCGGGAGACCCCGGCCCCCC

AGAGTCTGGGGAAATCGCCGTGTCCTGGGGAAGGGGTGCCGCCGGTGTACTGAGG

GTGCCGAGACGTTGTGGTCTCTGTGTTTCCTGGTGGCCGGAGCCAGTATCTCCGG

GGACACGGATGGCGCTCCCGGCTTCCTTTCCTTTCCAGCCACCGCCCTCCGCCCC

CTCCTGGGGCCTGCAGAAATGTAGTTAGTCCGTACCTCGTACCTCCTAACGCTTC

CGCGCCAACTGTCCCCCCGGAACCGAGGGAGGAGTGGTCTAGGCCCCTTTATTTT

CCGCAGCTTTTTCTTACCCCTCCTCTCAGATTGCTTAAGATCATCTCCGCGGGCT

CCTTGCCCCGGCTAGCCCCATCTCCTTACACCACCAAGCCCCCTCACCCCAGCA

CACACCCAGATACACTCACCCGTGATCTTGTCACCTGTGATGATAGTATGTCCTT

GGCGTCCATTTGGCCAGAGCTTTTCAGCTGTCACTGTGACAGACCCTGAGGTTCC

CCTCAAGCCAGTAGCTGCTGTCTCCACTTGCAACTTTCCTCTCCTCCCACTCCTA

ACAGCCAGTTTTGGCACCTCTTCTCAGCACCTGCGTTACTTTTAGCAGGAGTATA

CCTACTTCTTGAGTGTCTTGATTAAAAATTTGTTTTTGTGCCATGGATAGGCTGT

GTTCCTTCAGAAAGGTGTCAGTCTAATTTTTGTTTTTCTGAACAATGAATGTTCT

CATCTTCTAGGCGCTTTGATAACCCTGTCTGCCTTGGAATCTGTACTGACCTCCC

CAGAGGGAGACTCTTAGACCCAGCCTTTCTTGAACAACCTTGGTCCTGGGGAGCA

GCGCTAGATCCCAGGCTCTCACTTAGAGGCTGGGCTTAGAACTGTTGCTTTTTCT

CTATCCACGCTCTGCAGGTGACACCCAGGGCAGCTACACTCAGAAGCCACAAGGA

ATGCTAGTGGAGCCCCTCATCCCTCCCAGCTTCTCTTCCAAGCTGCCCCGTGGGG

CTTGATCCAGGAAGCTACTTCAGAAAGGTTGTGGGATAGCCTTGGGAGGAGGTTT

GTTGGTGGGAAGCGTGTGAACCGGAACAGTCTTGGATAACTTTCTGCTGTTACTA

TCTAGCATAAGAGGGTGGGCAGGGTTGGAGAGAGGACAGGAATTTTTCCTCCTAG

GACCAAACGCCTGGGATTCATAATCTTTCACCCTTTCTCCTCCAGCTATACCCTT

TTTGTACTCTGTGTATATACTATATTGCAGTAGACAATCATTCCAAGGGTACAAC

AAGGTTTACCACAATGTGAGGGACTCAGCCATTGCAAATTGTACAGATGAGGTAA

GTTACAGGTTTACATTTTTTTTCCCAGTAAATTTGGCACAGATTTAAAATGTGA

AACAGTTCTAGACCCCTTGTTTTGCTGTTCTCTCACCAGCAAACCCTTTAGTTT

GGCCAGCAATGGCTTTCTGCATGAACTTCAGATTTACTTCATTTGCTAGGTGGTG

GTTCTCAAACTTACTATAAGCACCTGAAGGGCTAGTTAAACGCATATTGCTGGGG

CCCACCCCTAGAGTTTCTGGTAATAGGTCTGTGCTGGGGCTTGAGAATTTATGCT

TCTAACAAGGCTCAGGTACTGATGCTGCAGATCTGGGTTCTTCACTTTGAGAACA

ACTACCTTTTGGCCAAATGTGATATACGTATTGCAGTAGGTTGAGGTTCAGAATA

CCTTTGTTTGAGTACTTCTGTGTTGGAAACTAGTAATCTGATCTTTTATAGATAA

TCACTTAGGTCTGAATATTCTGTTCGCAAAATTAAGAAAGCGTACTTAAAACAAC

TGAATGCTATATGCCAAATTTGAGGTGAAATATTGATGAGTTCTTCCCCTTGATT

TTCTTAATTCTCTTGATAGGGGCTTCACGTTTTGATCAAAAATATTACACCTGTA

TABLE 9-continued

CHD1 DNA and Protein Sequences

TTCTGGGCTTTTGCTGTGAATTCCTAGTATTGCTAAAATTCTGCAATTTCTTAAC

TACCTGTTAAGTTCCTCAAGGTCAGAGCTTCTGCTTTTTTATCTTTATTTGCCC

AGCACCTTGAATAGTGTGGGACACGTAATTGACGCTCAGTAGATATTTGTGTATT

GAACTCCATCCCTTGTCCTCCTCCCCTCTTGATGTTTTTCTCTACTGGCCTTATG

CTACACAGTAAAGCAGGGCATGATTATGCCACTTGATTACCCCCAAGAGATTGGA

ATAAATGCTAATGCCAAATTCCTACAGCTATCCCTGTGAATGGTTTATTACCCAG

GAGCCCTGACACTGGCTGATTTCTGAATTTTCAGTGCTTCTGTAATATATACTAG

TTGGGGGAGGAGAAATAGAAAGCTTAAACTCAATGTGCGTTTATTGAATACCTTT

TCTACTAAGGGCTTGACAAAGTGGTAGGCACTGGGAATATAAAAATGAATAAGGA

GACCCTTGCTCTCGAGGCAGGGCCCACAGTGGGGAGACAGACGTTAAGCCATGCC

CACGACAAGAATGACTTCTGAGATTCCTTCTTTGGATCATGATTTAGTCTTCAGT

GGAAACCTGGTACTCCTCAGATTCCTCTGGTTCAACAGGCGGGGATCCCATCCCT

TATCATCTCCTCAAATGCTAAAGGACCCTTGAGCAAAGCCAGGAGGAAGTCATCT

AGACGTGAAACAGGGAGTATCCACACAGGCTGTGTTAATGACAAAGCTAAAAACA

TAGTAAATGACTTTTGAATTTACTGCTGTTATGAATTATCTATAGCAACACCTCA

GGTCAGCTCTGTTATATATGTTATTGTGTTATTTCCCATTAAATGATGGTTCCTC

TGACTATCTGATTGGCATTGACTATGTTTGTTGTAGGGATTGCATACATCTAGTT

TAACTCTGGCTGTCAAATGAGAGAGCAGTTACTCTTATCAGGATGGGTGTCAGGT

TTGATGTCCCCTCCTTTTCCTGCTTCAGGTTAATTTGTCATGTTCTGTTTTAAAC

TGAGGCATATAGCTTGACCTCCTTTATTTAGGCCATTAACTGCTCTGGGGTAGTT

TTCCTGAAGGTTAAAAAGCCTAGCTTCATGATGGAGGTTAATCAACATGACCATG

ATGGCCAGGTGTATAAATCTGGCCTCTTAAAAATCTGTATTTGAGGCTGGGTGCA

GTGGCTCACACCTGTAATCCTAACACTTTGGGAGGCCAAAGCTGGCAGATCACTT

GAGCCCAGGTATTTGAGACCAGCCTGGGCAAGATGGCAAGACCCCTTCTCTATwA

AAAATTTAAACATTAGCTGGGCATGGTGGCATGTGCTGTAGTCCCAGATACTTAG

GAGGCTGGGGTGGAGGATGGCCTGAACCTGGGAGGCAGAGATTGCAGTGAGTTG

TGATCTTGCCACTGCACTCCAGTCTTAGCAACAGAGTAAACCCTATCTCAAAACT

TAAAAATCTGTGTTTGGCCCCTAGCCGTCCTCAGCTCTTGAGTAAATCTCAGCAT

CCTAGGCTGTTACATTATGGCCCAAATATTCAATAGAGATGCTGTATATCCTTGT

TCCTCTCAAAACCCCTCCTCATCACCATCAAAAAGCTGGTTTCGTTCTCTACCTT

TAGATAAAGAATCATCCCAAGACTCAACATGAGCTGCCGTGACTTGTCCAAGATG

ACACCTCTTTACAATGTAGAGCAGTGGACAGAACACAGGTCACCCTCCGCCGAAA

GCAACTATCTACTGTCTAACATTGCCTCCTAGGCCTGCCATATATAACCATCAAA

AACATTTTAGTTTAGAATAAAGTGAATTGTTACAATTTTTATTTTTCATTTTTGT

GTTTACATTTACTCTCAATGACATGTTTATTCCCACCTAATATCTTGAGGCTAAC

CACAAAATCTGCAGCATTTCCAGGCAGAAGATACTTGTGACTTCCCTGTACTATC

CACTACATACTTGACCTCTTTCTCTTTCTTCCTGTCTTCCCTTTCTCTATACCTT

ATTATCTTTCTTTGGAACCTCTTGTAACAAATTTTGAGCCATTTCTCCCCTCACT

TABLE 9-continued

CHD1 DNA and Protein Sequences

ACTCAAATATCACTTTTATGAAGGGGCGGGGGGGAAACTTAGGTGGCAAAAATAT

TTTACAGAAACAGTTTTAAACATGTTTTGAAGCATACTGGTCACGTGTTAGAAGG

CCAAAAGCCAGGGAATTCATTCCCTTTCATTCATTGTGCTGTCTAGGTTAAGTTT

TCACAGGACTTCTTGGTACACTGAGTTTGCCTCAGATTGTCTCCTGCCACTTACA

GGGAGTGGAGAGGACTTTGATATATTGGTAATTAGAAGCATTsCyGATATGGTCT

TCGGTGGGAGAACCTGTGTCTAAGGTTCCTTCTCATCTGTATTCCAACACTTTCA

TTTAATCCTACTTCATAAGTGCCTCCAAAGCAAGGATTTTTTTTTGGTTTAGCA

TGGTTTCTTTGATATAACAATAGACCGACCAAGATTTTCCTtATGCCATCTGTTT

TTTTGTAATTATGATGCAATAGAGAACTGTTTGCTTGTTTATCATTTAAATCTTG

CCTTCTTCCCAAAACGATTTCAAATAGCTTGAAGGAAAATGAATAAAATATATTG

AGCACCTACCCTATGCCAGACTCTATACTGAAGGGTTTCTATAGGTTATTTCATT

TACTCCTTAAAACAACCACATGAGATAAGTAGTATTAGCCACATTTTTGAGGATA

AGACTGAGGCTTAGGGAAATTGTGTTACAAGGCTAATAAGCGAGGTCAGGGATTC

GAGGTCAGGGATTCAAACCCAGCGTGCCAAGGCCACTAACCATTATGTGGAAAGC

TTAGGTAAGCGCTTGTATATAGGACAATCAAGAATAAAAGAATATGTCCATTAGA

AGGATTGTACTGGGCTAATCTTTCGTTTTAAAGAACAGCAGCAGCATTGGAAAAG

AGCGGTTAACAGTTTTTATTAGCCAATTTCTATTCTAGAACACTGAGAGGAGCTG

TTGACAGGCCCTGGTTAGCCCCAGCAAGTAGTTGTATTAAAATTACCAAACTATA

GGCCTGCATTAAGGTATAAAATAAGAATGGGGACTGGAAGGGATATAAATATCTG

CTAAATATAATAATTTCAGTTCTAATCACTATTTTCTTCTGAAGATTATTTGCCA

GTACATAGGCAGATCACTGTCTCTCCTTTAGGTTGATGGTATATGACTACAGACT

TTGTCATTTAGGGTCCAGAAAGATCACCCTAGCTAGTAGCGTTTTAAGGTAGAGA

ACTAGATATTGTTTCATTGCCTGTGGTTTTCTGTTCTTGTAAGAGAATTGAGCTT

GGGTCTTCACTGCCACGTGACACCTTCAGATAAGGGGCAGAGACAGCTGGCCTGA

GGATTGTACAGAGGTCTTACCTTGATAGCTCCTCTCCAATCCTATGCATCCTAGG

AACACTCAAGACACTAGGTTGTATCTTTGCAGATACTGTTTTAGTGTCTTCTGGA

ACCAAGTCTCTTACTTAATCCTGGCCTGGTTTCATATTCTCTCTATTGTATTCTC

TCTATAGTTTTTGTCTTACTCTGGAACTCTTCCAAGGACAGACATTGAAGAAAGG

TATTAGAATAGCAAAGGCAACAAATTGCAAGGTATACTTATGGCATAGCACATCC

CATTAATTATAGAATAAAAACACAACATCTGTTTTCTGCCTCTAATATTAAATCT

TGACATTTGCACAACACATTTTAGTTCATAAAGCTCTCATATCTCAGATAATCAC

TGAGTTAGGAGACTGGTTATCTGCAGAGGGCTTTATCCTTTACAAGGGCTCTTGG

GTACGTTACTTCACGAAACCCTCAGGGAAGCTCCAGTTTCTTGGGGATCTGGGGC

CGGGGCATATGTCTTTGGATACCCAGTTTGGTGCTGTGCACAGCACTGCTGTACC

TCCTATTCATTTCCCATCTCTTACCCCACAAAGACTCCTTCCTTCATTCCTTCTA

TTGCTGATCTGTTTTCCTTCATCTTCCTAGGCTGCCAAAGTAAATGCAAAACAAG

CACCFAGAAATCTCAGCTTGTGATTCTGAAGGGCATTTTTAAATGGCAAGTTTGG

TGTGGCACTGTTACATGTTCTTTTTTCTTTGGAGAGCAAAGCCCTTTGAGAGAGC

AGGAACTCTTCTGTCAATGCATACGTTGTACCATCCATACTGTGGAATCTCTTGT

TABLE 9-continued

CHD1 DNA and Protein Sequences

ACCTAGTGCTGCGTGAAAACAATGAGGATTCCAAGTCTACTTCACTGGACATCGG
TTCTCAAACTTTTAAGATACTAGAAGTCCTTTTCTTAAGCCAAAAGACCCTATGT
ATTAATTCTGTCTTCCAGGGGTAGGAGTTGGGGTGGGGTTTGGAAAGCTTTGTCT
GGATAAATAATTAGTATTGTAGTTCCATTTATTTGATGTCTGATTTTGCGCTTAT
TAAAATTGATTTAAATCCTCAATGGAAAATCATTTTTTTTTTTCAAATGCCAAGT
GTTGTGTGACTTGCATTTGGATTATTCCCGGTGCAACCTGAAGATTCCTTGTGAT
GAGTTGTGGTTCCATCATCTTGGGAACCACTAAGAGAATTCTGTTTTACTCACAA
TCCAAACAATAAATGTTTTTTTCCCTATGTATGCCTTTATCCAGCACACAGTTTG
CTAGACTTATGGATGAATATGGGTTAATATAACATGGTATCTATCCTTCTGGAAA
CAGACTTTTAAAACCTTACTAAGCATTCTCTGCATTCATCAAATGTGAAGTGAGT
GCCTGGTGTGTGCCAGGCATCGAGCTGGGCACAGCATATCCCTGCCcTCAGAGCT
TTACAGTCCAGTGAGTTCAACAGAAGATGAACAGTTTTGATGACACAAAAAATAG
ACACATGTGCATGCTGTGATAGGGGGAGATACAAgTTCCTGTGGAAGCATGATCT
GGGAGGACCAGGGAAGGCATCTTGGAAAAACTGAGCTCTGAAAGATGGATAGAGT
TAACCACATGAAGAGTGGAGAAGGGTACTTCAGACAAGGTGAACAGCATCAGGAA
AGCCCAGGGAGGGTATAGAAAAGAAAGAACAGTAATTCTTGCAGTGGCTTTCAAT
GGGAGTGGCAGTCATGGAAGGAAGGAGAGGTAGCAGGGACCAGCTTTTGAAGGGC
TTTGTGTATCACATTTTAAGAAGTTTAAATTTTAACCTAAGGTCACTGGGAAGCC
ATTGGCAGATTTTGTATGTTAGGAAGTTCACCACTCACCTACTTGGAGTATTGCA
GGTGGAGCTAATGTGGATGGGCCTCCTGCCCATTATTAAATCCTGTTCCTGTCAG
GAACAGGACAGCCCATGCTGTCTCTCCCTGTGTGTCTGTCTCTCCCTGTGTGTCT
GTCTCTCTCTCTCTCTGTCTCTCTCTCAAAAGCTAAAGGAAAGCGCATAGG
TTCCAGAAGGAAAAAGAAATAACCACTAGAAAAATAAGTATAAGCTGACTTTACC
ATGGCGCAGTGAGATTCCAAACCAAAATAAGGTTTCTAGGGATTGAGCTTTTAAT
ACTGGTACTCCAACAGGGAGATAGGACTTGGGAAACTGACGCTGTGTGAAAGTTA
CAGAATTAAGCAGCCTGCAAACCTGGACCTTTGAAAATCGTCCTACTGACCCAGG
AAAAGTGCAAGGAAGTGGGTTCTCCAGAACCTTGGGTAGGCCAAACATTACTTGA
AGGCATCGATCTAAATAATACACAAAAGCATTATTCAGGAACACCCTGAGAAATT
AACATAAAAACTGATTTGGCCAGGCATGGTGGCTCAGCCTCTGGTAACAGTGCTT
TGGGAGGCCAAGGTTGGAAAATCACTTGAGGCCAGGAGATCCAGGCTGTAGTGAG
CTATGATTGTACTACTGCACTCCAGCCTGGGCAACAGAGGGAGAGTCTTAAAAAA
GCAAACTGTCCAAGATCATTGAAACCATTAGCACTTAGGAAGAAACAAATGAAAT
TACATTCAAGGGGGTCACATTTAAATCCAGGGCTCTCAGGACTCCCAAAGTAAAA
AGATGGACATAAAATAAAAAAATTACAAGCCACTTGAGAAAAAAATAAATCACCA
TGAGGTAGAGATAGCAGAGGAAAAATTACACATGAAGATCTACCAATTAGGGAGC
TATCCAAGATAGACTGTGAAAGTATGTTGCAAGTGACTGAGGGTAATGAAAAAAA
TGTCATAAGAGCATGAATTAGAAGCGTTTTGAGAAAGAATGAAGATAATGTGGTC
ATTGACTGTAAACTCATTTGATGGGCAACGATAGATGAGACACAGCTATTAAGAG

TABLE 9-continued

CHD1 DNA and Protein Sequences

TGGATCGATAACCTTGAATGTGGATGTGAGGCAACTGTAGTATAGCACAAAAAGG

TTGAGAAATGATGGAGCCCTTAAGCTGCTTGTGGACACTGGTCTGGAGGGGACA

GGACCAAGAAAACCAGTCATGGAGGTTGAACTAAGTCATCTCTCCAATGTATCCG

TGCCTGTTACGTGCCAGTGCCGTTTAGGAGCAGAGGATATTGTAATTTTTTTAA

AGTTCCTATGAATACCTTCTAGTGGGTCATAATGGCTCAACCGGGAAATGGCAGT

AGAGATGAAGAGATGGATGGATTCGAAAGACATTTTTTGGAAGTTGGAATTAACA

GGATATGGTGAATAATCAAGAGATAGTAAAAGCATAATGGAGGAAACAATGGTTC

TTCCTGTTACCATAGGAAGAAGCTTTGGAGTAGAGTTTTATTCATTTTAAATGCA

TTTATTGTGCACTTTATTATAGGTATTGGAGATTGATGGAAAATAGTCTCTGACC

TCAAAGAGTTTCACAGGAAAGATGAGCGATGGCTATGTAATATGACCAATACTGG

GATAGAGAGGTGCCCAGGTCACTACGGGAGGACTTAGGTGATTTCTAACTATGTC

TGAGAGTAGGGGAAATGGGATCAAAGAAAACATCTCAGAAGACATGAAGCTTGAG

CTTATGTCTTGAAAAATTTAAAGTTTAACCTAACCAAGGATAAAGAATCAGAAGA

AACAGCATATTCAAAAGCTAAAGAACACGGGACTCTTGTGTGCTTTGCATGTACA

CACGTGTGTGCGTGTGTGTCTGAAAGGATTGGAGAGGAGGGCGAAGAGAATAACA

AGATGAACGTCAACCTAATGTAGAATGTTTGAAGTTTGTATTTCACTTAACAAGA

CAGCGGGGAGTGATGGAAGGATCTTAGATAGGAAAGGGACATGAGCACGTTTGCC

AAGAGAGCTCGTTCTGGTCATAGTGGGTACGTGAAGGTGACAAATCTGGAGGCAG

ATAGCTCACATTTGGAGGCAGCTGCAGTCATCCAGATGAGAAGTGAGAGGGACCT

AAGCTGTAAATTGTGGGAATAAAGACAAGACCCGTTAAAAAGAAAGAGAACACAC

CATGTAGCGTGGAAAGGAGAAGGGTGGAGAGTAGCCTGTGCAGAAGGAACAACCT

TCAAAAAGACATGGAAGACTGAAAAGACACCCTGTTGTAGGGAGATCAGCAATGC

ATTTTTTATAACCAGGTGATACAGGGAAAGGGTAGGATCTGAAGCTTGAAAAATA

GATTGGGGGCTGATTGTAAAGAGCTTCGTGTCATTCCCAGGATTTTGGAACTGAT

TTTACTAACATGAAAAGGTTTTGTTTTAAAATACTGAGTAATATAGTTGGAACT

ATAATTTAGAAAGATAATAGCTGGTGCCATCACTCTTCTAAGCAAAGATAGTAAT

ACATTTAATGCTCATAGGCTTTAGTAATACATTTAATCCTTACAGTAAGCCTATT

AGATAAAAACCATTATTATCTCCCTTCTATAGACAGAGAAACTGGCATTAGGAGA

ATGAGAACTTGCCTATGGTCCCACTCTGGAAATACCTAGTAAGCGACAGAGCCAG

GATTCAAACCCAGGCAGCTTGACTCCAGAACTTTCGCTCATAACCTTACACATCT

CCGTCATGGTTGGTGTTTCTCAACCATGGATACACATTCGAACTGCATGTAGCAT

CTCTAAACATACAGTTACCTGAATTGACTGAATCAGAGTGTCTGAAAAATGATGT

GTGATACTATGTTTTGCAAAATCTCCACAGGTAATTCTGTTGTACTTTGCTTATA

GTTGAGTACTGCAGGGATCTTAGGAAGTTAGAGCAGTAGTCCAGGCAGGAGATGA

TGAAGGCTCAGACTAAAGCAGTCTGTAGGAAGGAAGAGAAGGGAACCGGTTTGGA

GACTTAAGCGGGGAATTGGCAGTATTTGTGAAGTGGAAATGCAGTATTTTCTTG

TAGAGTATGAACCTTGCCTAGGAAAGGGAGTAGAGGACCATACCTTTAGTTGTAA

ATTATCCTCTCCCAACTGGATCTGTTGATTTATGGCTATGGTGGTTGGGGAAAAG

AGGATTTAACCATTTGAAGAAGTTTGTGTAGAGGATTATGATTGAACTCAGGCTG

TABLE 9-continued

CHD1 DNA and Protein Sequences

TTGTCCTTGTGTATAGTTTCATGCTTATACTCTTGTTTGTCTTTACTTCTCTATC
CAGGGCCCTTGGAAGAAAATCCTCGCTGTGTCCAGGCTGAGGCGGGGGGCTAATG
ACAGTGTGAGCTCTAGATGGTGTGAGACCACCCCAAAGCCAAGAAATGGCTACAG
CCGTGGAACCAGAGGACCAGGATCTTTGGGAAGAAGAGGGAATTCTGATGGTGAA
ACTGGAAGATGATTTCACCTGTCGGCCAGAGTCTGTCTTACAGAGGGATGACCCG
GTGCTGGAAACCTCCCACCAGAACTTCCGACGCTTCCGCTACCAGGAGGCAGCAA
GCCCTAGAGAAGCTCTCATCAGACTCCGAGAACTTTGTCACCAGTGGCTGAGACC
AGAGAGGCGGACAAAGGAGCAGATCCTAGAGCTGCTTGTGCTGGAACAATTTCTT
ACCGTCCTACCTGGAGAACTACAGAGCTGGGTGCGGGCCAACGGCCAGAAAGTG
GCGAGGAGGCAGTGACGCTGGTGGAGGGTTTGCAGAAACAACCCAGGAGACCAAG
GCGGTGGGTGAGGAGGGGAGTCCTGATCTGTGTGATGTGGAGGGGGACTATTTG
CTGGAAGGCTGGATTTGCGGGGAGAGCTTGCAGGATCCCCATAAATTATTAGTGG
CTCTGCCCTTGGGTTGCTCATATACCATGAGCCCCATGGATTAGGGGATGTGTG
TGTATGAATGTGACTTTCTGGATATTGGAACACCTGTATAGGGACCATCTGAGGG
GgTCTCAGCCACCAAAGGGTCATGGCTTTGGTTTTCCCTTCTTTGAATGTTGAGC
CGTGGGTTCCTGGAGAGGAGAATTTTGTGACTTCCTCGAAGGTTCTCATAGATCC
CCAGTCACAGATCCCCCTTCCTGGCTGGTCAGCTAGGGAAGCAGGCAGCAAGGAG
AGCTGCAGGTGGGACAGGTGGAGATGGGAAGGAACCTTGGGTGACAGGGGCCCAG
GCTGGGGGTGGTGAGAGAGCAGTGCAGGCCTGCGCATCCCCTGCCTTGTCCTGGG
GAGGATAACCTTCAGCTCCTCCTTGCCTGCTCCATTGAAACTGGAGTTTCCCCTC
CTTGTCTGGGTCCCTCTGGGAGTGTTTTCTCTAGGCATCTTCTCCTAAAATAAGC
TCCCGTGACAACCAAGAACTTCCTCCTGACTCCATGGTGACTGGAAGTTGGAATT
ATTCCCAGGTGACTGTCCATGTTCACGGCCAGGAAGTCCTGTCAGAGGAGACGGT
GCATTTAGGAGCGGAGCCTGAGTCACCTAATGAGCTGCAGGATCCTGTGCAAAGC
TCGACCCCCGAGCAGTCTCCTGAGGAAACCACACAGAGCCCAGATCTGGGGCAC
CGGCAGAGCAGCGTCCACACCAGGAAGAGGAGCTCCAGACCCTGCAGGAGAGCGG
TGGGAAGCATCAGCAGAAAGGGGGATTGTGGCAGAAGGCAGGCAAGGAGGGGGA
CATTTCTCCTATACCAAGGAAGCTGGGTAGATAGACTGTATGGAAAGACATCACA
GAATCCAGGATGTCAAGAGGAGACAGTACCGCCAGCTAGAGTCCCCCATAAACAG
GGCCAAGCTTAGACAGCAGATTGTTGCTTGTTCTCTTGGCATTCTGATAGTCTCA
TAGGTGATGGGATTGGGATATGGGAGCTACCCTTAGGCCAGTTTCTTGGTTCCCA
TAATAGAAAGGATAGGGCCACCTTCCTACCAAAGATGGTGGGGATGCCCAGATT
TTTGCCCATTATTGGGGCATGCTGCATATTACTGATCTTTGCCTTCTTTTCTTCA
TAGAGGTCCCAGTGCCCGAGGACCCAGACCTTCCTGCAGAGAGGAGCTCTGGAGA
CTCAGAGATGGTTGCTCTTCTTACTGCTCTGTCACAGGTGTGCCCTAGTTACCTC
TGTACCACAGAGAATTTGTTTGAAGAACCACTGGGCATAAGCCATACTAAACAGG
TGAAGCAGGATGCACATTTACACTCTTGCCAGTTTTAAGCTCACAGTTCTGCAGG
TACCTGGAAGGGGAGGAGATAATGAGATAAATTATCATACCTTATATTGGATCCA

TABLE 9-continued

CHD1 DNA and Protein Sequences

CAGGCACCAACACCAGTTTATTTGCCATTGACTAGAAGAACTAACAAAATGGGAT

TATTTTGTAACACTCCAGTACAACTGCGAAGTTGTCAAATGAGGGTTTTTTAGTT

TTTTTTTTTTTAAAGGAATAAATTTGATAGTCATTTGTAAGTATGACAGACTGT

ACTGCTGAGACATTTAGGAAGTATTCACCATGATCAAAGCTCTGAAACTAAGCCA

TGTGGCTGGAGAAAAGAAATAGAATTCATGTATGGTTTTAGATTGTAATCTAAC

TGAGGAAAAAAGTCTTGTTTTGGCTATAGAGTATAGAAACTATTGAAAGAGATTA

GAGTCTTTAGGGAAAGTGTACTAGAAAAGATGAATTTTGCAGAAATGTATATAGC

GTTAAAGTGTCAAGTAGGGAGCTGAATGATGATTTTTAAGACCTTTCCTAAATTT

TAAACAATACCTTAAAGAAGAAGAACATAAGCTGGTCCTCAGGAAAAGTGGTGGA

GTTGGAGGGGGCAGGGCCAGTGCCACAGGGGACACATGGCTCCCCCGAGAATGAG

TTTAAGCAGCCCGCCACTCAAGCTCCTTTCATCTCCTAGAGGAGTCCACCTATTG

TGTGACCTTCAACAGGGACAAAATACGAGGCTACCCGTAGCATCACGTTTTGATG

AAATCCTTATGTGGTTTCAGGGACTGGTAACGTTCAAGGATGTGGCCGTATGCTT

TTCCCAGGACCAGTGGAGTGATCTGGACCCAACACAGAAAGAGTTCTATGGAGAA

TATGTCTTGGAAGAAGACTGTGGAATTGTTGTCTCTCTGTGTAAGGAATTTCAAG

TATTCTAGAGTGTTCTAAGCCCAGAGATCTTTTTCCTGCTGGAAATTTTGGGGGA

TCTTAGACCTTAGATTGTATGCAGTGAACTTCTCTTATGCCTTCCCCACCAATAA

AATTGAGGGATTAGGTGAAAAATACGGTGTCCTTTCAAGTAAAAGATAAATGGAT

GGAAATGGAAACCTCTAATAGGAAAACAAACTTGTAATATTACAGCTTTAGTGCA

GAAATATTTGAAGTAAGCACATGAGTTTTAAAACAGTAAGAGTTGGAGATAATCT

TTCTTGAATATGGGAAAAGAGGATAAGGTGTACAATGGTATAATTATTAAGTTGC

AGGTGAAAACCACAAGAAAGGCAAGAGATACGCAGTCCTTGGTTAAAAGTACACA

AACTAAAGAGATGAAAGATTTCATCACCTGAGCTAGCTATGTATTTGCCCCACAA

CCTACCAAATAGAAAAGGACCGCTCTTAACACAGGGAATTGTTGAGCCAATCGTG

ATATCCTATTTTCCCTCTCTTGAGCAGCATTTCCAATCCCCAGACCTGATGAGAT

CTCCCAGGTTAGAGAGGAAGAGCCTTGGGTCCCAGATATCCAAGAGCCTCAGGAG

ACTCAAGAGCCAGAAATCCTGAGTTTTACCTACACAGGTGAGGAATGACAAAAAC

GGTGTTACCCACCCTGAGCCAGCAGTTCCTCTAGGCAGTGCTTCTCTCTCTCTGT

AGGGCCCCGCTCTCATCAGTTCTTCTAACATGTCAGCCAGTACTGCTTTCTCCCT

CTGACAGCCATTTCTTCTGTCATTGCCCTCCTCTTTTCTCCTCCCATCATTTGTC

TGATAGCAATGTAATACAAAAGGGTGAAAGAAAAATGTTAACTTTTGGAATTGCA

GCTATACCATTTACTGTACAATTCCCTTAAACCCTCGATTCTCAATCTCTGCATT

TGTAAAATGAAGATTATATTTGTGCATACCAAGGTTTGTTGATAGCATAACAATA

TGAGAAAGTGCTTGGCACAGGACAGGCATTCCATTTAGTCTTGCCATCTCAAAAC

CCTTTGTAAAAATCTCCCCATTGTGTAGAAGGCATTGTTGCCGCTACAGTCACCC

CCTTTTTCCTCTCACCCTTTCTACAGGAGATAGGAGTAAAGATGAGGAAGAGTGT

CTGGAGCAGGAAGATCTGAGTTTGGAGGATATACACAGGCCTGTTTTGGGAGAAC

CAGAAATTCACCAGACTCCAGATTGGGAAATAGTCTTTGAGGACAATCCAGGTAG

ACTTAATGAAAGAAGATTTGGTACTAATATTTCTCAAGTGAATAGTTTTGTGAAC

TABLE 9-continued

CHD1 DNA and Protein Sequences

CTTCGGGAAACTACACCCGTCCACCCCCTGTTAGGGAGGCATCATGACTGTTCTG
TGTGTGGAAAGAGCTTCACTTGTAACTCCCACCTTGTTAGACACCTGAGGACTCA
CACAGGAGAGAAACCCTATAAATGTATGGAATGTGGAAAAAGTTACACACGAAGC
TCACATCTTGCCAGGCACCAAAAGGTTCACAAGATGAACGCGCCTTACAAATATC
CCCTAAACCGGAAGAATTTGGAAGAGACCTCCCCTGTGACACAGGCTGAGAGAAC
TCCATCAGTGGAGAAACCCTATAGATGTGATGATTGCGGAAAGCACTTCCGCTGG
ACTTCAGACCTTGTCAGACATCAGAGGACACATACTGGAGAAAAACCCTTCTTTT
GTACTATTTGTGGCAAAAGCTTCAGCCAGAAATCTGTGTTAACAACACACCAAAG
AATCCACCTGGGAGGCAAACCCTACTTGTGTGGAGAGTGTGGTGAGGACTTCAGT
GAACACAGGCGGTACCTGGCGCACCGGAAGACGCACGCTGCTGAGGAACTCTACC
TCTGCAGCGAGTGCGGGCGCTGCTTGACCCACAGCGCAGCGTTCGCCAAGCACTT
GAGAGGACACGCCTCAGTGAGGCCCTGCCGATGCAACGAATGTGGGAAGAGCTTC
AGTCGCAGGGACCACCTCGTCAGGCATCAGAGAACACACACTGGGGAGAAACCAT
TCACGTGCCCTACCTGTGGAAAAAGCTTCAGCAGAGGATATCACTTAATTAGGCA
TCAGAGGACCCACTCAGAAAAGACCTCCTAGCTAGGTCCCCATGTGAGGAGATCT
GCTTTCAGCCCTCACCTAAGGGAGGTGAGGAAGAGGAAAAGCCCTCTTGTCAGCC
TGGGAAGACCTTTTCGACCCACTCTCCCTGACCTGCTCAGATCTGACATTACCTC
TTCCTGCAACTAAACACGAGCCTGGGCAGAACCTCTCAGCCTTCCTCTACGCCTT
GAGGGGATGTTTCATCCAAAGTACAACCTGAATTGAGGCTTCTCCTTCACTGGAG
TGCACCTGCCTCTACCTCATGGGTATAAAGTAGGAGAACTAAGAGACTTAAGAGG
TCGTCCTTCCTATATCGTCCAAAAAATAGGCTGTTACATATCCTAAAGACTGCTC
AACAGCTTCAAGTTGAAAGTGGCCAAGGACAGCCCCTTAGGTTTGGGAAGGGACG
AGCCTGAAGGATTCTGTCTTTACTGGGGTCAAATCTTAAAGCACACAGCTCTGGA
CTCAAGACAGGAGGTTTGCGTCCTGATGGCTTTGCACACATTCACAGGATAACTG
CATAGATCCCTCGCTGTCTGATTCACTTCTTACCATGCACTTTCCTTTGATGCTG
AGGAGAAATGGAAGTGGGCGAAAAATCTCAAGGCTGCTTCATGTGGACCTTGTCA
AGCTGCTCCCTCCCCCAGCGTCAAATTGTTATCAGGTGCCAaaCACTGCTAGAAA
GGAGGGCCTAGTCAGAAGCCTCTTTCCATACGAGTTTTGGTTTTGTTTTAATAT
TTTTTTCTATTAAAATACTCATGCATTTAACCTTCCCGTTATTCAACCAGTCTCT
TGGTTGCATCCCTAGCACTTCTACTACAAGTGAGATGGTAGTGTTTGAGTGCTTA
TTGAGTAAAGCATAATTCGGTCATAATGAAATCGTTCACATTCCCTCATATGCAC
AAGCCCACCAACCCCTTCACACCCCCCTTCACAGGGGTCGTATGAGTAAGGGGAT
TTGGAAACTGTCAACTTACAAAGGCACTATAACAATTACAGAATCATGATTGCCA
TGGGCCACTTTATTTACATGAAGACAACTGGAGAACGACTAAGACCAAATTATGG
AAAATAAGAAAAAGCTGTTGCTGGCAAGACCATCAAGACTGTTCTGACACCCTGT
CCCCATCATCCCTGACTGAGTACTCTGACATCACGGAAAGTGTTGAACCTGGGAC
CCTGAGGAATTCACCAGGAGTAAATGGCTTTCATGTATTTGTGTTGTTTGCTTTT
TATTACGTGATTTTATGTTCATAGAGCTAGAAAGTAGCATCTCATGATGGCCCAA

TABLE 9-continued

CHD1 DNA and Protein Sequences

CAATCTCTGTTGCCAGTTAAAGGTTCCTTGGAGATGAGGCTGAATAATTATGAAC

CTCACCTTCTCTGATTGTGGGAGTGGCAAGAACTGGGGAGACGTCCTCCATAAGT

GGAGCACAGGGTATGGGGTTAAAGCATGACAGGGAGAGTCTTCTGTGCCTGGTTT

CTTCTCCTCTATCTCATAATGCATTATGGGCCCGAGGAATAGGGGAGGGTTAATA

AGACTCCAACCCTAATGGCCCAACAGGGAAATTCTCATTTTGGTCGATGATATTC

TGATGGACTGGTTTGGTCTTAATACCAGTCAACCGTTGTCCTTCTGGAAATATAC

ATATATGAAATAAATAAAGGTAACACTTGCAGCCAAGTTCCCTGGTTTCTGGGAC

TTCCCATCTTACCCATTCCTTTTCCAGGGCTTCAGTGTCCTGATACTTCTGAGGG

TGGTTCATACTCAAATAGATCTGGGAGTACAGAGTATTTTCCTTGAGGAAAGGA

AGGGTTGGGATGATTAGCAGAGTCCGTGAAACATATGCACTCTGAGATAAGATC

CAAGCCTGGAGTTTGCAGAAGATACTGTCCTAATAAGCAGGCATTTCTAAAGGAA

GTATCTAAGCCTAAGCACAGCTTGTCCTGGGTGAAATGTCTGCCACAAAAGATAG

TTTCTCCTAGCTCAGACTTAACCATTTATAAAGGTTGGTAAAATACTGGCAGTGA

CAACAAATTGACTTTTTAATTTTCTTATTTGCATTATTCCAATAAATGAAAATCT

GTCAGAGTTCTACATGAGGGAAAGCTTGTGAGGCTGGGCCGGTTTGTTGGAACAT

CAAATAGTCCTTAATTACTGATCTCCCTGCAGAGTTTCATATGCAGACACTAAAT

CTCTGGTCCCTTTTGTAAATTACTGAATTTTCTGAGGTTCTGGGAGGGACATGTT

GTCTCCCAAATCTGAACAAACACAACCACAGTGTGCAGCGGCAGGAAACAAGTAG

TGCAGCTGAGCGTGAGCAGGGAGGTTGGAGCACAGGGTGTGTATTCGGAGGGGTC

CCCTCTAGTATCTTGTGAGCAGTAGAATTCTAGCATCCTTGAATACCATACTAAG

TTTCTGAGGGAGAAAACGGTGGGATTTTAAAGATATTATTTGGAGGAAGTTAATA

CGCTACTTAATTAACAGAATTGGCAGGTGGTTGGAAATGTGCTAAAGAGGTATGA

CACATTAAAAATGATAATATAAGGATGTTTGACCAGATAATTTAGGAATAACCAA

GGAATATTTAACCTCTTCACCACAAAGTCCGAGGAGAAATAAATGCCCAAGAGAT

CAAGCCAAAATACATTTTTATTATCTGGGACTTAGGCCTCATATTCCGGAGCAGA

ATCCGGTAAACTCAGATGAACTCCATGGAGAATTTCATAAATCAGATTAACATCA

AGGTACTAAAATCAAAACCCACTAAGAAACCTGTTGCCCCCTTCAAAGCACAACT

GAAGTAATGGATCTAATAGAAGATACATTGTTTGCACTGAGCAGTAGAGTAGTAG

AGGAGAAAAGCCCAGAGATGGCACAGACAAGTTGTTCCAGTCCCCTTCAGTCAAG

GCCTCTGGACCACCACCCTGCCACAGGCGAAAAATGGGATATTTAATAaATAaAA aATTTTGATTCACCAGACTGGCTGAAAGGACAGTAaTCCAaATGAGAGTTAACGG

CTCCATAGTAGTTTTCTAGAATGAAAGCTGAACTGAGAAATAGTAACTGATGACA

TGTTGAGCAGGTTAATAATTTGGTACCCTTCCACACCAGTATTTGTTTGTTTGTT

TGTTTTGAGATGGAGTCTCGCTCTGTCGCCCAGGCTGGACTGCAGTGGCGTGATC

TCGGCTCACTGCAAGCTCCGCCTCCCGGGTTCACGCCATTCTCCTGCCTCAGCCT

CCCCAGGAAGCTGGGACTACAGGCACCCACCACCACGCCCGGCTGATTTTCTGTA

ATTTTGGTAGAGACGGGGTTTCACCATGTTAGCCAGGATGGTCTCGATCTCCTGA

TABLE 9-continued

CHD1 DNA and Protein Sequences

CCTTGTGATCCGCCTGCCTTGGCCTCCCAAAGTGCTGGGATTGCAAGCGTGAGCC

ACCGCACCTGGCCCCACACCAGTATTTTTAAAAATAGTTTCTTTTACCTCTAGCG

TCTTCCCTCAGCTGACCTAAATAGTCCAGCCACAATAGCTGAGAGAAGTATACCT

ACAATTATTTCCATCTCCTTATATTTCTAGTGATGTTGGCTGACTAACCCACTAA

TCTAGTTTATGGGAGAGGGAAAGACTGAAAGAGCCACAAAGTGGATGGCCAACCC

ACGTGATTACTAACCTTTATTGTGGCAAAGTAACTGATACAATGTTTCAAATGTA

AGCACATCTCCTTGGAATAAGTGGAATAACTTAATTCATCCTTGCGGAAGTCCTG

AGGATCAAGCAAGGAGGAGCCCAGCTTTCTTTAGACACCACCTTTTTTATCTTTA

ATAACAAAAAGGAACAAAGTGATTGTCAGACCAGCACAAAGATACCTCTTAATGT

GCAATTTCTATTCTCTTTAGTGTGTGTGAGTGCACGCATGCACGTGTGTACACCG

AGGTTTCAGGTAGAAGGAGGAATGCAATTCAAATTCTAAAAAAGGAATCAGTCAG

CACAAACTAGTTTATTTGGCAATTCATAAAGATAGGGACTCTTCAGAGGAGGTTG

AGAGCATTGTAGGGTTATGTAAAGACTTCCAGAAGCTGTAAAGACTTCCAGAAGC

AAGAAGATTCAACCATCTAAAACGCCATGCAGGAAAATAGCCAAACCTTCTCCAT

TTAAGTAGAGAATAAATCTTAGTAGCGTTCTCTGCAGAATATAACAACGCTGCAA

AAAGGCCATTTCACAGGAATATAATCAAAACTGCAGATTCTCAGGGTTTCCCGTA

AGACGACTTCTCTGCTCTTCTGTTTGTGGTTTCTTTTTTAGTTGTACATCTCTCC

TAGACAAGTCCAAGGAACTACTAACGAGAAGATTTCAGGAAGAGGCCTACAGCAA

TTGCTTGGTGCTTGGGTTCATTTGCGGAATCTTGGCAACAGGTCTACAGAGAAGC

AGTTCCACGGCAAAAGAGCTGTGGGGCAGTTGAATAATCCATCCAAACAATGAGG

AGTAAACCCTGAGTCAAGAAACCAGCAAAAAGCAGAAGACTGGGTCAGCAAATAA

AGGGAGAAGATCCTTGCCTCCTTCAGTGCCCCTAGCATGATATTCTGAAAGGCCC

TCCACTAAAATACAACTACAGTTTTAATAAATTACTAAAATAGAGAATAGAAGTA

GTATGTAAGTTGGGATAGGGTGATCTGAATTAAGTGTTTTAACATTCATGAACTG

TTCAGGACAAAAGCTGTAAGATATTGGTTAACCTCAACATTGTTAAATTAAGTGT

GCACTGTAGTATCAAAGATACTCATAAGAATGGAGAGAGTAATTTTCTAAATAGT

GGAGGGAAAATAGGAATTAATTTTTTTCAAAAGTGGGACTTAGGTTGTCTAAAGA

AAGGCCAAAAAAGCATAAAAAGATGAAAAAATAGAACTACGAAGAACACAGCCC

AAATATATGAATAAAATAGAATAAATAGTAACTACCATTTAAGATACACATTGTC

AGAATGGGTAAAAAAAAAAGTAAATTATAACAAAGTATATACAACAGATATACAA

AAATAGTGATTTTTTTTTTTTTTT

TABLE 10

Alternatively Spliced transcripts of CHD1

| Transcript mRNA | exonF / intron protein genomic position | intron / exonA genomic position | length (nt) | length (AA) |
|---|---|---|---|---|
| cDNA1 | 10659 / 10660 | 11320 / 11321 | 3268 | 648 |
| cDNA2 | 10659 / 10660 | 11344 / 11345 | 3244 | 640 |
| cDNA3 | 10655 / 10656 | 11320 / 11321 | 3268 | 133 |
| cDNA4 | 10655 / 10656 | 11344 / 11345 | 3240 | 142 |

The CHD1 proteins have three conserved homology domains (FIG. 3). The most informative of these is a set of eight C2H2 zinc-finger motifs in the proteins encoded by cDNAs 1 and 2 (all in exonE, at amino acid residues 399–419, 427–447, 483–503, 511–531, 539–559, 567–587, 595–615 and 623–643 in the protein encoded by cDNA1). Zinc-finger motifs often serve as nucleic acid binding motifs, and can also serve as protein interaction motifs. A leucine-rich SCAN domain is found near the N-terminus of all of the alternative proteins (amino acids 49–125). This domain is found in at least 10 other putative transcription factors, but its function is currently unknown (Williams et al. 1995, Lee et al., 1997). FIG. 8 displays a comparison between the CHD1 SCAN domain and a consensus SCAN domain sequence derived from homology analysis of SCAN domain containing zinc finger proteins in the GenBank database. Yeast-two-hybrid experiments as well as in vitro interaction studies indicate that the SCAN domain acts as a protein-protein interaction surface leading to homo- and/or heterodimerization of two SCAN containing peptides. The functional form of CHD1 may therefore include a homo- and/or heterodimer of different CHD1 isoforms or CHD1 and other SCAN domain containing zinc finger proteins. Precedents for transcription factors acting as dimers include members of the bZIP family, bHLH proteins and nuclear receptors (Kouzarides and Ziff, 1988, Fairman et al. 1993, Fawell et al., 1990). A third domain, the KRAB domain (amino acids 235–276 in the protein encoded by cDNA1), is found in many zinc-finger containing transcription factors. It is often a site for protein-protein interaction that mediates transcriptional repression (Kim et al., 1996, Moosmann et al., 1996). These motifs together suggest that CHD1 serves as a sequence-specific DNA binding transcription factor. The presence of a KRAB domain raises the possibility that at least one function of CHD1 is that of a repressor, being able to reduce the transcriptional activity of genes it regulates.

Two of the alternative cDNAs (−3 and −4) encode small proteins largely identical to the N-terminus of the longer protein products (−1 and −2, respectively). Tagged fusion proteins have identified the subcellular localization of some of these proteins. The protein encoded by cDNA1 is largely localized to the nucleus, whereas the protein encoded by cDNA3 is found to be diffuse throughout the cell. These localizations were monitored by fusing the relevant CHD1 open reading frame to green fluoresent protein under the control of the cytomegalovirus promoter, transfecting these constructs into 293 cells and monitoring expression with fluorescent microscopy.

The presence of multiple protein products raises the interesting possibility that their relative proportion may influence function. For example, the N-terminus may interact with another protein, call it "protein X", and target protein X to the transcriptional control region of relevant genes. The presence of a fragment of the CHD1 protein that also binds protein X but lacks a DNA binding motif could regulate the effective concentration of protein X, and the function of the protein complex bound to the regulatory region. Such alternative transcripts retaining only partial function have been described for transcription factors and found to serve as competitive regulators (Chen et al., 1994, Arshura et al., 1995, and Walker et al., 1996).

EXAMPLE 8

Biochemical Characterization of the CHD1 Gene

CHD1 Fusion Proteins. Three coding sequence fragments corresponding to predicted zinc fingers 1 through 2, 1 through 8 and 3 through 8 of CHD1 were amplified from random-primed liver cDNA using PCR with Pfu enzyme (Strategene). The primer sequences are shown in Table 11. The PCR primers incorporated restriction sites in the same translational reading frame as the same sites in the polylinker of pGEX-4T-3 (Pharmacia), a GST fusion protein expression vector. The PCR fragments are cloned into this vector using these restriction sites. The ligation reactions were transformed into DH5α cells. Protein expression from these clones was confirmed by SDS-PAGE. The pGEX 4T-3 clones were transferred to BL21 cells for large scale production of proteins. Proteins for use in the in vitro selection and gel shift experiments were synthesized as according to manufacturer's instructions (Pharmacia). For in vitro selection experiments the fusion proteins were retained on the sepharose matrix. Proteins for gel shift experiments were eluted from the glutathione-sepharose and dialyzed to remove residual glutathione. Protein concentration was estimated from SDS-polyacrylamide gels.

TABLE 11

CHD1 Fusion Protein Primer Sequences (respectively (SEQ ID NOS: 190–198))

| Primer | Sequence | Used with |
|---|---|---|
| ZnP1.8F/ P1.2F | TTGTGAACCTTCGGGAAACTA | ZnP1.8R, P1.2R |
| ZnP3.8F | ACCGGAAGAATTTGGAAGAGA | ZnP1.8R, ZnP3.8R |
| ZnS1.8F/ S1.2F | cgat ggatcc TTGTTAGGGAGGCATCA | ZnS1.8R/ZnS3.8R, ZnS1.2R |
| ZnS3.8F | gca ggatcc CCATCAGTGGAGAAAC | ZnS1.8R/S3.8R |
| ZnP1.8R | CCCTTAGGTGAGGGCTGAAAG | ZnP1.8F, ZnP3.8F |
| ZnP3.8R | CCTTAGGTGAGGGCTGAAAG | ZnP1.8F, ZnP3.8F |
| ZnP1.2R | AGGGGAGGTCTCTTCCAAA | ZnP1.8F/P1.2F |
| ZnS1.8R/ S3.8R | caat gaattc GCTAGGAGGTCTTTTCTGAG | ZnS1.8F/S1.2F, ZnS3.8F |
| ZnS1.2R | caat gaattc GGTTTAGGGGATATTTGTAAG | ZnS1.SF/S1.2F |

Gel Shift Assays. Probes were prepared by PCR amplification of genomic DNA using Pfu and Taq plus long enzymes (Strategene), or by direct synthesis of plus and minus strands (ABI model 3948). Single stranded oligonucleotides were annealed to generate duplex DNA and the unannealed oligonucleotides were removed (Qiagen Gel Purification Kit). DNA fragments were end-labeled with $^{32}P$; unincorporated label and PCR primers were removed (Qiagen PCR Purification Kit); and the concentration of probe was determined by direct counting. Protein-DNA binding reactions and gel electrophoresis were similar to those described for other zinc finger proteins (see, for example, Pedone et al, 1996, Morris et al., 1994, Cook et al., 1996). Gels were exposed to phosphor screens for 14–20 hours and visualized with a phosphorimager (Molecular Dynamics Storm 860).

A GST fusion protein containing the last six zinc fingers of CHD1 (CHD1.ZnF3-8) was expressed in bacteria, purified and used to define a consensus binding site by selection of specific sequences from random oligonucleotides, essentially as described in Morris et al., 1994. A consensus binding motif (GGGGT) resulted. This motif was found in multiple copies in the regulatory regions upstream of the start of transcription in several genes known to be involved in lipid metabolism. Several promoter fragments containing these sequences were amplified from genomic DNA and gel shift assays were performed.

Examples of gel shift assays are shown for ApoAIV, ApoCIII, ApoE, LPL and LCAT promoter fragments in FIG. 5. GST protein alone does not cause a mobility shift of these fragments (FIG. 5C). In addition, poly dI:dC does not compete for binding of the fragments bound to CHD1.ZnF3-8 (FIGS. 5B, 5C). These two observations taken together indicate that binding of CHD1.ZnF3-8 to these promoter fragments is sequence specific. Protein dilution experiments indicate that binding of CHD1.ZnF3-8 to the ApoAIV fragment has an apparent Kd of approximately 10 nM, an upper limit assuming that all of the partially purified CHD1.ZnF3-8 protein is in active conformation. This is well with the range of biologically relevant DNA binding (Ausubel et al., 1992, Kriwacki et al., 1992). Several DNA fragments tested did not bind to CHD1, including sub-fragments of the ApoAIV and LPL promoters (FIGS. 5B, 6). These sub-fragments do not possess a CHD1 binding motif, again indicating specificity of binding. A summary of the promoter elements that bind CHD1 in vitro is provided in Table 12, and the positions of the fragments tested are shown in Table 13.

TABLE 12

Genes with binding sites for CHD1 protein

| Gene | function | reference |
| --- | --- | --- |
| ApoAIV | structural component of HDL | Kardassis, et al., 1996 |
| ApoCIII enhancer | regulates liver expression of ApoAI, ApoCIII and ApoAIV | Kardassis, et al., 1996 |
| ApoE | structural component of LDL, HDL - binds LDL-R | Davignon, et al., 1988 |
| LPL | lipoprotein lipase/interconversion of lipoproteins, metabolism of TG-rich lipoproteins | Olivercrona, et al., 1993 |
| LCAT | lecithin: cholesterol acyltransferase/metabolism of pre-beta-HDL | Kuivenhoven, et al., 1997 |
| PLTP | phospholipid transport protein/metabolism of pre-beta-HDL | Marques-Vidal, et al., 1997 |
| HTGL | hepatic triglyceride lipase (at -2,600)/liver TG metabolism | Chang, et al., 1997 |
| VEGF | vascular endothelial growth factor/growth regulation of endothelium - possible atherosclerosis | Ferrara and Davis-Smyth, 1997 |
| IA-1 | Ch 20 insulinoma-associated Zn-finger gene that may be regulated by glucokinase upstream promoter elements and a Pit-1 factor binding site (both cause MODY)/possible diabetes (db) | Lan, et al., 1994 |

TABLE 12-continued

Genes with binding sites for CHD1 protein

| Gene | function | reference |
| --- | --- | --- |
| β3AR | beta-3 adrenergic receptor gene/linked to diabetes, obesity and insulin resistance | Groop, 1997 |
| CRABP2 | retinoic acid (RA) responsive element −5.6 kb upstream of cellular retinoic acid-binding protein 2/region required for RAR-alpha induction of CRABP2 which is an uncharacterized homologue of CRABP, which binds RA | Astrom, et al., 1994 |
| CALRT1 | calretinin/brain-specific calcium binding protein | Parmentier and Lefort 1991 |
| GOS24 | Zn-finger putative lymphocyte G0/G1 switch regulatory gene | Heximer and Forsdyke, 1993 |
| p16/ALT | alternate exon 1-beta of p16INK4A | Merlo, et al., 1995 |
| PNMTA | phenylethanolamine N-methyltransferase (at −1,700)/conversion of norepinephrine to epinephrine | Baetge, et al., 1988 |
| PLP | Ch X proteolipid protein/myelin component, mutant in human dysmyelination disorders | Hudson, et al., 1989 |

TABLE 13

Positions of promoter fragments that bind CHD1 protein

| Gene | GenBank accession # | probe * |
| --- | --- | --- |
| ApoAIV | X13368 | 779–1187 |
| ApoCIII | X13367 | 675–1052 |
| ApoE | M10065 | 723–1062 |
| LPL | M29549 | 199–544 |
| LCAT | X51966 | 1411–1767 |
| PLTP | U38950 | 310–446 |
| HTGL | X58779 | 500–800 |
| VEGF | M63971 | 1193–1348 |
| IA-1 | U07172 | 641–725 |
| β3AR | M62473 | 1022–1245 |
| CRABP2 | U09967 | 73–235 |
| CALRT1 | X56668 | 3846–3941 |
| GOS24 | M92844 | 300–362 |
| p16/ALT | L41934 | 23–165 |
| PNMTA | J03280 | 115–260 |
| PLP | M27111 | 698–852 |

* bp are given according to numbering in the GenBank entry

The promoter fragments that CHD1 binds to can be grouped into several classes (Table 12). The promoters of a set of apolipoprotein (Apo) genes, which encode structural components of circulating lipoproteins, comprising the Class 1 genes potentially regulated by CHD1. Class 1 includes the HDL structural proteins ApoAIV and ApoE, as well as the ApoCIII enhancer, which regulate the liver specific expression of the ApoAI, CIII, AIV genes (reviewed in Kardassis et al., 1996). In all of these promoters the fragments that bind CHD1 have been shown to bind unidentified proteins from nuclear extracts, and to regulate gene expression in vitro (reviewed in Kardassis et al., 1996— FIG. 7). As described in the background section, the ApoAI, ApoCIII, ApoAIV loci have been genetically associated with several dyslipidemias and atherosclerosis. ApoE is a component of many circulating lipoproteins, and mediates interactions of these proteins with the LDL-receptor. Common polymorphisms of ApoE alter its affinity for the LDL receptor, and can cause dyslipidemic phenotypes and predisposition to atherosclerosis (Xu et al., 1991, Davignon et al., 1988).

The second class of promoters that bind to CHD1 includes several enzymes known to influence lipoprotein composition. Class 2 includes the lipoprotein lipase gene (LPL), the lecithin:cholesterol acyltransferase gene (LCAT), the phospholipid transport protein gene (PLTP) and the hepatic triglyceride lipase gene (HTGL). As described in the background section, LPL and LCAT deficiencies are associated with atherosclerosis and HDL-C levels (Cohen et al., 1994, Kuivenhoven et al, 1997). In addition, PLTP and HTGL can alter the composition of HDL particles in vitro (e.g. Marques-Vidal et al., 1997). Levels of plasma PTLP correlate with obesity and blood glucose, providing a possible link between insulin resistance, obesity and HDL metabolism (Dullart et al, 1994). The region of the HTGL promoter that binds CHD1 also regulates expression of the gene in liver cells (Chang et al., 1997).

The third class of promoters that bind to CHD1 protein includes several other genes implicated directly in the etiology of atherosclerosis, obesity and diabetes. Vascular endothelial growth factor (VEGF) is involved in atherosclerosis and angiogenesis, and modulation of its activity is the focus of several atherosclerosis intervention studies and drug discovery programs (Waltenberger 1997, Sueishi et al., 1997, Ferrara and Davie-Smyth, 1997). IA-1 is an insulinoma associated zinc finger gene, expression of which is regulated in a similar way to several genes involved in maturity onset diabetes of the young (MODY) (see background section for review of MODY). A common polymorphism of the beta-3 adrenergic receptor (β3AR) gene is associated with obesity (Silver et al., 1997), insulin resistance and weight control in NIDDM patients (Sakane et al., 1997), and with visceral obesity and decreased serum triglycerides (e.g. Kim-Motoyama et al., 1997). Thus, insulin resistant syndrome X may be partly explained by a common variant of β3AR (reviewed in Groop, 1997). This gene is the target of a number of drug discovery programs for the treatment of obesity and diabetes (reviewed in Strosberg and Pietr-Rouxel, 1996).

The remaining six genes, the promoters of which bind CHD1 protein, do not have a known link to either atherosclerosis or metabolic disease (Table 12).

In addition to the genes listed in Table 12, CHD1 has been found to bind to a promoter fragment of the HNF4 gene (hepatic nuclear factor 4). Transfection assays indicate that CHD1 represses transcription from this promoter suggesting that CHD1 may regulate HNF4 expression in vivo. Pathological consequences of CHD1 dysfunction are likely include deregulation of HNF4 expression that may be counteracted by agonists/antagonists of HNF4.

HNF4 is a member of the nuclear receptor superfamily, a class of ligand-activated transcription factors. HNF4 functions as a major regulator of liver-specific gene expression, and is involved in the expression of apolipoproteins AI, AII, AIV B and CIII (Kardassis et al., 1996). Mutations in HNF4 have been identified in MODY1 (maturity-onset diabetes of the young) cases (Yamagata et al., 1996, Furuta et al., 1997) linking HNF4 to diabetes. As a ligand-activated nuclear receptor HNF4 presents an excellent target for drug development.

Thus, CHD1 is a sequence specific DNA binding protein. It binds to fragments of the regulatory regions of a subset of apolipoprotein genes, a set of genes known to be intimately involved in the regulation of plasma lipoprotein metabolism, and a set of genes that have links to atherosclerosis, obesity, NIDDM and insulin resistant syndrome X. CHD1 has also been shown to bind to the regulatory region of HNF4, whose gene product is involved in regulating the expression of several apolipoprotein genes. The binding of CHD1 to these regulatory regions makes it very probable that CHD1 is involved in their regulation, and in the pathophysiology of these disorders.

TABLE 14

Polymorphisms in CHD1 and allele frequencies in CHD cases and CEPH controls

| location | amplicon | genomic position | cDNA position | | CHD 75 samples | CEPH 144 samples | |
| --- | --- | --- | --- | --- | --- | --- | --- |
| exonG | 7.7 bq | 9610 | −551 | C | 0.41 | 0.44 | non-coding |
| | | | | G | 0.59 | 0.55 | |
| exonG | 7.7 bq | 9655 | −506 | A | 0.26 | 0.29 | non-coding |
| | | | | T | 0.74 | 0.71 | |
| intronGF | 7.6 bq | 9838 | −323 | A | 0.41 | 0.44 | intron |
| | | | | G | 0.59 | 0.56 | |
| intronGF | 7.6 bq | 9921 | −240 | A | 0.86 | 0.87 | intron |
| | | | | T | 0.14 | 0.13 | |
| intronGF | 7.6 bq | 9938 | −223 | C | 0.27 | 0.28 | intron |
| | | | | T | 0.73 | 0.72 | |
| exonA | 7.1 bq | 11379 | 558 | C | 0.77 | 0.7 | GTG > GCG |
| | | | | T | 0.23 | 0.3 | Val > Ala |
| exonC | 7.2 bq | 12902 | 829 | A | 0.82 | 0.73 | GTA > GTG |
| | | | | G | 0.18 | 0.27 | Val > Val |
| exonC | 7.2 bq | 12945 | 872 | A > G | | | Lys > Glu |
| 3'UTR | 7.4 bq | 15140 | 2046 | G | 0.45 | 0.4 | non-coding |
| | | | | T | 0.55 | 0.6 | |
| 3'UTR | 7.4 ds | 15787 | 2693 | G | 0.76 | 0.68 | non-coding |
| | | | | A | 0.24 | 0.32 | |

EXAMPLE 9

Polymorphisms in CHD1 in CHD Cases and CEPH Controls

The DNA samples that were screened for CHD1 mutations were extracted from blood of patients with CHD or other metabolic disorders who were participating in research studies on the genetics of coronary heart disease. All subject signed appropriate informed consent. All exons of CHD1 and intron sequences within about 20–30 bases of the exons were screened for mutation in a set of 75 affected individuals from 43 kindreds, using the mutation screening protocol and primers described in Example 6. These represent individuals segregating haplotypes in the region of CHD1, and 9 spouses from the most likely linked families. In addition, a set of samples from diabetics were also screened for mutations. The number of samples screened for each exon is shown in Tables 14 and 15. Alterations of CHD1 sequence detected are shown in Table 14. One of the alterations in exonA results in a conservative change in the amino acid sequence of the CHD1 protein (an alanine to valine alteration, Table 14).

TABLE 15 number of individuals screened

| CHD-1 amplicon | # of individuals, mutation screened | | | # polymorph- isms | # mutations |
|---|---|---|---|---|---|
| | CHD families | CEPH controls | diabetes samples | | |
| exonG (5' UTR) | 75 | 134 | | 2 | |
| exonF | 75 | | 88 | | |
| exonA | 75 | 134 | 226 | 1 | |
| exonB | 75 | | | | |
| exonC | 75 | 134 | 226 | 1 | 1 |
| exonD | 75 | | 226 | | |
| exonE | 75 | | 88 | | |
| 3'UTR | 75 | 134 | | 2 | |

A second sequence alteration has only been seen in one sample form an obese diabetic individual, raising the possibility that this alteration disrupts gene function. This alteration in exonC at genomic nucleotide position 12945 and position 872 in cDNA1, results in a Lysine to Glutamic Acid substitution. This results in a change in the sign of a charged amino acid side chain, a highly significant alteration, very likely affecting protein structure. In addition, it occurs within a relatively conserved sequence motif, the KRAB domain (FIG. 4). As described above, KRAB domains often mediate transcriptional repression. Thus, one possible mechanism by which the diabetic mutation may mediate disease is through disruption of a protein interaction that normally reduces the level of gene expression from target genes.

The other polymorphisms are in the non-coding regions 5' or 3' to the open reading frame, in intronGF in positions unlikely to directly alter splicing patterns, or in third positions of codons that do not alter the sequence of the encoded protein. To test the possible association of these polymorphisms with CHD or metabolic disease, the frequency of selected common polymorphisms was compared between the 75 mutation screening samples (CHD in Table 14) and 120 CEPH control individuals (CEPH in Table 14). The CEPH controls are grandparents of the UTAH CEPH kindreds (obtained from the Coriell Institute for Medical Research), and represent a good population control for the CHD kindreds. None of the allele frequencies differed significantly between these two sets of individuals, indicating that they are not likely to be causal mutations.

The haplotypes associated with ten polymorphisms in CHD1, and the frequencies of these haplotypes in CHD patients and CEPH controls, are described in Table 16 The five most common haplotypes have all been observed in homozygous individuals. These haplotypes may be useful in identifying intragenic deletions in individual samples, or in segregation analysis of possible mutations in linked families.

In summary, one probable causal mutation in CHD1 has been found. This mutation causes a Lysine to Glutamic Acid substitution in an individual with morbid obesity (BMI=47), diabetes and low HDL-C.

Additionally, genomic sequences including exonJ and promoter elements for CHD1 have been identified (Example 7). Five additional polymorphisms and one insertion were found in CHD and CEPH samples. Their position and frequencies are listed in Table 17.

TABLE 16

Haplotypes of Ten Polymorphisms

| Haplotype | % in CEPH (148)* | % in CHD (90)** | exonG | exonG | intronGF | intronGF | intronGF | intronFA | exonA | exonC | 3UTR | 3UTR |
|---|---|---|---|---|---|---|---|---|---|---|---|---|
| 1-7 | 30% (44) | 22% (20) | G | T | G | A | T | C | C | A | G | A |
| 3-6 | 25% (37) | 26% (23) | C | A | A | A | C | C | T | G | T | G |
| 1-6 | 16% (23) | 23% (21) | G | T | G | A | T | C | C | A | T | G |
| 2-6 | 16% (24) | 12% (11) | C | T | A | T | T | T | C | A | T | G |
| 1-5 | 7% (11) | 11% (10) | G | T | G | A | T | C | C | A | G | G |
| 2-5 | 0.6% (1) | 2% (2) | C | T | A | T | T | T | C | A | G | G |
| 4-7 | 0.6% (1) | 0 | C | A | A | A | C | ? | T | A | G | A |
| 4-6 | 0 | 1% (1) | C | A | A | A | C | C | T | A | T | G |
| 8-5 | 0.6% (1) | 0 | G | T | A | A | T | ? | C | A | G | G |
| 8-6 | 0.6% (1) | 0 | G | T | A | A | T | ? | C | A | T | G |
| 8-7 | 1.2% (2) | 0 | G | T | A | A | T | ? | C | A | G | A |
| 9-6 | 0.6% (1) | 0 | G | A | A | A | C | ? | T | G | T | G |
| 10-6 | 0.6% (1) | 0 | G | T | G | A | T | ? | T | A | T | G |
| 11-6 | 0.6% (1) | 0 | G | T | A | G | A | ? | ? | C | ? | T | G |

* % in CEPH controls (number of observations)
** % in CHD samples (number of observations)

TABLE 17

Polymorphisms in the Promoter Region of CHD1* and Allele Frequencies in CHD Cases and CEPH Controls

| location | amplicon | genomic position | | CHD 45 samples | CEPH 82 samples | |
|---|---|---|---|---|---|---|
| promoter | 14 fu | −640 | G | 0.97 | | non-coding |
| | | | T | 0.03 | | |
| promoter | 14 ds | −1182 | A | 0.79 | 0.68 | non-coding |
| | | | G | 0.21 | 0.32 | |
| promoter | 15 bq | −2713 | A | 0.86 | | non-coding |
| | | | C | 0.14 | | |
| promoter | 15 bq | −2735 | T | 0.74 | | non-coding |
| | | | C | 0.26 | | |
| promoter | 15 bq | −2795 | A | 0.61 | | non-coding |
| | | | G | 0.39 | | |
| promoter | 15 bq | −2814/−2813 | wt | 0.99 | | non-coding |
| | | | T insertion | 0.01 | | |

* Genomic position of the polymorphisms was derived by setting the nucleotide position number 2,934 of SEQ ID NO: 210 as +1.

EXAMPLE 10
Analysis of the CHD1 Gene

The structure and function of CHD1 gene are determined according to the following methods.

Biological Studies. Because CHD1 binds to DNA sequence-specifically and it binds to promoter fragments of genes whose gene products are involved in lipid metabolism (Example 8), biological experiments are designed to address its role in transcription regulation. The full length protein is expressed in appropriate cells to assess the role of CHD1 in transcription. Inducible expression of the gene in tissue culture cells, such as HepG2 cells, will be used to study any alterations in the expression of other genes that are caused by CHD1, including those genes identified in Example 8. The ability of CHD1 to regulate transcription of these and other genes is analyzed by transient reporter expression systems in mammalian cells.

Molecular Genetics Studies. In vitro mutagenesis is performed to construct deletion mutants and missense mutants (by single base-pair substitutions in individual codons and alanine scanning mutagenesis). The mutants are used in biological, biochemical and biophysical studies.

Mechanistic Studies. Conventional procedures such as co-immunoprecipitation, affinity chromatography and the yeast two-hybrid system (details of which are provided in Example 15) are used to discover and identify any functional partners. The nature and functions of the partners are characterized. These partners in turn are targets for drug discovery. In addition, protein interaction motifs identified in these ways are further characterized by in vitro mutagenesis.

Structural Studies. Recombinant proteins are produced in E. coli, yeast, insect and/or mammalian cells and are used in crystallographic and NMR studies. Molecular modeling of the proteins is also employed. These studies facilitate structure-driven drug design.

EXAMPLE 11
Generation of Polyclonal Antibodies Against CHD1

Segments of CHD1 coding sequence are expressed as fusion proteins in E. coli. The proteins, expressed at high levels, are purified by gel elution and used to immunize rabbits and mice using a procedure similar to the one described by Harlow and Lane, 1988. This procedure has been shown to generate antibodies against various other proteins (for example, see Kraemer, et al., 1993).

Briefly, a stretch of CHD1 coding sequence was cloned as a fusion protein in plasmid PET5A (Novagen, Inc., Madison, Wis.). After induction with IPTG, the overexpression of a fusion protein with the expected molecular weight is verified by gel electrophoresis in the presence of sodium dodecyl sulphate (SDS-PAGE). Fusion proteins are purified from the gel by electroelution. The identification of the protein as the CHD1 fusion product is verified by protein sequencing at the N-terminus. Next, the purified protein is used as immunogen in rabbits. Rabbits are immunized with 100 mg of the protein in complete Freund's adjuvant and boosted twice in three-week intervals, first with 100 mg of immunogen in incomplete Freund's adjuvant followed by 100 mg of immunogen in phosphate buffer saline (PBS). Antibody containing serum is collected three weeks thereafter.

This procedure can be repeated to generate antibodies against the mutant forms of the CHD1 protein. These antibodies, in conjunction with antibodies to wild type CHD1, are used to detect the presence and the relative level of the mutant forms in various tissues and biological fluids.

EXAMPLE 12
Generation of Monoclonal Antibodies Specific for CHD1

Monoclonal antibodies are generated according to the following protocol. Mice are immunized with immunogen comprising intact CHD1 or CHD1 peptides (wild type or mutant) conjugated to keyhole limpet hemocyanin using glutaraldehyde or EDC as is well known in the art.

The immunogen is mixed with an adjuvant. Each mouse receives four injections of 10 to 100 mg of immunogen and after the fourth injection blood samples are taken from the mice to determine if the serum contains antibody to the immunogen. Serum titer is determined by ELISA or RIA. Mice with sera positive for the presence of antibody to the immunogen are selected for hybridoma production.

Spleens are removed from immune mice and a single cell suspension is prepared (see Harlow and Lane, 1988). Briefly, P3.65.3 myeloma cells (American Type Culture Collection, Rockville, Md.) are fused with immune spleen cells using polyethylene glycol as described by Harlow and Lane, 1988. Cells are plated at a density of 2×10$^5$ cells/well in 96 well tissue culture plates. Individual wells are examined for growth and the supernatants of wells with growth are tested for the presence of CHD1 specific antibodies by ELISA or RIA using wild type or mutant CHD1 target protein. Cells in positive wells are expanded and subcloned to establish and confirm monoclonality.

Clones with the desired specificities are expanded and grown as ascites in mice or in a hollow fiber system to produce sufficient quantities of antibody for characterization and assay development.

EXAMPLE 13
Isolation and Use of CHD1 Binding Peptides

Peptides that bind to the CHD1 gene product are isolated from both chemical and phage-displayed random peptide libraries as follows.

Fragments of the CHD1 gene product are expressed as glutathione-S-transferase (GST) and six histidine (His-tag) fusion proteins in both *E. coli* and SF9 cells. The fusion protein is isolated using either a glutathione matrix (for GST fusions proteins) or nickel chelation matrix (for His-tag fusion proteins). This target fusion protein preparation is either screened directly as described below, or eluted with glutathione or imidizole. The target protein is immobilized to either a surface such as polystyrene; or a resin such as agarose; or solid supports using either direct absorption, covalent linkage reagents such as glutaraldehyde, or linkage agents such as biotin-avidin.

Two types of random peptide libraries of varying lengths are generated: synthetic peptide libraries that may contain derivatized residues, for example by phosphorylation or myristylation, and phage-displayed peptide libraries which may be phosphorylated. These libraries are incubated with immobilized CHD1 gene product in a variety of physiological buffers. Next, unbound peptides are removed by repeated washes, and bound peptides recovered by a variety of elution reagents such as low or high pH, strong denaturants, glutathione, or imidizole. Recovered synthetic peptide mixtures are sent to commercial services for peptide microsequencing to identify enriched residues. Recovered phage are amplified and rescreened. The positive plaques are purified, and the DNAs encoding the peptides are then sequenced to determined the identity of the displayed peptides.

Peptides identified from the above screens are synthesized in larger quantities as biotin conjugates by commercial services. These peptides are used in both solid and solution phase competition assays with CHD1 and its interacting partners identified in yeast 2-hybrid screens. Versions of these peptides that are fused to membrane-permeable motifs (Lin et al., 1995; Rojas et al., 1996) will be chemically synthesized, added to cultured cells and the effects on growth, apoptosis, differentiation, cofactor response, and internal changes will be assayed.

EXAMPLE 14
Sandwich Assay for CHD1

Monoclonal antibody is attached to a solid surface such as a plate, tube, bead, or particle. Preferably, the antibody is attached to the well surface of a 96-well ELISA plate. 100 ml sample (e.g., serum, urine, tissue cytosol) containing the CHD1 peptide/protein (wild-type or mutant) is added to the solid phase antibody. The sample is incubated for 2 hours at room temperature. Next, the sample fluid is decanted, and the solid phase is washed with buffer to remove unbound material. 100 ml of a second monoclonal antibody (to a different antigenic determinant on the CHD1 peptide/protein) is added to the solid phase. This antibody is labeled with a detector molecule (e.g., $^{125}$I, enzyme, fluorophore, or a chromophore) and the solid phase with the second antibody is incubated for two hours at room temperature. The second antibody is decanted and the solid phase is washed with buffer to remove unbound material.

The amount of bound label, which is proportional to the amount of CHD1 peptide/protein present in the sample, is quantitated. Separate assays are performed using monoclonal antibodies that are specific for the wild-type CHD1 as well as monoclonal antibodies specific for each of the mutations identified in CHD1.

EXAMPLE 15
Two-hybrid Assay to Identify Proteins that Interact with CHD1

Sequence encoding all or portions of CHD1 are ligated to pAS2-1 (Clontech) such that the coding sequence of CHD1 is in-frame with the coding sequence for the DNA-binding domain of GAL4. This plasmid construct is introduced into the yeast reporter strain Y190 by transformation. A library of activation domain fusion plasmids prepared from human liver cDNA (Clontech) is then introduced into strain Y190 carrying the pAS2-1-based fusion construct. Transformants are spread onto 20–150 mm plates of yeast minimal media lacking leucine, tryptophan, and histidine, and containing 25 mM 3-amino-1,2,4-triazole. After one week incubation at 30° C., yeast colonies are assayed for expression of the lacZ reporter gene by β-galactosidase filter assay. Colonies that both grow in the absence of histidine and are positive for production of β-galactosidase are chosen for further characterization.

The activation domain fusion plasmid is purified from positive colonies by the smash-and-grab technique. These plasmids are introduced into *E. coli* DH5α by electroporation and purified from *E. coli* by the alkaline lysis method. To test for the specificity of the interaction, specific activation domain fusion plasmids are cotransformed into strain Y190 with plasmids encoding various DNA-binding domain fusion proteins, including fusions to CHD1 and human lamin C. Transformants from these experiments are assayed for expression of the HIS3 and lacZ reporter genes. Positives that express reporter genes with CHD1 constructs and not with lamin C constructs encode bona fide CHD1 interacting proteins. These proteins are identified and characterized by sequence analysis of the insert of the appropriate activation domain plasmid.

This procedure is repeated with mutant forms of the CHD1 gene, to identify proteins that interact with only the mutant protein or to determine whether a mutant form of the CHD1 protein can or cannot interact with a protein known to interact with wild-type CHD1.

References

Altschul, S. F. et al. (1990). *J. Mol. Biol.* 215:195–197.
Anand, R. (1992). *Techniques for the Analysis of Complex Genomes,* (Academic Press).
Anderson, et al. (1980). *Proc. Natl. Acad. Sci. USA* 77:5399–5403.
Arshura, et al. (1995). *Mol. Cell. Biol.,* 15:6702–6709.
Astrom, A., et al. (1994). *J. Biol. Chem.,* 269(35): 22334–22339.
Ausubel, F. M., et al. (1992). *Current Protocols in Molecular Biology,* (J. Wiley and Sons, N.Y.).
Baetge, E. E., et al. (1988). *Proc. Natl. Acad. Sci.,* 85(10):3648–3652.
Berkner, et al. (1988). *BioTechniques* 6:616–629.
Berkner (1992). *Curr. Top. Microbiol. Immunol.* 158:39–61.
Blangero, J., S. Williams-Blangero, et al. (1996). *Arterioscler Thromb Vasc Biol* 16(9):1177–83.
Botstein, et al. (1980). *Am. J. Hum. Genet.* 32:314–331.
Brandyopadhyay and Temin (1984). *Mol. Cell. Biol.* 4:749–754.

Breakfield and Geller (1987). *Mol. Neurobiol.* 1:337–371.
Brinster, et al. (1981). *Cell* 27:223–231.
Bu, X., C. H. Warden, et al. (1994). *Hum Genet* 93(6):639–648.
Buchschacher and Panganiban (1992). *J. Virol.* 66:2731–2739.
Capecchi, M. R. (1989). *Science* 244:1288.
Castro Cabezas, M., T. W. de Bruin, et al. (1993). *J Clin Invest* 92(1):160–8.
Chang, S. F., Scharf, J. G., Will, H. (1997). *Eur. J. Biochem.*, 247(1):148–159.
Chen, B. P., et al. (1994). *Biol. Chem.*, 269:15819–15826.
Claverie, J. M. and States, D. J. (1993). Information Enhancement Methods for Large Scale Sequence Analysis. *Computers and Chemistry* 17:191–201.
Cohen, J. C., et al. (1994). *J. Clin. Invest.*, 94(6):2377–2384.
Conner, B. J., et al. (1983). *Proc. Natl. Acad. Sci. USA* 80:278–282.
Constantini and Lacy (1981). *Nature* 294:92–94.
Cook, et al. (1996). *Oncogene* 13, 1789–1799.
Cotten, et al. (1990). *Proc. Natl. Acad. Sci. USA* 87:4033–4037.
Cotton, et al. (1988). *Proc. Natl. Acad. Sci. USA* 85:4397–4401.
Cottingham R W, Idury R M, Schaffer A A (1993). Faster sequential genetic linkage computations. *Am J Hum Genet* 53:252–263.
Culver, et al. (1992). *Science* 256:1550–1552.
Curiel, et al. (1991a). *Proc. Natl. Acad. Sci. USA* 88:8850–8854.
Curiel, et al. (1991b). *Hum. Gene Ther.* 3:147–154.
Dallinga-Thie, G. M., M. V. Trip, et al. (1997). *J Clin Invest* 99(5):953–961.
Davignon, J, et al. (1988). *Arteriosclerosis* 8, 1–21.
De Bruin, T. W., H. van Barlingen, et al. (1993). *J Clin Endocrinol Metab* 76(1):121–6.
De Bruin, T. W., F. Mailly, et al. (1996). *Eur J Clin Invest* 26(8):631–9.
Deeb, S. S., D. N. Nevin, et al. (1996). *Hum Mutat* 8(4):319–25.
DeMeester, C. A., et al. (1995). *Am. J. Hum. Genet.,* 56(1):287–293.
Donehower, L. A., et al. (1992). *Nature* 356:215.
Dullaart, R P, et al. (1994). *Eur J Clin Invest* 24, 188–194.
Durbin R and Thierry-Mieg J (1991). A *C. elegans* Database. Documentation, code and data available from anonymous FTP servers at lirmm.lirmm.fr, cele.mrc-lmb.cam.ac.uk and ncbi.nlm.nih.gov. *Enhancers and Eurkaryotic Gene Expression,* Cold Spring Harbor Press, Cold Spring Harbor, N.Y. (1983).
Fairman, R., R. K. Beran-Steed, S. J. Athony-Cahill, J. D. Lear, W. F. Stafford, W. F. DeGrado, P. A. Benfield and S. L. Brenner (1993) *Proc. Natl. Acad. Sci.* 90, 10429–10433.
Fawell S. E., J. A. Less, R. White and M. G. Parker (1990) *Cell* 60, 953–962.
Felgner, et al. (1987). *Proc. Natl. Acad. Sci. USA* 84:7413–7417.
Ferrara, N and Davis-Smyth, T. (1997). *Endocr Rev* 18, 4–25.
Fiers, et al. (1978). *Nature* 273:113.
Fink, et al. (1992). *Hum. Gene Ther.* 3:11–19.
Finkelstein, J., et al. (1990). *Genomics* 7:167–172.
Fodor, S. P. A. (1997). DNA Sequencing. Massively Parallel Genomics. *Science* 277:393–395.
Freese, et al. (1990). *Biochem. Pharmacol.* 40:2189–2199.
Friedlander, Y., Kark, J. D., Stein, Y. (1986). *Hum. Hered.,* 36(3):143–153.
Friedlander, Y., Kark, J. D., Stein, Y. (1986). *Genet. Epidemiol.,* 3(2):95–112.
Friedlander, Y., Leitersdorf, E. (1996). *Genet. Epidemiol.,* 13(2):159–177.
Friedman, T. (1991). In *Therapy for Genetic Diseases,* T. Friedman, ed., Oxford University Press, pp. 105–121.
Funke, H. (1997). *Current Opinion in Lipidology* 8:189–196.
Glover, D. (1985). *DNA Cloning,* I and II (Oxford Press).
Goding (1986). *Monoclonal Antibodies: Principles and Practice,* 2d ed. (Academic Press, N.Y.).
Goldstein, J. L., et al. (1973). *J. Clin Invest.,* 52(7):1544–1568.
Gordon, et al. (1980). *Proc. Natl. Acad. Sci. USA* 77:7380–7384.
Gorziglia and Kapikian (1992). *J. Virol.* 66:4407–4412.
Graham and van der Eb (1973). *Virology* 52:456–467.
Grompe, M., et al., (1989). *Proc. Natl. Acad. Sci. USA* 86:5855–5892.
Groop, L C. (1997). *J Intern Med* 241, 95–101.
Guthrie, G. and Fink, G. R. (1991). *Guide to Yeast Genetics and Molecular Biology* (Academic Press).
Gyapay, G., et al. (1994). *Nat. Genet.,* 7(2 Spec No):246–339.
Harlow and Lane (1988). *Antibodies: A Laboratory Manual* (Cold Spring Harbor Laboratory, Cold Spring Harbor, N.Y.
Habener, J. F., Stoffers, D. A. (1998). *Proc. Assoc. Am. Physicians,* 110(1):12–21.
Hacia, J. G., et al. (1996). *Nat. Genet.,* 14(4):441–447.
Hasty, P., K., et al. (1991). *Nature* 350:243.
Hazzard, W. R., G. R. Warnick, et al. (1981). *Metabolism* 30(1): 79–88.
Helseth, et al. (1990). *J. Virol.* 64:2416–2420.
Heximer, S. P., Forsdyke, D. R. (1993). *DNA Cell Biol.,* 12(1):73–88.
Hjermann, I. (1992). *J Cardiovasc Pharmacol* 20(8):S5–10.
Hopkins, P. N., R. R. Williams, et al. (1988). *Am J Cardiol* 62(10 Pt 1):703–7.
Hopkins, P. N., S. C. Hunt, et al. (1996). *Curr Opin Lipidol* 7(4):241–53.
Horikawa, Y., et al. (1997). *Nat. Genet.,* 17(4):384–385.
Hudson, L. D., et al. (1989). *Proc. Natl. Acad. Sci.,* 86(20):8128–8131.
Innis, et al. (1990). *PCR Protocols: A Guide to Methods and Applications* (Academic Press, San Diego, Calif.).
Iverius, P. H. and J. D. Brunzell (1985). *Ann Intern Med* 103:1050–1.
Jablonski, E., et al. (1986). *Nuc. Acids Res.* 14:6115–6128.
Jakoby, W. B. and Pastan, I. H. (eds.) (1979). *Cell Culture. Methods in Enzymology,* volume 58 (Academic Press, Inc., Harcourt Brace Jovanovich (New York)).
Jeffreys, et al. (1985). *Nature* 314:67–73.
Johnson, et al. (1992). *J. Virol.* 66:2952–2965.
Jorde, L. B., Williams, R. R. & Hunt, S. C. (1984). *West J Med* 140, 220–3
Kaneda, et al. (1989). *J. Biol. Chem.* 264:12126–12129.
Kanehisa (1984). *Nucl. Acids Res.* 12:203–213.
Kardassis, D., et al. (1996). *Hypertension,* 27:980–1008.
Kawamoto, T. and K. Ishikawa (1996). *Hypertens Res* 19(1):S69–74.
Kim, S. S., et al. (1996). *Proc. Natl. Acad. Sci.,* 93:15299–15304.
Kim-Motoyama, H, et al. (1997). *Diabetologia* 40, 469–472.
Kinszler, K. W., et al. (1991). *Science* 251:1366–1370.
Kouzarides, T. and E. Ziff 1988 *Nature* 336, 646–651.
Kriwacki, R. W., et al., (1992). *Proc. Natl. Acad. Sci.,* 89:9759–9763.

Kubo, T., et al. (1988). *FEBS Letts.* 241:119.
Kuivenhoven, et al. (1997). *J Lipid Res* 38, 191–205.
Lan, M. S., et al. (1994). *J. Biol. Chem.,* 269(19):14170–14174.
Landegren, et al. (1988). *Science* 242:229.
Landsberg, L. (1996). *Hypertens Res* 19(1): S51–5.
Lathrop G M, Lalouel J M, Julier C, Ott J (1985). Multilocus linkage analysis in humans: detection of linkage and estimation of recombination. *Am J Hum Genet.* 37:482–489.
Lee, P. L., et al. (1997). *Genomics,* 43:191–201.
Lim, et al. (1992). *Circulation* 83:2007–2011.
Lin, Y. Z., Yao, S., Veach, R. A., Torgerson, T. R., and Hawiger, J. (1995). *J. Biol. Chem.* 270:14255–14258.
Litt, et al. (1989). *Am. J. Hum. Genet.* 44:397–401.
Ma, J., Ptashne, M. (1987). *Cell,* 51(1):113–119.
Madzak, et al. (1992). *J. Gen. Virol.* 73:1533–1536.
Mahaney, M. C., J. Blangero, et al. (1995). *Arterioscler Thromb Vasc Biol* 15(10): 1730–9.
Maniatis T., et al. (1982). *Molecular Cloning: A Laboratory Manual* (Cold Spring Harbor Laboratory, Cold Spring Harbor, N.Y.).
Mann and Baltimore (1985). *J. Virol.* 54:401–407.
Mao, L., et al. (1995). *Cancer Res.,* 55(14):2995–2997.
Marcil, M., B. Boucher, et al. (1996). *J Lipid Res* 37(2):309–19.
Margolskee (1992). *Curr. Top. Microbiol. Immunol.* 158:67–90.
Marques-Vidal, P, et al. (1997). *Atherosclerosis* 133, 87–95.
Martin, R., et al. (1990). *BioTechniques* 9:762–768.
Matthews and Kricka (1988). *Anal. Biochem.* 169:1.
Metzger, et al. (1988). *Nature* 334:31–36.
Miller, et al. (1985). *Mol. Cell. Biol.* 5:431–437.
Miller, et al. (1988). *J. Virol.* 62:4337–4345.
Mittlin (1989). *Clinical Chem.* 35:1819.
Modrich, P. (1991). *Ann. Rev. Genet.* 25:229–253.
Moll, P. P., et al. (1989). *Am. J. Hum. Genet.,* 44(1):124–139.
Mombaerts, P., et al. (1992). *Cell* 68:869.
Morris, et al. (1994). *Mol Cell Biol* 14, 1786–1795.
Moosmann, P., et al. (1996). *Nucleic Acid Res.,* 24:4859–4867.
Moss (1992). *Curr. Top. Microbiol. Immunol.* 158:25–38.
Muzyczka (1992). *Curr. Top. Microbiol. Immunol.* 158:97–123.
Nabel (1992). *Hum. Gene Ther.* 3:399–410.
Nabel, et al. (1990). *Science* 249:1285–1288.
Nakamura, et al. (1987). *Science* 235:1616–1622.
Nguyen, Q., et al. (1992). *BioTechniques* 13:116–123.
Novack, et al. (1986). *Proc. Natl. Acad. Sci. USA* 83:586.
O'Connell, J R and Weeks, D E (1995). The VITESSE algorithm for rapid exact multilocus linkage analysis via genotype set-recoding and fuzzy inheritance. *Nature Genetics* 11:402–408.
Ohi, et al. (1990). *Gene* 89:279–282.
Olivecrona, T., et al. (1993). *Haemostasis,* 23(Suppl 1):150–160.
Orita, et al. (1989). *Proc. Natl. Acad. Sci. USA* 86:2776–2770.
Ott, J. (1986). *Genet. Epidemiol. Suppl.,* 1:251–257.
Page, et al. (1990). *J. Virol.* 64:5370–5276.
Parmentier, M., Lefort, A. (1991). *Eur. J. Biochem.,* 196(1):79–85.
Peacock, R., A. Dunning, et al. (1992). *Atherosclerosis* 92(2–3): 151–64.
Pedone, et al. (1996). *Proc Natl Acad Sci, USA* 93, 2822–2826.
Pellicer, et al. (1980). *Science* 209:1414–1422.
Perusse, L., et al. (1989). *Arteriosclerosis,* 9(3):308–318.
Philpott, K. L., et al. (1992). *Science* 256:1448.
Prenger, V. L., Beaty, T. H., Kwiterovich, P. O. (1992). *Am. J. Hum. Genet.,* 51(5):1047–1057.
Quantin, et al. (1992). *Proc. Natl. Acad. Sci. USA* 89:2581–2584.
Ramsay, G. (1998). *Nat. Biotechnol.,* 16(1):40–44.
Rano and Kidd (1989). *Nucl. Acids Res.* 17:8392.
Rigby, P. W. J., et al. (1977). *J. Mol. Biol.* 113:237–251.
Rojas, M., Yao, S., and Lin, Y. Z. (1996). *J. Biol. Chem.* 271:27456–27461.
Rosenfeld, et al. (1992). *Cell* 68:143–155.
Sakane, N., et al. (1997). *Diabetes Care* 20, 1887–1890.
Sambrook, J., et al. (1989). *Molecular Cloning: A Laboratory Manual,* 2nd Ed. (Cold Spring Harbor Laboratory, Cold Spring Harbor, N.Y.).
Schaffer A A, Gupta S K, Shriram K, Cottingham R W (1994). Avoiding recomputation in linkage analysis. *Human Heredity* 44:225–237.
Schena, M., et al. (1996). *Proc. Natl. Acad. Sci.,* 93(20):10614–10619.
Sheffield, V. C., et al. (1989). *Proc. Natl. Acad. Sci. USA* 86:232–236.
Sheffield, V. C., et al. (1991). *Am. J. Hum. Genet.* 49:699–706.
Shenk, et al. (1975). *Proc. Natl. Acad. Sci. USA* 72:989.
Shimada, et al. (1991). *J. Clin. Invest.* 88:1043–1047.
Shinkai, Y., et al. (1992). *Cell* 68:855.
Silver, K, et al. (1997). *Hum Genet* 101, 306–311.
Skolnick, M. H. and Wallace, B. R. (1988). *Genomics* 2:273–279.
Smith S W, Overbee, R, Woese C R, Gilbert W, Gillevet P M (1994). The Genetic Data Environment: An expandable GUI for multiple sequence analysis. *CABIOS* 10:671–675.
Snouwaert, J. N., et al. (1992). *Science* 257:1083.
Sorge, et al. (1984). *Mol. Cell. Biol.* 4:1730–1737.
Stewart, et al. (1992). *Hum. Gene Ther.* 3:267–275.
Stoffers, D. A., et al. (1997). *Nat. Genet.,* 17(2):138–139.
Stratford-Perricaudet, et al. (1990). *Hum. Gene Ther.* 1:241–256.
Strosberg, A D and Pietri-Rouxel, F. (1996). *Trends Pharmacol Sci* 17, 373–381.
Sueishi, K, et al. (1997). *Ann NY Acad Sci* 811, 311–324.
Tenkanen, H., M. R. Taskinen, et al. (1994). *J Lipid Res* 35(2): 220–8.
Thierry-Mieg D, Thierry-Mieg J and Sauvage U (1995). Ace.mbly. A graphic interactive program to support shotgun and directed sequencing projects.
Tybjaerg-Hansen, A., B. G. Nordestgaard, et al. (1993). *Atherosclerosis* 100(2): 157–69.
Vague, P. and D. Raccah (1992). *Horm Res* 38(1–2):28–32.
Valancius, V. and Smithies, 0. (1991). *Mol. Cell Biol.* 11:1402.
Wagner, et al. (1990). *Proc. Natl. Acad. Sci. USA* 87:3410–3414.
Wagner, et al. (1991). *Proc. Natl. Acad. Sci. USA* 88:4255–4259.
Walker, W. H., et al. (1996). *Biol. Chem.,* 271:20145–20150.
Waltenberger, J. (1997). *Circulation* 96, 4083–4094.
Wang and Huang (1989). *Biochemistry* 28:9508–9514.
Wartell, R. M., et al. (1990). *Nucl. Acids Res.* 18:2699–2705.
Weber and May (1989). *Am. J. Hum. Genet.* 44:388–396.
Wells, J. A. (1991). *Methods in Enzymol.* 202:390–411.
Wetmur and Davidson (1968). *J. Mol. Biol.* 31:349–370.
White, M. B., et al., (1992). *Genomics* 12:301–306.
White and Lalouel (1988). *Ann. Rev. Genet.* 22:259–279.

Wilkinson, et al. (1992). *Nucleic Acids Res.* 20:2233–2239.
Williams, R. R., P. N. Hopkins, et al. (1990). *Arch Intern Med* 150(3):582–8.
Williams, R. R., S. C. Hunt, et al. (1993). *Am J Hypertens* 6(11 Pt 2):319S–327S.
Williams, R. R., S. C. Hunt, et al. (1990). *Klin Wochenschr* 20:53–9.
Williams, A. J., L. M. Khachigian, T. Shows and T. Collins (1995) *J.Biol.Chem.* 270(38), 22143–22152.
Wojciechowski, A. P., M. Farrall, et al. (1991). *Nature* 349(6305):161–4.
Wolff, et al. (1990). *Science* 247:1465–1468.
Wolff, et al. (1991). *BioTechniques* 11:474–485.
Wu, et al. (1989a). *Genomics* 4:560–569.
Wu, et al. (1989b). *J. Biol. Chem.* 264:16985–16987.
Wu, et al. (1991). *J. Biol. Chem.* 266:14338–14342.
Xu, C. F., et al. (1991). *Genetic Epidemiol.* 8, 389–398.
Xu, C. F., P. Talmud, et al. (1994). *Clin Genet* 46(6):385–97.
Yamagata, K., et al. (1996). *Nature,* 384(6608):455–458.
Yamagata, K., et al. (1996). *Nature,* 384(6608):458–460.
Yang, W. S., D. N. Nevin, et al. (1996). *J Lipid Res* 37(12):2627–37.
Zenke, et al. (1990). *Proc. Natl. Acad. Sci. USA* 87:3655–3659.

We claim:

1. An isolated, recombinant or synthetic DNA wherein the DNA comprises a nucleic acid sequence selected from the group consisting of SEQ ID NO: 1, SEQ ID NO: 3, SEQ ID NO: 5 and SEQ ID NO: 7.

2. The DNA according to claim 1 wherein the DNA comprises a nucleic acid sequence of SEQ ID NO: 206.

3. An isolated, recombinant or synthetic DNA comprising a nucleic acid sequence selected from the group consisting of SEQ ID NO: 169, SEQ ID NO: 170, position 19 to position 40 of SEQ ID NO: 169, and position 19 to position 41 of SEQ ID NO: 170.

4. An isolated, recombinant or synthetic DNA comprising a nucleic acid sequence selected from the group consisting of SEQ ID NO: 209 and SEQ ID NO: 210.

5. An isolated, recombinant or synthetic DNA or polynucleotide comprising a nucleic acid sequence that is at least 60% homologous to any of the DNAs selected from the group consisting of SEQ ID NO: 1, SEQ ID NO: 3, SEQ ID NO: 5, SEQ ID NO: 7, SEQ ID NO: 169, SEQ ID NO: 170, SEQ ID NO: 206, SEQ ID NO: 209, SEQ ID NO: 210, position 19 to position 40 of SEQ ID NO: 169 and position 19 to position 41 of SEQ ID NO: 170.

6. An isolated, recombinant or synthetic DNA or polynucleotide comprising a nucleic acid sequence that hybridizes under stringent conditions to and that is at least 80% complementary to any of the nucleic acid sequences selected from the group consisting of SEQ ID NO: 1, SEQ ID NO: 3, SEQ ID NO: 5, SEQ ID NO: 7, SEQ ID NO: 169, SEQ ID NO: 170, SEQ ID NO: 206, SEQ ID NO: 209, SEQ ID NO: 210, position 19 to position 40 of SEQ ID NO: 169 and position 19 to position 41 SEQ ID NO: 170.

7. The polynucleotide according to any one of claims 5 or 6, wherein said polynucleotide is selected from the group comprising:
   (a) RNA;
   (b) cDNA;
   (c) genomic DNA;
   (d) synthetic nucleic acids;
   (e) chemically or biochemically modified nucleic acid comprising non-natural or derivatized nucleic acid bases; and
   (f) mixed polymers comprising any of (a)–(e).

8. An isolated, recombinant or synthetic DNA or polynucleotide comprising the antisense RNA or antisense DNA sequence of the DNA or polynucleotide according to any one of claims 1–6.

9. A vector comprising a DNA according to claim 1, 2, 3, or 4 or a polynucleotide according to claims 5–6 or 8.

10. A host cell characterized by any one of the DNAs of claims 1, 2, 3, or 4, the polynucleotides of claims 5–6 or 8, vectors of claim 9.

11. A diagnostic kit for detecting or characterizing in a biological sample any one of the DNAs of claims 1, 2, 3 or 4, or the polynucleotides of claims 5–6 or 8, said kit comprising a composition comprising a probe or probes selected from the group consisting of the DNAs of claims 1, 2, 3 and 4, and the polynucleotides of claims 5–6 and 8.

12. A diagnostic kit for detecting or characterizing in a biological sample any one of the DNAs of claims 1, 2, 3 or 4, or the polynucleotides of claims 5–6 or 8, wherein: an isolated polynucleotide with at least 60% homology to SEQ ID NOs: 1, 2, 3 or 4 or the polynucleotide of claim 8 is provided.

13. The DNA according to claim 1 wherein the DNA comprises a nucleic acid sequence of SEQ ID NO: 9.

14. An isolated, recombinant or synthetic DNA or polynucleotide comprising a nucleic acid sequence that is substantially homologous to any of the DNAs of claims 1 or 13.

15. An isolated, recombinant or synthetic DNA or polynucleotide comprising a nucleic acid sequence that hybridizes under stringent conditions to and that is at least 80% complementary to any of the nucleic acid sequences of claims 1 or 13.

16. The polynucleotide according to any one of claims 14 or 15, wherein said polynucleotide is selected from the group comprising:
   (a) RNA;
   (b) cDNA;
   (c) genomic DNA;
   (d) synthetic nucleic acids;
   (e) chemically or biochemically modified nucleic acid comprising non-natural or derivatized nucleic acid bases; and
   (f) mixed polymers comprising any of (a)–(e).

17. An isolated, recombinant or synthetic DNA or polynucleotide comprising the antisense RNA or antisense DNA sequence of the DNA or polynucleotide according to any one of claims 1, 13, 14, or 15.

18. A vector comprising a DNA according to claim 1 or 13 or a polynucleotide according to claims 14–17.

19. A host cell characterized by any one of the DNAs of claims 1 or 13, the polynucleotides of claims 14–17, or vectors of claim 18.

20. A diagnostic kit for detecting or characterizing in a biological sample any one of the DNAs of claims 1 or 13, or the polynucleotides of claims 14–15 or 17, said kit comprising a composition comprising a probe or probes selected from the group consisting of the DNAs of claims 1 and 13, and the polynucleotides of claims 14–15 or 17.

21. A diagnostic kit for detecting or characterizing in a biological sample any one of the DNAs of claims 1 or 13, or the polynucleotides of claims 14–15 or 17, wherein: an isolated polynucleotide with at least 60% homology to SEQ ID Nos: 1, 2, 3, 4 or 34, or the polynucleotide of claim 17 is provided.

* * * * *

UNITED STATES PATENT AND TRADEMARK OFFICE
CERTIFICATE OF CORRECTION

PATENT NO. : 6,225,451 B1
DATED : May 1, 2001
INVENTOR(S) : Dennis G. Ballinger, Wei Ding, Suzanne Wagner and Mark A. Hess It is certified that error appears in the above-identified patent and that said Letters Patent is hereby corrected as shown below:

Title page,
Item [60], Related U.S. Application Data, add -- Provisional Application No. 60,135,113, filed on March 4, 1998. --

Column 17,
Line 20, change "indicate" to -- indicate: --.

Column 25,
Line 34, change "The" to -- the --.

Column 28,
Line 10, change "that" to -- that: --.

Column 33,
Line 13, change "(I)" to -- (1) --.
Line 14, change "(ii)" to -- (2) --.

Column 36,
Line 37, change "Receptor-mediated" to -- Receptor-mediated --.

Column 37,
Line 38, change "the examples" to -- The examples --.

Column 40,
Line 26, change "B138-a" to -- B138-2 --.

UNITED STATES PATENT AND TRADEMARK OFFICE
CERTIFICATE OF CORRECTION

PATENT NO.    : 6,225,451 B1
DATED         : May 1, 2001
INVENTOR(S)   : Dennis G. Ballinger, Wei Ding, Suzanne Wagner and Mark A. Hess It is certified that error appears in the above-identified patent and that said Letters Patent is hereby corrected as shown below:

<u>Column 144,</u>
Line 23, change "16 The" to -- 16.  The --.

Signed and Sealed this

Twenty-third Day of April, 2002

*Attest:*

JAMES E. ROGAN
*Attesting Officer*        *Director of the United States Patent and Trademark Office*

SEQUENCE LISTING

<160> NUMBER OF SEQ ID NOS: 210

<210> SEQ ID NO 1
<211> LENGTH: 3268
<212> TYPE: DNA
<213> ORGANISM: human
<220> FEATURE:
<221> NAME/KEY: CDS
<222> LOCATION: (98)..(2041)

<400> SEQUENCE: 1

```
ggcccttgga agaaaatcct cgctgtgtcc aggctgaggc gggggggctaa tgacagtgtg       60 agctctagat ggtgtgagac caccccaaag ccaagaa atg gct aca gcc gtg gaa       115
                                        Met Ala Thr Ala Val Glu
                                        1               5 cca gag gac cag gat ctt tgg gaa gaa gag gga att ctg atg gtg aaa       163
Pro Glu Asp Gln Asp Leu Trp Glu Glu Glu Gly Ile Leu Met Val Lys
        10                  15                  20 ctg gaa gat gat ttc acc tgt cgg cca gag tct gtc tta cag agg gat       211
Leu Glu Asp Asp Phe Thr Cys Arg Pro Glu Ser Val Leu Gln Arg Asp
    25                  30                  35 gac ccg gtg ctg gaa acc tcc cac cag aac ttc cga cgc ttc cgc tac       259
Asp Pro Val Leu Glu Thr Ser His Gln Asn Phe Arg Arg Phe Arg Tyr
40                  45                  50 cag gag gca gca agc cct aga gaa gct ctc atc aga ctc cga gaa ctt       307
Gln Glu Ala Ala Ser Pro Arg Glu Ala Leu Ile Arg Leu Arg Glu Leu
55                  60                  65                  70 tgt cac cag tgg ctg aga cca gag agg cgg aca aag gag cag atc cta       355
Cys His Gln Trp Leu Arg Pro Glu Arg Arg Thr Lys Glu Gln Ile Leu
                75                  80                  85 gag ctg ctt gtg ctg gaa caa ttt ctt acc gtc cta cct gga gaa cta       403
Glu Leu Leu Val Leu Glu Gln Phe Leu Thr Val Leu Pro Gly Glu Leu
            90                  95                  100 cag agc tgg gtg cgg ggc caa cgg cca gaa agt ggc gag gag gca gtg       451
Gln Ser Trp Val Arg Gly Gln Arg Pro Glu Ser Gly Glu Glu Ala Val
        105                 110                 115 acg ctg gtg gag ggt ttg cag aaa caa ccc agg aga cca agg cgg tgg       499
Thr Leu Val Glu Gly Leu Gln Lys Gln Pro Arg Arg Pro Arg Arg Trp
    120                 125                 130 gtg act gtc cat gtt cac ggc cag gaa gtc ctg tca gag gag acg gtg       547
Val Thr Val His Val His Gly Gln Glu Val Leu Ser Glu Glu Thr Val
135                 140                 145                 150 cat tta gga gcg gag cct gag tca cct aat gag ctg cag gat cct gtg       595
His Leu Gly Ala Glu Pro Glu Ser Pro Asn Glu Leu Gln Asp Pro Val
                155                 160                 165 caa agc tcg acc ccc gag cag tct cct gag gaa acc aca cag agc cca       643
Gln Ser Ser Thr Pro Glu Gln Ser Pro Glu Glu Thr Thr Gln Ser Pro
```

```
              170                 175                 180
gat ctg ggg gca ccg gca gag cag cgt cca cac cag gaa gag gag ctc    691
Asp Leu Gly Ala Pro Ala Glu Gln Arg Pro His Gln Glu Glu Glu Leu
            185                 190                 195 cag acc ctg cag gag agc gag gtc cca gtg ccc gag gac cca gac ctt    739
Gln Thr Leu Gln Glu Ser Glu Val Pro Val Pro Glu Asp Pro Asp Leu
200                 205                 210 cct gca gag agg agc tct gga gac tca gag atg gtt gct ctt ctt act    787
Pro Ala Glu Arg Ser Ser Gly Asp Ser Glu Met Val Ala Leu Leu Thr
215                 220                 225                 230 gct ctg tca cag gga ctg gta acg ttc aag gat gtg gcc gta tgc ttt    835
Ala Leu Ser Gln Gly Leu Val Thr Phe Lys Asp Val Ala Val Cys Phe
                235                 240                 245 tcc cag gac cag tgg agt gat ctg gac cca aca cag aaa gag ttc tat    883
Ser Gln Asp Gln Trp Ser Asp Leu Asp Pro Thr Gln Lys Glu Phe Tyr
                250                 255                 260 gga gaa tat gtc ttg gaa gaa gac tgt gga att gtt gtc tct ctg tca    931
Gly Glu Tyr Val Leu Glu Glu Asp Cys Gly Ile Val Val Ser Leu Ser
            265                 270                 275 ttt cca atc ccc aga cct gat gag atc tcc cag gtt aga gag gaa gag    979
Phe Pro Ile Pro Arg Pro Asp Glu Ile Ser Gln Val Arg Glu Glu Glu
280                 285                 290 cct tgg gtc cca gat atc caa gag cct cag gag act caa gag cca gaa   1027
Pro Trp Val Pro Asp Ile Gln Glu Pro Gln Glu Thr Gln Glu Pro Glu
295                 300                 305                 310 atc ctg agt ttt acc tac aca gga gat agg agt aaa gat gag gaa gag   1075
Ile Leu Ser Phe Thr Tyr Thr Gly Asp Arg Ser Lys Asp Glu Glu Glu
                315                 320                 325 tgt ctg gag cag gaa gat ctg agt ttg gag gat ata cac agg cct gtt   1123
Cys Leu Glu Gln Glu Asp Leu Ser Leu Glu Asp Ile His Arg Pro Val
                330                 335                 340 ttg gga gaa cca gaa att cac cag act cca gat tgg gaa ata gtc ttt   1171
Leu Gly Glu Pro Glu Ile His Gln Thr Pro Asp Trp Glu Ile Val Phe
            345                 350                 355 gag gac aat cca ggt aga ctt aat gaa aga aga ttt ggt act aat att   1219
Glu Asp Asn Pro Gly Arg Leu Asn Glu Arg Arg Phe Gly Thr Asn Ile
360                 365                 370 tct caa gtg aat agt ttt gtg aac ctt cgg gaa act aca ccc gtc cac   1267
Ser Gln Val Asn Ser Phe Val Asn Leu Arg Glu Thr Thr Pro Val His
375                 380                 385                 390 ccc ctg tta ggg agg cat cat gac tgt tct gtg tgt gga aag agc ttc   1315
Pro Leu Leu Gly Arg His His Asp Cys Ser Val Cys Gly Lys Ser Phe
                395                 400                 405 act tgt aac tcc cac ctt gtt aga cac ctg agg act cac aca gga gag   1363
Thr Cys Asn Ser His Leu Val Arg His Leu Arg Thr His Thr Gly Glu
                410                 415                 420 aaa ccc tat aaa tgt atg gaa tgt gga aaa agt tac aca cga agc tca   1411
Lys Pro Tyr Lys Cys Met Glu Cys Gly Lys Ser Tyr Thr Arg Ser Ser
                425                 430                 435 cat ctt gcc agg cac caa aag gtt cac aag atg aac gcg cct tac aaa   1459
His Leu Ala Arg His Gln Lys Val His Lys Met Asn Ala Pro Tyr Lys
                440                 445                 450 tat ccc cta aac cgg aag aat ttg gaa gag acc tcc cct gtg aca cag   1507
Tyr Pro Leu Asn Arg Lys Asn Leu Glu Glu Thr Ser Pro Val Thr Gln
455                 460                 465                 470 gct gag aga act cca tca gtg gag aaa ccc tat aga tgt gat gat tgc   1555
Ala Glu Arg Thr Pro Ser Val Glu Lys Pro Tyr Arg Cys Asp Asp Cys
                475                 480                 485 gga aag cac ttc cgc tgg act tca gac ctt gtc aga cat cag agg aca   1603
```

-continued

```
Gly Lys His Phe Arg Trp Thr Ser Asp Leu Val Arg His Gln Arg Thr
        490                 495                 500 cat act gga gaa aaa ccc ttc ttt tgt act att tgt ggc aaa agc ttc      1651
His Thr Gly Glu Lys Pro Phe Phe Cys Thr Ile Cys Gly Lys Ser Phe
        505                 510                 515 agc cag aaa tct gtg tta aca aca cac caa aga atc cac ctg gga ggc      1699
Ser Gln Lys Ser Val Leu Thr Thr His Gln Arg Ile His Leu Gly Gly
        520                 525                 530 aaa ccc tac ttg tgt gga gag tgt ggt gag gac ttc agt gaa cac agg      1747
Lys Pro Tyr Leu Cys Gly Glu Cys Gly Glu Asp Phe Ser Glu His Arg
535                 540                 545                 550 cgg tac ctg gcg cac cgg aag acg cac gct gct gag gaa ctc tac ctc      1795
Arg Tyr Leu Ala His Arg Lys Thr His Ala Ala Glu Glu Leu Tyr Leu
                555                 560                 565 tgc agc gag tgc ggg cgc tgc ttc acc cac agc gca gcg ttc gcc aag      1843
Cys Ser Glu Cys Gly Arg Cys Phe Thr His Ser Ala Ala Phe Ala Lys
            570                 575                 580 cac ttg aga gga cac gcc tca gtg agg ccc tgc cga tgc aac gaa tgt      1891
His Leu Arg Gly His Ala Ser Val Arg Pro Cys Arg Cys Asn Glu Cys
        585                 590                 595 ggg aag agc ttc agt cgc agg gac cac ctc gtc agg cat cag aga aca      1939
Gly Lys Ser Phe Ser Arg Arg Asp His Leu Val Arg His Gln Arg Thr
    600                 605                 610 cac act ggg gag aaa cca ttc acg tgc cct acc tgt gga aaa agc ttc      1987
His Thr Gly Glu Lys Pro Phe Thr Cys Pro Thr Cys Gly Lys Ser Phe
615                 620                 625                 630 agc aga gga tat cac tta att agg cat cag agg acc cac tca gaa aag      2035
Ser Arg Gly Tyr His Leu Ile Arg His Gln Arg Thr His Ser Glu Lys
                635                 640                 645 acc tcc tagctaggtc cccatgtgag gagatctgct ttcagccctc acctaaggga      2091
Thr Ser ggtgaggaag aggaaaagcc ctcttgtcag cctgggaaga ccttttcgag ggagtctccc    2151
tgacctgctc agatctgaca ttacctcttc ctgcaactaa acacgagcct gggcagaacc    2211
tctcagcctt cctctacgcc ttgagggat gtttcatcca agtacaacc tgaattgagg     2271 cttctccttc actggagtgc acctgcctct acctcatggg tataaagtag gagaactaag    2331
agacttaaga ggtcgtggtt cctatatcgt ccaaaaaata ggctgttaca tatcctaaag    2391
actgctcaac agcttcaagt tgaaagtggc caaggacagc cccttaggtt tgggaaggga    2451
cgagcctgaa ggattctgtc tttactgggg tcaaatctta aagcacacag ctctggactc    2511
aagacaggag gtttgcgtcc tgatggcttt gcacacattc acaggataac tgcatagatc    2571
cctcgctgtc tgattcactt cttaccatgc actttccttt gatgctgagg agaaatggaa    2631
gtgggcgaaa atctcaagg ctgcttcatg tggaccttgt caagctgctc cctcccccag     2691
cgtcaaattg ttatcaggtg ccaaacactg ctagaaagga gggcctagtc agaagcctct    2751
ttccatacga gttttggttt tgttttttaat atttttttct attaaaatac tcatgcattt    2811
aaccttcccg ttattcaacc agtctcttgg ttgcatccct agcacttcta ctacaagtga    2871
gatggtagtg tttgagtgct tattgagtaa agcataattc ggtcataatg aaatcgttca    2931
cattccctca tatgcacaag cccaccaacc ccttcacacc cccttcaca ggggtcgtat      2991 gagtaagggg atttggaaac tgtcaactta caaaggcact ataacaatta cagaatcatg    3051
attgccatgg gccactttat ttacatgaag acaactggag aacgactaag accaaattat    3111
ggaaaataag aaaaagctgt tgctggcaag accatcaaga ctgttctgac accctgtccc    3171
catcatccct gactgagtac tctgacatca cggaaagtgt tgaacctggg accctgagga    3231
```

```
attcaccagg agtaaatggc tttcatgtaa aaaaaaa                                      3268
```

<210> SEQ ID NO 2
<211> LENGTH: 648
<212> TYPE: PRT
<213> ORGANISM: human

<400> SEQUENCE: 2

```
Met Ala Thr Ala Val Glu Pro Glu Asp Gln Asp Leu Trp Glu Glu
  1               5                  10                  15

Gly Ile Leu Met Val Lys Leu Glu Asp Asp Phe Thr Cys Arg Pro Glu
                 20                  25                  30

Ser Val Leu Gln Arg Asp Asp Pro Val Leu Glu Thr Ser His Gln Asn
             35                  40                  45

Phe Arg Arg Phe Arg Tyr Gln Glu Ala Ala Ser Pro Arg Glu Ala Leu
         50                  55                  60

Ile Arg Leu Arg Glu Leu Cys His Gln Trp Leu Arg Pro Glu Arg Arg
 65                  70                  75                  80

Thr Lys Glu Gln Ile Leu Glu Leu Leu Val Leu Glu Gln Phe Leu Thr
                 85                  90                  95

Val Leu Pro Gly Glu Leu Gln Ser Trp Val Arg Gly Gln Arg Pro Glu
                100                 105                 110

Ser Gly Glu Glu Ala Val Thr Leu Val Glu Gly Leu Gln Lys Gln Pro
            115                 120                 125

Arg Arg Pro Arg Arg Trp Val Thr Val His Val His Gly Gln Glu Val
        130                 135                 140

Leu Ser Glu Glu Thr Val His Leu Gly Ala Glu Pro Glu Ser Pro Asn
145                 150                 155                 160

Glu Leu Gln Asp Pro Val Gln Ser Ser Thr Pro Glu Gln Ser Pro Glu
                165                 170                 175

Glu Thr Thr Gln Ser Pro Asp Leu Gly Ala Pro Ala Glu Gln Arg Pro
            180                 185                 190

His Gln Glu Glu Glu Leu Gln Thr Leu Gln Glu Ser Glu Val Pro Val
        195                 200                 205

Pro Glu Asp Pro Asp Leu Pro Ala Glu Arg Ser Ser Gly Asp Ser Glu
    210                 215                 220

Met Val Ala Leu Leu Thr Ala Leu Ser Gln Gly Leu Val Thr Phe Lys
225                 230                 235                 240

Asp Val Ala Val Cys Phe Ser Gln Asp Gln Trp Ser Asp Leu Asp Pro
                245                 250                 255

Thr Gln Lys Glu Phe Tyr Gly Glu Tyr Val Leu Glu Glu Asp Cys Gly
            260                 265                 270

Ile Val Val Ser Leu Ser Phe Pro Ile Pro Arg Pro Asp Glu Ile Ser
        275                 280                 285

Gln Val Arg Glu Glu Pro Trp Val Pro Asp Ile Gln Glu Pro Gln
    290                 295                 300

Glu Thr Gln Glu Pro Glu Ile Leu Ser Phe Thr Tyr Thr Gly Asp Arg
305                 310                 315                 320

Ser Lys Asp Glu Glu Cys Leu Glu Gln Glu Asp Leu Ser Leu Glu
                325                 330                 335

Asp Ile His Arg Pro Val Leu Gly Glu Pro Glu Ile His Gln Thr Pro
            340                 345                 350

Asp Trp Glu Ile Val Phe Glu Asp Asn Pro Gly Arg Leu Asn Glu Arg
        355                 360                 365
```

-continued

```
Arg Phe Gly Thr Asn Ile Ser Gln Val Asn Ser Phe Val Asn Leu Arg
    370                 375                 380
Glu Thr Thr Pro Val His Pro Leu Leu Gly Arg His His Asp Cys Ser
385                 390                 395                 400
Val Cys Gly Lys Ser Phe Thr Cys Asn Ser His Leu Val Arg His Leu
                405                 410                 415
Arg Thr His Thr Gly Glu Lys Pro Tyr Lys Cys Met Glu Cys Gly Lys
            420                 425                 430
Ser Tyr Thr Arg Ser Ser His Leu Ala Arg His Gln Lys Val His Lys
        435                 440                 445
Met Asn Ala Pro Tyr Lys Tyr Pro Leu Asn Arg Lys Asn Leu Glu Glu
    450                 455                 460
Thr Ser Pro Val Thr Gln Ala Glu Arg Thr Pro Ser Val Glu Lys Pro
465                 470                 475                 480
Tyr Arg Cys Asp Asp Cys Gly Lys His Phe Arg Trp Thr Ser Asp Leu
                485                 490                 495
Val Arg His Gln Arg Thr His Thr Gly Glu Lys Pro Phe Phe Cys Thr
            500                 505                 510
Ile Cys Gly Lys Ser Phe Ser Gln Lys Ser Val Leu Thr Thr His Gln
        515                 520                 525
Arg Ile His Leu Gly Gly Lys Pro Tyr Leu Cys Gly Glu Cys Gly Glu
    530                 535                 540
Asp Phe Ser Glu His Arg Arg Tyr Leu Ala His Arg Lys Thr His Ala
545                 550                 555                 560
Ala Glu Glu Leu Tyr Leu Cys Ser Glu Cys Gly Arg Cys Phe Thr His
                565                 570                 575
Ser Ala Ala Phe Ala Lys His Leu Arg Gly His Ala Ser Val Arg Pro
            580                 585                 590
Cys Arg Cys Asn Glu Cys Gly Lys Ser Phe Ser Arg Arg Asp His Leu
        595                 600                 605
Val Arg His Gln Arg Thr His Thr Gly Glu Lys Pro Phe Thr Cys Pro
    610                 615                 620
Thr Cys Gly Lys Ser Phe Ser Arg Gly Tyr His Leu Ile Arg His Gln
625                 630                 635                 640
Arg Thr His Ser Glu Lys Thr Ser
                645
```

<210> SEQ ID NO 3
<211> LENGTH: 3244
<212> TYPE: DNA
<213> ORGANISM: human
<220> FEATURE:
<221> NAME/KEY: CDS
<222> LOCATION: (98)..(2017)

<400> SEQUENCE: 3

```
ggcccttgga agaaaatcct cgctgtgtcc aggctgaggc gggggggctaa tgacagtgtg      60 agctctagat ggtgtgagac caccccaaag ccaagaa atg gct aca gcc gtg gaa     115
                                         Met Ala Thr Ala Val Glu
                                           1               5 cca gag gac cag gat ctt tgg gaa gaa gag gga att ctg atg gtg aaa     163
Pro Glu Asp Gln Asp Leu Trp Glu Glu Glu Gly Ile Leu Met Val Lys
         10                  15                  20 ctg gaa gat gat ttc acc tgt cgg cca gag tct gtc tta cag agg gat     211
Leu Glu Asp Asp Phe Thr Cys Arg Pro Glu Ser Val Leu Gln Arg Asp
     25                  30                  35
```

```
gac ccg gtg ctg gaa acc tcc cac cag aac ttc cga cgc ttc cgc tac      259
Asp Pro Val Leu Glu Thr Ser His Gln Asn Phe Arg Arg Phe Arg Tyr
     40                  45                  50 cag gag gca gca agc cct aga gaa gct ctc atc aga ctc cga gaa ctt      307
Gln Glu Ala Ala Ser Pro Arg Glu Ala Leu Ile Arg Leu Arg Glu Leu
 55                  60                  65                  70 tgt cac cag tgg ctg aga cca gag agg cgg aca aag gag cag atc cta      355
Cys His Gln Trp Leu Arg Pro Glu Arg Arg Thr Lys Glu Gln Ile Leu
             75                  80                  85 gag ctg ctt gtg ctg gaa caa ttt ctt acc gtc cta cct gga gaa cta      403
Glu Leu Leu Val Leu Glu Gln Phe Leu Thr Val Leu Pro Gly Glu Leu
             90                  95                 100 cag agc tgg gtg cgg ggc caa cgg cca gaa agt ggc gag gag gca gtg      451
Gln Ser Trp Val Arg Gly Gln Arg Pro Glu Ser Gly Glu Glu Ala Val
            105                 110                 115 acg ctg gtg gag ggt ttg cag aaa caa ccc agg aga cca agg cgg tgg      499
Thr Leu Val Glu Gly Leu Gln Lys Gln Pro Arg Arg Pro Arg Arg Trp
120                 125                 130 gaa gtc ctg tca gag gag acg gtg cat tta gga gcg gag cct gag tca      547
Glu Val Leu Ser Glu Glu Thr Val His Leu Gly Ala Glu Pro Glu Ser
135                 140                 145                 150 cct aat gag ctg cag gat cct gtg caa agc tcg acc ccc gag cag tct      595
Pro Asn Glu Leu Gln Asp Pro Val Gln Ser Ser Thr Pro Glu Gln Ser
            155                 160                 165 cct gag gaa acc aca cag agc cca gat ctg ggg gca ccg gca gag cag      643
Pro Glu Glu Thr Thr Gln Ser Pro Asp Leu Gly Ala Pro Ala Glu Gln
            170                 175                 180 cgt cca cac cag gaa gag gag ctc cag acc ctg cag gag agc gag gtc      691
Arg Pro His Gln Glu Glu Glu Leu Gln Thr Leu Gln Glu Ser Glu Val
            185                 190                 195 cca gtg ccc gag gac cca gac ctt cct gca gag agg agc tct gga gac      739
Pro Val Pro Glu Asp Pro Asp Leu Pro Ala Glu Arg Ser Ser Gly Asp
200                 205                 210 tca gag atg gtt gct ctt ctt act gct ctg tca cag gga ctg gta acg      787
Ser Glu Met Val Ala Leu Leu Thr Ala Leu Ser Gln Gly Leu Val Thr
215                 220                 225                 230 ttc aag gat gtg gcc gta tgc ttt tcc cag gac cag tgg agt gat ctg      835
Phe Lys Asp Val Ala Val Cys Phe Ser Gln Asp Gln Trp Ser Asp Leu
            235                 240                 245 gac cca aca cag aaa gag ttc tat gga gaa tat gtc ttg gaa gaa gac      883
Asp Pro Thr Gln Lys Glu Phe Tyr Gly Glu Tyr Val Leu Glu Glu Asp
            250                 255                 260 tgt gga att gtt gtc tct ctg tca ttt cca atc ccc aga cct gat gag      931
Cys Gly Ile Val Val Ser Leu Ser Phe Pro Ile Pro Arg Pro Asp Glu
            265                 270                 275 atc tcc cag gtt aga gag gaa gag cct tgg gtc cca gat atc caa gag      979
Ile Ser Gln Val Arg Glu Glu Glu Pro Trp Val Pro Asp Ile Gln Glu
280                 285                 290 cct cag gag act caa gag cca gaa atc ctg agt ttt acc tac aca gga     1027
Pro Gln Glu Thr Gln Glu Pro Glu Ile Leu Ser Phe Thr Tyr Thr Gly
295                 300                 305                 310 gat agg agt aaa gat gag gaa gag tgt ctg gag cag gaa gat ctg agt     1075
Asp Arg Ser Lys Asp Glu Glu Glu Cys Leu Glu Gln Glu Asp Leu Ser
            315                 320                 325 ttg gag gat ata cac agg cct gtt ttg gga gaa cca gaa att cac cag     1123
Leu Glu Asp Ile His Arg Pro Val Leu Gly Glu Pro Glu Ile His Gln
            330                 335                 340 act cca gat tgg gaa ata gtc ttt gag gac aat cca ggt aga ctt aat     1171
Thr Pro Asp Trp Glu Ile Val Phe Glu Asp Asn Pro Gly Arg Leu Asn
```

-continued

| | | | |
|---|---|---|---|
| gaa aga aga ttt ggt act aat att tct caa gtg aat agt ttt gtg aac<br>Glu Arg Arg Phe Gly Thr Asn Ile Ser Gln Val Asn Ser Phe Val Asn<br>360                             365                   370 | 1219 |
| ctt cgg gaa act aca ccc gtc cac ccc ctg tta ggg agg cat cat gac<br>Leu Arg Glu Thr Thr Pro Val His Pro Leu Leu Gly Arg His His Asp<br>375                       380                   385                   390 | 1267 |
| tgt tct gtg tgt gga aag agc ttc act tgt aac tcc cac ctt gtt aga<br>Cys Ser Val Cys Gly Lys Ser Phe Thr Cys Asn Ser His Leu Val Arg<br>                       395                   400                   405 | 1315 |
| cac ctg agg act cac aca gga gag aaa ccc tat aaa tgt atg gaa tgt<br>His Leu Arg Thr His Thr Gly Glu Lys Pro Tyr Lys Cys Met Glu Cys<br>410                             415                   420 | 1363 |
| gga aaa agt tac aca cga agc tca cat ctt gcc agg cac caa aag gtt<br>Gly Lys Ser Tyr Thr Arg Ser Ser His Leu Ala Arg His Gln Lys Val<br>                       425                   430                   435 | 1411 |
| cac aag atg aac gcg cct tac aaa tat ccc cta aac cgg aag aat ttg<br>His Lys Met Asn Ala Pro Tyr Lys Tyr Pro Leu Asn Arg Lys Asn Leu<br>440                             445                   450 | 1459 |
| gaa gag acc tcc cct gtg aca cag gct gag aga act cca tca gtg gag<br>Glu Glu Thr Ser Pro Val Thr Gln Ala Glu Arg Thr Pro Ser Val Glu<br>455                       460                   465                   470 | 1507 |
| aaa ccc tat aga tgt gat gat tgc gga aag cac ttc cgc tgg act tca<br>Lys Pro Tyr Arg Cys Asp Asp Cys Gly Lys His Phe Arg Trp Thr Ser<br>                       475                   480                   485 | 1555 |
| gac ctt gtc aga cat cag agg aca cat act gga gaa aaa ccc ttc ttt<br>Asp Leu Val Arg His Gln Arg Thr His Thr Gly Glu Lys Pro Phe Phe<br>490                             495                   500 | 1603 |
| tgt act att tgt ggc aaa agc ttc agc cag aaa tct gtg tta aca aca<br>Cys Thr Ile Cys Gly Lys Ser Phe Ser Gln Lys Ser Val Leu Thr Thr<br>                       505                   510                   515 | 1651 |
| cac caa aga atc cac ctg gga ggc aaa ccc tac ttg tgt gga gag tgt<br>His Gln Arg Ile His Leu Gly Gly Lys Pro Tyr Leu Cys Gly Glu Cys<br>520                             525                   530 | 1699 |
| ggt gag gac ttc agt gaa cac agg cgg tac ctg gcg cac cgg aag acg<br>Gly Glu Asp Phe Ser Glu His Arg Arg Tyr Leu Ala His Arg Lys Thr<br>535                       540                   545                   550 | 1747 |
| cac gct gct gag gaa ctc tac ctc tgc agc gag tgc ggg cgc tgc ttc<br>His Ala Ala Glu Glu Leu Tyr Leu Cys Ser Glu Cys Gly Arg Cys Phe<br>                       555                   560                   565 | 1795 |
| acc cac agc gca gcg ttc gcc aag cac ttg aga gga cac gcc tca gtg<br>Thr His Ser Ala Ala Phe Ala Lys His Leu Arg Gly His Ala Ser Val<br>                       570                   575                   580 | 1843 |
| agg ccc tgc cga tgc aac gaa tgt ggg aag agc ttc agt cgc agg gac<br>Arg Pro Cys Arg Cys Asn Glu Cys Gly Lys Ser Phe Ser Arg Arg Asp<br>585                             590                   595 | 1891 |
| cac ctc gtc agg cat cag aga aca cac act ggg gag aaa cca ttc acg<br>His Leu Val Arg His Gln Arg Thr His Thr Gly Glu Lys Pro Phe Thr<br>600                             605                   610 | 1939 |
| tgc cct acc tgt gga aaa agc ttc agc aga gga tat cac tta att agg<br>Cys Pro Thr Cys Gly Lys Ser Phe Ser Arg Gly Tyr His Leu Ile Arg<br>615                       620                   625                   630 | 1987 |
| cat cag agg acc cac tca gaa aag acc tcc tagctaggtc cccatgtgag<br>His Gln Arg Thr His Ser Glu Lys Thr Ser<br>                     635                   640 | 2037 |
| gagatctgct ttcagccctc acctaaggga ggtgaggaag aggaaaagcc ctcttgtcag | 2097 |
| cctgggaaga ccttttcgag ggagtctccc tgacctgctc agatctgaca ttacctcttc | 2157 |
| ctgcaactaa acacgagcct gggcagaacc tctcagcctt cctctacgcc ttgaggggat | 2217 |

-continued

```
gtttcatcca aagtacaacc tgaattgagg cttctccttc actggagtgc acctgcctct    2277
acctcatggg tataaagtag gagaactaag agacttaaga ggtcgtggtt cctatatcgt    2337
ccaaaaaata ggctgttaca tatcctaaag actgctcaac agcttcaagt tgaaagtggc    2397
caaggacagc cccttaggtt tgggaaggga cgagcctgaa ggattctgtc tttactgggg    2457
tcaaatctta aagcacacag ctctggactc aagacaggag gtttgcgtcc tgatggcttt    2517
gcacacattc acaggataac tgcatagatc cctcgctgtc tgattcactt cttaccatgc    2577
actttccttt gatgctgagg agaaatggaa gtgggcgaaa atctcaagg ctgcttcatg     2637 tggaccttgt caagctgctc cctcccccag cgtcaaattg ttatcaggtg ccaaacactg    2697
ctagaaagga gggcctagtc agaagcctct ttccatacga gttttggttt tgtttttaat    2757
atttttttct attaaaatac tcatgcattt aaccttcccg ttattcaacc agtctcttgg    2817
ttgcatccct agcacttcta ctacaagtga atggtagtg tttgagtgct tattgagtaa     2877
agcataattc ggtcataatg aaatcgttca cattccctca tatgcacaag cccaccaacc    2937
ccttcacacc cccttcaca ggggtcgtat gagtaagggg atttggaaac tgtcaactta     2997
caaaggcact ataacaatta cagaatcatg attgccatgg ccactttat ttacatgaag     3057 acaactggag aacgactaag accaaattat ggaaaataag aaaaagctgt tgctggcaag    3117
accatcaaga ctgttctgac accctgtccc catcatccct gactgagtac tctgacatca    3177
cggaaagtgt tgaacctggg accctgagga attccaggg agtaaatggc tttcatgtaa     3237
aaaaaaa                                                              3244
```

<210> SEQ ID NO 4
<211> LENGTH: 640
<212> TYPE: PRT
<213> ORGANISM: human

<400> SEQUENCE: 4

```
Met Ala Thr Ala Val Glu Pro Glu Asp Gln Asp Leu Trp Glu Glu
 1               5                  10                  15

Gly Ile Leu Met Val Lys Leu Glu Asp Asp Phe Thr Cys Arg Pro Glu
                20                  25                  30

Ser Val Leu Gln Arg Asp Asp Pro Val Leu Glu Thr Ser His Gln Asn
            35                  40                  45

Phe Arg Arg Phe Arg Tyr Gln Glu Ala Ala Ser Pro Arg Glu Ala Leu
        50                  55                  60

Ile Arg Leu Arg Glu Leu Cys His Gln Trp Leu Arg Pro Glu Arg Arg
 65                 70                  75                  80

Thr Lys Glu Gln Ile Leu Glu Leu Leu Val Leu Glu Gln Phe Leu Thr
                85                  90                  95

Val Leu Pro Gly Glu Leu Gln Ser Trp Val Arg Gly Gln Arg Pro Glu
            100                 105                 110

Ser Gly Glu Glu Ala Val Thr Leu Val Glu Gly Leu Gln Lys Gln Pro
        115                 120                 125

Arg Arg Pro Arg Arg Trp Glu Val Leu Ser Glu Glu Thr Val His Leu
    130                 135                 140

Gly Ala Glu Pro Glu Ser Pro Asn Glu Leu Gln Asp Pro Val Gln Ser
145                 150                 155                 160

Ser Thr Pro Glu Gln Ser Pro Glu Glu Thr Thr Gln Ser Pro Asp Leu
                165                 170                 175

Gly Ala Pro Ala Glu Gln Arg Pro His Gln Glu Glu Glu Leu Gln Thr
```

-continued

```
                180                 185                 190
Leu Gln Glu Ser Glu Val Pro Val Pro Glu Asp Pro Asp Leu Pro Ala
            195                 200                 205
Glu Arg Ser Ser Gly Asp Ser Glu Met Val Ala Leu Leu Thr Ala Leu
    210                 215                 220
Ser Gln Gly Leu Val Thr Phe Lys Asp Val Ala Val Cys Phe Ser Gln
225                 230                 235                 240
Asp Gln Trp Ser Asp Leu Asp Pro Thr Gln Lys Glu Phe Tyr Gly Glu
                245                 250                 255
Tyr Val Leu Glu Glu Asp Cys Gly Ile Val Val Ser Leu Ser Phe Pro
            260                 265                 270
Ile Pro Arg Pro Asp Glu Ile Ser Gln Val Arg Glu Glu Pro Trp
    275                 280                 285
Val Pro Asp Ile Gln Glu Pro Gln Glu Thr Gln Glu Pro Glu Ile Leu
    290                 295                 300
Ser Phe Thr Tyr Thr Gly Asp Arg Ser Lys Asp Glu Glu Cys Leu
305                 310                 315                 320
Glu Gln Glu Asp Leu Ser Leu Glu Asp Ile His Arg Pro Val Leu Gly
                325                 330                 335
Glu Pro Glu Ile His Gln Thr Pro Asp Trp Glu Ile Val Phe Glu Asp
            340                 345                 350
Asn Pro Gly Arg Leu Asn Glu Arg Arg Phe Gly Thr Asn Ile Ser Gln
        355                 360                 365
Val Asn Ser Phe Val Asn Leu Arg Glu Thr Thr Pro Val His Pro Leu
    370                 375                 380
Leu Gly Arg His His Asp Cys Ser Val Cys Gly Lys Ser Phe Thr Cys
385                 390                 395                 400
Asn Ser His Leu Val Arg His Leu Arg Thr His Thr Gly Glu Lys Pro
                405                 410                 415
Tyr Lys Cys Met Glu Cys Gly Lys Ser Tyr Thr Arg Ser Ser His Leu
            420                 425                 430
Ala Arg His Gln Lys Val His Lys Met Asn Ala Pro Tyr Lys Tyr Pro
        435                 440                 445
Leu Asn Arg Lys Asn Leu Glu Glu Thr Ser Pro Val Thr Gln Ala Glu
    450                 455                 460
Arg Thr Pro Ser Val Glu Lys Pro Tyr Arg Cys Asp Asp Cys Gly Lys
465                 470                 475                 480
His Phe Arg Trp Thr Ser Asp Leu Val Arg His Gln Arg Thr His Thr
                485                 490                 495
Gly Glu Lys Pro Phe Phe Cys Thr Ile Cys Gly Lys Ser Phe Ser Gln
            500                 505                 510
Lys Ser Val Leu Thr Thr His Gln Arg Ile His Leu Gly Gly Lys Pro
        515                 520                 525
Tyr Leu Cys Gly Glu Cys Gly Glu Asp Phe Ser Glu His Arg Arg Tyr
    530                 535                 540
Leu Ala His Arg Lys Thr His Ala Ala Glu Leu Tyr Leu Cys Ser
545                 550                 555                 560
Glu Cys Gly Arg Cys Phe Thr His Ser Ala Ala Phe Ala Lys His Leu
                565                 570                 575
Arg Gly His Ala Ser Val Arg Pro Cys Arg Cys Asn Glu Cys Gly Lys
            580                 585                 590
Ser Phe Ser Arg Arg Asp His Leu Val Arg His Gln Arg Thr His Thr
        595                 600                 605
```

```
Gly Glu Lys Pro Phe Thr Cys Pro Thr Cys Gly Lys Ser Phe Ser Arg
    610                 615                 620

Gly Tyr His Leu Ile Arg His Gln Arg Thr His Ser Glu Lys Thr Ser
625                 630                 635                 640

<210> SEQ ID NO 5
<211> LENGTH: 3264
<212> TYPE: DNA
<213> ORGANISM: human
<220> FEATURE:
<221> NAME/KEY: CDS
<222> LOCATION: (98)..(496)

<400> SEQUENCE: 5
ggcccttgga agaaaatcct cgctgtgtcc aggctgaggc gggggggctaa tgacagtgtg      60 agctctagat ggtgtgagac caccccaaag ccaagaa atg gct aca gcc gtg gaa      115
                                         Met Ala Thr Ala Val Glu
                                           1               5 cca gag gac cag gat ctt tgg gaa gaa gag gga att ctg atg gtg aaa      163
Pro Glu Asp Gln Asp Leu Trp Glu Glu Glu Gly Ile Leu Met Val Lys
         10                  15                  20 ctg gaa gat gat ttc acc tgt cgg cca gag tct gtc tta cag agg gat      211
Leu Glu Asp Asp Phe Thr Cys Arg Pro Glu Ser Val Leu Gln Arg Asp
     25                  30                  35 gac ccg gtg ctg gaa acc tcc cac cag aac ttc cga cgc ttc cgc tac      259
Asp Pro Val Leu Glu Thr Ser His Gln Asn Phe Arg Arg Phe Arg Tyr
 40                  45                  50 cag gag gca gca agc cct aga gaa gct ctc atc aga ctc cga gaa ctt      307
Gln Glu Ala Ala Ser Pro Arg Glu Ala Leu Ile Arg Leu Arg Glu Leu
55                  60                  65                  70 tgt cac cag tgg ctg aga cca gag agg cgg aca aag gag cag atc cta      355
Cys His Gln Trp Leu Arg Pro Glu Arg Arg Thr Lys Glu Gln Ile Leu
                 75                  80                  85 gag ctg ctt gtg ctg gaa caa ttt ctt acc gtc cta cct gga gaa cta      403
Glu Leu Leu Val Leu Glu Gln Phe Leu Thr Val Leu Pro Gly Glu Leu
             90                  95                 100 cag agc tgg gtg cgg ggc caa cgg cca gaa agt ggc gag gag gca gtg      451
Gln Ser Trp Val Arg Gly Gln Arg Pro Glu Ser Gly Glu Glu Ala Val
         105                 110                 115 acg ctg gtg gag ggt ttg cag aaa caa ccc agg aga cca agg cgg           496
Thr Leu Val Glu Gly Leu Gln Lys Gln Pro Arg Arg Pro Arg Arg
     120                 125                 130 tgactgtcca tgttcacggc caggaagtcc tgtcagagga gacggtgcat ttaggagcgg      556
agcctgagtc acctaatgag ctgcaggatc ctgtgcaaag ctcgaccccc gagcagtctc      616
ctgaggaaac cacacagagc ccagatctgg gggcaccggc agagcagcgt ccacaccagg      676
aagaggagct ccagaccctg caggagagcg aggtcccagt gcccgaggac ccagaccttc      736
ctgcagagag gagctctgga gactcagaga tggttgctct tcttactgct ctgtcacagg      796
gactggtaac gttcaaggat gtggccgtat gcttttccca ggaccagtgg agtgatctgg      856
acccaacaca gaaagagttc tatggagaat atgtcttgga agaagactgt ggaattgttg      916
tctctctgtc atttccaatc cccagacctg atgagatctc caggttaga gaggaagagc      976 cttgggtccc agatatccaa gagcctcagg agactcaaga gccagaaatc ctgagtttta     1036
cctacacagg agataggagt aaagatgagg aagagtgtct ggagcaggaa gatctgagtt     1096
tggaggatat acacaggcct gttttgggag aaccagaaat tcaccagact ccagattggg     1156
aaatagtctt tgaggacaat ccaggtagac ttaatgaaag aagatttggt actaatattt     1216
```

-continued

```
ctcaagtgaa tagttttgtg aaccttcggg aaactacacc cgtccacccc ctgttaggga    1276
ggcatcatga ctgttctgtg tgtggaaaga gcttcacttg taactcccac cttgttagac    1336
acctgaggac tcacacagga gagaaaccct ataaatgtat ggaatgtgga aaaagttaca    1396
cacgaagctc acatcttgcc aggcaccaaa aggttcacaa gatgaacgcg ccttacaaat    1456
atcccctaaa ccggaagaat ttggaagaga cctcccctgt gacacaggct gagagaactc    1516
catcagtgga gaaaccctat agatgtgatg attgcggaaa gcacttccgc tggacttcag    1576
accttgtcag acatcagagg acacatactg gagaaaaacc cttcttttgt actatttgtg    1636
gcaaaagctt cagccagaaa tctgtgttaa caacacacca agaatccac ctgggaggca     1696
aaccctactt gtgtggagag tgtggtgagg acttcagtga acacaggcgg tacctggcgc    1756
accggaagac gcacgctgct gaggaactct acctctgcag cgagtgcggg cgctgcttca    1816
cccacagcgc agcgttcgcc aagcacttga aggacacgc tcagtgagg ccctgccgat      1876
gcaacgaatg tgggaagagc ttcagtcgca gggaccacct cgtcaggcat cagagaacac    1936
acactgggga gaaccattc acgtgcccta cctgtggaaa aagcttcagc agaggatatc     1996
acttaattag gcatcagagg acccactcag aaaagacctc ctagctaggt ccccatgtga    2056
ggagatctgc tttcagccct cacctaaggg aggtgaggaa gaggaaaagc cctcttgtca    2116
gcctgggaag acctttcga gggagtctcc ctgacctgct cagatctgac attacctctt     2176
cctgcaacta aacacgagcc tgggcagaac ctctcagcct tcctctacgc cttgagggga    2236
tgtttcatcc aaagtacaac ctgaattgag gcttctcctt cactggagtg cacctgcctc    2296
tacctcatgg gtataaagta ggagaactaa gagacttaag aggtcgtggt tcctatatcg    2356
tccaaaaaat aggctgttac atatcctaaa gactgctcaa cagcttcaag ttgaaagtgg    2416
ccaaggacag cccctaggt ttgggaaggg acgagcctga aggattctgt ctttactggg     2476
gtcaaatctt aaagcacaca gctctggact caagacagga ggtttgcgtc ctgatggctt    2536
tgcacacatt cacaggataa ctgcatagat ccctcgctgt ctgattcact tcttaccatg    2596
cactttcctt tgatgctgag gagaaatgga agtgggcgaa aaatctcaag gctgcttcat    2656
gtggaccttg tcaagctgct ccctccccca gcgtcaaatt gttatcaggt gccaaacact    2716
gctagaaagg agggcctagt cagaagcctc tttccatacg agttttggtt ttgttttttaa   2776
tattttttc tattaaaata ctcatgcatt taaccttccc gttattcaac cagtctcttg     2836
gttgcatccc tagcacttct actacaagtg agatggtagt gtttgagtgc ttattgagta    2896
aagcataatt cggtcataat gaaatcgttc acattccctc atatgcacaa gcccaccaac    2956
cccttcacac cccccttcac aggggtcgta tgagtaaggg gatttggaaa ctgtcaactt    3016
acaaaggcac tataacaatt acagaatcat gattgccatg gccactttta tttacatgaa    3076
gacaactgga gaacgactaa gaccaaatta tggaaaataa gaaaaagctg ttgctggcaa    3136
gaccatcaag actgttctga caccctgtcc ccatcatccc tgactgagta ctctgacatc    3196
acggaaagtg ttgaacctgg gaccctgagg aattcaccag gagtaaatgg ctttcatgta    3256
aaaaaaaa                                                             3264
```

<210> SEQ ID NO 6
<211> LENGTH: 133
<212> TYPE: PRT
<213> ORGANISM: human

<400> SEQUENCE: 6

```
Met Ala Thr Ala Val Glu Pro Glu Asp Gln Asp Leu Trp Glu Glu
 1               5                  10                  15

Gly Ile Leu Met Val Lys Leu Glu Asp Asp Phe Thr Cys Arg Pro Glu
                 20                  25                  30

Ser Val Leu Gln Arg Asp Asp Pro Val Leu Glu Thr Ser His Gln Asn
             35                  40                  45

Phe Arg Arg Phe Arg Tyr Gln Glu Ala Ala Ser Pro Arg Glu Ala Leu
         50                  55                  60

Ile Arg Leu Arg Glu Leu Cys His Gln Trp Leu Arg Pro Glu Arg Arg
 65                  70                  75                  80

Thr Lys Glu Gln Ile Leu Glu Leu Leu Val Leu Glu Gln Phe Leu Thr
                 85                  90                  95

Val Leu Pro Gly Glu Leu Gln Ser Trp Val Arg Gly Gln Arg Pro Glu
            100                 105                 110

Ser Gly Glu Glu Ala Val Thr Leu Val Glu Gly Leu Gln Lys Gln Pro
            115                 120                 125

Arg Arg Pro Arg Arg
            130
```

<210> SEQ ID NO 7
<211> LENGTH: 3240
<212> TYPE: DNA
<213> ORGANISM: human
<220> FEATURE:
<221> NAME/KEY: CDS
<222> LOCATION: (98)..(523)

<400> SEQUENCE: 7

```
ggcccttgga agaaaatcct cgctgtgtcc aggctgaggc gggggggctaa tgacagtgtg      60 agctctagat ggtgtgagac caccccaaag ccaagaa atg gct aca gcc gtg gaa     115
                                         Met Ala Thr Ala Val Glu
                                          1               5 cca gag gac cag gat ctt tgg gaa gaa gag gga att ctg atg gtg aaa     163
Pro Glu Asp Gln Asp Leu Trp Glu Glu Glu Gly Ile Leu Met Val Lys
                10                  15                  20 ctg gaa gat gat ttc acc tgt cgg cca gag tct gtc tta cag agg gat     211
Leu Glu Asp Asp Phe Thr Cys Arg Pro Glu Ser Val Leu Gln Arg Asp
             25                  30                  35 gac ccg gtg ctg gaa acc tcc cac cag aac ttc cga cgc ttc cgc tac     259
Asp Pro Val Leu Glu Thr Ser His Gln Asn Phe Arg Arg Phe Arg Tyr
     40                  45                  50 cag gag gca gca agc cct aga gaa gct ctc atc aga ctc cga gaa ctt     307
Gln Glu Ala Ala Ser Pro Arg Glu Ala Leu Ile Arg Leu Arg Glu Leu
 55                  60                  65                  70 tgt cac cag tgg ctg aga cca gag agg cgg aca aag gag cag atc cta     355
Cys His Gln Trp Leu Arg Pro Glu Arg Arg Thr Lys Glu Gln Ile Leu
                 75                  80                  85 gag ctg ctt gtg ctg gaa caa ttt ctt acc gtc cta cct gga gaa cta     403
Glu Leu Leu Val Leu Glu Gln Phe Leu Thr Val Leu Pro Gly Glu Leu
             90                  95                 100 cag agc tgg gtg cgg ggc caa cgg cca gaa agt ggc gag gag gca gtg     451
Gln Ser Trp Val Arg Gly Gln Arg Pro Glu Ser Gly Glu Glu Ala Val
         105                 110                 115 acg ctg gtg gag ggt ttg cag aaa caa ccc agg aga cca agg cgg aag     499
Thr Leu Val Glu Gly Leu Gln Lys Gln Pro Arg Arg Pro Arg Arg Lys
     120                 125                 130 tcc tgt cag agg aga cgg tgc att taggagcgga gcctgagtca cctaatgagc    553
Ser Cys Gln Arg Arg Arg Cys Ile
135                 140
```

```
tgcaggatcc tgtgcaaagc tcgaccccg  agcagtctcc tgaggaaacc acacagagcc    613
cagatctggg ggcaccggca gagcagcgtc cacaccagga agaggagctc cagaccctgc    673
aggagagcga ggtcccagtg cccgaggacc cagaccttcc tgcagagagg agctctggag    733
actcagagat ggttgctctt cttactgctc tgtcacaggg actggtaacg ttcaaggatg    793
tggccgtatg cttttcccag gaccagtgga gtgatctgga cccaacacag aaagagttct    853
atggagaata tgtcttggaa gaagactgtg aattgttgt  ctctctgtca tttccaatcc    913
ccagacctga tgagatctcc caggttagag aggaagagcc ttgggtccca gatatccaag    973
agcctcagga gactcaagag ccagaaatcc tgagttttac ctacacagga gataggagta   1033
aagatgagga agagtgtctg gagcaggaag atctgagttt ggaggatata cacaggcctg   1093
ttttgggaga accagaaatt caccagactc cagattggga aatagtcttt gaggacaatc   1153
caggtagact taatgaaaga agatttggta ctaatatttc tcaagtgaat agttttgtga   1213
accttcggga aactacaccc gtccaccccc tgttagggag gcatcatgac tgttctgtgt   1273
gtggaaagag cttcacttgt aactcccacc ttgttagaca cctgaggact cacacaggag   1333
agaaacccta taaatgtatg gaatgtggaa aaagttacac acgaagctca catcttgcca   1393
ggcaccaaaa ggttcacaag atgaacgcgc cttacaaata tcccctaaac cggaagaatt   1453
tggaagagac ctcccctgtg acacaggctg agagaactcc atcagtggag aaaccctata   1513
gatgtgatga ttgcggaaag cacttccgct ggacttcaga ccttgtcaga catcagagga   1573
cacatactgg agaaaaaccc ttcttttgta ctatttgtgg caaaagcttc agccagaaat   1633
ctgtgttaac aacacaccaa agaatccacc tgggaggcaa accctacttg tgtgagagt    1693 gtggtgagga cttcagtgaa cacaggcggt acctggcgca ccggaagacg cacgctgctg   1753
aggaactcta cctctgcagc gagtgcgggc gctgcttcac ccacagcgca gcgttcgcca   1813
agcacttgag aggacacgcc tcagtgaggc cctgccgatg caacgaatgt gggaagagct   1873
tcagtcgcag ggaccacctc gtcaggcatc agagaacaca cactggggag aaaccattca   1933
cgtgccctac ctgtggaaaa agcttcagca gaggatatca cttaattagg catcagagga   1993
cccactcaga aaagacctcc tagctaggtc cccatgtgag gagatctgct ttcagccctc   2053
acctaaggga ggtgaggaag aggaaaagcc ctcttgtcag cctgggaaga ccttttcgag   2113
ggagtctccc tgacctgctc agatctgaca ttacctcttc ctgcaactaa acacgagcct   2173
gggcagaacc tctcagcctt cctctacgcc ttgagggat  gtttcatcca agtacaacc    2233 tgaattgagg cttctccttc actggagtgc acctgcctct acctcatggg tataaagtag   2293
gagaactaag agacttaaga ggtcgtggtt cctatatcgt ccaaaaaata ggctgttaca   2353
tatcctaaag actgctcaac agcttcaagt tgaaagtggc caaggacagc cccttaggtt   2413
tgggaaggga cgagcctgaa ggattctgtc tttactgggg tcaaatctta aagcacacag   2473
ctctggactc aagacaggag gtttgcgtcc tgatggcttt gcacacattc acaggataac   2533
tgcatagatc cctcgctgtc tgattcactt cttaccatgc actttccttt gatgctgagg   2593
agaaatggaa gtgggcgaaa atctcaagg  ctgcttcatg tggaccttgt caagctgctc   2653
cctcccccag cgtcaaattg ttatcaggtg ccaaacactg ctagaaagga gggcctagtc   2713
agaagcctct ttccatacga gttttggttt tgtttttaat atttttttct attaaaatac   2773
tcatgcattt aaccttcccg ttattcaacc agtctcttgg ttgcatccct agcacttcta   2833
ctacaagtga gatggtagtg tttgagtgct tattgagtaa agcataattc ggtcataatg   2893
```

```
aaatcgttca cattccctca tatgcacaag cccaccaacc ccttcacacc cccttcaca      2953 ggggtcgtat gagtaagggg atttggaaac tgtcaactta caaggcact ataacaatta      3013 cagaatcatg attgccatgg ccactttat ttacatgaag acaactggag aacgactaag      3073
accaaattat ggaaaataag aaaaagctgt tgctggcaag accatcaaga ctgttctgac      3133
accctgtccc catcatccct gactgagtac tctgacatca cggaaagtgt tgaacctggg      3193
accctgagga attcaccagg agtaaatggc tttcatgtaa aaaaaaa                   3240

<210> SEQ ID NO 8
<211> LENGTH: 142
<212> TYPE: PRT
<213> ORGANISM: human

<400> SEQUENCE: 8

Met Ala Thr Ala Val Glu Pro Glu Asp Gln Asp Leu Trp Glu Glu
 1               5                  10                  15

Gly Ile Leu Met Val Lys Leu Glu Asp Asp Phe Thr Cys Arg Pro Glu
                20                  25                  30

Ser Val Leu Gln Arg Asp Asp Pro Val Leu Glu Thr Ser His Gln Asn
            35                  40                  45

Phe Arg Arg Phe Arg Tyr Gln Glu Ala Ala Ser Pro Arg Glu Ala Leu
        50                  55                  60

Ile Arg Leu Arg Glu Leu Cys His Gln Trp Leu Arg Pro Glu Arg Arg
    65                  70                  75                  80

Thr Lys Glu Gln Ile Leu Glu Leu Leu Val Leu Glu Gln Phe Leu Thr
                85                  90                  95

Val Leu Pro Gly Glu Leu Gln Ser Trp Val Arg Gly Gln Arg Pro Glu
            100                 105                 110

Ser Gly Glu Glu Ala Val Thr Leu Val Glu Gly Leu Gln Lys Gln Pro
        115                 120                 125

Arg Arg Pro Arg Arg Lys Ser Cys Gln Arg Arg Cys Ile
    130                 135                 140

<210> SEQ ID NO 9
<211> LENGTH: 20138
<212> TYPE: DNA
<213> ORGANISM: human

<400> SEQUENCE: 9
cctcctctca gattgcttaa gatcatctcc gcgggctcct tgccccggct agccccatct       60
ccttacacca ccaagccccc ctcaccccag cacacaccca gatacactca cccgtgatct      120
tgtcacctgt gatgatagta tgtccttggc gtccatttgg ccagagcttt tcagctgtca      180
ctgtgacaga ccctgaggtt cccctcaagc cagtagctgc tgtctccact tgcaactttc      240
ctctcctccc actcctaaca gccagttttg gcacctcttc tcagcacctg cgttactttt      300
agcaggagta tacctacttc ttgagtgtct tgattaaaaa tttgtttttg tgccatggat      360
aggctgtgtt ccttcagaaa ggtgtcagtc taatttttgt ttttctgaac aatgaatgtt      420
ctcatcttct aggcgctttg ataaccctgt ctgccttgga atctgtactg acctccccag      480
agggagactc ttagacccag cctttcttga acaaccttgg tcctggggag cagcgctaga      540
tcccaggctc tcacttagag gctgggctta gaactgttgc ttttctcta tccacgctct      600 gcaggtgaca cccagggcag ctacactcag aagccacaag gaatgctagt ggagcccctc      660
atccctccca gcttctcttc caagctgccc cgtggggctt gatccaggaa gctacttcag      720
```

-continued

```
aaaggttgtg ggatagcctt gggaggaggt ttgttggtgg gaagcgtgtg aaccggaaca      780
gtcttggata actttctgct gttactatct agcataagag ggtgggcagg gttggagaga      840
ggacaggaat ttttcctcct aggaccaaac gcctgggatt cataatcttt caccctttct      900
cctccagcta tacccttttt gtactctgtg tatatactat attgcagtag acaatcattc      960
caagggtaca acaaggttta ccacaatgtg agggactcag ccattgcaaa ttgtacagat     1020
gaggtaagtt acaggtttac attttttttt cccagtaaat ttggcacaga tttaaaatgt     1080
gaaacagttc tagacccctt gttttgctg ttctctcacc agcaaaccct ttagtttggc      1140
cagcaatggc tttctgcatg aacttcagat ttacttcatt tgctaggtgg tggttctcaa     1200
acttactata agcacctgaa gggctagtta acgcatatt gctggggccc acccctagag      1260
tttctggtaa taggtctgtg ctgggcttg agaatttatg cttctaacaa ggctcaggta      1320
ctgatgctgc agatctgggt tcttcacttt gagaacaact accttttggc caaatgtgat     1380
atacgtattg cagtaggttg aggttcagaa tacctttgtt tgagtacttc tgtgttggaa     1440
actagtaatc tgatctttta tagataatca cttaggtctg aatattctgt tcgcaaaatt     1500
aagaaagcgt acttaaaaca actgaatgct atatgccaaa tttgaggtga aatattgatg     1560
agttcttccc cttgattttc ttaattctct tgataggggc ttcacgtttt gatcaaaaat     1620
attacacctg tattctgggc ttttgctgtg aattcctagt attgctaaaa ttctgcaatt     1680
tcttaactac ctgttaagtt cctcaaggtc agagcttctg ctttttttat ctttctttgc     1740
ccagcacctt gaatagtgtg ggacacgtaa ttgacgctca gtagatattt gtgtattgaa     1800
ctccatccct tgtcctcctc ccctcttgat gtttttctct actggcctta tgctacacag     1860
taaagcaggg catgattatg ccacttgatt accccaaga gattggaata aatgctaatg      1920
ccaaattcct acagctatcc ctgtgaatgg tttattaccc aggagccctg acactggctg     1980
atttctgaat tttcagtgct tctgtaatat atactagttg ggggaggaga aatagaaagc     2040
ttaaactcaa tgtgcgttta ttgaatacct tttctactaa gggcttgaca agtggtagg      2100 cactgggaat ataaaaatga ataaggagac ccttgctctc gaggcagggc ccacagtggg     2160
gagacagacg ttaagccatg cccacgacaa gaatgacttc tgagattcct tctttggatc     2220
atgatttagt cttcagtgga aacctggtac tcctcagatt cctctggttc aacaggcggg     2280
gatcccatcc cttatcatct cctcaaatgc taaaggaccc ttgagcaaag ccaggaggaa     2340
gtcatctaga cgtgaaacag ggagtatcca cacaggctgt gttaatgaca aagctaaaaa     2400
catagtaaat gacttttgaa tttactgctg ttatgaatta tctatagcaa cacctcaggt     2460
cagctctgtt atatatgtta ttgtgttatt tcccattaaa tgatggttcc tctgactatc     2520
tgattggcat tgactatgtt tgttgtaggg attgcataca tctagtttaa ctctggctgt     2580
caaatgagag agcagttact cttatcagga tgggtgtcag gtttgatgtc ccctcctttt     2640
cctgcttcag gttaatttgt catgttctgt tttaaactga ggcatatagc ttgacctcct     2700
ttatttaggc cattaactgc tctgggtag ttttcctgaa ggttaaaaag cctagcttca      2760
tgatggaggt taatcaacat gaccatgatg gccaggtgta taaatctggc ctcttaaaaa     2820
tctgtatttg aggctgggtg cagtggctca cacctgtaat cctaacactt ggggaggcca     2880
aagctggcag atcacttgag cccaggtatt tgagaccagc ctgggcaaca tggcaagacc     2940
ccttctctat waaaattta aacattagct gggcatggtg gcatgtgctg tagtcccaga     3000
tacttaggag gctgggtgg gaggatggcc tgaacctggg aggcagagat tgcagtgagt      3060
tgtgatcttg ccactgcact ccagtcttag caacagagta aaccctatct caaaacttaa     3120
```

```
aaatctgtgt ttggcccta gccgtcctca gctcttgagt aaatctcagc atcctaggct      3180
gttacattat ggcccaaata ttcaatagag atgctgtata tccttgttcc tctcaaaacc      3240
cctcctcatc accatcaaaa agctggttta gttctctacc tttagataaa gaatcatccc      3300
aagactcaac atgagctgcc gtgacttgtc caagatgaca cctctttaca atgtagagca      3360
gtggacagaa cacaggtcac cctccgccga aagcaactat ctactgtcta acattgcctc      3420
ctaggcctgc catatataac catcaaaaac attttagttt agaataaagt gaattgttac      3480
aatttttatt tttcattttt gtgtttacat ttactctcaa tgacatgttt attcccacct      3540
aatatcttga ggctaaccac aaaatctgca gcatttccag gcagaagata cttgtgactt      3600
ccctgtacta tccactacat acttgacctc tttctctttc ttcctgtctt ccctttctct      3660
ataccttatt atctttcttt ggaacctctt gtaacaaatt ttgagccatt tctcccctca      3720
ctactcaaat atcacttttta tgaaggggcg ggggggaaac ttaggtggca aaatatttt      3780 acagaaacag ttttaaacat gttttgaagc atactggtca cgtgttagaa ggccaaaagc      3840
cagggaattc attccctttc attcattgtg ctgtctaggt taagttttca caggacttct      3900
tggtacactg agtttgcctc agattgtctc ctgccagtta cagggagtgg agaggacttt      3960
gatatattgg taattagaag cattscygat atggtcttcg gtgggagaac ctgtgtctaa      4020
ggttccttct catctgtatt ccaacacttt catttaatcc tacttcataa gtgcctccaa      4080
agcaaggatt ttttttttgg tttagcatgg tttctttgat ataacaatag accgaccaag      4140
attttcctta tgccatctgt tttttgtaa ttatgatgca atagagaact gtttgcttgt      4200
ttatcattta aatcttgcct tcttcccaaa acgatttcaa atagcttgaa ggaaaatgaa      4260
taaaatatat tgagcaccta ccctatgcca gactctatac tgaagggttt ctataggtta      4320
tttcatttac tccttaaaac aaccacatga gataagtagt attagccaca ttttttgagga      4380 taagactgag gcttagggaa attgtgttac aaggctaata agcgaggtca gggattcgag      4440
gtcagggatt caaacccagc gtgccaaggc cactaaccat tatgtggaaa gcttaggtaa      4500
gcgcttgtat ataggacaat caagaataaa agaatatgtc cattagaagg attgtactgg      4560
gctaatcttt cgttttaaag aacagcagca gcattggaaa agagcggtta acagttttta      4620
ttagccaatt tctattctag aacactgaga ggagctgttg acaggccctg gttagcccca      4680
gcaagtagtt gtattaaaat taccaaacta taggcctgca ttaaggtata aaataagaat      4740
ggggactgga agggatataa atatctgcta aatataataa tttcagttct aatcactatt      4800
ttcttctgaa gattatttgc cagtacatag gcagatcact gtctctcctt taggttgatg      4860
gtatatgact acagactttg tcatttaggg tccagaaaga tcaccctagc tagtagcgtt      4920
ttaaggtaga gaactagata ttgtttcatt gcctgtggtt ttctgttctt gtaagagaat      4980
tgagcttggg tcttcactgc cacgtgacac cttcagataa ggggcagaga cagctggcct      5040
gaggattgta cagaggtctt accttgatag ctcctctcca atcctatgca tcctaggaac      5100
actcaagaca ctaggttgta tctttgcaga tactgtttta gtgtcttctg gaaccaagtc      5160
tcttacttaa tcctggcctg gtttcatatt ctctctattg tattctctct atagttttttg      5220 tcttactctg gaactcttcc aaggacagac attgaagaaa ggtattagaa tagcaaaggc      5280
aacaaattgc aaggtatact tatggcatag cacatcccat taattataga ataaaaacac      5340
aacatctgtt ttctgcctct aatattaaat cttgacattt gcacaacaca ttttagttca      5400
taaagctctc atatctcaga taatcactga gttaggagac tggttatctg cagagggctt      5460
```

-continued

```
tatcctttac aagggctctt gggtacgtta cttcacgaaa ccctcaggga agctccagtt    5520
tcttggggat ctggggccgg ggcatatgtc tttggatacc cagtttggtg ctgtgcacag    5580
cactgctgta cctcctattc atttcccatc tcttacccca caaagactcc ttccttcatt    5640
ccttctattg ctgatctgtt ttccttcatc ttcctaggct gccaaagtaa atgcaaaaca    5700
agcaccagaa atctcagctt gtgatttctg aagggcattt ttaaatggca agtttggtgt    5760
ggcactgtta catgttcttt tttctttgga gagcaaagcc ctttgagaga gcaggaactc    5820
ttctgtcaat gcatacgttg taggatccat actgtggaat ctcttgtacc tagtgctgcg    5880
tgaaaacaat gaggattcca gtctacttc actggacatc ggttctcaaa cttttaagat    5940
actagaagtc cttttattaa gccaaaagac cctatgtatt aattctgtct tccaggggta    6000
ggagttgggg tggggtttgg aaagctttgt ctggataaat aattagtatt gtagttccat    6060
ttatttgatg tctgattttg cgcttattaa aattgattta aatcctcaat ggaaaatgat    6120
tttttttttt caaatgccaa gtgttgtgtg acttgcattt ggattattcc cggtgcaacc    6180
tgaagattcc ttgtgatgag ttgtggttcc atcatcttgg gaaccactaa gagaattctg    6240
ttttactcac aatccaaaca ataaatgttt ttttccctat gtatgccttt atccagcaca    6300
cagtttgcta gacttatgga tgaatatggg ttaatataac atggtatcta tccttctgga    6360
aacagacttt taaaacctta ctaagcattc tctgcattca tcaaatgtga agtgagtgcc    6420
tggtgtgtgc caggcatcga gctgggcaca gcatatccct gccctcagag ctttacagtc    6480
cagtgagttc aacagaagat gaacagtttt gatgacacaa aaaatagaca catgtgcatg    6540
ctgtgatagg gggagataca agttcctgtg gaagcatcat ctgggaggac cagggaaggc    6600
atcttggaaa aactgagctc tgaaagatgg atagagttaa ccacatgaag agtggagaag    6660
ggtacttcag acaaggtgaa cagcatcagg aaagcccagg gagggtatag aaaagaaaga    6720
acagtaattc ttgcagtggc tttcaatggg agtggcagtc atggaaggaa ggagaggtag    6780
cagggaccag cttttgaagg gctttgtgta tcacatttta agaagtttaa atttaaccct    6840
aaggtcactg ggaagccatt ggcagatttt gtatgttagg aagttcacca ctcacctact    6900
tggagtattg caggtggagc taatgtggat gggcctcctg cccattatta aatcctgttc    6960
ctgtcaggaa caggacagcc catgctgtct ctccctgtgt gtctgtctct ccctgtgtgt    7020
ctgtctctct ctctctctct gtctctctct ctcaaaagct aaaggaaagc gcataggttc    7080
cagaaggaaa aagaaataac cactagaaaa ataagtataa gctgacttta ccatggcgca    7140
gtgagattcc aaaccaaaat aaggtttcta gggattgagc ttttaatact ggtactccaa    7200
cagggagata ggacttggga aactgacgct gtgtgaaagt tacagaatta agcagcctgc    7260
aaacctggac ctttgaaaat cgtcctactg acccaggaaa agtgcaagga agtgggttct    7320
ccagaacctt gggtaggcca acattactt gaaggcatcg atctaaataa tacacaaaag    7380
cattattcag gaacaccctg agaaattaac ataaaactg atttggccag gcatggtggc    7440
tcagcctctg gtaacagtgc tttgggaggc caaggttgga aaatcacttg aggccaggag    7500
atccaggctg tagtgagcta tgattgtact actgcactcc agcctgggca acagagggag    7560
agtcttaaaa aagcaaactg tccaagatca ttgaaaccat tagcacttag gaagaaacaa    7620
atgaaattac attcaagggg gtcacattta aatccagggc tctcaggact cccaaagtaa    7680
aaagatggac ataaaataaa aaattacaa gccacttgag aaaaaaataa atcaccatga    7740
ggtagagata gcagaggaaa aattacacat gaagatctag gaattaggga gctatccaag    7800
atagactgtg aaagtatgtt gcaagtgact gagggtaatg aaaaaaatgt cataagagca    7860
```

```
tgaattagaa gcgttttgag aaagaatgaa gataatgtgg tcattgactg taaactcatt   7920
tgatgggcaa cgatagatga gacacagcta ttaagagtgg atcgataacc ttgaatgtgg   7980
atgtgaggca actgtagtat agcacaaaaa ggttgagaaa tgatggagcc cttaagctgc   8040
ttgtggacac tggtctggag ggggacagga ccaagaaaac cagtcatgga ggttgaacta   8100
agtcatctct ccaatgtatc cgtgcctgtt acgtgccagt gccgtttagg agcagaggat   8160
attgtaattt tttttaaagt tcctatgaat accttctagt gggtcataat ggctcaaccg   8220
ggaaatggca gtagagatga agagatggat ggattcgaaa gacatttttt ggaagttgga   8280
attaacagga tatggtgaat aatcaagaga tagtaaaagc ataatggagg aaacaatggt   8340
tcttcctgtt accataggaa gaagctttgg agtagagttt tattcatttt aaatgcattt   8400
attgtgcact ttattatagg tattggagat tgatggaaaa tagtctctga cctcaaagag   8460
tttcacagga aagatgagcg atggctatgt aatatgacca atactgggat agagaggtgc   8520
ccaggtcact acgggaggac ttaggtgatt tctaactatg tctgagagta ggggaaatgg   8580
gatcaaagaa aacatctcag aagacatgaa gcttgagctt atgtcttgaa aaatttaaag   8640
tttaacctaa ccaaggataa agaatcagaa gaaacagcat attcaaaagc taagaacac    8700 gggactcttg tgtgctttgc atgtacacac gtgtgtgcgt gtgtgtctga aaggattgga   8760
gaggagggcg aagagaataa caagatgaac gtcaacctaa tgtagaatgt ttgaagtttg   8820
tatttcactt aacaagacag cggggagtga tggaaggatc ttagatagga aagggacatg   8880
agcacgtttg ccaagagagc tcgttctggt catagtgggt acgtgaaggt gacaaatctg   8940
gaggcagata gctcacattt ggaggcagct gcagtcatcc agatgagaag tgagagggac   9000
ctaagctgta aattgtggga ataaagacaa gacccgttaa aaagaaagag aacacaccat   9060
gtagcgtgga aaggagaagg gtggagagta gcctgtgcag aaggaacaac cttcaaaaag   9120
acatggaaga ctgaaaagac accctgttgt agggagatca gcaatgcatt ttttataacc   9180
aggtgataca gggaaagggt aggatctgaa gcttgaaaaa tagattgggg gctgattgta   9240
aagagcttcg tgtcattccc aggattttgg aactgatttt actaacatga aaaaggtttt   9300 gtttaaaat actgagtaat atagttggaa ctataattta gaaagataat agctggtgcc   9360
atcactcttc taagcaaaga tagtaataca tttaatgctc ataggcttta gtaatacatt   9420
taatccttac agtaagccta ttagataaaa accattatta tctcccttct atagacagag   9480
aaactggcat taggagaatg agaacttgcc tatggtccca ctctggaaat acctagtaag   9540
cgacagagcc aggattcaaa cccaggcagc ttgactccag aactttcgct cataacctta   9600
cacatctccg tcatggttgg tgtttctcaa ccatggatac acattcgaac tgcatgtagc   9660
atctctaaac atacagttac ctgaattgac tgaatcagag tgtctgaaaa atgatgtgtg   9720
atactatgtt ttgcaaaatc tccacaggta attctgttgt actttgctta tagttgagta   9780
ctgcagggat cttaggaagt tagagcagta gtccaggcag gagatgatga aggctcagac   9840
taaagcagtc tgtaggaagg aagagaaggg aaccggtttg gagacttaag cggggaatt    9900 ggcagtattt gtgaagtgga aatgcagtat tttcttgtag agtatgaacc ttgcctagga   9960
aagggagtag aggaccatac ctttagttgt aaattatcct ctcccaactg gatctgttga  10020
tttatggcta tggtggttgg ggaaaagagg atttaaccat ttgaagaagt ttgtgtagag  10080
gattatgatt gaactcaggc tgttgtcctt gtgtatagtt tcatgcttat actcttgttt  10140
gtctttactt ctctatccag ggcccttgga agaaaatcct cgctgtgtcc aggctgaggc  10200
```

-continued

```
gggggggctaa tgacagtgtg agctctagat ggtgtgagac cacccaaag ccaagaaatg    10260 gctacagccg tggaaccaga ggaccaggat ctttgggaag aagagggaat tctgatggtg    10320
aaactggaag atgatttcac ctgtcggcca gagtctgtct tacagaggga tgacccggtg    10380
ctggaaacct cccaccagaa cttccgacgc ttccgctacc aggaggcagc aagccctaga    10440
gaagctctca tcagactccg agaactttgt caccagtggc tgagaccaga gaggcggaca    10500
aaggagcaga tcctagagct gcttgtgctg aacaatttc ttaccgtcct acctggagaa     10560
ctacagagct gggtgcgggg ccaacggcca gaaagtggcg aggaggcagt gacgctggtg    10620
gagggtttgc agaaacaacc caggagacca aggcggtggg tgaggagggg gagtcctgat    10680
ctgtgtgatg tggaggggga ctatttgctg gaaggctgga tttgcgggga gagcttgcag    10740
gatccccata aattattagt ggctctgccc ttgggttgct catataccat gagccccatg    10800
gattaggggg atgtgtgtgt atgaatgtga ctttctggat attggaacac ctgtataggg    10860
accatctgag ggggtctcag ccaccaaagg gtcatggctt tggttttccc ttctttgaat    10920
gttgagccgt gggttcctgg agaggagaat tttgtgactt cctcgaaggt tctcatagat    10980
ccccagtcac agatccccct tcctggctgg tcagctaggg aagcaggcag caaggagagc    11040
tgcaggtggg acaggtggag atgggaagga accttgggtg acaggggccc aggctggggg    11100
tggtgagaga gcagtgcagg cctgcgcatc ccctgccttg tcctggggag gataaccttc    11160
agctcctcct tgcctgctcc attgaaactg gagtttcccc tccttgtctg ggtccctctg    11220
ggagtgtttt ctctaggcat cttctcctaa aataagctcc cgtgacaacc aagaacttcc    11280
tcctgactcc atggtgactg gaagttggaa ttattcccag gtgactgtcc atgttcacgg    11340
ccaggaagtc ctgtcagagg agacggtgca tttaggagcg gagcctgagt cacctaatga    11400
gctgcaggat cctgtgcaaa gctcgacccc cgagcagtct cctgaggaaa ccacacagag    11460
cccagatctg ggggcaccgg cagagcagcg tccacaccag gaagaggagc tccagacccct   11520 gcaggagagc ggtgggaagc atcagcagaa agggggggatt gtggcagaag gcaggcaagg   11580 aggggggacat ttctcctata ccaaggaagc tgggtagata gactgtatgg aaagacatca   11640
cagaatccag gatgtcaaga ggagacagta ccgccagcta gagtccccca taaacagggc   11700
caagcttaga cagcagattg ttgcttgttc tcttggcatt ctgatagtct cataggtgat   11760
gggattggga tatgggagct acccttaggc cagtttcttg gttcccataa tagaaaggat   11820
agggccacct tcctaccaaa gatggtgggg gatgcccaga ttttttgccca ttattggggc    11880 atgctgcata ttactgatct ttgccttctt ttcttcatag aggtcccagt gcccgaggac    11940
ccagaccttc ctgcagagag gagctctgga gactcagaga tggttgctct tcttactgct    12000
ctgtcacagg tgtgccctag ttacctctgt accacagaga atttgtttga agaaccactg    12060
ggcataagcc atactaaaca ggtgaagcag gatgcacatt tacactcttg ccagttttaa    12120
gctcacagtt ctgcaggtac ctggaagggg aggagataat gagataaatt atcatacctt    12180
atattggatc cacaggcacc aacaccagtt tatttgccat tgactagaag aactaacaaa    12240
atgggattat tttgtaacac tccagtacaa ctgcgaagtt gtcaaatgag ggttttttag    12300 ttttttttt ttttaaagga ataaatttga tagtcatttg taagtatgac agactgtact     12360
gctgagacat ttaggaagta ttcaccatga tcaaagctct gaaactaagc catgtggctg    12420
gagaaaaaga aatagaattc atgtatggtt ttagattgta atctaactga ggaaaaaagt    12480
cttgttttgg ctatagagta tagaaactat tgaaagtgat tagagtcttt agggaaagtg    12540
tactagaaaa gatgaatttt gcagaaatgt atatagcgtt aaagtgtcaa gtagggagct    12600
```

```
gaatgatgat ttttaagacc tttcctaaat tttaaacaat accttaaaga agaagaacat    12660
aagctggtcc tcaggaaaag tggtggagtt ggaggggggca gggccagtgc cacaggggac    12720
acatggctcc cccgagaatg agtttaagca gcccgccact caagctcctt tcatctccta    12780
gaggagtcca cctattgtgt gaccttcaac agggacaaaa tacgaggcta cccgtagcat    12840
cacgttttga tgaaatcctt atgtggtttc agggactggt aacgttcaag gatgtggccg    12900
tatgcttttc ccaggaccag tggagtgatc tggacccaac acagaaagag ttctatggag    12960
aatatgtctt ggaagaagac tgtggaattg ttgtctctct gtgtaaggaa tttcaagtat    13020
tctagagtgt tctaagccca gagatctttt tcctgctgga aattttgggg gatcttagac    13080
cttagattgt atgcagtgaa cttctcttat gccttcccca ccaataaaat tgagggatta    13140
ggtgaaaaat acggtgtcct ttcaagtaaa agataaatgg atggaaatgg aaacctctaa    13200
taggaaaaca aacttgtaat attacagctt tagtgcagaa atatttgaag taagcacatg    13260
agttttaaaa cagtaagagt tggagataat ctttcttgaa tatgggaaaa gaggataagg    13320
tgtacaatgg tataattatt aagttgcagg tgaaaaccac aagaaaggca agagatacgc    13380
agtccttggt taaaagtaca caaactaaag agatgaaaga tttcatcacc tgagctagct    13440
atgtatttgc cccacaacct accaaataga aaaggaccgc tcttaacaca gggaattgtt    13500
gagccaatcg tgatatccta ttttccctct cttgagcagc atttccaatc cccagacctg    13560
atgagatctc ccaggttaga gaggaagagc cttgggtccc agatatccaa gagcctcagg    13620
agactcaaga gccagaaatc ctgagttttta cctacacagg tgaggaatga caaaaacggt    13680
gttacccacc ctgagccagc agttcctcta ggcagtgctt ctctctctct gtagggcccc    13740
gctctcatca gttcttctaa catgtcagcc agtactgctt tctccctctg acagccattt    13800
cttctgtcat tgccctcctc ttttctcctc ccatcatttg tctgatagca atgtaataca    13860
aaagggtgaa agaaaaatgt taacttttgg aattgcagct ataccattta ctgtacaatt    13920
cccttaaacc ctcgattctc aatctctgca tttgtaaaat gaagattata tttgtgcata    13980
ccaaggtttg ttgatagcat aacaatatga gaaagtgctt ggcacaggac aggcattcca    14040
tttagtcttg ccatctcaaa acccttttgta aaaatctccc cattgtgtag aaggcattgt    14100
tgccgctaca gtgaccccct ttttcctctc acccttctta caggagatag gagtaaagat    14160
gaggaagagt gtctggagca ggaagatctg agtttggagg atatacacag gcctgttttg    14220
ggagaaccag aaattcacca gactccagat tgggaaatag tctttgagga caatccaggt    14280
agacttaatg aaagaagatt tggtactaat atttctcaag tgaatagttt tgtgaacctt    14340
cgggaaacta cacccgtcca cccctgtta gggaggcatc atgactgttc tgtgtgtgga    14400
aagagcttca cttgtaactc ccaccttgtt agacacctga ggactcacac aggagagaaa    14460
ccctataaat gtatggaatg tggaaaaagt tacacacgaa gctcacatct tgccaggcac    14520
caaaaggttc acaagatgaa cgcgccttac aaatatcccc taaaccggaa gaatttggaa    14580
gagacctccc ctgtgacaca ggctgagaga actccatcag tggagaaacc ctatagatgt    14640
gatgattgcg gaaagcactt ccgctggact tcagaccttg tcagacatca gaggacacat    14700
actggagaaa aaccccttctt ttgtactatt tgtggcaaaa gcttcagcca gaaatctgtg    14760
ttaacaacac accaaagaat ccacctggga ggcaaaccct acttgtgtgg agagtgtggt    14820
gaggacttca gtgaacacag gcggtacctg gcgcaccgga agacgcacgc tgctgaggaa    14880
ctctacctct gcagcgagtg cgggcgctgc ttcacccaca gcgcagcgtt cgccaagcac    14940
```

-continued

```
ttgagaggac acgcctcagt gaggccctgc cgatgcaacg aatgtgggaa gagcttcagt    15000
cgcagggacc acctcgtcag gcatcagaga acacacactg gggagaaacc attcacgtgc    15060
cctacctgtg gaaaaagctt cagcaggaga tatcacttaa ttaggcatca gaggacccac    15120
tcagaaaaga cctcctagct aggtccccat gtgaggagat ctgctttcag ccctcaccta    15180
agggaggtga ggaagaggaa aagccctctt gtcagcctgg gaagaccttt tcgagggagt    15240
ctccctgacc tgctcagatc tgacattacc tcttcctgca actaaacacg agcctgggca    15300
gaacctctca gccttcctct acgccttgag gggatgtttc atccaaagta caacctgaat    15360
tgaggcttct ccttcactgg agtgcacctg cctctacctc atgggtataa agtaggagaa    15420
ctaagagact taagaggtcg tggttcctat atcgtccaaa aaataggctg ttacatatcc    15480
taaagactgc tcaacagctt caagttgaaa gtggccaagg acagcccctt aggtttggga    15540
agggacgagc ctgaaggatt ctgtctttac tggggtcaaa tcttaaagca cacagctctg    15600
gactcaagac aggaggtttg cgtcctgatg gctttgcaca cattcacagg ataactgcat    15660
agatccctcg ctgtctgatt cacttcttac catgcacttt cctttgatgc tgaggagaaa    15720
tggaagtggg cgaaaaatct caaggctgct tcatgtggac cttgtcaagc tgctccctcc    15780
cccagcgtca aattgttatc aggtgccaaa cactgctaga aaggagggcc tagtcagaag    15840
cctcttttcca tacgagtttt ggttttgttt ttaatatttt tttctattaa aatactcatg    15900
catttaacct tcccgttatt caaccagtct cttggttgca tccctagcac ttctactaca    15960
agtgagatgg tagtgtttga gtgcttattg agtaaagcat aattcggtca taatgaaatc    16020
gttcacattc cctcatatgc acaagcccac caaccccttc acaccccct tcacagggt    16080
cgtatgagta aggggatttg gaaactgtca acttacaaag gcactataac aattacagaa    16140
tcatgattgc catgggccac tttatttaca tgaagacaac tggagaacga ctaagaccaa    16200
attatgaaaa ataagaaaaa gctgttgctg gcaagaccat caagactgtt ctgacaccct    16260
gtccccatca tccctgactg agtactctga catcacggaa agtgttgaac ctgggaccct    16320
gaggaattca ccaggagtaa atggctttca tgtatttgtg ttgtttgctt tttcttacgt    16380
gattttatgt tcatagagct agaaagtagc atctcatgat ggcccaacaa tctctgttgc    16440
cagttaaagg ttccttggag atgaggctga ataattatga acctcacctt ctctgattgt    16500
gggagtggca agaactgggg agacgtcctc cataagtgga gcacagggta tggggttaaa    16560
gcatgacagg gagagtcttc tgtgcctggt ttcttctcct ctatctcata atgcattatg    16620
ggcccgagga ataggggagg gttaataaga ctccaaccct aatggcccaa cagggaaatt    16680
ctcattttgg tcgatgatat tctgatggac tggtttggtc ttaataccag tcaaccgttg    16740
tccttctgga aatatacata tatgaaataa ataaaggtaa cacttgcagc caagttccct    16800
ggtttctggg acttcccatc ttacccattc cttttccagg gcttcagtgt cctgatactt    16860
ctgagggtgg ttcatactca aatagatctg ggagtacaga gtattttttcc ttgaggaaag    16920
gaagggttgg gatgattagc agagtccggt gaaacatatg cactctgaga taagatccaa    16980
gcctggagtt tgcagaagat actgtcctaa taagcaggca tttctaaacc aagtatctaa    17040
gcctaagcac agcttgtcct gggtgaaatg tctgccacaa aagatagttt ctcctagctc    17100
agacttaacc atttataaag gttggtaaaa tactggcagt gacaacaaat tgactttta    17160
attttcttat ttgcattatt ccaataaatg aaaatctgtc agagttctac atgagggaaa    17220
gcttgtgagg ctgggccggt ttgttggaac atcaaatagt ccttaattac tgatctccct    17280
gcagagtttc atatgctgac actaaatctc tggtcccttt tgtaaattac tgaattttct    17340
```

```
gaggttctgg gagggacatg ttgtctccca aatctgaaca aacacaacca cagtgtgcag    17400
cggcaggaaa gaagtagtgc agctgagcgt gagcagggag gttggagcac agggtgtgta    17460
ttcggagggg tcccctctag tatcttgtga gcagtagaat tctagcatcc ttgaatacca    17520
tactaagttt ctgagggaga aaacggtggg atttttaaaga tattatttgg aggaagttaa    17580
tacgctactt aattaacaga attggcaggt ggttggaaat gtgctaaaga ggtatgacac    17640
attaaaaatg ataatataag gatgtttgac cagataattt aggaataacc aaggaatatt    17700
taacctcttc accacaaagt ccgaggagaa ataaatgccc aagagatcaa gccaaaatac    17760
atttttatta tctgggactt aggcctcata ttccggagca gaatccggta aactcagatg    17820
aactccatgg agaatttcat aaatcagatt aacatcaagg tactaaaatc aaaacccact    17880
aagaaacctg ttgcccccctt caaagcacaa ctgaagtaat ggatctaata gaagatacat    17940
tgtttgcact gagcagtaga gtagtagagg agaaaagccc agagatggca cagacaagtt    18000
gttccagtcc ccttcagtca aggcctctgg accaccaccc tgccacaggc gaaaaatggg    18060
atatttaata aataaaaaat tttgattcac cagactggct gaaaggacag taatccaaat    18120
gagagttaac ggctccatag tagttttcta gaatgaaagc tgaactgaga aatagtaact    18180
gatgacatgt tgagcaggtt aataatttgg tacccttcca caccagtatt tgtttgtttg    18240
tttgttttga gatggagtct cgctctgtcg cccaggctgg agtgcagtgg cgtgatctcg    18300
gctcactgca agctccgcct cccgggttca cgccattctc ctgcctcagc ctccccagga    18360
agctgggact acaggcaccc accaccacgc ccggctgatt ttctgtaatt ttggtagaga    18420
cggggtttca ccatgttagc caggatggtc tcgatctcct gaccttgtga tccgcctgcc    18480
ttggcctccc aaagtgctgg gattgcaagc gtgagccacc gcacctggcc ccacaccagt    18540 attttttaaaa atagtttgtt ttacctctag cgtcttccct cagctgacct aaatagtcca    18600
gccacaatag ctgagagaag tatacctaca attatttcca tctccttata tttctagtga    18660
tgttggctga ctaacccact aatctagttt atgggagagg gaaagactga aagagccaca    18720
aagtggatgg ccaacccacg tgattactaa cctttattgt ggcaaagtaa ctgatacaat    18780
gtttcaaatg taagcacatc tccttggaat aagtggaata acttaattca tccttgcgga    18840
agtcctgagg atcaagcaag gaggagccca gctttcttta gacaccacct tttttatctt    18900
taataacaaa aaggaacaaa gtgattgtca gaccagcaca aagataccct ttaatgtgca    18960
atttctattc tctttagtgt gtgtgagtgc acgcatgcac gtgtgtacac cgaggtttca    19020
ggtagaagga ggaatgcaat tcaaattcta aaaaaggaat cagtcagcac aaactagttt    19080
atttggcaat tcataaagat agggactctt cagaggaggt tgagagcatt gtagggttat    19140
gtaaagactt ccagaagctg taaagacttc cagaagcaag aagattcaac catctaaaac    19200
gccatgcagg aaaatagcca aaccttctcc atttaagtag agaataaatc ttagtagcgt    19260
tctctgcaga atataacaac gctgcaaaaa ggccatttca caggaatata atcaaaactg    19320
cagattctca gggtttcccg taagacgact tctctgctct tctgtttgtg gtttcttttt    19380
tagttgtaca tctctcctag acaagtccaa ggaactacta acgagaagat ttcaggaaga    19440
ggcctacagc aattgcttgg tgcttgggtt catttgcgga atcttggcaa caggtctaca    19500
gagaagcagt tccacggcaa aagagctgtg gggcagttga ataatccatc caaacaatga    19560
ggagtaaacc ctgagtcaag aaaccagcaa aaagcagaag actgggtcag caaataaagg    19620
gagaagatcc ttgcctcctt cagtgcccct agcatgatat tctgaaaggc cctccactaa    19680
```

```
aatacaacta cagtttaat aaattactaa aatagagaat agaagtagta tgtaagttgg    19740
gataggtgta tctgaattaa gtgttttaac attcatgaac tgttcaggac aaaagctgta    19800
agatattggt taacctcaac attgttaaat taagtgtgca ctgtagtatc aaagatactc    19860
ataagaatgg agagagtaat tttctaaata gtggagggaa aataggaatt aattttttc     19920 aaaagtggga cttaggttgt ctaaagaaag gccaaaaaaa gcataaaaag atgaaaaaat   19980
agaactacga agaacacagc ccaaatatat gaataaaata gaataaatag taactaccat   20040
ttaagataga gattgtcaga atgggtaaaa aaaaaagtaa attataacaa agtatataca   20100
acagatatac aaaaatagtg atttttttt  tttttttt                           20138
```

```
<210> SEQ ID NO 10
<211> LENGTH: 114
<212> TYPE: DNA
<213> ORGANISM: human

<400> SEQUENCE: 10
ggtgttccga cccgctaggc cccgcgcggc tcggatccgg cggcgctgtt tcggtcggga    60
gtgggtggga gagaagccgg ggcaggggag gagccgccgg agctgtcgga gccg          114

<210> SEQ ID NO 11
<211> LENGTH: 119
<212> TYPE: DNA
<213> ORGANISM: human

<400> SEQUENCE: 11
tgacacccag ggcagctaca ctcagaagcc acaaggaatg ctagtggagc ccctcatccc    60
tcccagcttc tcttccaagc tgccccgtgg ggcttgatcc aggaagctac ttcagaaag    119

<210> SEQ ID NO 12
<211> LENGTH: 140
<212> TYPE: DNA
<213> ORGANISM: human

<400> SEQUENCE: 12
tgacacccag ggcagctaca ctcagaagcc acaaggaatg ctagtggagc ccctcatccc    60
tcccagcttc tcttccaagc tgccccgtgg ggcttgatcc aggaagctac ttcagaaagg   120
ttgtgggata gccttgggag                                                140

<210> SEQ ID NO 13
<211> LENGTH: 116
<212> TYPE: DNA
<213> ORGANISM: human

<400> SEQUENCE: 13
ctataccctt tttgtactct gtgtatatac tatattgcag tagacaatca ttccaagggt    60
acaacaaggt ttaccacaat gtgagggact cagccattgc aaattgtaca gatgag       116

<210> SEQ ID NO 14
<211> LENGTH: 156
<212> TYPE: DNA
<213> ORGANISM: human

<400> SEQUENCE: 14
ataaccttac acatctccgt catggttggt gtttctcaac catggataca cattcgaact    60
gcatgtagca tctctaaaca tacagttacc tgaattgact gaatcagagt gtctgaaaaa   120
tgatgtgtga tactatgttt tgcaaaatct ccacag                              156
```

<210> SEQ ID NO 15
<211> LENGTH: 27
<212> TYPE: DNA
<213> ORGANISM: polylinker sequence

<400> SEQUENCE: 15
atgaccatag tcgacctggc cgtcgtt                                27

<210> SEQ ID NO 16
<211> LENGTH: 39
<212> TYPE: DNA
<213> ORGANISM: polylinker sequence

<400> SEQUENCE: 16
atgaccatag tcgacggatc cgtcgacctg gccgtcgtt                   39

<210> SEQ ID NO 17
<211> LENGTH: 32
<212> TYPE: DNA
<213> ORGANISM: primer
<220> FEATURE:
<223> OTHER INFORMATION: "n" base designation at various positions
      throughout the sequence represents A,T,C, G or
      unknown

<400> SEQUENCE: 17
gtcagatcta ctacgtacag nnnnnnnnnn nn                          32

<210> SEQ ID NO 18
<211> LENGTH: 34
<212> TYPE: DNA
<213> ORGANISM: primer
<220> FEATURE:
<223> OTHER INFORMATION: "n" base designation at various positions
      throughout the sequence represents A,T,C, G or
      unknown

<400> SEQUENCE: 18
gtcagatcta ctacgtacag nnttttttttt tttt                       34

<210> SEQ ID NO 19
<211> LENGTH: 29
<212> TYPE: DNA
<213> ORGANISM: primer

<400> SEQUENCE: 19
gtgactaatc gatacgcgtg tgaaggtgc                              29

<210> SEQ ID NO 20
<211> LENGTH: 33
<212> TYPE: DNA
<213> ORGANISM: primer
<220> FEATURE:
<223> OTHER INFORMATION: "n" base designation at various positions
      throughout the sequence represents A,T,C, G or
      unknown

<400> SEQUENCE: 20
ccttcacacg cgtatcgatt agtcacnnnn nnn                         33

<210> SEQ ID NO 21
<211> LENGTH: 20
<212> TYPE: DNA
<213> ORGANISM: primer

-continued

<400> SEQUENCE: 21
gtcagatcta ctacgtacag                                                20

<210> SEQ ID NO 22
<211> LENGTH: 19
<212> TYPE: DNA
<213> ORGANISM: primer

<400> SEQUENCE: 22
caccttcaca cgcgtatcg                                                 19

<210> SEQ ID NO 23
<211> LENGTH: 22
<212> TYPE: DNA
<213> ORGANISM: primer

<400> SEQUENCE: 23
ccttcacacg cgtatcgatt ag                                             22

<210> SEQ ID NO 24
<211> LENGTH: 19
<212> TYPE: DNA
<213> ORGANISM: primer

<400> SEQUENCE: 24
acatggacag tcaccgcct                                                 19

<210> SEQ ID NO 25
<211> LENGTH: 19
<212> TYPE: DNA
<213> ORGANISM: primer

<400> SEQUENCE: 25
acagtcaccg ccttggtct                                                 19

<210> SEQ ID NO 26
<211> LENGTH: 20
<212> TYPE: DNA
<213> ORGANISM: primer

<400> SEQUENCE: 26
gctggtggag ggtttgcaga                                                20

<210> SEQ ID NO 27
<211> LENGTH: 20
<212> TYPE: DNA
<213> ORGANISM: primer

<400> SEQUENCE: 27
ctgtgtatat cctccaaact                                                20

<210> SEQ ID NO 28
<211> LENGTH: 23
<212> TYPE: DNA
<213> ORGANISM: primer

<400> SEQUENCE: 28
ggaatgtgga aaagttaca cac                                             23

<210> SEQ ID NO 29
<211> LENGTH: 20
<212> TYPE: DNA
<213> ORGANISM: primer

-continued

<400> SEQUENCE: 29
ctcttcctca cctcccttag                                               20

<210> SEQ ID NO 30
<211> LENGTH: 20
<212> TYPE: DNA
<213> ORGANISM: primer

<400> SEQUENCE: 30
gtgaggagat ctgctttcag                                               20

<210> SEQ ID NO 31
<211> LENGTH: 20
<212> TYPE: DNA
<213> ORGANISM: primer

<400> SEQUENCE: 31
caggttcaac actttccgtg                                               20

<210> SEQ ID NO 32
<211> LENGTH: 21
<212> TYPE: DNA
<213> ORGANISM: primer

<400> SEQUENCE: 32
ctcattaggt gactcaggct c                                             21

<210> SEQ ID NO 33
<211> LENGTH: 19
<212> TYPE: DNA
<213> ORGANISM: primer

<400> SEQUENCE: 33
gactcaggct ccgctccta                                                19

<210> SEQ ID NO 34
<211> LENGTH: 19
<212> TYPE: DNA
<213> ORGANISM: primer

<400> SEQUENCE: 34
aacatggaca gtcacccac                                                19

<210> SEQ ID NO 35
<211> LENGTH: 19
<212> TYPE: DNA
<213> ORGANISM: primer

<400> SEQUENCE: 35
ctctgacagg acttcccac                                                19

<210> SEQ ID NO 36
<211> LENGTH: 20
<212> TYPE: DNA
<213> ORGANISM: primer

<400> SEQUENCE: 36
tgaacatgga cagtcaccgc                                               20

<210> SEQ ID NO 37
<211> LENGTH: 19
<212> TYPE: DNA

```
<213> ORGANISM: primer

<400> SEQUENCE: 37
cctctgacag gacttccgc                                          19

<210> SEQ ID NO 38
<211> LENGTH: 21
<212> TYPE: DNA
<213> ORGANISM: primer

<400> SEQUENCE: 38
ccgtgacaac caagaacttc c                                       21

<210> SEQ ID NO 39
<211> LENGTH: 24
<212> TYPE: DNA
<213> ORGANISM: primer

<400> SEQUENCE: 39
gtttagtatg gcttatgccc agtg                                    24

<210> SEQ ID NO 40
<211> LENGTH: 20
<212> TYPE: DNA
<213> ORGANISM: primer

<400> SEQUENCE: 40
ctcccgtgac aaccaagaac                                         20

<210> SEQ ID NO 41
<211> LENGTH: 24
<212> TYPE: DNA
<213> ORGANISM: primer

<400> SEQUENCE: 41
gtgagcttaa aactggcaag agtg                                    24

<210> SEQ ID NO 42
<211> LENGTH: 39
<212> TYPE: DNA
<213> ORGANISM: primer

<400> SEQUENCE: 42
gttttcccag tcacgacgcc aagaacttcc tcctgactc                    39

<210> SEQ ID NO 43
<211> LENGTH: 41
<212> TYPE: DNA
<213> ORGANISM: primer

<400> SEQUENCE: 43
aggaaacagc tatgaccatc ttggtatagg agaaatgtcc c                 41

<210> SEQ ID NO 44
<211> LENGTH: 41
<212> TYPE: DNA
<213> ORGANISM: primer

<400> SEQUENCE: 44
gttttcccag tcacgacgct tcctcctgac tccatggtga c                 41

<210> SEQ ID NO 45
<211> LENGTH: 38
```

```
<212> TYPE: DNA
<213> ORGANISM: primer

<400> SEQUENCE: 45
aggaaacagc tatgaccatc tccttgcctg ccttctgc                               38

<210> SEQ ID NO 46
<211> LENGTH: 39
<212> TYPE: DNA
<213> ORGANISM: primer

<400> SEQUENCE: 46
gttttcccag tcacgacggg ggcatgctgc atattactg                              39

<210> SEQ ID NO 47
<211> LENGTH: 43
<212> TYPE: DNA
<213> ORGANISM: primer

<400> SEQUENCE: 47
aggaaacagc tatgaccatg tgagcttaaa actggcaaga gtg                         43

<210> SEQ ID NO 48
<211> LENGTH: 41
<212> TYPE: DNA
<213> ORGANISM: primer

<400> SEQUENCE: 48
gttttcccag tcacgacggc ccagattttt gcccattatt g                           41

<210> SEQ ID NO 49
<211> LENGTH: 43
<212> TYPE: DNA
<213> ORGANISM: primer

<400> SEQUENCE: 49
aggaaacagc tatgaccatg tgcatcctgc ttcacctgtt tag                         43

<210> SEQ ID NO 50
<211> LENGTH: 22
<212> TYPE: DNA
<213> ORGANISM: primer

<400> SEQUENCE: 50
cgttaaagtg tcaagtaggg ag                                                22

<210> SEQ ID NO 51
<211> LENGTH: 21
<212> TYPE: DNA
<213> ORGANISM: primer

<400> SEQUENCE: 51
ccgaagttca caaaactatt c                                                 21

<210> SEQ ID NO 52
<211> LENGTH: 22
<212> TYPE: DNA
<213> ORGANISM: primer

<400> SEQUENCE: 52
gttaaagtgt caagtaggga gc                                                22

<210> SEQ ID NO 53
```

```
<211> LENGTH: 20
<212> TYPE: DNA
<213> ORGANISM: primer

<400> SEQUENCE: 53
gactaaatgg aatgcctgtc                                              20

<210> SEQ ID NO 54
<211> LENGTH: 36
<212> TYPE: DNA
<213> ORGANISM: primer

<400> SEQUENCE: 54
gttttcccag tcacgacgcc gtagcatcac gttttg                            36

<210> SEQ ID NO 55
<211> LENGTH: 41
<212> TYPE: DNA
<213> ORGANISM: primer

<400> SEQUENCE: 55
aggaaacagc tatgaccatg atctctgggc ttagaacact c                      41

<210> SEQ ID NO 56
<211> LENGTH: 39
<212> TYPE: DNA
<213> ORGANISM: primer

<400> SEQUENCE: 56
gttttcccag tcacgacgct tcaacaggga caaaatacg                         39

<210> SEQ ID NO 57
<211> LENGTH: 41
<212> TYPE: DNA
<213> ORGANISM: primer

<400> SEQUENCE: 57
aggaaacagc tatgaccatg gaaaaagatc tctgggctta g                      41

<210> SEQ ID NO 58
<211> LENGTH: 38
<212> TYPE: DNA
<213> ORGANISM: primer

<400> SEQUENCE: 58
gttttcccag tcacgacgga attgttgagc caatcgtg                          38

<210> SEQ ID NO 59
<211> LENGTH: 41
<212> TYPE: DNA
<213> ORGANISM: primer

<400> SEQUENCE: 59
aggaaacagc tatgaccatg aagcactgcc tagaggaact g                      41

<210> SEQ ID NO 60
<211> LENGTH: 40
<212> TYPE: DNA
<213> ORGANISM: primer

<400> SEQUENCE: 60
gttttcccag tcacgacggg gaattgttga gccaatcgtg                        40
```

```
<210> SEQ ID NO 61
<211> LENGTH: 39
<212> TYPE: DNA
<213> ORGANISM: primer

<400> SEQUENCE: 61
aggaaacagc tatgaccatg agagcgggc cctacagag                    39

<210> SEQ ID NO 62
<211> LENGTH: 23
<212> TYPE: DNA
<213> ORGANISM: primer

<400> SEQUENCE: 62
gcattccatt tagtcttgcc atc                                    23

<210> SEQ ID NO 63
<211> LENGTH: 20
<212> TYPE: DNA
<213> ORGANISM: primer

<400> SEQUENCE: 63
gctgacaaga gggcttttcc                                        20

<210> SEQ ID NO 64
<211> LENGTH: 23
<212> TYPE: DNA
<213> ORGANISM: primer

<400> SEQUENCE: 64
gttgcaggaa gaggtaatgt cag                                    23

<210> SEQ ID NO 65
<211> LENGTH: 20
<212> TYPE: DNA
<213> ORGANISM: primer

<400> SEQUENCE: 65
catcccctca aggcgtagag                                        20

<210> SEQ ID NO 66
<211> LENGTH: 39
<212> TYPE: DNA
<213> ORGANISM: primer

<400> SEQUENCE: 66
gttttcccag tcacgacggc tacagtgacc cccttttc                    39

<210> SEQ ID NO 67
<211> LENGTH: 43
<212> TYPE: DNA
<213> ORGANISM: primer

<400> SEQUENCE: 67
aggaaacagc tatgaccatg tctaacaagg tgggagttac aag              43

<210> SEQ ID NO 68
<211> LENGTH: 38
<212> TYPE: DNA
<213> ORGANISM: primer

<400> SEQUENCE: 68
gttttcccag tcacgacgca gtgacccct ttttcctc                     38
```

<210> SEQ ID NO 69
<211> LENGTH: 43
<212> TYPE: DNA
<213> ORGANISM: primer

<400> SEQUENCE: 69
aggaaacagc tatgaccatg ggagttacaa gtgaagctct ttc           43

<210> SEQ ID NO 70
<211> LENGTH: 38
<212> TYPE: DNA
<213> ORGANISM: primer

<400> SEQUENCE: 70
gttttcccag tcacgacggg catcatgact gttctgtg                 38

<210> SEQ ID NO 71
<211> LENGTH: 41
<212> TYPE: DNA
<213> ORGANISM: primer

<400> SEQUENCE: 71
aggaaacagc tatgaccatg ggttttttctc cagtatgtgt c            41

<210> SEQ ID NO 72
<211> LENGTH: 38
<212> TYPE: DNA
<213> ORGANISM: primer

<400> SEQUENCE: 72
gttttcccag tcacgacgga ggcatcatga ctgttctg                 38

<210> SEQ ID NO 73
<211> LENGTH: 41
<212> TYPE: DNA
<213> ORGANISM: primer

<400> SEQUENCE: 73
gttttcccag tcacgacgac acaggctgag agaactccat c             41

<210> SEQ ID NO 74
<211> LENGTH: 39
<212> TYPE: DNA
<213> ORGANISM: primer

<400> SEQUENCE: 74
aggaaacagc tatgaccatg ctcttcccac attcgttgc                39

<210> SEQ ID NO 75
<211> LENGTH: 37
<212> TYPE: DNA
<213> ORGANISM: primer

<400> SEQUENCE: 75
aggaaacagc tatgaccata ctgcgctgtg ggtgaag                  37

<210> SEQ ID NO 76
<211> LENGTH: 38
<212> TYPE: DNA
<213> ORGANISM: primer

<400> SEQUENCE: 76
gttttcccag tcacgacgct ctacctctgc agcgagtg                 38

<210> SEQ ID NO 77
<211> LENGTH: 39
<212> TYPE: DNA
<213> ORGANISM: primer

<400> SEQUENCE: 77
aggaaacagc tatgaccatc cttaggtgag ggctgaaag        39

<210> SEQ ID NO 78
<211> LENGTH: 39
<212> TYPE: DNA
<213> ORGANISM: primer

<400> SEQUENCE: 78
aggaaacagc tatgaccatc tcttcctcac ctcccttag        39

<210> SEQ ID NO 79
<211> LENGTH: 37
<212> TYPE: DNA
<213> ORGANISM: primer

<400> SEQUENCE: 79
gttttcccag tcacgacggc tgctgaggaa ctctacc          37

<210> SEQ ID NO 80
<211> LENGTH: 21
<212> TYPE: DNA
<213> ORGANISM: primer

<400> SEQUENCE: 80
ctccgtcatg gttggtgttt c                           21

<210> SEQ ID NO 81
<211> LENGTH: 20
<212> TYPE: DNA
<213> ORGANISM: primer

<400> SEQUENCE: 81
ctcctttgtc cgcctctctg                             20

<210> SEQ ID NO 82
<211> LENGTH: 22
<212> TYPE: DNA
<213> ORGANISM: primer

<400> SEQUENCE: 82
cacatctccg tcatggttgg tg                          22

<210> SEQ ID NO 83
<211> LENGTH: 21
<212> TYPE: DNA
<213> ORGANISM: primer

<400> SEQUENCE: 83
gctcctttgt ccgcctctct g                           21

<210> SEQ ID NO 84
<211> LENGTH: 38
<212> TYPE: DNA
<213> ORGANISM: primer

<400> SEQUENCE: 84

```
gttttcccag tcacgacggg tggttgggga aaagagga                              38

<210> SEQ ID NO 85
<211> LENGTH: 39
<212> TYPE: DNA
<213> ORGANISM: primer

<400> SEQUENCE: 85
aggaaacagc tatgaccatc ggaagcgtcg gaagttctg                             39

<210> SEQ ID NO 86
<211> LENGTH: 40
<212> TYPE: DNA
<213> ORGANISM: primer

<400> SEQUENCE: 86
gttttcccag tcacgacggg ctatggtggt tggggaaaag                            40

<210> SEQ ID NO 87
<211> LENGTH: 40
<212> TYPE: DNA
<213> ORGANISM: primer

<400> SEQUENCE: 87
aggaaacagc tatgaccatg aagcgtcgga agttctggtg                            40

<210> SEQ ID NO 88
<211> LENGTH: 39
<212> TYPE: DNA
<213> ORGANISM: primer

<400> SEQUENCE: 88
gttttcccag tcacgacggt actgcaggga tcttaggaa                             39

<210> SEQ ID NO 89
<211> LENGTH: 41
<212> TYPE: DNA
<213> ORGANISM: primer

<400> SEQUENCE: 89
aggaaacagc tatgaccatc agcctgagtt caatcataat c                          41

<210> SEQ ID NO 90
<211> LENGTH: 40
<212> TYPE: DNA
<213> ORGANISM: primer

<400> SEQUENCE: 90
gttttcccag tcacgacgga gtactgcagg gatcttagga                            40

<210> SEQ ID NO 91
<211> LENGTH: 40
<212> TYPE: DNA
<213> ORGANISM: primer

<400> SEQUENCE: 91
aggaaacagc tatgaccatg acaacagcct gagttcaatc                            40

<210> SEQ ID NO 92
<211> LENGTH: 21
<212> TYPE: DNA
<213> ORGANISM: primer

<400> SEQUENCE: 92
```

```
cagggcccct tggaagaaaat c                                            21

<210> SEQ ID NO 93
<211> LENGTH: 20
<212> TYPE: DNA
<213> ORGANISM: primer

<400> SEQUENCE: 93
gaacccacgg ctcaacattc                                               20

<210> SEQ ID NO 94
<211> LENGTH: 21
<212> TYPE: DNA
<213> ORGANISM: primer

<400> SEQUENCE: 94
ctatggtggt tgggaaaag a                                              21

<210> SEQ ID NO 95
<211> LENGTH: 21
<212> TYPE: DNA
<213> ORGANISM: primer

<400> SEQUENCE: 95
cggctcaaca ttcaaagaag g                                             21

<210> SEQ ID NO 96
<211> LENGTH: 38
<212> TYPE: DNA
<213> ORGANISM: primer

<400> SEQUENCE: 96
gttttcccag tcacgacggg ggctaatgac agtgtgag                           38

<210> SEQ ID NO 97
<211> LENGTH: 40
<212> TYPE: DNA
<213> ORGANISM: primer

<400> SEQUENCE: 97
aggaaacagc tatgaccatg acggtaagaa attgttccag                         40

<210> SEQ ID NO 98
<211> LENGTH: 38
<212> TYPE: DNA
<213> ORGANISM: primer

<400> SEQUENCE: 98
gttttcccag tcacgacggg aagaaaatcc tcgctgtg                           38

<210> SEQ ID NO 99
<211> LENGTH: 40
<212> TYPE: DNA
<213> ORGANISM: primer

<400> SEQUENCE: 99
aggaaacagc tatgaccatc tccaggtagg acggtaagaa                         40

<210> SEQ ID NO 100
<211> LENGTH: 37
<212> TYPE: DNA
<213> ORGANISM: primer
```

```
<400> SEQUENCE: 100
gttttcccag tcacgacgct agagctgctt gtgctgg                             37

<210> SEQ ID NO 101
<211> LENGTH: 39
<212> TYPE: DNA
<213> ORGANISM: primer

<400> SEQUENCE: 101
aggaaacagc tatgaccatc atgggctca tggtatatg                            39

<210> SEQ ID NO 102
<211> LENGTH: 38
<212> TYPE: DNA
<213> ORGANISM: primer

<400> SEQUENCE: 102
gttttcccag tcacgacggt gctggaacaa tttcttac                            38

<210> SEQ ID NO 103
<211> LENGTH: 38
<212> TYPE: DNA
<213> ORGANISM: primer

<400> SEQUENCE: 103
aggaaacagc tatgaccatc atggtatatg agcaaccc                            38

<210> SEQ ID NO 104
<211> LENGTH: 21
<212> TYPE: DNA
<213> ORGANISM: primer

<400> SEQUENCE: 104
ggtgccatca ctcttctaag c                                              21

<210> SEQ ID NO 105
<211> LENGTH: 21
<212> TYPE: DNA
<213> ORGANISM: primer

<400> SEQUENCE: 105
catctcctgc ctggactact g                                              21

<210> SEQ ID NO 106
<211> LENGTH: 21
<212> TYPE: DNA
<213> ORGANISM: primer

<400> SEQUENCE: 106
gataatagct ggtgccatca c                                              21

<210> SEQ ID NO 107
<211> LENGTH: 21
<212> TYPE: DNA
<213> ORGANISM: primer

<400> SEQUENCE: 107
cccttctctt ccttcctaca g                                              21

<210> SEQ ID NO 108
<211> LENGTH: 39
<212> TYPE: DNA
<213> ORGANISM: primer
```

```
<400> SEQUENCE: 108
gttttcccag tcacgacgat acatttaatg ctcataggc                              39

<210> SEQ ID NO 109
<211> LENGTH: 40
<212> TYPE: DNA
<213> ORGANISM: primer

<400> SEQUENCE: 109
aggaaacagc tatgaccatg caaagtacaa cagaattacc                             40

<210> SEQ ID NO 110
<211> LENGTH: 38
<212> TYPE: DNA
<213> ORGANISM: primer

<400> SEQUENCE: 110
gttttcccag tcacgacggc catcactctt ctaagcaa                               38

<210> SEQ ID NO 111
<211> LENGTH: 40
<212> TYPE: DNA
<213> ORGANISM: primer

<400> SEQUENCE: 111
aggaaacagc tatgaccatg ctctaacttc ctaagatccc                             40

<210> SEQ ID NO 112
<211> LENGTH: 20
<212> TYPE: DNA
<213> ORGANISM: primer

<400> SEQUENCE: 112
gtgggaagag cttcagtcgc                                                   20

<210> SEQ ID NO 113
<211> LENGTH: 21
<212> TYPE: DNA
<213> ORGANISM: primer

<400> SEQUENCE: 113
cttgccactc ccacaatcag a                                                 21

<210> SEQ ID NO 114
<211> LENGTH: 20
<212> TYPE: DNA
<213> ORGANISM: primer

<400> SEQUENCE: 114
cgtcaggcat cagagaacac                                                   20

<210> SEQ ID NO 115
<211> LENGTH: 21
<212> TYPE: DNA
<213> ORGANISM: primer

<400> SEQUENCE: 115
ccactcccac aatcagagaa g                                                 21

<210> SEQ ID NO 116
<211> LENGTH: 39
<212> TYPE: DNA
```

<213> ORGANISM: primer

<400> SEQUENCE: 116
gttttcccag tcacgacgca cttaattagg catcagagg        39

<210> SEQ ID NO 117
<211> LENGTH: 39
<212> TYPE: DNA
<213> ORGANISM: primer

<400> SEQUENCE: 117
aggaaacagc tatgaccatg acgatatagg aaccacgac        39

<210> SEQ ID NO 118
<211> LENGTH: 38
<212> TYPE: DNA
<213> ORGANISM: primer

<400> SEQUENCE: 118
gttttcccag tcacgacggc atcagaggac ccactcag         38

<210> SEQ ID NO 119
<211> LENGTH: 40
<212> TYPE: DNA
<213> ORGANISM: primer

<400> SEQUENCE: 119
aggaaacagc tatgaccatg tagaggcagg tgcactccag       40

<210> SEQ ID NO 120
<211> LENGTH: 39
<212> TYPE: DNA
<213> ORGANISM: primer

<400> SEQUENCE: 120
gttttcccag tcacgacgca acctgaattg aggcttctc        39

<210> SEQ ID NO 121
<211> LENGTH: 38
<212> TYPE: DNA
<213> ORGANISM: primer

<400> SEQUENCE: 121
aggaaacagc tatgaccatg acagcgaggg atctatgc         38

<210> SEQ ID NO 122
<211> LENGTH: 39
<212> TYPE: DNA
<213> ORGANISM: primer

<400> SEQUENCE: 122
gttttcccag tcacgacgga attgaggctt ctccttcac        39

<210> SEQ ID NO 123
<211> LENGTH: 36
<212> TYPE: DNA
<213> ORGANISM: primer

<400> SEQUENCE: 123
gttttcccag tcacgacggc tttgcacaca ttcaca           36

<210> SEQ ID NO 124
<211> LENGTH: 40

```
<212> TYPE: DNA
<213> ORGANISM: primer

<400> SEQUENCE: 124
aggaaacagc tatgaccatc aaacactacc atctcacttg                            40

<210> SEQ ID NO 125
<211> LENGTH: 39
<212> TYPE: DNA
<213> ORGANISM: primer

<400> SEQUENCE: 125
gttttcccag tcacgacggt ttgcgtcctg atggctttg                             39

<210> SEQ ID NO 126
<211> LENGTH: 38
<212> TYPE: DNA
<213> ORGANISM: primer

<400> SEQUENCE: 126
aggaaacagc tatgaccatg gtgtgaaggg gttggtgg                              38

<210> SEQ ID NO 127
<211> LENGTH: 38
<212> TYPE: DNA
<213> ORGANISM: primer

<400> SEQUENCE: 127
gttttcccag tcacgacgga agcctctttc catacgag                              38

<210> SEQ ID NO 128
<211> LENGTH: 40
<212> TYPE: DNA
<213> ORGANISM: primer

<400> SEQUENCE: 128
aggaaacagc tatgaccata gtttccaaat ccccttactc                            40

<210> SEQ ID NO 129
<211> LENGTH: 38
<212> TYPE: DNA
<213> ORGANISM: primer

<400> SEQUENCE: 129
gttttcccag tcacgacgca gaagcctctt tccatacg                              38

<210> SEQ ID NO 130
<211> LENGTH: 40
<212> TYPE: DNA
<213> ORGANISM: primer

<400> SEQUENCE: 130
aggaaacagc tatgaccatg tttccaaatc cccttactca                            40

<210> SEQ ID NO 131
<211> LENGTH: 38
<212> TYPE: DNA
<213> ORGANISM: primer

<400> SEQUENCE: 131
gttttcccag tcacgacgca ttccctcata tgcacaag                              38

<210> SEQ ID NO 132
```

```
<211> LENGTH: 40
<212> TYPE: DNA
<213> ORGANISM: primer

<400> SEQUENCE: 132
aggaaacagc tatgaccatg aacctttaac tggcaacaga                     40

<210> SEQ ID NO 133
<211> LENGTH: 39
<212> TYPE: DNA
<213> ORGANISM: primer

<400> SEQUENCE: 133
gttttcccag tcacgacgca cagggtcgt atgagtaag                       39

<210> SEQ ID NO 134
<211> LENGTH: 38
<212> TYPE: DNA
<213> ORGANISM: primer

<400> SEQUENCE: 134
aggaaacagc tatgaccatg gccatcatga gatgctac                       38

<210> SEQ ID NO 135
<211> LENGTH: 21
<212> TYPE: DNA
<213> ORGANISM: primer

<400> SEQUENCE: 135
ccgtcctacc tggagaacta c                                         21

<210> SEQ ID NO 136
<211> LENGTH: 21
<212> TYPE: DNA
<213> ORGANISM: primer

<400> SEQUENCE: 136
cctggtgtgg acgctgctct g                                         21

<210> SEQ ID NO 137
<211> LENGTH: 21
<212> TYPE: DNA
<213> ORGANISM: primer

<400> SEQUENCE: 137
ccgctctcct gcagggtctg g                                         21

<210> SEQ ID NO 138
<211> LENGTH: 40
<212> TYPE: DNA
<213> ORGANISM: primer

<400> SEQUENCE: 138
gttttcccag tcacgacgcg aggaggcagt gacgctggtg                     40

<210> SEQ ID NO 139
<211> LENGTH: 41
<212> TYPE: DNA
<213> ORGANISM: primer

<400> SEQUENCE: 139
aggaaacagc tatgaccatc ccacggctca acattcaaag a                   41
```

<210> SEQ ID NO 140
<211> LENGTH: 41
<212> TYPE: DNA
<213> ORGANISM: primer

<400> SEQUENCE: 140
aggaaacagc tatgaccatc acggctcaac attcaaagaa g					41

<210> SEQ ID NO 141
<211> LENGTH: 39
<212> TYPE: DNA
<213> ORGANISM: primer

<400> SEQUENCE: 141
gttttcccag tcacgacgag ggggtctcag ccaccaaag					39

<210> SEQ ID NO 142
<211> LENGTH: 40
<212> TYPE: DNA
<213> ORGANISM: primer

<400> SEQUENCE: 142
aggaaacagc tatgaccata aggaggagct gaaggttatc					40

<210> SEQ ID NO 143
<211> LENGTH: 39
<212> TYPE: DNA
<213> ORGANISM: primer

<400> SEQUENCE: 143
gttttcccag tcacgacgaa gggtcatggc tttggtttt					39

<210> SEQ ID NO 144
<211> LENGTH: 40
<212> TYPE: DNA
<213> ORGANISM: primer

<400> SEQUENCE: 144
aggaaacagc tatgaccatg ggatgcgcag gcctgcactg					40

<210> SEQ ID NO 145
<211> LENGTH: 39
<212> TYPE: DNA
<213> ORGANISM: primer

<400> SEQUENCE: 145
gttttcccag tcacgacgca ggctgggggt ggtgagaga					39

<210> SEQ ID NO 146
<211> LENGTH: 40
<212> TYPE: DNA
<213> ORGANISM: primer

<400> SEQUENCE: 146
aggaaacagc tatgaccatc cgctcctaaa tgcaccgtct					40

<210> SEQ ID NO 147
<211> LENGTH: 39
<212> TYPE: DNA
<213> ORGANISM: primer

<400> SEQUENCE: 147
gttttcccag tcacgacggg gaaggaacct tgggtgaca					39

<210> SEQ ID NO 148
<211> LENGTH: 40
<212> TYPE: DNA
<213> ORGANISM: primer

<400> SEQUENCE: 148
aggaaacagc tatgaccatg cagctcatta ggtgactcag          40

<210> SEQ ID NO 149
<211> LENGTH: 21
<212> TYPE: DNA
<213> ORGANISM: primer

<400> SEQUENCE: 149
ctatgaatac cttctagtgg g          21

<210> SEQ ID NO 150
<211> LENGTH: 21
<212> TYPE: DNA
<213> ORGANISM: primer

<400> SEQUENCE: 150
caaaatcctg ggaatgacac g          21

<210> SEQ ID NO 151
<211> LENGTH: 21
<212> TYPE: DNA
<213> ORGANISM: primer

<400> SEQUENCE: 151
gtgcctgtta cgtgccagtg c          21

<210> SEQ ID NO 152
<211> LENGTH: 21
<212> TYPE: DNA
<213> ORGANISM: primer

<400> SEQUENCE: 152
caccagctat tatctttcta a          21

<210> SEQ ID NO 153
<211> LENGTH: 39
<212> TYPE: DNA
<213> ORGANISM: primer

<400> SEQUENCE: 153
gttttcccag tcacgacgga tagtaaaagc ataatggag          39

<210> SEQ ID NO 154
<211> LENGTH: 40
<212> TYPE: DNA
<213> ORGANISM: primer

<400> SEQUENCE: 154
aggaaacagc tatgaccata gcttcatgtc ttctgagatg          40

<210> SEQ ID NO 155
<211> LENGTH: 39
<212> TYPE: DNA
<213> ORGANISM: primer

<400> SEQUENCE: 155
gttttcccag tcacgacgga tatggtgaat aatcaagag          39

<210> SEQ ID NO 156
<211> LENGTH: 40
<212> TYPE: DNA
<213> ORGANISM: primer

<400> SEQUENCE: 156
aggaaacagc tatgaccatc tcaagcttca tgtcttctga                40

<210> SEQ ID NO 157
<211> LENGTH: 39
<212> TYPE: DNA
<213> ORGANISM: primer

<400> SEQUENCE: 157
gttttcccag tcacgacgga aatgggatca agaaaaca                  39

<210> SEQ ID NO 158
<211> LENGTH: 40
<212> TYPE: DNA
<213> ORGANISM: primer

<400> SEQUENCE: 158
aggaaacagc tatgaccatc ttggcaaacg tgctcatgtc                40

<210> SEQ ID NO 159
<211> LENGTH: 39
<212> TYPE: DNA
<213> ORGANISM: primer

<400> SEQUENCE: 159
gttttcccag tcacgacggt agggaaatg ggatcaaag                  39

<210> SEQ ID NO 160
<211> LENGTH: 40
<212> TYPE: DNA
<213> ORGANISM: primer

<400> SEQUENCE: 160
aggaaacagc tatgaccatc gagctctctt ggcaaacgtg                40

<210> SEQ ID NO 161
<211> LENGTH: 39
<212> TYPE: DNA
<213> ORGANISM: primer

<400> SEQUENCE: 161
gttttcccag tcacgacggt gatggaagga tcttagata                 39

<210> SEQ ID NO 162
<211> LENGTH: 40
<212> TYPE: DNA
<213> ORGANISM: primer

<400> SEQUENCE: 162
aggaaacagc tatgaccatc tttacaatca gcccccaatc                40

<210> SEQ ID NO 163
<211> LENGTH: 39
<212> TYPE: DNA
<213> ORGANISM: primer

<400> SEQUENCE: 163
gttttcccag tcacgacgga tggaaggatc ttagatagg                          39

<210> SEQ ID NO 164
<211> LENGTH: 40
<212> TYPE: DNA
<213> ORGANISM: primer

<400> SEQUENCE: 164
aggaaacagc tatgaccatg cccccaatct atttttcaag                         40

<210> SEQ ID NO 165
<211> LENGTH: 22
<212> TYPE: DNA
<213> ORGANISM: primer

<400> SEQUENCE: 165
ctgccttgga atctgtactg ac                                            22

<210> SEQ ID NO 166
<211> LENGTH: 22
<212> TYPE: DNA
<213> ORGANISM: primer

<400> SEQUENCE: 166
agccccagca cagacctatt ac                                            22

<210> SEQ ID NO 167
<211> LENGTH: 22
<212> TYPE: DNA
<213> ORGANISM: primer

<400> SEQUENCE: 167
gcgctttgat aaccctgtct gc                                            22

<210> SEQ ID NO 168
<211> LENGTH: 22
<212> TYPE: DNA
<213> ORGANISM: primer

<400> SEQUENCE: 168
caggtgctta tagtaagttt ga                                            22

<210> SEQ ID NO 169
<211> LENGTH: 40
<212> TYPE: DNA
<213> ORGANISM: primer

<400> SEQUENCE: 169
gttttcccag tcacgacggc agcgctagat cccaggctct                         40

<210> SEQ ID NO 170
<211> LENGTH: 41
<212> TYPE: DNA
<213> ORGANISM: primer

<400> SEQUENCE: 170
aggaaacagc tatgaccatc ccaccctctt atgctagata g                       41

<210> SEQ ID NO 171
<211> LENGTH: 40
<212> TYPE: DNA
<213> ORGANISM: primer

<400> SEQUENCE: 171

```
gttttcccag tcacgacggc gctagatccc aggctctcac              40

<210> SEQ ID NO 172
<211> LENGTH: 41
<212> TYPE: DNA
<213> ORGANISM: primer

<400> SEQUENCE: 172
aggaaacagc tatgaccata accctgccca ccctcttatg c           41

<210> SEQ ID NO 173
<211> LENGTH: 40
<212> TYPE: DNA
<213> ORGANISM: primer

<400> SEQUENCE: 173
gttttcccag tcacgacgaa acgcctggga ttcataatct              40

<210> SEQ ID NO 174
<211> LENGTH: 41
<212> TYPE: DNA
<213> ORGANISM: primer

<400> SEQUENCE: 174
aggaaacagc tatgaccata agggtctag aactgtttca c            41

<210> SEQ ID NO 175
<211> LENGTH: 40
<212> TYPE: DNA
<213> ORGANISM: primer

<400> SEQUENCE: 175
gttttcccag tcacgacgcc tgggattcat aatctttcac              40

<210> SEQ ID NO 176
<211> LENGTH: 22
<212> TYPE: DNA
<213> ORGANISM: primer

<400> SEQUENCE: 176
gtgctggaac aatttcttac cg                                 22

<210> SEQ ID NO 177
<211> LENGTH: 22
<212> TYPE: DNA
<213> ORGANISM: primer

<400> SEQUENCE: 177
cccaaggctc ttcctctcta ac                                 22

<210> SEQ ID NO 178
<211> LENGTH: 22
<212> TYPE: DNA
<213> ORGANISM: primer

<400> SEQUENCE: 178
cagatcctag agctgcttgt gc                                 22

<210> SEQ ID NO 179
<211> LENGTH: 21
<212> TYPE: DNA
<213> ORGANISM: primer
```

<400> SEQUENCE: 179
ggctcttgag tctcctgagg c                                                        21

<210> SEQ ID NO 180
<211> LENGTH: 40
<212> TYPE: DNA
<213> ORGANISM: primer

<400> SEQUENCE: 180
gttttcccag tcacgacgcc atgttcacgg ccaggaagtc                                    40

<210> SEQ ID NO 181
<211> LENGTH: 46
<212> TYPE: DNA
<213> ORGANISM: primer

<400> SEQUENCE: 181
aggaaacagc tatgaccatg gccatcctgg tgtggacgct gctctc                             46

<210> SEQ ID NO 182
<211> LENGTH: 46
<212> TYPE: DNA
<213> ORGANISM: primer

<400> SEQUENCE: 182
aggaaacagc tatgaccatg gccatctcgc tctcctgcag ggtctc                             46

<210> SEQ ID NO 183
<211> LENGTH: 39
<212> TYPE: DNA
<213> ORGANISM: primer

<400> SEQUENCE: 183
gttttcccag tcacgacggt tgctcttctt actgctctg                                     39

<210> SEQ ID NO 184
<211> LENGTH: 46
<212> TYPE: DNA
<213> ORGANISM: primer

<400> SEQUENCE: 184
aggaaacagc tatgaccatg gccatcttct tccaagacat attctc                             46

<210> SEQ ID NO 185
<211> LENGTH: 38
<212> TYPE: DNA
<213> ORGANISM: primer

<400> SEQUENCE: 185
gttttcccag tcacgacgct cagagatggt tgctcttc                                      38

<210> SEQ ID NO 186
<211> LENGTH: 22
<212> TYPE: DNA
<213> ORGANISM: primer

<400> SEQUENCE: 186
gaaaccattc acgtgcccta cc                                                       22

<210> SEQ ID NO 187
<211> LENGTH: 22
<212> TYPE: DNA
<213> ORGANISM: primer

```
<400> SEQUENCE: 187
gacagtttcc aaatcccctt ac                                          22

<210> SEQ ID NO 188
<211> LENGTH: 22
<212> TYPE: DNA
<213> ORGANISM: primer

<400> SEQUENCE: 188
ctcgtcaggc atcagagaac ac                                          22

<210> SEQ ID NO 189
<211> LENGTH: 22
<212> TYPE: DNA
<213> ORGANISM: primer

<400> SEQUENCE: 189
gtgcatatga gggaatgtga ac                                          22

<210> SEQ ID NO 190
<211> LENGTH: 21
<212> TYPE: DNA
<213> ORGANISM: primer

<400> SEQUENCE: 190
ttgtgaacct tcgggaaact a                                           21

<210> SEQ ID NO 191
<211> LENGTH: 21
<212> TYPE: DNA
<213> ORGANISM: primer

<400> SEQUENCE: 191
accggaagaa tttggaagag a                                           21

<210> SEQ ID NO 192
<211> LENGTH: 27
<212> TYPE: DNA
<213> ORGANISM: primer

<400> SEQUENCE: 192
cgatggatcc ttgttaggga ggcatca                                     27

<210> SEQ ID NO 193
<211> LENGTH: 25
<212> TYPE: DNA
<213> ORGANISM: primer

<400> SEQUENCE: 193
gcaggatccc catcagtgga gaaac                                       25

<210> SEQ ID NO 194
<211> LENGTH: 21
<212> TYPE: DNA
<213> ORGANISM: primer

<400> SEQUENCE: 194
cccttaggtg agggctgaaa g                                           21

<210> SEQ ID NO 195
<211> LENGTH: 20
<212> TYPE: DNA
```

```
<213> ORGANISM: primer

<400> SEQUENCE: 195
ccttaggtga gggctgaaag                                              20

<210> SEQ ID NO 196
<211> LENGTH: 19
<212> TYPE: DNA
<213> ORGANISM: primer

<400> SEQUENCE: 196
aggggaggtc tcttccaaa                                               19

<210> SEQ ID NO 197
<211> LENGTH: 30
<212> TYPE: DNA
<213> ORGANISM: primer

<400> SEQUENCE: 197
caatgaattc gctaggaggt cttttctgag                                   30

<210> SEQ ID NO 198
<211> LENGTH: 31
<212> TYPE: DNA
<213> ORGANISM: primer

<400> SEQUENCE: 198
caatgaattc ggtttagggg atatttgtaa g                                 31

<210> SEQ ID NO 199
<211> LENGTH: 42
<212> TYPE: PRT
<213> ORGANISM: human

<400> SEQUENCE: 199

Glu Ser Val Thr Phe Lys Asp Val Ala Val Asp Phe Ser Glu Glu
 1               5                  10                  15

Trp Gln Leu Leu Asp Pro Ala Gln Arg Lys Leu Tyr Arg Asp Val Met
                20                  25                  30

Leu Glu Asn Phe Arg Asn Leu Val Ser Leu
        35                  40

<210> SEQ ID NO 200
<211> LENGTH: 42
<212> TYPE: PRT
<213> ORGANISM: human

<400> SEQUENCE: 200

Gly Leu Val Thr Phe Lys Asp Val Ala Val Asp Phe Ser Gln Asp Glu
 1               5                  10                  15

Trp Gln Leu Leu Asp Pro Ala Gln Lys Asp Leu Tyr Arg Glu Tyr Met
                20                  25                  30

Leu Glu Asn Phe Arg Asn Leu Val Ser Leu
        35                  40

<210> SEQ ID NO 201
<211> LENGTH: 42
<212> TYPE: PRT
<213> ORGANISM: human

<400> SEQUENCE: 201

Gly Leu Val Thr Phe Lys Asp Val Ala Val Cys Phe Ser Gln Asp Gln
```

```
                 1               5                  10                 15
             Trp Ser Asp Leu Asp Pro Thr Gln Lys Glu Phe Tyr Gly Glu Tyr Val
                            20                  25                  30
             Leu Glu Glu Asp Cys Gly Ile Val Val Ser
                            35                  40

<210> SEQ ID NO 202
<211> LENGTH: 42
<212> TYPE: PRT
<213> ORGANISM: human

<400> SEQUENCE: 202

Gly Leu Val Thr Phe Lys Asp Val Ala Val Cys Phe Ser Gln Asp Gln
              1               5                  10                  15

Trp Ser Asp Leu Asp Pro Thr Gln Glu Glu Phe Tyr Gly Glu Tyr Val
                            20                  25                  30

Leu Glu Glu Asp Cys Gly Ile Val Val Ser
                            35                  40

<210> SEQ ID NO 203
<211> LENGTH: 23
<212> TYPE: DNA
<213> ORGANISM: DNA fragment

<400> SEQUENCE: 203
ttggtggggt ggggtgggg gtg                                               23

<210> SEQ ID NO 204
<211> LENGTH: 20
<212> TYPE: DNA
<213> ORGANISM: DNA fragment

<400> SEQUENCE: 204 gggtggggc gggtgggggg                                                   20

<210> SEQ ID NO 205
<211> LENGTH: 24
<212> TYPE: DNA
<213> ORGANISM: DNA fragment

<400> SEQUENCE: 205
gggggtgggg atggggtgcg gggt                                             24

<210> SEQ ID NO 206
<211> LENGTH: 20137
<212> TYPE: DNA
<213> ORGANISM: human

<400> SEQUENCE: 206
cctcctctca gattgcttaa gatcatctcc gcgggctcct tgccccggct agccccatct      60
ccttacacca ccaagccccc ctcaccccag cacacaccca gatacactca cccgtgatct     120
tgtcacctgt gatgatagta tgtccttggc gtccatttgg ccagagcttt tcagctgtca     180
ctgtgacaga ccctgaggtt cccctcaagc cagtagctgc tgtctccact gcaactttc     240 ctctcctccc actcctaaca gccagttttg gcacctcttc tcagcacctg cgttactttt    300
agcaggagta tacctacttc ttgagtgtct tgattaaaaa tttgttttttg tgccatggat    360 aggctgtgtt cctttcagaaa ggtgtcagtc taatttttgt ttttctgaac aatgaatgtt    420
ctcatcttct aggcgctttg ataaccctgt ctgccttgga atctgtactg acctccccag    480
```

```
agggagactc ttagacccag cctttcttga caaaccttgg tcctggggag cacgctagat      540
cccaggctct cacttagagg ctgggcttag aactgttgct ttttctctat ccacgctctg      600
caggtgacac ccagggcagc tacactcaga agccacaagg aatgctagtg gagcccctca      660
tccctcccag cttctcttcc aagctgcccc gtggggcttg atccaggaag ctacttcaga      720
aaggttgtgg gatagccttg ggaggaggtt tgttggtggg aagcgtgtga accggaacag      780
tcttggataa ctttctgctg ttactatcta gcataagagg gtgggcaggg ttggagagag      840
gacaggaatt tttcctccta ggaccaaacg cctgggattc ataatctttc accctttctc      900
ctccagctat acccttttgt actctgtgt atatactata ttgcagtaga caatcattcc       960
aagggtacaa caaggtttac cacaatgtga gggactcagc cattgcaaat tgtacagatg     1020
aggtaagtta caggtttaca ttttttttc ccagtaaatt tggcacagat ttaaaatgtg      1080
aaacagttct agacccttg ttttgctgt tctctcacca gcaaacccct tagtttggcc       1140
agcaatggct ttctgcatga acttcagatt tacttcattt gctaggtggt ggttctcaaa     1200
cttactataa gcacctgaag ggctagttaa acgcatattg ctgggcccca ccctagagt      1260 ttctggtaat aggtctgtgc tggggcttga aatttatgc ttctaacaag gctcaggtac      1320
tgatgctgca gatctgggtt cttcactttg agaacaacta ccttttggcc aaatgtgata     1380
tacgtattgc agtaggttga ggttcagaat acctttgttt gagtacttct gtgttggaaa     1440
ctagtaatct gatcttttat agataatcac ttaggtctga atattctgtt cgcaaaatta     1500
agaaagcgta cttaaaacaa ctgaatgcta tatgccaaat ttgaggtgaa atattgatga     1560
gttcttcccc ttgattttct taattctctt gatagggct tcacgttttg atcaaaaata     1620 ttacctgt attctgggct tttgctgtga attcctagta ttgctaaaat ctgcaatttt      1680
cttaactacc tgttaagttc ctcaaggtca gagcttctgc tttttttatc tttctttgcc     1740
cagcaccttg aatagtgtgg gacacgtaat tgacgctcag tagatatttg tgtattgaac     1800
tccatccctt gtcctcctcc cctcttgatg tttttctcta ctggccttat gctacacagt     1860
aaagcagggc atgattatgc cacttgatta cccccaagag attggaataa atgctaatgc     1920
caaattccta cagctatccc tgtgaatggt ttattaccca ggagccctga cactggctga     1980
tttctgaatt tcagtgctt ctgtaatata tactagttgg gggaggagaa atagaaagct      2040
taaactcaat gtgcgtttat tgaataccttt ttctactaag ggcttgacaa agtggtaggc    2100
actgggaata taaaaatgaa taaggagacc cttgctctcg aggcagggcc cacagtgggg    2160
agacagacgt taagccatgc ccacgacaag aatgacttct gagattcctt ctttggatca    2220
tgatttagtc ttcagtggaa acctggtact cctcagattc ctctggttca acaggcgggg    2280
atcccatccc ttatcatctc ctcaaatgct aaaggaccct tgagcaaagc caggaggaag    2340
tcatctagac gtgaaacagg gagtatccac acaggctgtg ttaatgacaa agctaaaaac    2400
atagtaaatg acttttgaat ttactgctgt tatgaattat ctatagcaac acctcaggtc    2460
agctctgtta tatatgttat tgtgttattt cccattaaat gatggttcct ctgactatct    2520
gattggcatt gactatgttt gttgtaggga ttgcatacat ctagtttaac tctggctgtc    2580
aaatgagaga gcagttactc ttatcaggat gggtgtcagg tttgatgtcc cctccttttc    2640
ctgcttcagg ttaatttgtc atgttctgtt ttaaactgag gcatatagct tgacctcctt    2700
tatttaggcc attaactgct ctggggtagt tttcctgaag gttaaaaagc ctagcttcat    2760
gatggaggtt aatcaacatg accatgatgg ccaggtgtat aaatctggcc tcttaaaaat    2820
ctgtatttga ggctgggtgc agtggctcac acctgtaatc ctaacacttt gggaggccaa    2880
```

```
agctggcaga tcacttgagc ccaggtattt gagaccagcc tgggcaacat ggcaagaccc    2940
cttctctatw aaaaatttaa acattagctg gcatggtgg catgtgctgt agtcccagat    3000
acttaggagg ctggggtggg aggatggcct gaacctggga ggcagagatt gcagtgagtt    3060
gtgatcttgc cactgcactc cagtcttagc aacagagtaa accctatctc aaaacttaaa    3120
aatctgtgtt tggcccctag ccgtcctcag ctcttgagta aatctcagca tcctaggctg    3180
ttacattatg gcccaaatat tcaatagaga tgctgtatat ccttgttcct ctcaaaaccc    3240
ctcctcatca ccatcaaaaa gctggtttag ttctctacct ttagataaag aatcatccca    3300
agactcaaca tgagctgccg tgacttgtcc aagatgacac ctctttacaa tgtagagcag    3360
tggacagaac acaggtcacc ctccgccgaa agcaactatc tactgtctaa cattgcctcc    3420
taggcctgcc atatataacc atcaaaaaca ttttagttta gaataaagtg aattgttaca    3480
atttttattt ttcattttg tgtttacatt tactctcaat gacatgttta ttcccaccta    3540
atatcttgag gctaaccaca aaatctgcag catttccagg cagaagatac ttgtgacttc    3600
cctgtactat ccactacata cttgacctct ttctcttttct tcctgtcttc cctttctcta    3660
taccttatta tctttctttg gaacctcttg taacaaattt tgagccattt ctcccctcac    3720
tactcaaata tcacttttat gaaggggcgg gggggaaact taggtggcaa aaatatttta    3780
cagaaacagt tttaaacatg ttttgaagca tactggtcac gtgttagaag gccaaaagcc    3840
agggaattca ttcccttca ttcattgtgc tgtctaggtt aagttttcac aggacttctt    3900
ggtacactga gtttgcctca gattgtctcc tgccagttac agggagtgga gaggactttg    3960
atatattggt aattagaagc attscygata tggtcttcgg tgggagaacc tgtgtctaag    4020
gttccttctc atctgtattc caacactttc atttaatcct acttcataag tgcctccaaa    4080
gcaaggattt ttttttggt ttagcatggt ttctttgata taacaataga ccgaccaaga    4140
ttttccttat gccatctgtt ttttgtaat tatgatgcaa tagagaactg tttgcttgtt    4200
tatcatttaa atcttgcctt cttcccaaaa cgatttcaaa tagcttgaag gaaaatgaat    4260
aaaatatatt gagcacctac cctatgccag actctatact gaagggtttc tataggttat    4320
ttcatttact ccttaaaaca accacatgag ataagtagta ttagccacat ttttgaggat    4380
aagactgagg cttagggaaa ttgtgttaca aggctaataa gcgaggtcag ggattcgagg    4440
tcagggattc aaacccagcg tgccaaggcc actaaccatt atgtggaaag cttaggtaag    4500
cgcttgtata taggacaatc aagaataaaa gaatatgtcc attagaagga ttgtactggg    4560
ctaatctttc gttttaaaga acagcagcag cattggaaaa gagcggttaa cagttttat    4620 tagccaattt ctattctaga acactgagag gagctgttga caggccctgg ttagccccag    4680
caagtagttg tattaaaatt accaaactat aggcctgcat taaggtataa aataagaatg    4740
gggactggaa gggatataaa tatctgctaa atataataat ttcagttcta atcactattt    4800
tcttctgaag attatttgcc agtacatagg cagatcactg tctctccttt aggttgatgg    4860
tatatgacta cagactttgt catttagggt ccagaaagat caccctagct agtagcgttt    4920
taaggtagag aactagatat tgtttcattg cctgtggttt tctgttcttg taagagaatt    4980
gagcttgggt cttcactgcc acgtgacacc ttcagataag gggcagagac agctggcctg    5040
aggattgtac agaggtctta ccttgatagc tcctctccaa tcctatgcat cctaggaaca    5100
ctcaagacac taggttgtat ctttgcagat actgttttag tgtcttctgg aaccaagtct    5160
cttacttaat cctggcctgg tttcatattc tctctattgt attctctcta tagttttgt    5220
```

```
cttactctgg aactcttcca aggacagaca ttgaagaaag gtattagaat agcaaaggca      5280
acaaattgca aggtatactt atggcatagc acatcccatt aattatagaa taaaaacaca      5340
acatctgttt tctgcctcta atattaaatc ttgacatttg cacaacacat tttagttcat      5400
aaagctctca tatctcagat aatcactgag ttaggagact ggttatctgc agagggcttt      5460
atcctttaca agggctcttg ggtacgttac ttcacgaaac cctcagggaa gctccagttt      5520
cttggggatc tggggccggg gcatatgtct ttggataccc agtttggtgc tgtgcacagc      5580
actgctgtac ctcctattca tttcccatct cttaccccac aaagactcct tccttcattc      5640
cttctattgc tgatctgttt tccttcatct tcctaggctg ccaaagtaaa tgcaaaacaa      5700
gcaccagaaa tctcagcttg tgatttctga agggcatttt taaatggcaa gtttggtgtg      5760
gcactgttac atgttctttt ttctttggag agcaaagccc tttgagagag caggaactct      5820
tctgtcaatg catacgttgt aggatccata ctgtggaatc tcttgtacct agtgctgcgt      5880
gaaaacaatg aggattccaa gtctacttca ctggacatcg gttctcaaac ttttaagata      5940
ctagaagtcc ttttattaag ccaaaagacc ctatgtatta attctgtctt ccaggggtag      6000
gagttggggt ggggtttgga aagctttgtc tggataaata attagtattg tagttccatt      6060
tatttgatgt ctgattttgc gcttattaaa attgatttaa atcctcaatg gaaaatgatt      6120
tttttttttc aaatgccaag tgttgtgtga cttgcatttg gattattccc ggtgcaacct      6180
gaagattcct tgtgatgagt tgtggttcca tcatcttggg aaccactaag agaattctgt      6240
tttactcaca atccaaacaa taaatgtttt tttccctatg tatgccttta tccagcacac      6300
agtttgctag acttatggat gaatatgggt taatataaca tggtatctat ccttctggaa      6360
acagactttt aaaaccttac taagcattct ctgcattcat caaatgtgaa gtgagtgcct      6420
ggtgtgtgcc aggcatcgag ctgggcacag catatccctg ccctcagagc tttacagtcc      6480
agtgagttca acagaagatg aacagttttg atgacacaaa aaatagacac atgtgcatgc      6540
tgtgataggg ggagatacaa gttcctgtgg aagcatcatc tgggaggacc agggaaggca      6600
tcttggaaaa actgagctct gaaagatgga tagagttaac cacatgaaga gtggagaagg      6660
gtacttcaga caaggtgaac agcatcagga aagcccaggg agggtataga aagaaagaa      6720 cagtaattct tgcagtggct ttcaatggga gtggcagtca tggaaggaag agaggtagc      6780 agggaccagc ttttgaaggg ctttgtgtat cacattttaa gaagtttaaa ttttaaccta      6840
aggtcactgg gaagccattg gcagattttg tatgttagga agttcaccac tcacctactt      6900
ggagtattgc aggtggagct aatgtggatg ggcctcctgc ccattattaa atcctgttcc      6960
tgtcaggaac aggacagccc atgctgtctc tccctgtgtg tctgtctctc cctgtgtgtc      7020
tgtctctctc tctctctctg tctctctctc tcaaaagcta aggaaagcg cataggttcc      7080 agaaggaaaa agaaataacc actagaaaaa taagtataag ctgactttac catggcgcag      7140
tgagattcca aaccaaaata aggtttctag ggattgagct tttaatactg gtactccaac      7200
agggagatag gacttgggaa actgacgctg tgtgaaagtt acagaattaa gcagcctgca      7260
aacctggacc tttgaaaatc gtcctactga cccaggaaaa gtgcaaggaa gtgggttctc      7320
cagaaccttg ggtaggccaa acattacttg aaggcatcga tctaaataat acacaaaagc      7380
attattcagg aacaccctga gaaattaaca taaaaactga tttggccagg catggtggct      7440
cagcctctgg taacagtgct ttgggaggcc aaggttggaa aatcacttga ggccaggaga      7500
tccaggctgt agtgagctat gattgtacta ctgcactcca gcctgggcaa cagagggaga      7560
gtcttaaaaa agcaaactgt ccaagatcat tgaaaccatt agcacttagg aagaaacaaa      7620
```

-continued

```
tgaaattaca ttcaaggggg tcacatttaa atccagggct ctcaggactc ccaaagtaaa      7680
aagatggaca taaaataaaa aaattacaag ccacttgaga aaaaaataaa tcaccatgag      7740
gtagagatag cagaggaaaa attacacatg aagatctagg aattagggag ctatccaaga      7800
tagactgtga agtatgttg caagtgactg agggtaatga aaaaaatgtc ataagagcat       7860
gaattagaag cgttttgaga aagaatgaag ataatgtggt cattgactgt aaactcattt     7920
gatgggcaac gatagatgag acacagctat taagagtgga tcgataacct tgaatgtgga     7980
tgtgaggcaa ctgtagtata gcacaaaaag gttgagaaat gatggagccc ttaagctgct     8040
tgtggacact ggtctggagg gggacaggac caagaaaacc agtcatggag gttgaactaa     8100
gtcatctctc caatgtatcc gtgcctgtta cgtgccagtg ccgtttagga gcagaggata    8160
ttgtaatttt ttttaaagtt cctatgaata ccttctagtg ggtcataatg gctcaaccgg    8220
gaaatggcag tagagatgaa gagatggatg gattcgaaag acattttttg gaagttggaa     8280
ttaacaggat atggtgaata atcaagagat agtaaaagca taatggagga aacaatggtt    8340
cttcctgtta ccataggaag aagctttgga gtagagtttt attcatttta aatgcattta     8400
ttgtgcactt tattataggt attggagatt gatggaaaat agtctctgac ctcaaagagt    8460
ttcacaggaa agatgagcga tggctatgta atatgaccaa tactgggata gagaggtgcc    8520
caggtcacta cgggaggact taggtgattt ctaactatgt ctgagagtag gggaaatggg    8580
atcaaagaaa acatctcaga agacatgaag cttgagctta tgtcttgaaa aatttaaagt    8640
ttaacctaac caaggataaa gaatcagaag aaacagcata ttcaaaagct aaagaacacg    8700
ggactcttgt gtgctttgca tgtacacacg tgtgtgcgtg tgtgtctgaa aggattggag    8760
aggagggcga agagaataac aagatgaacg tcaacctaat gtagaatgtt tgaagtttgt    8820
atttcactta acaagacagc ggggagtgat ggaaggatct tagataggaa agggacatga    8880
gcacgtttgc caagagagct cgttctggtc atagtgggta cgtgaaggtg acaaatctgg    8940
aggcagatag ctcacatttg gaggcagctg cagtcatcca gatgagaagt gagagggacc    9000
taagctgtaa attgtgggaa taaagacaag acccgttaaa aagaaagaga acacaccatg    9060
tagcgtggaa aggagaaggg tggagagtag cctgtgcaga aggaacaacc ttcaaaaaga    9120
catggaagac tgaaaagaca ccctgttgta gggagatcag caatgcattt tttataacca    9180
ggtgatacag ggaaagggta ggatctgaag cttgaaaaat agattggggg ctgattgtaa    9240
agagcttcgt gtcattccca ggattttgga actgatttta ctaacatgaa aaaggttttg    9300
ttttaaaata ctgagtaata tagttggaac tataatttag aaagataata gctggtgcca    9360
tcactcttct aagcaaagat agtaatacat ttaatgctca taggctttag taatacattt    9420
aatccttaca gtaagcctat tagataaaaa ccattattat ctcccttcta tagacagaga    9480
aactggcatt aggagaatga gaacttgcct atggtcccac tctggaaata cctagtaagc    9540
gacagagcca ggattcaaac ccaggcagct tgactccaga actttcgctc ataaccttac    9600
acatctccgt catggttggt gtttctcaac catggataca cattcgaact gcatgtagca    9660
tctctaaaca tacagttacc tgaattgact gaatcagagt gtctgaaaaa tgatgtgtga    9720
tactatgttt tgcaaaatct ccacaggtaa ttctgttgta ctttgcttat agttgagtac    9780
tgcagggatc ttaggaagtt agagcagtag tccaggcagg agatgatgaa ggctcagact    9840
aaagcagtct gtaggaagga agagaaggga accggtttgg agacttaagc gggggaattg    9900
gcagtatttg tgaagtggaa atgcagtatt ttcttgtaga gtatgaacct tgcctaggaa    9960
```

```
agggagtaga ggaccatacc tttagttgta aattatcctc tcccaactgg atctgttgat    10020
ttatggctat ggtggttggg gaaaagagga tttaaccatt tgaagaagtt tgtgtagagg    10080
attatgattg aactcaggct gttgtccttg tgtatagttt catgcttata ctcttgtttg    10140
tctttacttc tctatccagg gcccttggaa gaaaatcctc gctgtgtcca ggctgaggcg    10200
gggggctaat gacagtgtga gctctagatg gtgtgagacc accccaaagc caagaaatgg    10260
ctacagccgt ggaaccagag gaccaggatc tttgggaaga gagggaatt ctgatggtga     10320 aactggaaga tgatttcacc tgtcggccag agtctgtctt acagagggat gacccggtgc    10380
tggaaacctc ccaccagaac ttccgacgct tccgctacca ggaggcagca agccctagag    10440
aagctctcat cagactccga gaactttgtc accagtggct gagaccagag aggcggacaa    10500
aggagcagat cctagagctg cttgtgctgg aacaatttct taccgtccta cctggagaac    10560
tacagagctg ggtgcgggc caacggccag aaagtggcga ggaggcagtg acgctggtgg     10620
agggtttgca gaaacaaccc aggagaccaa ggcggtgggt gaggaggggg agtcctgatc    10680
tgtgtgatgt ggagggggac tatttgctgg aaggctggat ttgcggggag agcttgcagg    10740
atccccataa attattagtg gctctgccct tgggttgctc ataccatg agccccatgg       10800 attagggga tgtgtgtgta tgaatgtgac tttctggata ttggaacacc tgtatagga      10860 ccatctgagg gggtctcagc caccaaaggg tcatggcttt ggttttccct tctttgaatg    10920
ttgagccgtg ggttcctgga gaggagaatt ttgtgacttc ctcgaaggtt ctcatagatc    10980
cccagtcaca gatcccccctt cctggctggt cagctaggga agcaggcagc aaggagagct   11040
gcaggtggga caggtggaga tgggaaggaa ccttgggtga caggggccca ggctgggggt    11100
ggtgagagag cagtgcaggc ctgcgcatcc cctgccttgt cctggggagg ataaccttca    11160
gctcctcctt gcctgctcca ttgaaactgg agtttcccct ccttgtctgg gtccctctgg    11220
gagtgttttc tctaggcatc ttctcctaaa ataagctccc gtgacaacca agaacttcct    11280
cctgactcca tggtgactgg aagttggaat tattcccagg tgactgtcca tgttcacggc    11340
caggaagtcc tgtcagagga gacggtgcat ttaggagcgg agcctgagtc acctaatgag    11400
ctgcaggatc ctgtgcaaag ctcgaccccc gagcagtctc ctgaggaaac cacacagagc    11460
ccagatctgg gggcaccggc agagcagcgt ccacaccagg aagaggagct ccagaccctg    11520
caggagagcg gtgggaagca tcagcagaaa gggggattg tggcagaagg caggcaagga     11580
gggggacatt tctcctatac caaggaagct gggtagatag actgtatgga aagacatcac    11640
agaatccagg atgtcaagag gagacagtac cgccagctag agtcccccat aaacagggcc    11700
aagcttagac agcagattgt tgcttgttct cttggcattc tgatagtctc ataggtgatg    11760
ggattgggat atgggagcta cccttaggcc agtttcttgg ttcccataat agaaaggata    11820
gggccacctt cctaccaaag atggtggggg atgcccagat ttttgcccat tattgggca     11880 tgctgcatat tactgatctt tgccttcttt tcttcataga ggtcccagtg cccgaggacc    11940
cagaccttcc tgcagagagg agctctggag actcagagat ggttgctctt cttactgctc    12000
tgtcacaggt gtgccctagt tacctctgta ccacagagaa tttgtttgaa gaaccactgg    12060
gcataagcca tactaaacag gtgaagcagg atgcacattt acactcttgc cagttttaag    12120
ctcacagttc tgcaggtacc tggaagggga ggagataatg agataaatta tcatacctta    12180
tattggatcc acaggcacca acaccagttt atttgccatt gactagaaga actaacaaaa    12240
tgggattatt ttgtaacact ccagtacaac tgcgaagttg tcaaatgagg gttttttagt    12300
tttttttttt tttaaaggaa taaatttgat agtcatttgt aagtatgaca gactgtactg    12360
```

-continued

```
ctgagacatt taggaagtat tcaccatgat caaagctctg aaactaagcc atgtggctgg     12420
agaaaaagaa atagaattca tgtatggttt tagattgtaa tctaactgag gaaaaaagtc     12480
ttgttttggc tatagagtat agaaactatt gaaagtgatt agagtcttta gggaaagtgt     12540
actagaaaag atgaattttg cagaaatgta tatagcgtta aagtgtcaag tagggagctg     12600
aatgatgatt tttaagacct ttcctaaatt ttaaacaata ccttaaagaa gaagaacata     12660
agctggtcct caggaaaagt ggtggagttg gaggggggcag ggccagtgcc acagggggaca     12720 catggctccc ccgagaatga gtttaagcag cccgccactc aagctccttt catctcctag     12780
aggagtccac ctattgtgtg accttcaaca gggacaaaat acgaggctac ccgtagcatc     12840
acgttttgat gaaatcctta tgtggtttca gggactggta acgttcaagg atgtggccgt     12900
atgcttttcc caggaccagt ggagtgatct ggacccaaca cagaaagagt tctatggaga     12960
atatgtcttg gaagaagact gtggaattgt tgtctctctg tgtaaggaat ttcaagtatt     13020
ctagagtgtt ctaagcccag agatcttttt cctgctggaa attttggggg atcttagacc     13080
ttagattgta tgcagtgaac ttctcttatg ccttccccac caataaaatt gagggattag     13140
gtgaaaaata cggtgtcctt tcaagtaaaa gataaatgga tggaaatgga aacctctaat     13200
aggaaaacaa acttgtaata ttacagcttt agtgcagaaa tatttgaagt aagcacatga     13260
gttttaaaac agtaagagtt ggagataatc tttcttgaat atgggaaaag aggataaggt     13320
gtacaatggt ataattatta agttgcaggt gaaaaccaca agaaaggcaa gagatacgca     13380
gtccttggtt aaaagtacac aaactaaaga gatgaaagat ttcatcacct gagctagcta     13440
tgtatttgcc ccacaaccta ccaaatagaa aaggaccgct cttaacacag ggaattgttg     13500
agccaatcgt gatatcctat tttccctctc ttgagcagca tttccaatcc ccagacctga     13560
tgagatctcc caggttagag aggaagagcc ttgggtccca gatatccaag agcctcagga     13620
gactcaagag ccagaaatcc tgagttttac ctacacaggt gaggaatgac aaaaacggtg     13680
ttacccaccc tgagccagca gttcctctag gcagtgcttc tctctctctg tagggccccg     13740
ctctcatcag ttcttctaac atgtcagcca gtactgcttt ctccctctga cagccatttc     13800
ttctgtcatt gccctcctct tttctcctcc catcatttgt ctgatagcaa tgtaatacaa     13860
aagggtgaaa gaaaaatgtt aacttttgga attgcagcta taccatttac tgtacaattc     13920
ccttaaaccc tcgattctca atctctgcat ttgtaaaatg aagattatat ttgtgcatac     13980
caaggtttgt tgatagcata acaatatgag aaagtgcttg gcacaggaca ggcattccat     14040
ttagtcttgc catctcaaaa cccttttgtaa aaatctcccc attgtgtaga aggcattgtt     14100
gccgctacag tgaccccctt tttcctctca ccctttctac aggagatagg agtaaagatg     14160
aggaagagtg tctggagcag gaagatctga gtttggagga tatacacagg cctgttttgg     14220
gagaaccaga aattcaccag actccagatt gggaaatagt ctttgaggac aatccaggta     14280
gacttaatga agaagatttt ggtactaata tttctcaagt gaatagtttt gtgaaccttc     14340
gggaaactac acccgtccac cccctgttag ggaggcatca tgactgttct gtgtgtggaa     14400
agagcttcac ttgtaactcc caccttgtta gacacctgag gactcacaca ggagagaaac     14460
cctataaatg tatggaatgt ggaaaaagtt acacacgaag ctcacatctt gccaggcacc     14520
aaaaggttca caagatgaac gcgccttaca aatatcccct aaaccggaag aatttggaag     14580
agacctcccc tgtgacacag gctgagagaa ctccatcagt ggagaaaccc tatagatgtg     14640
atgattgcgg aaagcacttc cgctggactt cagaccttgt cagacatcag aggacacata     14700
```

-continued

```
ctggagaaaa accottctttt tgtactatttt gtggcaaaag cttcagccag aaatctgtgt    14760
taacaacaca ccaaagaatc cacctgggag gcaaaccota cttgtgtgga gagtgtggtg    14820
aggacttcag tgaacacagg cggtacctgg cgcaccggaa gacgcacgct gctgaggaac    14880
tctacctctg cagcgagtgc gggcgctgct tcacccacag cgcagcgttc gccaagcact    14940
tgagaggaca cgcctcagtg aggccctgcc gatgcaacga atgtgggaag agcttcagtc    15000
gcagggacca cctcgtcagg catcagagaa cacacactgg ggagaaacca ttcacgtgcc    15060
ctacctgtgg aaaaagcttc agcagaggat atcacttaat taggcatcag aggacccact    15120
cagaaaagac ctcctagcta ggtccccatg tgaggagatc tgctttcagc cctcacctaa    15180
gggaggtgag gaagaggaaa agccctcttg tcagcctggg aagaccttt cgagggagtc    15240 tccctgacct gctcagatct gacattacct cttcctgcaa ctaaacacga gcctgggcag    15300
aacctctcag ccttcctcta cgccttgagg ggatgtttca tccaaagtac aacctgaatt    15360
gaggcttctc cttcactgga gtgcacctgc ctctacctca tgggtataaa gtaggagaac    15420
taagagactt aagaggtcgt ggttcctata tcgtccaaaa aataggctgt tacatatcct    15480
aaagactgct caacagcttc aagttgaaag tggccaagga cagccccttaa ggtttgggaa    15540 gggacgagcc tgaaggattc tgtctttact ggggtcaaat cttaaagcac acagctctgg    15600
actcaagaca ggaggtttgc gtcctgatgg cttttgcacac attcacagga taactgcata    15660
gatccctcgc tgtctgattc acttcttacc atgcactttc ctttgatgct gaggagaaat    15720
ggaagtgggc gaaaaatctc aaggctgctt catgtgacc ttgtcaagct gctccctccc    15780
ccagcgtcaa attgttatca ggtgccaaac actgctagaa aggagggcct agtcagaagc    15840
ctctttccat acgagttttg gttttgtttt taatatttt ttctattaaa atactcatgc    15900
atttaacctt cccgttattc aaccagtctc ttggttgcat ccctagcact tctactacaa    15960
gtgagatggt agtgtttgag tgcttattga gtaaagcata attcggtcat aatgaaatcg    16020
ttcacattcc ctcatatgca caagcccacc aaccccttca cccccccctt cacaggggtc    16080
gtatgagtaa ggggatttgg aaactgtcaa cttacaaagg cactataaca attacagaat    16140
catgattgcc atgggccact ttatttacat gaagacaact ggagaacgac taagaccaaa    16200
ttatggaaaa taagaaaaag ctgttgctgg caagaccatc aagactgttc tgacaccctg    16260
tccccatcat ccctgactga gtactctgac atcacggaaa gtgttgaacc tgggaccctg    16320
aggaattcac caggagtaaa tggctttcat gtatttgtgt tgtttgcttt ttcttacgtg    16380
attttatgtt catagagcta gaaagtagca tctcatgatg gcccaacaat ctctgttgcc    16440
agttaaaggt tccttggaga tgaggctgaa taattatgaa cctcaccttc tctgattgtg    16500
ggagtggcaa gaactgggga gacgtcctcc ataagtggag cacagggtat ggggttaaag    16560
catgacaggg agagtcttct gtgcctggtt tcttctcctc tatctcataa tgcattatgg    16620
gcccgaggaa taggggaggg ttaataagac tccaaccota atgcccaac agggaaattc    16680 tcattttggt cgatgatatt ctgatggact ggtttggtct taataccagt caaccgttgt    16740
ccttctggaa atatacatat atgaaataaa taaaggtaac acttgcagcc aagttccctg    16800
gtttctggga cttcccatct tacccattcc ttttccaggg cttcagtgtc ctgatacttc    16860
tgagggtggt tcatactcaa atagatctgg gagtacagag tatttttcct tgaggaaagg    16920
aagggttggg atgattagca gagtccggtg aaacatatgc actctgagat aagatccaag    16980
cctggagttt gcagaagata ctgtcctaat aagcaggcat ttctaaacca agtatctaag    17040
cctaagcaca gcttgtcctg ggtgaaatgt ctgccacaaa agatagtttc tcctagctca    17100
```

```
gacttaacca tttataaagg ttggtaaaat actggcagtg acaacaaatt gactttttaa   17160
ttttcttatt tgcattattc caataaatga aaatctgtca gagttctaca tgagggaaag   17220
cttgtgaggc tgggccggtt tgttggaaca tcaaatagtc cttaattact gatctccctg   17280
cagagtttca tatgctgaca ctaaatctct ggtcccttt  gtaaattact gaattttctg   17340
aggttctggg agggacatgt tgtctcccaa atctgaacaa acacaaccac agtgtgcagc   17400
ggcaggaaag aagtagtgca gctgagcgtg agcagggagg ttggagcaca gggtgtgtat   17460 tcggagggt  cccctctagt atcttgtgag cagtagaatt ctagcatcct tgaataccat   17520
actaagtttc tgagggagaa aacggtggga ttttaaagat attatttgga ggaagttaat   17580
acgctactta attaacagaa ttggcaggtg gttggaaatg tgctaaagag gtatgacaca   17640
ttaaaaatga taatataagg atgtttgacc agataattta ggaataacca aggaatattt   17700
aacctcttca ccacaaagtc cgaggagaaa taaatgccca agagatcaag ccaaaataca   17760
tttttattat ctgggactta ggcctcatat tccggagcag aatccggtaa actcagatga   17820
actccatgga gaatttcata aatcagatta acatcaaggt actaaaatca aaacccacta   17880
agaaacctgt tgccccttc  aaagcacaac tgaagtaatg gatctaatag aagatacatt   17940
gtttgcactg agcagtagag tagtagagga gaaaagccca gagatggcac agacaagttg   18000
ttccagtccc cttcagtcaa ggcctctgga ccaccaccct gccacaggcg aaaaatggga   18060
tatttaataa ataaaaaatt ttgattcacc agactggctg aaaggacagt aatccaaatg   18120
agagttaacg gctccatagt agttttctag aatgaaagct gaactgagaa atagtaactg   18180
atgacatgtt gagcaggtta ataatttggt acccttccac accagtattt gtttgtttgt   18240 ttgtttttgag atggagtctc gctctgtcgc ccaggctgga gtgcagtggc gtgatctcgg   18300
ctcactgcaa gctccgcctc ccgggttcac gccattctcc tgcctcagcc tcccaggaa   18360 gctgggacta caggcaccca ccaccacgcc cggctgattt tctgtaattt tggtagagac   18420
ggggtttcac catgttagcc aggatggtct cgatctcctg accttgtgat ccgcctgcct   18480
tggcctccca aagtgctggg attgcaagcg tgagccaccg cacctggccc cacaccagta   18540 ttttaaaaa  tagtttgttt tacctctagc gtcttccctc agctgaccta aatagtccag   18600
ccacaatagc tgagagaagt atacctacaa ttatttccat ctccttatat ttctagtgat   18660
gttggctgac taacccacta atctagttta tgggagaggg aaaagactgaa agagccacaa   18720 agtggatggc caacccacgt gattactaac ctttattgtg gcaaagtaac tgatacaatg   18780
tttcaaatgt aagcacatct ccttggaata agtggaataa cttaattcat ccttgcggaa   18840
gtcctgagga tcaagcaagg aggagcccag ctttctttag acaccacctt ttttatcttt   18900
aataacaaaa aggaacaaag tgattgtcag accagcacaa agatacctct taatgtgcaa   18960
tttctattct ctttagtgtg tgtgagtgca cgcatgcacg tgtgtacacc gaggtttcag   19020
gtagaaggag gaatgcaatt caaattctaa aaaaggaatc agtcagcaca aactagttta   19080
tttggcaatt cataaagata gggactcttc agaggaggtt gagagcattg tagggttatg   19140
taaagacttc cagaagctgt aaagacttcc agaagcaaga agattcaacc atctaaaacg   19200
ccatgcagga aaatagccaa accttctcca tttaagtaga gaataaatct tagtagcgtt   19260
ctctgcagaa tataacaacg ctgcaaaaag gccatttcac aggaatataa tcaaaactgc   19320
agattctcag ggtttcccgt aagacgactt ctctgctctt ctgtttgtgg tttctttttt   19380
agttgtacat ctctcctaga caagtccaag gaactactaa cgagaagatt tcaggaagag   19440
```

-continued

```
gcctacagca attgcttggt gcttgggttc atttgcggaa tcttggcaac aggtctacag    19500
agaagcagtt ccacggcaaa agagctgtgg ggcagttgaa taatccatcc aaacaatgag    19560
gagtaaaccc tgagtcaaga aaccagcaaa aagcagaaga ctgggtcagc aaataaaggg    19620
agaagatcct tgcctccttc agtgcccta gcatgatatt ctgaaaggcc ctccactaaa     19680
atacaactac agtttaata aattactaaa atagagaata gaagtagtat gtaagttggg     19740 ataggtgat ctgaattaag tgttttaaca ttcatgaact gttcaggaca aaagctgtaa     19800
gatattggtt aacctcaaca ttgttaaatt aagtgtgcac tgtagtatca aagatactca    19860
taagaatgga gagagtaatt ttctaaatag tggagggaaa ataggaatta attttttttca   19920 aaagtgggac ttaggttgtc taaagaaagg ccaaaaaaag cataaaaaga tgaaaaaata    19980
gaactacgaa gaacacagcc caaatatatg aataaaatag aataaatagt aactaccatt    20040
taagatagag attgtcagaa tgggtaaaaa aaaaagtaaa ttataacaaa gtatatacaa    20100
cagatataca aaaatagtga ttttttttttt ttttttt                            20137
```

<210> SEQ ID NO 207
<211> LENGTH: 77
<212> TYPE: PRT
<213> ORGANISM: human

<400> SEQUENCE: 207

```
Phe Arg Arg Phe Arg Tyr Gln Glu Ala Ala Ser Pro Arg Glu Ala Leu
  1               5                  10                  15

Ile Arg Leu Arg Glu Leu Cys His Gln Trp Leu Arg Pro Glu Arg Arg
             20                  25                  30

Thr Lys Glu Gln Ile Leu Glu Leu Leu Val Leu Glu Gln Phe Leu Thr
         35                  40                  45

Val Leu Pro Gly Glu Leu Gln Ser Trp Val Arg Gly Gln Arg Pro Glu
     50                  55                  60

Ser Gly Glu Glu Ala Val Thr Leu Val Glu Gly Leu Gln
 65                  70                  75
```

<210> SEQ ID NO 208
<211> LENGTH: 77
<212> TYPE: PRT
<213> ORGANISM: SCAN consensus peptide

<400> SEQUENCE: 208

```
Phe Arg Gln Leu Cys Tyr Gln Glu Thr Ser Gly Pro Arg Glu Ala Leu
  1               5                  10                  15

Ser Arg Leu Arg Glu Leu Cys Arg Gln Trp Leu Arg Pro Glu Leu His
             20                  25                  30

Thr Lys Glu Gln Ile Leu Glu Leu Leu Val Leu Glu Gln Phe Leu Thr
         35                  40                  45

Ile Leu Pro Gly Glu Leu Leu Ala Trp Val Arg Glu His His Pro Glu
     50                  55                  60

Ser Gly Glu Glu Ala Val Thr Leu Val Glu Asp Leu Gln
 65                  70                  75
```

<210> SEQ ID NO 209
<211> LENGTH: 2933
<212> TYPE: DNA
<213> ORGANISM: human

<400> SEQUENCE: 209

```
gtcattagct ttatccattg acaaaatctc ttttcttcgc caaacttgtc aggcttctga    60
```

```
aacttctcct agggctatcg gcgtacttcc ttgtaaaatc tactgttagc aaagaactct    120
aagtcctttg gcaggaacac ccccatcctt gatatctgac catccttaat acctggtcag    180
tgtcctcatc ctccatcatg ccccaggtga tgtctgatca acctggcctg tcttcagcaa    240
gaatcctatt aggttgactt agccagaatc cgccttaagc ctgatgtttc cccttagtaa    300
ttttcaatcc atcgacgtcc caaactccaa aaaagttcc ttgactataa attcccactt     360
gcccattctg tattcagagt tcagcccaat ctctcatccc tacagcaaga cttcattgca    420
gtggtttctt tacctttcct ggtcctgaat aaggtctccc ttaccatgct ctaacaagta    480
tcactgaata attttttcctt taacactgta atgcattaaa tgtttagaag aagatgttta   540
tgtattattt atgcacttaa taccaatatt ttaaaatatt caatgagatt tacagagaaa    600
aatatttggt acacagtagg ctttcatgaa atgtatattt ctctttgtat tgggtaattt    660
tatgtgtcaa cttgactagc taagggatgc ccagacaaca gaaaacatta ttagtcggtg    720
tgtctgtgag ggtgtttctg gccaatatgg tgaaccccc tctctactaa aaatacacac     780
acacaaaaaa aaaatagctg gcatggtgg cacatgcctg taatcccagc tattcgggag     840
gctgaggcag gagaattgct tgaacccagg aggcagacat tgcagtaagc cgagatcgct    900
gggcgacaga gcaagactct gtccaaaaaa aaaaaaaaaa aaaaaaaaga gagagagaga    960
ttagcatttg aatcagtaga ctgagtaaag aaaatcactc tcaccactat gcgtaggcac   1020
catccaatcc attgagggcc caaatagtat aaaaaggcag ggaaagtaa attcacctct    1080 ctcttcttga gctgggacat catctcctcc tgctctctgg ccttcagaca ccagcacctc   1140
aatccctttc cagttctcag gccttcagct ttagactgaa ttataccacc aacctcctta   1200
tttctccagc ttgcagtaag cagatggtgg gacttctcaa cgtccataat tatgtaagcc   1260 aactcctat aataaatctc cttttatatg tttatacata ccccgtgtga aggaaagtg     1320 atttggggcc cccaaaatca ctaaagggaa aattcatgct gggaactgct tagggcaaac   1380
ctgcctcccc ttctattcaa agtcacctct ctgctcactg agataaatgc atatctgatt   1440
gcctccttcc ggagaggcta atcagcaact caatgcaacc atttgtgtct tatctaccta   1500
tgacctggaa gccccctccc cgctttgagt tgtcctgcct tctgggttca cacctattag   1560
ttctgtttcg ctaatacact gccgctccac caaaagtaac taatcctttg gttcaaaccc   1620
agtaaacaga tcccagcaat gtgtcccatg aaaaggaagt ggcacatggc acgtggagag   1680
tggtgactta cagggtaaaa gggacagaga gcaaggaaa atgtcaggta tgggcagaaa    1740
ggtcaccgaa cagacaaaaa tgaacaaatg agatcaggga agacagcctg aaagtaaaga   1800
aatacgaagc aacactcaaa ggaaaagaaa gaacagtgat accataacta tttctttct    1860 gagcttctga tgttccattc agttcatgtg caatgtatca tttagtcctc agagtaacgg   1920
tattattatg cccgttttat atgatgcaca atagggttca aagatggaga gattcggccg   1980
aggccctgct gctgatggtg actgcaagag ccagtattca aacctaacgc tgccctttc    2040 taccatgttg cagcggacaa tgcaagaaa aaaaatcaa gaaaaacacg tagaggtatc    2100
caaatgaaaa caaacacaca aaagatcaaa aacagaaaag aaaaagaaa agaaaaagaa    2160 aacccttgca gaaggtatgc ctgtaaatga aaggcccaag atgttaattt attcgctgca   2220
gagtggagtt aggggtcgcg gacggcagct gtgggtccg aggcttcttc gcactgggtc    2280
cttggggagc actgagccgc aacccgcgga gggcgcatag agaggatcaa acctcccaca   2340
gcctagaaag gctcctactc ggcgagaagg cggggcgagc gatcgcttcc ggttccgggc   2400
```

```
gcaaaggccc cacgtgttcc gacccgctag gccccgcgcg gctcggatcc ggcggcgctg    2460
tttcggtcgg gagtgggtgg gagagaagcc ggggcagggg aggagccgcc ggagctgtcg    2520
gagccgtgag tcctgagtgg gctgggctgg gccggccgg gctggaccgg gccggaccag    2580
atcgggcaga gccgggcagg gcggngagga gggggaggga ccgggagacc ccggcccccc    2640
agagtctggg gaaatcgccg tgtcctgggg aaggggtgcc gccggtgtac tgagggtgcc    2700
gagacgttgt ggtctctgtg tttcctggtg gccggagcca gtatctccgg ggacacggat    2760
ggcgctcccg gcttcctttc ctttccagcc accgccctcc gcccctcct ggggcctgca    2820 gaaatgtagt tagtccgtac ctcgtacctc ctaacgcttc cgcgccaact gtcccccgg    2880 aaccgaggga ggagtggtct aggcccttt attttccgca gcttttcctt acc           2933
```

<210> SEQ ID NO 210
<211> LENGTH: 23071
<212> TYPE: DNA
<213> ORGANISM: human

<400> SEQUENCE: 210

```
gtcattagct ttatccattg acaaaatctc ttttcttcgc caaacttgtc aggcttctga      60
aacttctcct agggctatcg gcgtacttcc ttgtaaaatc tactgttagc aaagaactct     120
aagtcctttg gcaggaacac ccccatcctt gatatctgac catccttaat acctggtcag     180
tgtcctcatc ctccatcatg ccccaggtga tgtctgatca acctggcctg tcttcagcaa     240
gaatcctatt aggttgactt agccagaatc cgccttaagc ctgatgtttc ccttagtaa      300 ttttcaatcc atcgacgtcc caaactccaa aaaagttcc ttgactataa attcccactt      360
gcccattctg tattcagagt tcagcccaat ctctcatccc tacagcaaga cttcattgca     420
gtggtttctt taccttcct ggtcctgaat aaggtctccc ttaccatgct ctaacaagta     480
tcactgaata attttccctt taacactgta atgcattaaa tgtttagaag aagatgttta    540
tgtattattt atgcacttaa taccaatatt ttaaatatt caatgagatt tacagagaaa     600
aatatttggt acacagtagg ctttcatgaa atgtatattt ctctttgtat tgggtaattt    660
tatgtgtcaa cttgactagc taaggggatgc ccagacaaca gaaaacatta ttagtcggtg    720
tgtctgtgag ggtgtttctg gccaatatgg tgaaaccccc tctctactaa aaatacacac    780
acacaaaaaa aaaatagctg ggcatggtgg cacatgcctg taatcccagc tattcgggag    840
gctgaggcag gagaattgct tgaacccagg aggcagacat tgcagtaagc cgagatcgct    900
gggcgacaga gcaagactct gtccaaaaaa aaaaaaaaa aaaaaaaga gagagagaga      960 ttagcatttg aatcagtaga ctgagtaaag aaaatcactc tcaccactat gcgtaggcac   1020
catccaatcc attgagggcc caaatagtat aaaaaggcag ggaaaagtaa attcacctct   1080
ctcttcttga gctgggacat catctcctcc tgctctctgg ccttcagaca ccagcacctc   1140
aatccctttc cagttctcag gccttcagct ttagactgaa ttataccacc aacctcctta   1200
tttctccagc ttgcagtaag cagatggtgg gacttctcaa cgtccataat tatgtaagcc   1260
aactccttat aataaatctc cttttatatg tttatacata ccccgtgtga aaggaaagtg   1320
atttggggcc cccaaaatca ctaaaggaa aattcatgct gggaactgct tagggcaaac    1380
ctgcctcccc ttctattcaa agtcacctct ctgctcactg agtaaaatgc atatctgatt   1440
gcctccttcc ggagaggcta atcagcaact caatgcaacc atttgtgtct tatctaccta   1500
tgacctggaa gccccctccc cgctttgagt tgtcctgcct tctgggttca cacctattag   1560
ttctgtttcg ctaatacact gccgctccac caaaagtaac taatcctttg gttcaaaccc   1620
```

```
agtaaacaga tcccagcaat gtgtcccatg aaaaggaagt ggcacatggc acgtggagag    1680
tggtgactta cagggtaaaa gggacagaga gcaaaggaaa atgtcaggta tgggcagaaa    1740
ggtcaccgaa cagacaaaaa tgaacaaatg agatcaggga agacagcctg aaagtaaaga    1800
aatacgaagc aacactcaaa ggaaaagaaa gaacagtgat accataacta ttttcttcct    1860
gagcttctga tgttccattc agttcatgtg caatgtatca tttagtcctc agagtaacgg    1920
tattattatg cccgttttat atgatgcaca atagggttca agatggaga gattcggccg     1980 aggccctgct gctgatggtg actgcaagag ccagtattca aacctaacgc tgccttttc     2040 taccatgttg cagcggacaa tgcaaagaaa aaaaatcaa gaaaacacg tagaggtatc      2100 caaatgaaaa caaacacaca aaagatcaaa acagaaaag aaaaagaaa agaaaaagaa      2160 aacccttgca gaaggtatgc ctgtaaatga aaggcccaag atgttaattt attcgctgca    2220
gagtggagtt aggggtcgcg gacggcagct gtggggtccg aggcttcttc gcactgggtc    2280 cttgggagc actgagccgc aacccgcgga gggcgcatag agaggatcaa acctcccaca     2340
gcctagaaag gctcctactc ggcgagaagg cgggcgagc gatcgcttcc ggttccgggc     2400
gcaaaggccc cacgtgttcc gacccgctag ccccgcgcg gctcggatcc ggcggcgctg     2460
tttcggtcgg gagtgggtgg gagagaagcc ggggcagggg aggagccgcc ggagctgtcg    2520
gagccgtgag tcctgagtgg gctgggctgg gccgggccgg gctggaccgg gccggaccag    2580
atcgggcaga gccgggcagg gcggngagga ggggagggga ccgggagacc ccggcccccc    2640
agagtctggg gaaatcgccg tgtcctgggg aagggtgcc gccggtgtac tgagggtgcc     2700
gagacgttgt ggtctctgtg tttcctggtg gccgagccca gtatctccgg ggacacggat    2760
ggcgctcccg gcttcctttc ctttccagcc accgccctcc gcccctcct ggggcctgca     2820 gaaatgtagt tagtccgtac ctcgtacctc ctaacgcttc cgcgccaact gtccccccgg    2880
aaccgaggga ggagtggtct aggccccttt attttccgca gcttttcctt acccctcctc    2940
tcagattgct taagatcatc tccgcgggct ccttgccccg gctagcccca tctccttaca    3000
ccaccaagcc cccctcaccc cagcacacac ccagatacac tcaccgtga tcttgtcacc     3060 tgtgatgata gtatgtcctt ggcgtccatt tggccagagc ttttcagctg tcactgtgac    3120
agaccctgag gttcccctca agccagtagc tgctgtctcc acttgcaact ttcctctcct    3180
cccactccta acagccagtt ttggcacctc ttctcagcac ctgcgttact tttagcagga    3240
gtatacctac ttcttgagtg tcttgattaa aaatttgttt ttgtgccatg gataggctgt    3300
gttccttcag aaaggtgtca gtctaatttt tgttttttctg aacaatgaat gttctcatct   3360
tctaggcgct ttgataaccc tgtctgcctt ggaatctgta ctgacctccc cagagggaga    3420
ctcttagacc cagccttctc tgaacaacct tggtcctggg gagcagcgct agatcccagg    3480
ctctcactta gaggctgggc ttagaactgt tgcttttct ctatccacgc tctgcaggtg     3540
acacccaggg cagctacact cagaagccac aaggaatgct agtggagccc ctcatccctc    3600
ccagcttctc ttccaagctg ccccgtgggg cttgatccag gaagctactt cagaaaggtt    3660
gtgggatagc cttgggagga ggtttgttgg tgggaagcgt gtgaaccgga acagtcttgg    3720
ataactttct gctgttacta tctagcataa gagggtgggc agggttggag agaggacagg    3780 aattttttcct cctaggacca aacgcctggg attcataatc tttcacccctt tctcctccag  3840 ctatacccctt tttgtactct gtgtatatac tatattgcag tagacaatca ttccaagggt   3900
acaacaaggt ttaccacaat gtgagggact cagccattgc aaattgtaca gatgaggtaa    3960
```

```
gttacaggtt tacattttt  tttcccagta aatttggcac agatttaaaa tgtgaaacag    4020
ttctagaccc cttgttttg  ctgttctctc accagcaaac cctttagttt ggccagcaat    4080
ggctttctgc atgaacttca gatttacttc atttgctagg tggtggttct caaacttact    4140
ataagcacct gaagggctag ttaaacgcat attgctgggg cccaccccta gagtttctgg    4200
taataggtct gtgctggggc ttgagaattt atgcttctaa caaggctcag gtactgatgc    4260
tgcagatctg ggttcttcac tttgagaaca actaccttt  ggccaaatgt gatatacgta    4320
ttgcagtagg ttgaggttca gaataccttt gtttgagtac ttctgtgttg gaaactagta    4380
atctgatctt ttatagataa tcacttaggt ctgaatattc tgttcgcaaa attaagaaag    4440
cgtacttaaa acaactgaat gctatatgcc aaatttgagg tgaaatattg atgagttctt    4500 cccttgatt  ttcttaattc tcttgatagg ggcttcacgt tttgatcaaa aatattacac    4560
ctgtattctg ggcttttgct gtgaattcct agtattgcta aaattctgca atttcttaac    4620
tacctgttaa gttcctcaag gtcagagctt ctgcttttt  tatctttctt tgcccagcac    4680
cttgaatagt gtgggacacg taattgacgc tcagtagata tttgtgtatt gaactccatc    4740
ccttgtcctc ctccctctt  gatgttttt  tctactggcc ttatgctaca cagtaaagca    4800
gggcatgatt atgccacttg attacccca  agagattgga ataaatgcta atgccaaatt    4860
cctacagcta tccctgtgaa tggtttatta cccaggagcc ctgacactgg ctgatttctg    4920
aattttcagt gcttctgtaa tatatactag ttgggggagg agaaatagaa agcttaaact    4980
caatgtgcgt ttattgaata ccttttctac taagggcttg acaaagtggt aggcactggg    5040
aatataaaaa tgaataagga gacccttgct ctcgaggcag ggcccacagt ggggagacag    5100
acgttaagcc atgcccacga caagaatgac ttctgagatt ccttctttgg atcatgattt    5160
agtcttcagt ggaaacctgg tactcctcag attcctctgg ttcaacaggc ggggatccca    5220
tcccttatca tctcctcaaa tgctaaagga cccttgagca agccaggag  gaagtcatct    5280 agacgtgaaa cagggagtat ccacacaggc tgtgttaatg acaaagctaa aacatagta    5340 aatgactttt gaatttactg ctgttatgaa ttatctatag caacacctca ggtcagctct    5400
gttatatatg ttattgtgtt atttcccatt aaatgatggt tcctctgact atctgattgg    5460
cattgactat gtttgttgta gggattgcat acatctagtt taactctggc tgtcaaatga    5520
gagagcagtt actcttatca ggatgggtgt caggtttgat gtcccctcct tttcctgctt    5580
caggttaatt tgtcatgttc tgttttaaac tgaggcatat agcttgacct cctttattta    5640
ggccattaac tgctctgggg tagttttcct gaaggttaaa aagcctagct tcatgatgga    5700
ggttaatcaa catgaccatg atggccaggt gtataaatct ggcctcttaa aaatctgtat    5760
ttgaggctgg gtgcagtggc tcacacctgt aatcctaaca ctttgggagg ccaaagctgg    5820
cagatcactt gagcccaggt atttgagacc agcctgggca acatggcaag accccttctc    5880
tatwaaaaat ttaaacatta gctgggcatg gtggcatgtg ctgtagtccc agatacttag    5940
gaggctgggg tggaggatg  gcctgaacct gggaggcaga gattgcagtg agttgtgatc    6000
ttgccactgc actccagtct tagcaacaga gtaaacccta tctcaaaact taaaaatctg    6060
tgtttggccc ctagccgtcc tcagctcttg agtaaatctc agcatccatg gctgttacat    6120
tatggcccaa atattcaata gagatgctgt atatccttgt tcctctcaaa accctcctc    6180 atcaccatca aaaagctggt ttagttctct acctttagat aaagaatcat cccaagactc    6240
aacatgagct gccgtgactt gtccaagatg acacctcttt acaatgtaga gcagtggaca    6300
gaacacaggt caccctccgc cgaaagcaac tatctactgt ctaacattgc ctcctaggcc    6360
```

```
tgccatatat aaccatcaaa aacattttag tttagaataa agtgaattgt tacaattttt    6420 attttttcatt tttgtgttta catttactct caatgacatg tttattccca cctaatatct    6480
tgaggctaac cacaaaatct gcagcatttc caggcagaag atacttgtga cttccctgta    6540
ctatccacta catacttgac ctctttctct ttcttcctgt cttccctttc tctatacctt    6600
attatctttc tttggaacct cttgtaacaa attttgagcc atttctcccc tcactactca    6660
aatatcactt ttatgaaggg gcggggggga aacttaggtg gcaaaaatat tttacagaaa    6720 cagtttttaaa catgttttga agcatactgg tcacgtgtta gaaggccaaa agccagggaa    6780
ttcattccct ttcattcatt gtgctgtcta ggttaagttt tcacaggact tcttggtaca    6840
ctgagtttgc ctcagattgt ctcctgccag ttacagggag tggagaggac tttgatatat    6900
tggtaattag aagcattscy gatatggtct tcggtgggag aacctgtgtc taaggttcct    6960
tctcatctgt attccaacac tttcatttaa tcctacttca taagtgcctc caaagcaagg    7020
attttttttt tggtttagca tggtttcttt gatataacaa tagaccgacc aagattttcc    7080
ttatgccatc tgtttttttg taattatgat gcaatagaga actgtttgct tgtttatcat    7140
ttaaatcttg ccttcttccc aaaacgattt caaatagctt gaaggaaaat gaataaaata    7200
tattgagcac ctaccctatg ccagactcta tactgaaggg tttctatagg ttatttcatt    7260
tactccttaa aacaaccaca tgagataagt agtattagcc acattttga ggataagact    7320 gaggcttagg gaaattgtgt tacaaggcta ataagcgagg tcagggattc gaggtcaggg    7380
attcaaaccc agcgtgccaa ggccactaac cattatgtgg aaagcttagg taagcgcttg    7440
tatataggac aatcaagaat aaaagaatat gtccattaga aggattgtac tgggctaatc    7500
tttcgtttta aagaacagca gcagcattgg aaaagagcgg ttaacagttt ttattagcca    7560
atttctattc tagaacactg agaggagctg ttgacaggcc ctggttagcc ccagcaagta    7620
gttgtattaa aattaccaaa ctataggcct gcattaaggt ataaaataag aatgggact    7680 ggaagggata taaatatctg ctaaatataa taatttcagt tctaatcact attttcttct    7740
gaagattatt tgccagtaca taggcagatc actgtctctc ctttaggttg atggtatatg    7800
actacagact ttgtcattta gggtccagaa agatcaccct agctagtagc gttttaaggt    7860
agagaactag atattgtttc attgcctgtg gtttttctgtt cttgtaagag aattgagctt    7920
gggtcttcac tgccacgtga caccttcaga taagggcag agacagctgg cctgaggatt    7980
gtacagaggt cttaccttga tagctcctct ccaatcctat gcatcctagg aacactcaag    8040
acactaggtt gtatctttgc agatactgtt ttagtgtctt ctggaaccaa gtctcttact    8100
taatcctggc ctggtttcat attctctcta ttgtattctc tctatagttt ttgtcttact    8160
ctggaactct tccaaggaca gacattgaag aaaggtatta gaatagcaaa ggcaacaaat    8220
tgcaaggtat acttatggca tagcacatcc cattaattat agaataaaaa cacaaacatct    8280 gttttctgcc tctaatatta aatcttgaca tttgcacaac acattttagt tcataaagct    8340
ctcatatctc agataatcac tgagttagga gactggttat ctgcagaggg ctttatcctt    8400
tacaagggct cttgggtacg ttacttcacg aaaccctcag ggaagctcca gtttcttggg    8460
gatctggggc cggggcatat gtctttggat acccagtttg gtgctgtgca cagcactgct    8520
gtacctccta ttcatttccc atctcttacc ccacaaagac tccttccttc attccttcta    8580
ttgctgatct gttttccttc atcttcctag gctgccaaag taaatgcaaa acaagcacca    8640
gaaatctcag cttgtgattt ctgaagggca tttttaaatg gcaagtttgg tgtggcactg    8700
```

```
ttacatgttc ttttttcttt ggagagcaaa gcccttgag agagcaggaa ctcttctgtc    8760
aatgcatacg ttgtaggatc catactgtgg aatctcttgt acctagtgct gcgtgaaaac    8820
aatgaggatt ccaagtctac ttcactggac atcggttctc aaacttttaa gatactagaa    8880
gtccttttat taagccaaaa gaccctatgt attaattctg tcttccaggg gtaggagttg    8940
gggtggggtt tggaaagctt tgtctggata ataattagt attgtagttc catttatttg    9000
atgtctgatt ttgcgcttat taaaattgat ttaaatcctc aatggaaaat gatttttttt    9060
tttcaaatgc caagtgttgt gtgacttgca tttggattat tcccggtgca acctgaagat    9120
tccttgtgat gagttgtggt tccatcatct tgggaaccac taagagaatt ctgttttact    9180
cacaatccaa acaataaatg ttttttttccc tatgtatgcc tttatccagc acacagtttg    9240
ctagacttat ggatgaatat gggttaatat aacatggtat ctatccttct ggaaacagac    9300
ttttaaaacc ttactaagca ttctctgcat tcatcaaatg tgaagtgagt gcctggtgtg    9360
tgccaggcat cgagctgggc acagcatatc cctgccctca gagctttaca gtccagtgag    9420
ttcaacagaa gatgaacagt tttgatgaca caaaaaatag acacatgtgc atgctgtgat    9480
agggggagat acaagttcct gtggaagcat catctgggag gaccagggaa ggcatcttgg    9540
aaaaactgag ctctgaaaga tggatagagt taaccacatg aagagtggag aagggtactt    9600
cagacaaggt gaacagcatc aggaaagccc agggagggta tagaaaagaa agaacagtaa    9660
ttcttgcagt ggctttcaat gggagtggca gtcatggaag gaaggagagg tagcagggac    9720
cagcttttga agggctttgt gtatcacatt ttaagaagtt taaattttaa cctaaggtca    9780
ctgggaagcc attggcagat tttgtatgtt aggaagttca ccactcacct acttggagta    9840
ttgcaggtgg agctaatgtg gatgggcctc ctgcccatta ttaaatcctg ttcctgtcag    9900
gaacaggaca gcccatgctg tctctccctg tgtgtctgtc tctccctgtg tgtctgtctc    9960
tctctctctc tctgtctctc tctctcaaaa gctaaaggaa agcgcatagg ttccagaagg   10020
aaaaagaaat aaccactaga aaaataagta taagctgact ttaccatggc gcagtgagat   10080
tccaaaccaa aataaggttt ctagggattg agcttttaat actggtactc caacagggag   10140
ataggacttg ggaaactgac gctgtgtgaa agttacagaa ttaagcagcc tgcaaacctg   10200
gacctttgaa aatcgtccta ctgacccagg aaaagtgcaa ggaagtgggt tctccagaac   10260
cttgggtagg ccaaacatta cttgaaggca tcgatctaaa taatacacaa aagcattatt   10320
caggaacacc ctgagaaatt aacataaaaa ctgatttggc caggcatggt ggctcagcct   10380
ctggtaacag tgctttggga ggccaaggtt ggaaaatcac ttgaggccag gagatccagg   10440
ctgtagtgag ctatgattgt actactgcac tccagcctgg gcaacagagg gagagtctta   10500
aaaaagcaaa ctgtccaaga tcattgaaac cattagcact taggaagaaa caaatgaaat   10560
tacattcaag ggggtcacat ttaaatccag ggctctcagg actcccaaag taaaagatg   10620 gacataaaat aaaaaaatta caagccactt gagaaaaaaa taaatcacca tgaggtagag   10680
atagcagagg aaaaattaca catgaagatc taggaattag ggagctatcc aagatagact   10740
gtgaaagtat gttgcaagtg actgagggta atgaaaaaaa tgtcataaga gcatgaatta   10800
gaagcgtttt gagaaagaat gaagataatg tggtcattga ctgtaaactc atttgatggg   10860
caacgataga tgagacacag ctattaagag tggatcgata accttgaatg tggatgtgag   10920
gcaactgtag tatagcacaa aaaggttgag aaatgatgga gcccttaagc tgcttgtgga   10980
cactggtctg gaggggaca ggaccaagaa aaccagtcat ggaggttgaa ctaagtcatc   11040
tctccaatgt atccgtgcct gttacgtgcc agtgccgttt aggagcagag gatattgtaa   11100
```

-continued

```
tttttttttaa agttcctatg aataccttct agtgggtcat aatggctcaa ccgggaaatg  11160
gcagtagaga tgaagagatg gatggattcg aaagacattt tttggaagtt ggaattaaca  11220
ggatatggtg aataatcaag agatagtaaa agcataatgg aggaaacaat ggttcttcct  11280
gttaccatag gaagaagctt tggagtagag ttttattcat tttaaatgca tttattgtgc  11340
actttattat aggtattgga gattgatgga aaatagtctc tgacctcaaa gagtttcaca  11400
ggaaagatga gcgatggcta tgtaatatga ccaatactgg gatagagagg tgcccaggtc  11460
actacgggag gacttaggtg atttctaact atgtctgaga gtaggggaaa tgggatcaaa  11520
gaaaacatct cagaagacat gaagcttgag cttatgtctt gaaaaattta agtttaacc  11580 taaccaagga taaagaatca gaagaaacag catattcaaa agctaaagaa cacgggactc  11640
ttgtgtgctt tgcatgtaca cacgtgtgtg cgtgtgtgtc tgaaaggatt ggagaggagg  11700
gcgaagagaa taacaagatg aacgtcaacc taatgtagaa tgtttgaagt ttgtatttca  11760
cttaacaaga cagcggggag tgatggaagg atcttagata ggaaagggac atgagcacgt  11820
ttgccaagag agctcgttct ggtcatagtg ggtacgtgaa ggtgacaaat ctggaggcag  11880
atagctcaca tttggaggca gctgcagtca tccagatgag aagtgagagg gacctaagct  11940
gtaaattgtg ggaataaaga caagacccgt taaaaagaaa gagaacacac catgtagcgt  12000
ggaaaggaga agggtggaga gtagcctgtg cagaaggaac aaccttcaaa aagacatgga  12060
agactgaaaa gacaccctgt tgtagggaga tcagcaatgc atttttttata accaggtgat  12120 acagggaaag ggtaggatct gaagcttgaa aaatagattg ggggctgatt gtaaagagct  12180
tcgtgtcatt cccaggattt tggaactgat tttactaaca tgaaaaaggt tttgttttaa  12240
aatactgagt aatatagttg gaactataat ttagaaagat aatagctggt gccatcactc  12300
ttctaagcaa agatagtaat acatttaatg ctcataggct ttagtaatac atttaatcct  12360
tacagtaagc ctattagata aaaaccatta ttatctccct tctatagaca gagaaactgg  12420
cattaggaga atgagaactt gcctatggtc ccactctgga aatacctagt aagcgacaga  12480
gccaggattc aaacccaggc agcttgactc cagaactttc gctcataacc ttacacatct  12540
ccgtcatggt tggtgtttct caaccatgga tacacattcg aactgcatgt agcatctcta  12600
aacatacagt tacctgaatt gactgaatca gagtgtctga aaaatgatgt gtgatactat  12660
gttttgcaaa atctccacag gtaattctgt tgtactttgc ttatagttga gtactgcagg  12720
gatcttagga agttagagca gtagtccagg caggagatga tgaaggctca gactaaagca  12780
gtctgtagga aggaagagaa gggaaccggt ttggagactt aagcggggga attggcagta  12840
tttgtgaagt ggaaatgcag tattttcttg tagagtatga accttgccta ggaaagggag  12900
tagaggacca tacctttagt tgtaaattat cctctcccaa ctggatctgt tgatttatgg  12960
ctatggtggt tggggaaaag aggatttaac catttgaaga agtttgtgta gaggattatg  13020
attgaactca ggctgttgtc cttgtgtata gtttcatgct tatactcttg tttgtctttta 13080 cttctctatc cagggccctt ggaagaaaat cctcgctgtg tccaggctga ggcgggggc  13140 taatgacagt gtgagctcta gatggtgtga gaccacccca aagccaagaa atggctacag  13200
ccgtggaacc agaggaccag gatctttggg aagaagaggg aattctgatg gtgaaactgg  13260
aagatgattt cacctgtcgg ccagagtctg tcttacagag ggatgacccg gtgctggaaa  13320
cctcccacca gaacttccga cgcttccgct accaggaggc agcaagccct agagaagctc  13380
tcatcagact ccgagaactt tgtcaccagt ggctgagacc agagaggcgg acaaaggagc  13440
```

```
agatcctaga gctgcttgtg ctggaacaat ttcttaccgt cctacctgga gaactacaga    13500
gctgggtgcg gggccaacgg ccagaaagtg gcgaggaggc agtgacgctg gtggagggtt    13560
tgcagaaaca acccaggaga ccaaggcggt gggtgaggag ggggagtcct gatctgtgtg    13620
atgtggaggg ggactatttg ctggaaggct ggatttgcgg ggagagcttg caggatcccc    13680
ataaattatt agtggctctg cccttgggtt gctcatatac catgagcccc atggattagg    13740
gggatgtgtg tgtatgaatg tgactttctg gatattggaa cacctgtata gggaccatct    13800 gaggggtct cagccaccaa aggtcatgg ctttggtttt cccttctttg aatgttgagc    13860
cgtgggttcc tggagaggag aattttgtga cttcctcgaa ggttctcata gatccccagt    13920
cacagatccc ccttcctggc tggtcagcta gggaagcagg cagcaaggag agctgcaggt    13980
gggacaggtg gagatgggaa ggaaccttgg gtgacagggg cccaggctgg gggtggtgag    14040
agagcagtgc aggcctgcgc atcccctgcc ttgtcctggg gaggataacc ttcagctcct    14100
ccttgcctgc tccattgaaa ctggagtttc ccctccttgt ctgggtccct ctgggagtgt    14160
tttctctagg catcttctcc taaaataagc tcccgtgaca accaagaact tcctcctgac    14220
tccatggtga ctggaagttg gaattattcc caggtgactg tccatgttca cggccaggaa    14280
gtcctgtcag aggagacggt gcatttagga gcggagcctg agtcacctaa tgagctgcag    14340
gatcctgtgc aaagctcgac ccccgagcag tctcctgagg aaaccacaca gagcccagat    14400 ctggggcac cggcagagca gcgtccacac caggaagagg agctccagac cctgcaggag    14460
agcggtggga agcatcagca gaaagggggg attgtgcag aaggcaggca aggaggggga    14520
catttctcct ataccaagga agctgggtag atagactgta tggaaagaca tcacagaatc    14580
caggatgtca agaggagaca gtaccgccag ctagagtccc ccataaacag ggccaagctt    14640
agacagcaga ttgttgcttg ttctcttggc attctgatag tctcataggt gatgggattg    14700
ggatatggga gctaccctta ggccagtttc ttggttccca taatagaaag gataggggcca    14760 ccttcctacc aaagatggtg ggggatgccc agattttttgc ccattattgg ggcatgctgc    14820
atattactga tctttgcctt cttttcttca tagaggtccc agtgcccgag gacccagacc    14880
ttcctgcaga gaggagctct ggagactcag agatggttgc tcttcttact gctctgtcac    14940
aggtgtgccc tagttacctc tgtaccacag agaatttgtt tgaagaacca ctgggcataa    15000
gccatactaa acaggtgaag caggatgcac atttacactc ttgccagttt taagctcaca    15060
gttctgcagg tacctggaag gggaggagat aatgagataa attatcatac cttatattgg    15120
atccacaggc accaacacca gtttatttgc cattgactag aagaactaac aaaatgggat    15180
tattttgtaa cactccagta caactgcgaa gttgtcaaat gagggttttt tagtttttttt    15240 ttttttttaaa ggaataaatt tgatagtcat ttgtaagtat gacagactgt actgctgaga    15300
catttaggaa gtattcacca tgatcaaagc tctgaaacta agccatgtgg ctggagaaaa    15360
agaaatagaa ttcatgtatg gttttagatt gtaatctaac tgaggaaaaa agtcttgttt    15420
tggctataga gtatagaaac tattgaaagt gattagagtc tttagggaaa gtgtactaga    15480
aaagatgaat tttgcagaaa tgtatatagc gttaaagtgt caagtaggga gctgaatgat    15540
gatttttaag accttcccta aattttaaac aataccttaa agaagaagaa cataagctgg    15600
tcctcaggaa aagtggtgga gttggagggg gcagggccag tgccacaggg gacacatggc    15660
tcccccgaga atgagtttaa gcagcccgcc actcaagctc ctttcatctc ctagaggagt    15720
ccacctattg tgtgaccttc aacagggaca aaatacgagg ctacccgtag catcacgttt    15780
tgatgaaatc cttatgtggt ttcagggact ggtaacgttc aaggatgtgg ccgtatgctt    15840
```

-continued

```
ttcccaggac cagtggagtg atctggaccc aacacagaaa gagttctatg agaatatgt    15900
cttggaagaa gactgtggaa ttgttgtctc tctgtgtaag gaatttcaag tattctagag    15960
tgttctaagc ccagagatct ttttcctgct ggaaattttg ggggatctta gaccttagat    16020
tgtatgcagt gaacttctct tatgccttcc ccaccaataa aattgaggga ttaggtgaaa    16080
aatacggtgt cctttcaagt aaaagataaa tggatgaaaa tggaaacctc taataggaaa    16140
acaaacttgt aatattacag ctttagtgca gaaatatttg aagtaagcac atgagtttta    16200
aaacagtaag agttggagat aatctttctt gaatatggga aaagaggata aggtgtacaa    16260
tggtataatt attaagttgc aggtgaaaac cacaagaaag gcaagagata cgcagtcctt    16320
ggttaaaagt acacaaacta aagagatgaa agatttcatc acctgagcta gctatgtatt    16380
tgccccacaa cctaccaaat agaaaaggac cgctcttaac acagggaatt gttgagccaa    16440
tcgtgatatc ctatttccc tctcttgagc agcatttcca atcccagac ctgatgagat    16500
ctcccaggtt agagaggaag agccttgggt cccagatatc caagagcctc aggagactca    16560
agagccagaa atcctgagtt ttacctacac aggtgaggaa tgacaaaaac ggtgttaccc    16620
accctgagcc agcagttcct ctaggcagtg cttctctctc tctgtagggc cccgctctca    16680
tcagttcttc taacatgtca gccagtactg cttttctccct ctgacagcca tttcttctgt    16740
cattgccctc ctcttttctc ctcccatcat ttgtctgata gcaatgtaat acaaaagggt    16800
gaaagaaaaa tgttaacttt tggaattgca gctataccat ttactgtaca attcccttaa    16860
accctcgatt ctcaatctct gcatttgtaa aatgaagatt atatttgtgc ataccaaggt    16920
ttgttgatag cataacaata tgagaaagtg cttggcacag acaggcatt ccatttagtc    16980
ttgccatctc aaaacccttt gtaaaaatct cccccattgtg tagaaggcat tgttgccgct    17040
acagtgaccc ccttttcct ctcacccttt ctacaggaga taggagtaaa gatgaggaag    17100
agtgtctgga gcaggaagat ctgagtttgg aggatataca caggcctgtt ttgggagaac    17160
cagaaattca ccagactcca gattgggaaa tagtctttga ggacaatcca ggtagactta    17220
atgaaagaag atttggtact aatatttctc aagtgaatag ttttgtgaac cttcgggaaa    17280
ctacacccgt ccaccccctg ttagggaggc atcatgactg ttctgtgtgt ggaaagagct    17340
tcacttgtaa ctcccacctt gttagacacc tgaggactca cacaggagag aaaccctata    17400
aatgtatgga atgtgaaaaa agttacacac gaagctcaca tcttgccagg caccaaaagg    17460
ttcacaagat gaacgcgcct tacaaatatc ccctaaaccg gaagaatttg gaagagacct    17520
cccctgtgac acaggctgag agaactccca cagtggagaa acccctataga tgtgatgatt    17580
gcggaaagca cttccgctgg acttcagacc ttgtcagaca tcagaggaca catactggag    17640
aaaaaccctt cttttgtact atttgtggca aaagcttcag ccagaaatct gtgttaacaa    17700
cacaccaaag aatccacctg ggaggcaaac cctacttgtg tggagagtgt ggtgaggact    17760
tcagtgaaca caggcggtac ctggcgcacc ggaagacgca cgctgctgag gaactctacc    17820
tctgcagcga gtgcgggcgc tgcttcaccc acagcgcagc gttcgccaag cacttgagag    17880
gacacgcctc agtgaggccc tgccgatgca acgaatgtgg gaagagcttc agtcgcaggg    17940
accacctcgt caggcatcag agaacacaca ctggggagaa accattcacg tgccctacct    18000
gtggaaaaag cttcagcaga ggatatcact taattaggca tcagaggacc cactcagaaa    18060
agacctccta gctaggtccc catgtgagga gatctgcttt cagccctcac ctaagggagg    18120
tgaggaagag gaaaagccct cttgtcagcc tgggaagacc ttttcgaggg agtctccctg    18180
```

```
acctgctcag atctgacatt acctcttcct gcaactaaac acgagcctgg gcagaacctc   18240
tcagccttcc tctacgcctt gagggggatgt ttcatccaaa gtacaacctg aattgaggct   18300
tctccttcac tggagtgcac ctgcctctac ctcatgggta taaagtagga gaactaagag   18360
acttaagagg tcgtggttcc tatatcgtcc aaaaaatagg ctgttacata tcctaaagac   18420
tgctcaacag cttcaagttg aaagtggcca aggacagccc cttaggtttg ggaagggacg   18480
agcctgaagg attctgtctt tactggggtc aaatcttaaa gcacacagct ctggactcaa   18540
gacaggaggt ttgcgtcctg atggctttgc acacattcac aggataactg catagatccc   18600
tcgctgtctg attcacttct taccatgcac tttcctttga tgctgaggag aaatggaagt   18660
gggcgaaaaa tctcaaggct gcttcatgtg gaccttgtca agctgctccc tcccccagcg   18720
tcaaattgtt atcaggtgcc aaacactgct agaaggagg gcctagtcag aagcctcttt   18780
ccatacgagt tttggttttg tttttaatat ttttttctat taaatactc atgcatttaa   18840 ccttcccgtt attcaaccag tctcttggtt gcatccctag cacttctact acaagtgaga   18900
tggtagtgtt tgagtgctta ttgagtaaag cataattcgg tcataatgaa atcgttcaca   18960
ttccctcata tgcacaagcc caccaacccc ttcacacccc ccttcacagg ggtcgtatga   19020
gtaaggggat ttggaaactg tcaacttaca aaggcactat aacaattaca gaatcatgat   19080
tgccatgggc cactttattt acatgaagac aactggagaa cgactaagac caaattatgg   19140
aaaataagaa aaagctgttg ctggcaagac catcaagact gttctgacac cctgtcccca   19200
tcatccctga ctgagtactc tgacatcacg gaaagtgttg aacctgggac cctgaggaat   19260
tcaccaggag taaatggctt tcatgtattt gtgttgtttg cttttttctta cgtgatttta   19320 tgttcataga gctagaaagt agcatctcat gatggcccaa caatctctgt tgccagttaa   19380
aggttccttg gagatgaggc tgaataatta tgaacctcac cttctctgat tgtgggagtg   19440
gcaagaactg gggagacgtc ctccataagt ggagcacagg gtatggggtt aaagcatgac   19500
agggagagtc ttctgtgcct ggtttcttct cctctatctc ataatgcatt atgggcccga   19560
ggaatagggg agggttaata agactccaac cctaatggcc caacagggaa attctcattt   19620
tggtcgatga tattctgatg gactggtttg gtcttaatac cagtcaaccg ttgtccttct   19680
ggaaatatac atatatgaaa taaataaagg taacacttgc agccaagttc cctggttttct   19740 gggacttccc atcttaccca ttcctttttcc agggcttcag tgtcctgata cttctgaggg   19800
tggttcatac tcaaatagat ctgggagtac agagtatttt tccttgagga aggaagggt   19860 tgggatgatt agcagagtcc ggtgaaacat atgcactctg agataagatc caagcctgga   19920
gtttgcagaa gatactgtcc taataagcag gcatttctaa accaagtatc taagcctaag   19980
cacagcttgt cctgggtgaa atgtctgcca caaagatag tttctcctag ctcagactta   20040
accatttata aaggttggta aaatactggc agtgacaaca aattgacttt ttaattttct   20100
tatttgcatt attccaataa atgaaaatct gtcagagttc tacatgaggg aaagcttgtg   20160
aggctgggcc ggtttgttgg aacatcaaat agtccttaat tactgatctc cctgcagagt   20220
ttcatatgct gacactaaat ctctggtccc ttttgtaaat tactgaattt tctgaggttc   20280
tgggagggac atgttgtctc ccaaatctga acaaacacaa ccacagtgtg cagcggcagg   20340
aaagaagtag tgcagctgag cgtgagcagg gaggttggag cacagggtgt gtattcggag   20400
gggtcccctc tagtatcttg tgagcagtag aattctagca tccttgaata ccatactaag   20460
tttctgaggg agaaaacggt gggatttaaa agatattatt tggaggaagt taatacgcta   20520
cttaattaac agaattggca ggtggttgga aatgtgctaa agaggtatga cacattaaaa   20580
```

```
atgataatat aaggatgttt gaccagataa tttaggaata accaaggaat atttaacctc    20640
ttcaccacaa agtccgagga gaaataaatg cccaagagat caagccaaaa tacattttta    20700
ttatctggga cttaggcctc atattccgga gcagaatccg gtaaactcag atgaactcca    20760
tggagaattt cataaatcag attaacatca aggtactaaa atcaaaaccc actaagaaac    20820
ctgttgcccc cttcaaagca caactgaagt aatggatcta atagaagata cattgtttgc    20880
actgagcagt agagtagtag aggagaaaag cccagagatg gcacagacaa gttgttccag    20940
tccccttcag tcaaggcctc tggaccacca ccctgccaca ggcgaaaaat gggatattta    21000
ataaataaaa aattttgatt caccagactg gctgaaagga cagtaatcca aatgagagtt    21060
aacggctcca tagtagtttt ctagaatgaa agctgaactg agaaatagta actgatgaca    21120
tgttgagcag gttaataatt tggtaccctt ccacaccagt atttgtttgt tgtttgttt    21180 tgagatggag tctcgctctg tcgcccaggc tggagtgcag tggcgtgatc tcggctcact    21240
gcaagctccg cctcccgggt tcacgccatt ctcctgcctc agcctcccca ggaagctggg    21300
actacaggca cccaccacca cgcccggctg attttctgta attttggtag agacggggtt    21360
tcaccatgtt agccaggatg gtctcgatct cctgaccttg tgatccgcct gccttggcct    21420
cccaaagtgc tgggattgca agcgtgagcc accgcacctg gccccacacc agtattttta    21480
aaaatagttt gttttacctc tagcgtcttc cctcagctga cctaaatagt ccagccacaa    21540
tagctgagag aagtatacct acaattattt ccatctcctt atatttctag tgatgttggc    21600
tgactaaccc actaatctag tttatgggag agggaaagac tgaaagagcc acaaagtgga    21660
tggccaaccc acgtgattac taacctttat tgtggcaaag taactgatac aatgtttcaa    21720
atgtaagcac atctccttgg aataagtgga ataacttaat tcatccttgc ggaagtcctg    21780
aggatcaagc aaggaggagc ccagctttct ttagacacca cctttttat ctttaataac    21840 aaaaaggaac aaagtgattg tcagaccagc acaaagatac ctcttaatgt gcaatttcta    21900
ttctctttag tgtgtgtgag tgcacgcatg cacgtgtgta caccgaggtt tcaggtagaa    21960
ggaggaatgc aattcaaatt ctaaaaaagg aatcagtcag cacaaactag tttatttggc    22020
aattcataaa gatagggact cttcagagga ggttgagagc attgtagggt tatgtaaaga    22080
cttccagaag ctgtaaagac ttccagaagc aagaagattc aaccatctaa aacgccatgc    22140
aggaaaatag ccaaaccttc tccatttaag tagagaataa atcttagtag cgttctctgc    22200
agaatataac aacgctgcaa aaaggccatt tcacaggaat ataatcaaaa ctgcagattc    22260
tcagggtttc ccgtaagacg acttctctgc tcttctgttt gtggtttctt ttttagttgt    22320
acatctctcc tagacaagtc caaggaacta ctaacgagaa gatttcagga agaggcctac    22380
agcaattgct tggtgcttgg gttcatttgc ggaatcttgg caacaggtct acagagaagc    22440
agttccacgg caaaagagct gtggggcagt tgaataatcc atccaaacaa tgaggagtaa    22500
accctgagtc aagaaaccag caaaaagcag aagactgggt cagcaaataa agggagaaga    22560
tccttgcctc cttcagtgcc cctagcatga tattctgaaa ggccctccac taaaatacaa    22620
ctacagtttt aataaattac taaaatagag aatagaagta gtatgtaagt tgggataggg    22680
tgatctgaat taagtgtttt aacattcatg aactgttcag gacaaaagct gtaagatatt    22740
ggttaacctc aacattgtta aattaagtgt gcactgtagt atcaaagata ctcataagaa    22800
tggagagagt aattttctaa atagtggagg gaaaatagga attaatttttt ttcaaaagtg    22860 ggacttaggt tgtctaaaga aaggccaaaa aaagcataaa aagatgaaaa aatagaacta    22920
```

-continued

```
cgaagaacac agcccaaata tatgaataaa atagaataaa tagtaactac catttaagat   22980
agagattgtc agaatgggta aaaaaaaaag taaattataa caaagtatat acaacagata   23040
tacaaaaata gtgatttttt tttttttttt t                                  23071
```